United States Patent
Ji et al.

(10) Patent No.: US 11,761,963 B2
(45) Date of Patent: Sep. 19, 2023

(54) BIOMARKER SIGNATURE FOR PREDICTING TUMOR RESPONSE TO ANTI-CD200 THERAPY

(71) Applicant: Alexion Pharmaceuticals, Inc., Boston, MA (US)

(72) Inventors: Rui-Ru Ji, Belmont, MA (US); Mark Hamilton, Ridgefield, CT (US); Sharon Barr, Madison, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 531 days.

(21) Appl. No.: 16/648,503

(22) PCT Filed: Sep. 26, 2018

(86) PCT No.: PCT/US2018/052792
§ 371 (c)(1),
(2) Date: Mar. 18, 2020

(87) PCT Pub. No.: WO2019/067499
PCT Pub. Date: Apr. 4, 2019

(65) Prior Publication Data
US 2020/0232990 A1    Jul. 23, 2020

Related U.S. Application Data

(60) Provisional application No. 62/578,643, filed on Oct. 30, 2017, provisional application No. 62/564,052, filed on Sep. 27, 2017.

(51) Int. Cl.
| | | |
|---|---|---|
| *G01N 33/574* | (2006.01) | |
| *A61K 39/395* | (2006.01) | |
| *A61K 39/00* | (2006.01) | |

(52) U.S. Cl.
CPC ... *G01N 33/57484* (2013.01); *A61K 39/3955* (2013.01); *G01N 33/57407* (2013.01); *A61K 2039/545* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 3,940,475 A | 2/1976 | Gross |
| 4,289,747 A | 9/1981 | Chu |
| 4,376,110 A | 3/1983 | David et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,434,131 A | 7/1995 | Linsley et al. |
| 5,508,717 A | 4/1996 | Miller |
| 5,530,101 A | 6/1996 | Queen et al. |
| 5,571,698 A | 11/1996 | Ladner et al. |
| 5,580,717 A | 12/1996 | Dower et al. |
| 5,780,279 A | 7/1998 | Matthews et al. |
| 5,859,205 A | 1/1999 | Adair et al. |
| 5,902,583 A | 5/1999 | Buchsbaum et al. |
| 5,916,560 A | 6/1999 | Larsen et al. |
| 6,011,138 A | 1/2000 | Reff et al. |
| 6,040,136 A | 3/2000 | Garrard et al. |
| 6,632,927 B2 | 10/2003 | Adair et al. |
| 6,652,858 B2 | 11/2003 | Gorczynski et al. |
| 6,709,832 B1 | 3/2004 | Von Knebel Doeberitz et al. |
| 6,737,056 B1 | 5/2004 | Presta |
| 6,749,854 B2 | 6/2004 | Gorczynski et al. |
| 6,955,811 B2 | 10/2005 | Gorczynski et al. |
| 6,984,625 B2 | 1/2006 | Gorczynski |

(Continued)

FOREIGN PATENT DOCUMENTS

| | | |
|---|---|---|
| EP | 2178561 A1 | 4/2010 |
| EP | 2523976 A1 | 11/2012 |

(Continued)

OTHER PUBLICATIONS

Sun et al, Immunology Letter, Aug. 2016, vol. 178, pp. 105-113.*
Kretz-Rommel et al, The Journal of Immunology, 2007, vol. 178, pp. 5595-5605.*
Wong et al, Journal of Leukocyte Biology 2010, vol. 88, pp. 361-372.*
Siva et al, (Cancer Immunology, Immunotherapy, 2008, vol. 57, pp. 987-996.*
Mahadevan et al, Blood, 2010, vol. 21, pp. 2465.*
Kotwica-Mojzych, (International Journal of Molecular, 2021, vol. 22, 1-21).*

(Continued)

*Primary Examiner* — Bridget E Bunner
*Assistant Examiner* — Fozia M Hamud
(74) *Attorney, Agent, or Firm* — Nelson Mullins Riley & Scarborough LLP; Jane E. Remillard, Esq.; Jill Gorny Sloper, Esq.

(57) ABSTRACT

Provided herein are methods for treating cancer in a patient who has been determined to have positive expression of CD200 receptor (CD200R1) and one or more biomarkers (i.e., ICOS, TIGIT, TNFRSF9, HAVCR2, PDCD1, FCGR2A, FCGR1A, CD163, and/or CD14) by administering to the patient a CD200 inhibitor. Also provided are methods for monitoring responsiveness of a patient having cancer to treatment with a CD200 inhibitor, the method comprising: determining expression levels of CD200R1 and one or more biomarkers (i.e., ICOS, TIGIT, TNFRSF9, HAVCR2, PDCD1, FCGR2A, FCGR1A, CD163, and/or CD14) in a biological sample from the patient, wherein increased expression levels of CD200R1 and the one or more biomarkers, as compared to expression levels in a biological sample of the same type obtained from the subject prior to treatment with the CD200 inhibitor, indicates that the subject is responsive to treatment with the CD200 inhibitor.

21 Claims, 25 Drawing Sheets

Specification includes a Sequence Listing.

(56) References Cited

U.S. PATENT DOCUMENTS

| | | | |
|---|---|---|---|
| 7,238,352 B2 | 7/2007 | Gorczynski et al. |
| 7,368,535 B2 | 5/2008 | Gorczynski et al. |
| 7,408,041 B2 | 8/2008 | Bowdish et al. |
| 7,427,665 B2 | 9/2008 | Bowdish et al. |
| 7,435,412 B2 | 10/2008 | Bowdish et al. |
| 7,452,536 B2 | 11/2008 | Gorczynski et al. |
| 7,598,353 B2 | 10/2009 | Bowdish et al. |
| 7,714,110 B2 | 5/2010 | Bowdish et al. |
| 7,887,798 B2 | 2/2011 | Gorczynski et al. |
| 7,915,000 B2 | 3/2011 | Bowdish et al. |
| 8,075,884 B2 | 12/2011 | Bowdish et al. |
| 8,114,403 B2 | 2/2012 | Bowdish et al. |
| 8,187,877 B2 | 5/2012 | Bowdish et al. |
| 8,252,285 B2 | 8/2012 | Rother et al. |
| 8,637,014 B2 | 1/2014 | Rother et al. |
| 8,709,415 B2 | 4/2014 | Bowdish et al. |
| 8,840,885 B2 | 9/2014 | Bowdish et al. |
| 8,999,328 B2 | 4/2015 | Bowdish et al. |
| 9,000,133 B2 | 4/2015 | Bowdish et al. |
| 9,085,623 B2 | 7/2015 | Rother et al. |
| 9,150,661 B2 | 10/2015 | Bowdish et al. |
| 9,180,186 B2 | 11/2015 | Faas McKnight et al. |
| 9,249,229 B2 | 2/2016 | Bowdish et al. |
| 9,447,187 B2 | 9/2016 | Wang et al. |
| RE46,323 E | 2/2017 | Rother et al. |
| 9,862,767 B2 | 1/2018 | Rother et al. |
| 2002/0031515 A1 | 3/2002 | Caligiuri et al. |
| 2002/0168364 A1 | 11/2002 | Gorczynski et al. |
| 2002/0192215 A1 | 12/2002 | Hoek et al. |
| 2003/0017491 A1 | 1/2003 | Shi et al. |
| 2004/0018972 A1 | 1/2004 | Gorczynski et al. |
| 2004/0054145 A1 | 3/2004 | Gorczynski |
| 2004/0175692 A1 | 9/2004 | Bowdish et al. |
| 2004/0198661 A1 | 10/2004 | Bowdish et al. |
| 2005/0074452 A1 | 4/2005 | Bowdish et al. |
| 2005/0100957 A1 | 5/2005 | Bowdish et al. |
| 2005/0107314 A1 | 5/2005 | Gorczynski et al. |
| 2005/0129690 A1 | 6/2005 | Bowdish et al. |
| 2005/0169870 A1 | 8/2005 | Truitt et al. |
| 2006/0024231 A1 | 2/2006 | Schnitzer et al. |
| 2007/0036786 A1 | 2/2007 | Tuaillon et al. |
| 2007/0065438 A1 | 3/2007 | Liversidge et al. |
| 2008/0131428 A1 | 6/2008 | Young et al. |
| 2009/0017046 A1 | 1/2009 | Bowdish et al. |
| 2009/0022745 A1 | 1/2009 | Bowdish et al. |
| 2010/0239598 A1 | 9/2010 | Bowdish et al. |
| 2010/0249382 A1 | 9/2010 | Desjarlais et al. |
| 2010/0291085 A1 | 11/2010 | Rother et al. |
| 2011/0129471 A1 | 6/2011 | Bowdish et al. |
| 2011/0135633 A1 | 6/2011 | Bowdish et al. |
| 2011/0236387 A1 | 9/2011 | Bowdish et al. |
| 2012/0148579 A1 | 6/2012 | Bowdish et al. |
| 2012/0321625 A1 | 12/2012 | Rother et al. |
| 2013/0158236 A1 | 6/2013 | Bowdish et al. |
| 2013/0172534 A1 | 7/2013 | Bowdish et al. |
| 2013/0189258 A1 | 7/2013 | Rother et al. |
| 2013/0202602 A1 | 8/2013 | Faas McKnight et al. |
| 2014/0170143 A1 | 6/2014 | Wang et al. |
| 2015/0368341 A1 | 12/2015 | Bowdish et al. |
| 2016/0009803 A1 | 1/2016 | Rother et al. |
| 2016/0033514 A1 | 2/2016 | McKnight et al. |

FOREIGN PATENT DOCUMENTS

| | | | |
|---|---|---|---|
| EP | 2534178 A1 | 12/2012 |
| EP | 2670487 A1 | 12/2013 |
| WO | 84/03508 A1 | 9/1984 |
| WO | 85/03508 A1 | 8/1985 |
| WO | 88/06630 A1 | 9/1988 |
| WO | 9215679 A1 | 9/1992 |
| WO | 94/28027 A1 | 12/1994 |
| WO | 95/18825 A1 | 7/1995 |
| WO | 96/27011 A1 | 9/1996 |
| WO | 96/38557 A1 | 12/1996 |
| WO | 97/08320 A1 | 3/1997 |
| WO | 97/21450 A1 | 6/1997 |
| WO | 98/27230 A1 | 6/1998 |
| WO | 99/24565 A1 | 5/1999 |
| WO | 01/87336 A1 | 11/2001 |
| WO | 02/11762 A2 | 2/2002 |
| WO | 02/42332 A2 | 5/2002 |
| WO | 02/46227 A2 | 6/2002 |
| WO | 02/059280 A2 | 8/2002 |
| WO | 02/095030 A2 | 11/2002 |
| WO | 03/025202 A2 | 3/2003 |
| WO | 2003/074679 A2 | 9/2003 |
| WO | 2004/060295 A2 | 7/2004 |
| WO | 2004/078937 A2 | 9/2004 |
| WO | 2004/078938 A2 | 9/2004 |
| WO | 2005/007809 A2 | 1/2005 |
| WO | 2006/053301 A2 | 5/2006 |
| WO | 2007/084321 A2 | 7/2007 |
| WO | 2008/089022 A2 | 7/2008 |
| WO | 2009014745 A1 | 1/2009 |
| WO | 2011085343 A1 | 7/2011 |
| WO | 2011100538 A1 | 8/2011 |
| WO | 2012106634 A1 | 8/2012 |
| WO | 2018/075408 A1 | 4/2018 |
| WO | 2018102594 A1 | 6/2018 |
| WO | 2019126133 A1 | 6/2019 |
| WO | 2019126536 A1 | 6/2019 |

OTHER PUBLICATIONS

Xiong et al, (Clin Cancer Res; 2020; vol. 26:232).*

Erin et al, (Oncotarget, 2018, vol. 9, No. 27; pp. 19147-19158).*

Ebert et al., "Selective Immunosuppressive Action of a Factor Produced by Colon Cancer Cells," Cancer Res. 60:6158-6161 (1990).

Elgert, K. D. "Immunology: Understanding the Immune System," The Genetic Basis of Antibody Diversity, 123 (1996).

Ennishi, D. et al., "CD5 expression is potentially predictive of poor outcome among biomarkers in patients with diffuse large B-cell lymphoma receiving rituximab plus CHOP therapy," Annals of Oncology, vol. 19:1921-1926 (2008).

Faguet et al., "Blood Kinectics, Tissue Distribution, and Radioimaging of Anti-Common Chronic Lymphatic Leukemia Antigen (cCLLa) Monoclonal Antibody CLL.sub.2 in Mice Transplanted With cCLLa-Bearing Human Leukemia Cells." Blood, vol. 75, No. 9(1990) pp. 1853-1861.

Faisal et al., "Cell-surface Associated p43/Endothelial-monocyte-activating-polypeptide-II in Hepatocellular Carcinoma Cells Induces Apoptosis in T-lymphocytes," Asian Journal of Surgery, 30(1):13-22 (2007).

Fallarino, F., et al., "Murine Plasmacytoid Dendritic Cells Initiate the Immunosupressive Pathway of Tryptophan Catabolism in Response to CD200 Receptor Engagement," J. Immunol., 173:3748-3754 (2004).

Farber, U., et al., "Loss of heterozygosity on chromosome 3, bands q24→qter, in a diploid meningioma," Cytogenet Cell Genet, 57:157-158 (1991).

Feurstein et al., "Induction of Autoimmunity in a Transgenic Model of B Cell Receptor Peripheral Tolerance: Changes in Coreceptors and B Cell Receptor-Induced Tyrosine-Phosphoproteins", J. Immunol., vol. 163:5287-5297 (1999).

Friedberg, Jonathan W., "Unique Toxicities and Resistance Mechanisms Associated with Monoclonal Antibody Therapy," Hematology, pp. 329-334 (2005).

Funakoshi et al., "Antitumor Effects of Nonconjugated Murine Lym-2 and Human-Mouse Chimeric CLL-1 Monoclonal Antibodies Against Various Human Lumphoma Cell Lines In Vitro and In Vivo." Blood vol. 90, No. 8 (1997) pp. 3160-3166.

Ginaldi et al., "Levels of expression of CD52 in normal and leukemic B and T cells: correlation with in vivo therapeutic responses to Campath-1H," Leukemia Res. 22(2):185-191 (1998).

Giusti et al., "Somatic diversification of S107 from an antiphosphocholine to an anti-DNA autoantibody is due to a single base change in its heavy chain variable region," PNAS, 84(9):2926-2930 (1987).

(56) References Cited

OTHER PUBLICATIONS

Gorczynski and Marsden, "Modulation of CD200 receptors as a novel method of immunosuppression," Expert Opin. Ther. Patents, 13(5):711-715(2003).
Gorczynski et al., "Anti-CD200R Ameliorates Collagen-Induced Arthritis in Mice," Clinical Immunol., 104(3):256-264 (2002).
Gorczynski et al., "Does Successful Allopregnancy Mimic Transplantation Tolerance?", Graft, 4(5):338-345(2001).
Gorczynski et al., "Evidence of a role for CD200 in regulation of immune rejection of leukaemic tumour cells in C57BL/6 mice," Clin. Exp. Immunol., 126:220-229(2001).
Gorczynski, "CD200 and its receptors as targets for immunoregulation," Current Opinion in Investigational Drugs, 6:483-488(2005).
Gorczynski, L., et al., "Evidence That an OX-2-Positive Cell Can Inhibit the Stimulation of Type 1 Cytokine Production by Bone Marrow-Derived B7-1 (and B7-2)-Positive Dendtritic Cells," J. Immunol, 162:774-781 (1999).
Gorczynski, R., et al., "CD200 Is a Ligand for All Members of the CD200R Family of Immunoregulatory Molecules," J. Immunol., 172:7744-7749 (2004).
Gorczynski, R., et al., "Dendritic Cells Expressing TGFBeta/IL-10, and CHO Cells With OX-2, Increase Graft Survival," Transplantation Proceedings, 33:1565-1566 (2001).
Gorczynski, R.M., "Evidence for an Immunoregulatory Role of OX2 with its Counter Ligand (OX2L) in the Regulation of Transplant Rejection, Fetal Loss, Autoimmunity and Tumor Growth", Archivum Immunologiae et Therapiae Experimentalis, Polish Academyof Sciences, vol. 49(4), pp. 303-309 (2001).
Gorczynski, R.M., "Role of Cytokines in Allograft Rejection," Current Pharmaceutical Design, 7:1039-1057 (2001).
Gorczynski, R.M., "Synergy in Induction of Increased Renal Allograft Survival after Portal Vein Infusion of Dendtritic Cells Transduced to Express TGFbeta and IL-10, along with Administration of CHO Cells Expressing the Regulatory Molecule OX-2,"Clinical Immunology, 95(3):182-189 (2000).
Gorczynski, R.M., "Transplant tolerance modifying antibody to CD200 receptor, but not CD200, alters cytokine production profile from stimulated macrophages," Eur. J. Immunol., 31:2331-2337 (2001).
Gorczynski, R.M., et al., "A CD200FC Immunoadhesin Prolongs Rat Islet Xenograft Survival in Mice," Transplantation, 73(12):1948-1953 (2002).
Gorczynski, R.M., et al., "An Immunoadhesin Incorporating the Molecule OX-2 Is a Potent Immunosuppressant That Prolongs Allo- and Xenograft Survival," J. Immunol., 163:1654-1660(1999).
Gorczynski, R.M., et al., "Anti-Rat OX-2 Blocks Increased Small Intestinal Transplant Survival After Portal Vein Immunization," Transplantation Proceedings, 31:577-578 (1999).
Gorczynski, R.M., et al., "Augmented Induction of CD4+ CD25+ Treg using Monoclonal Antibodies to CD200R," Transplantation, 79(4):488-491 (2005).
Gorczynski, R.M., et al., "Augmented Induction of CD4+ CD25+ Treg using Monoclonal Antibodies to CD200R," Transplantation, 79(9), pp. 1180-1183 (2005).
Gorczynski, R.M., et al., "CD200 Immunoadhesin Supresses Collagen-Induced Arthritis in Mice," Clinical Immunology, 101(3):328-334 (2001).
Gorczynski, R.M., et al., "Evidence for Persistent Expression of OX2 as a Necessary Component of Prolonged Renal Allograft Survival Following Portal Vein Immunization," Clinical Immunol., 97(1):69-78 (2000).
Gorczynski, R.M., et al., "Induction of Tolerance-Inducing Antigen-Presenting Cells in Bone Marrow Cultures in Vitor Using Monoclonal Antibodies to CD200R," Transplantation, 77(8):1138-1144 (2004).
Gorczynski, R.M., et al., "Interleukin-13, in Combination with Anti-Interleukin-12, Increases Graft Prolongation After Portal Venous Immunization with Cultured Allogeneic Bone Marrow-Derived Dendtritic Cells," Transplantation, 62(11):1592-1600(1996).

Gorczynski, R.M., et al., "Persistent expression of OX-2 is necessary for renal allograft survival," FASEB Journal, 14(6):A1069 (2000).
Gorczynski, R.M., et al., "Receptor Engagement on Cells Expressing a Ligand for the Tolerance-Inducing Molecule OX2 Induces an Immunoregulatory Population That Inhibits Alloreactivity in Vitro and in Vivo," J. Immunol., 165:4854-4860 (2000).
Gorczynski, R.M., et al., "Regulation of Gene Expression of Murine MD-1 Regulates Subsequent T Cell Activation and Cytokine Production," J. of Immunology, 165:1925-1932 (2000).
Gorczynski, R.M., et al., "Structural and Functional Heterogeneity in the CD200R Family of Immunoregulatory Molecules and their Expression at the Fetomatemal Interface," AJRI, 52:147-163 (2004).
Gorczynski, R.M., et al., "The Same Immunoregulatory Molecules Contribute to Successful Pregnancy and Transplantation," AJRI, 48:18-26 (2002).
Greenwood, J.D. and Clark, M., "Protein Engineering of Antibody Molecules for Prophylactic and Therapeutic Applications in Man," (ed. Clark, M.) Pub. Academic Titles, UK, pp. 4-5 (1993).
Gura, T. "Systems for Identifying New Drugs are Often Faulty", Science, 278: 1041-1042 (1997).
Gussow and Seemann, "Humanization of Monoclonal Antibodies," Meth. Enzymol. 203:99-121 (1991).
Hardy et al., "A lymphocyte-activating monoclonal antibody induces regression of human tumors in severe combined immunodeficient mice," Proc. Natl. Acad. Sci. USA 94:5756-5760 (1997).
Hart, P.H., "Modulation of Monocyte Effector Functions by Lipopolysacc-haride and Interferon-Y," Dept. of Medicine, University of Melbourne, Royal Melbourne Hospital, Parkville, Vic., 3050 (1987) (Abstract).
Hatherley, Deborah et al., "The CD200 and CD200 receptor cell surface proteins interact through their N-terminal immunoglobulin-like domains," Eur. J. Immunol., vol. 34:1688-1694 (2004).
Heaney et al., "Severe asthma treatment: need for characterising patients," Lancet, 365:974-976(2005).
Hegen et al., "Utility of animal models for identification of potential therapeutics for rheumatoid arthritis," Ann. Rheum. Dis., vol. 67, pp. 1505-1515 (2008).
Hernandez-Ilizaliturri, F.J. et al., "Strategies to overcoming rituximab-chemotherapy resistance by targeting the autophagy pathway using bortezomib in combination with the Bcl-2 inhibitor obatoclax in non-Hodgkin's lymphomas (NHL)," Journal ofClinical Oncology, 2009 ASCO Annual Meeting Proceedings, vol. 27(15S), 1 page, Poster No. 8543 (2009).
Hoek, R.M., et al., "Down-Regulation of the Macrophage Lineage Through Interaction with OX2 (CD200)," Science, 290:1768-1771 (2000).
Hoek, R.M., et al., "Macrophage regulation by the B7.1/2 homologue OX2?", FASB Journal, 14(6):A1232 (2000).
Holodick, Nichol E. et al., "Adult BM generates CD5+ B1 cells containing abundant N-region additions," Eur. J. Immunol., vol. 39(9):2383-2394 (2009).
Petermann, Kimberly B. et al., "CD200 is induced by ERK and is a potential therapeutic target in melanoma," The Journal of Clinical Investigation, vol. 117(12):3922-3929 (2007).
Presta, L., "Antibody engineering for therapeutics," Current Opinion in Structural Biology, 13(4):519-525 (2003).
Preston et al., "The leukocyte/neuron cell surface antigen OX2 binds to a ligand on macrophages", European J. of Immunol., 27(8):1911-1918(1997).
Ragheb et al., "Preparation and functional properties of monoclonal antibodies to human, mouse and rat OX-2", Immunol. Letters, 68(2,3):311-315(1999).
Ragheb, R.F., "Exploration of OX-2 function in tolerance induction and graft acceptance using an anti-mouse OX-2 monoclonal antibody," University of Toronto, Masters Abstracts International, 38(4):971-972 (2000).
Reddy, N.M. et al., "Rituximab resistance and its association with changes in the internal domain of CD20 antigen and down-regulation of pro-apoptotic protein Bax and Bak in both rituximab-resistant cell lines (RRCL) and diffuse large B-celllymphoma (DLBCL)

(56) References Cited

OTHER PUBLICATIONS patient (pt) samples," Journal of Clinical Oncology, 2006 ASCO Annual Meeting Proceedings, vol. 24(18S), 1 page, Poster No. 17509 (2006).
Richards, S.J., et al., "Reported Sequence Homology Between Alzheimer Amyloid770 and the MCR OX-2 Antigen Does Not Predict Function," Brain Research Bulletin, 38(3):305-306 (1995).
Rijkers, Eva S.K. et al., "The inhibitory CD200R is differentially expressed on human and mouse T and B lymphocytes," Molecular Immunology, vol. 45:1126-1135 (2008).
Riley, "Melanoma and the Problem Malignancy," J. Exp. Med., 204:1-9 (2004).
Rindfleisch et al., "Diagnosis and Management of Rheumatoid Arthritis," American Family Physician, vol. 72(6), pp. 1037-1047(2005).
Rioux, P., Campath-1H (Cambridge Univeristy), IDrugs, vol. 2(2); pp. 153-167, Database Medline, abstract No. NLM16160950 (Abstract Only) (1999).
Romagnani, Sergio., "Short Analytical Review: TH1 and TH2 in Human Diseases," Clin. Immunol. Immunopath, 80 (3):225-235(1996).
Rosenblum, M.D., et al., "CD200 is a novel p53-target gene involved in apoptosis-associated immune tolerance," Blood, 103(7):2691-2698 (2004).
Rosenwald et al., "Relation of Gene Expression Phenotype to Immunoglobulin Mutation Genotype in B Cell Chronic Lymphocytic Leukemia," J. of Exp. Medicine, 194(11):1639-1647(2001).
Rudicoff et al., "Single amino acid substitution altering antigen-binding specificity," Proc. Natl. Acad. Sci. USA 79:1979-1983 (1982).
Sahin et al., "New monoclonal antibody specific for a 6.5 kDa glycoprotein which presents mainly on a B cell of chronic lymphocytic leukemia (CLL)" Immunology Letters, 2001, 76, 1-6.
Schlom, Jeffrey :Monoclonal Antiboides They're More and Less Than You Think, Molecular and Cellular Research for Future Diagnosis and Therapy, 95-134, 1991.
Schultes et al., "Immunotherapy of Human Ovarian Carcinoma With Ovarex.TM. Mab-B43.13 in a Human-PBL-SCID/BG Mouse Model," Hybridoma, 18(1):47-55 (1999).
Sebestyen et al., Syndecan-1 (CD138) expression in human non-Hodgkin lymphomas. British Journal of Hematology. vol. 104, 1999, p. 412-419.
Sehgal, et al., "Generation of the Primary Antibody Repertoire in Rabbits: Expression of a Diverse Set of Igk-V Genes May Compensate for Limited Combinatorial Diversity at the Heavy Chain Locus," Immunogenetics, vol. 50, pp. 31-42 (1999). cited byapplicant.
Shields, R. L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," Journal of Biological Chemistry,276(9):6591-6604 (2001).
Simelyte et al., "CD200-Fc, A Novel Antiarthritic Biologic Agent That Targets Proinflammatory Cytokine Expression in the Joints of Mice With Collagen-Induced Arthritis," Arthritis & Rheumatism, vol. 58(4), pp. 1038-1043 (2008).
Smith-Gill, Sandra J., "Biology of Antibody-Mediated Responses," Biologic Therapy of Cancer: Principles and Practice, Chapter 2, pp. 39-51 (1995).
Snyder et al., "Enhanced Targeting and Killing of Tumor Cells Expressing the CXC Chemokine Receptor 4 by Transducible Anticancer Peptides," Cancer Res 65(23):10646-10650 (2005).
Srivastava, P.K., "Immunotherapy of human cancer: lessons from mice," Nature Immunology, 1(5):363-366 (2000).
Steinman, Lawrence., "Assessment of Animal Models for MS and Demyelinating Disease in the Design of Rational Therapy," Neuron, 24:511-514(1999).
Stuart et al., "Monkeying Around with Collagen Autoimmunity and Arthritis," Lab. Invest., 54(1):1-3(1986).
Syme, R., et al., "Comparison of CD34 and Monocyte-Derived Dendritic Cells from Mobilized Peripheral Blood from Cancer Patients," Stem Cells, 23:74-81 (2005).
Tanaka et al., "The Anti-Human Tumor Effect and Generation of Human Cytotoxic T Cells in SCID Mice Given Human Peripheral Blood Lymphocytes by the in Vivo transfer of the Interleukin-6 Gene Using Adenovirus Vector," Cancer Research, 57:1335-1343(1997).
Tang et al., Pathogenesis of collagen-induced arthritis: modulation of disease by arthritogenic T-Cell epitope location, J. of Immunology, 113: 384-391 (2004).
Tangri and Raghupathy, "Expression of Cytokines in'Placentas of Mice Undergoing Immunologically Mediated Spontaneous Fetal Resorptions," Biology of Reprod., 49:850-856(1993).
Tao et al., "Structural Features of Human Immunoglobulin G that Determine Isotype-specific Differences in Complement Activation," J. Exp. Med., vol. 178, pp. 661-667 (1993).
Taylor, N., et al., "Enhanced Tolerance to Autoimmune Uveitis in CD200-Deficient Mice Correlates with a Pronounced Th2 Switch in Response to Antigen Challenge," J. Immunol., 174:143-154 (2005).
Tedder, Thomas F et al., "Isolation and structure of a cDNA encoding the B1 (CD20) cell-surface antigen of human B lymphocytes," Proc. Natl. Acad. Sci. USA, vol. 85:208-212 (1988).
Teeling, Jessica L. et al., "The Biological Activity of Human CD20 Monoclonal Antibodies Is Linked to Unique Epitopes on CD20," The Journal of Immunology, vol. 177:362-371 (2006).
Thomsen et al., "Reconstitution of a human immune system in immunodeficient mice: models of human alloreaction in vivo," Tissue Antigens, 66:73-82 (2005).
Toder et al., "Mouse Model for the Treatment of Immune Pregnancy Loss," Am. J. of Reprod. Immunol., 26:42-46 (1991).
Webb, M., et al., "Localisation of the MRC OX-2 Glycoprotein on the Surfaces of Neurones," J. Neurochemistry, 43:1061-1067 (1984).
Wilczynski, J.R., "Immunoligical Analogy Between Allograft Rejection, Recurrent Abortion and Pre-Eclampsia—the Same Basic Mechanism?," Human Ummunology, 67:492-511 (2006).
Wright et al., "The unusual distribution of the neuronal/lymphoid cell surface CD200 (OX2) glycoprotein is conserved in himans," Immunology 102:173-179 (2001).
Wright, G.J., et al., "Lymphoid/Neuronal Cell Surface OX2 Glycoprotein Recognizes a Novel Receptor on Macrophages Implicated in the Control of Their Function," Immunity, 13:233-242 (2000).
Wright, G.J., et al., "The lymphoid/neuronal OX-2 glycoprotein interacts with a novel protein expressed by macrophages," Tissue Antigens, 55(Supplement 1): 11 (2000).
Wright, G.J., et al., "Viral homologues of cell surface proteins OX2 and CD47 have potential to regulate macrophage function," Annual Congress of the British Society for Immunology, vol. 101 (Supplement 1): 50; Dec. 5-8, 2000.
Yamaguchi et al., "Application of tumor marker for immunotargeting therapy of cancer," Nihon Rinsho, vol. 54(6), pp. 1674-1679 (1996).
Yamaguchi et al., "Biological Response Modifier and Missile Cancer Chemotherapy," Biotherapy, vol. 10(4), pp. 605-609 (1996).
Yamaguchi et al., "Immunomissile Therapy Using Tumor Markers: Application of tumor marker for immunotargeting therapy of cancer," Nihon Rinsho, vol. 54(6), pp. 1674-1679 (1996).
Yang, C., et al., "Functional maturation and recent thymic emigrants in the periphery: development of alloreactivity correlates with the cyclic expression of CD45RC isoforms," Eur. J. Immunol., 22:2261-2269 (1992).
Yu, X., et al., "The role of B7-CD28 co-stimulation in tumor rejection," International Immunology, 10(6):791-797 (1998).
Zhang, S., et al., "Molecular Mechanisms of CD200 Inhibition of Mast Cell Activation," J. Immunol., 173:6786-6793 (2004).
Zheng, P., et al., "B7-CTLA4 interaction enhances both production of antitumor cytotoxic T lymphocytes and resistance to tumor challenge," Proc. Natl. Acad. Sci. USA, 95:6284-6289 (1998).
Zhu et al., "Radioimmunotherapy of Human B-Cell Chronic Lymphocytic Leukemia in Nude Mice." Cancer Research. 54, 5111-5117 (1994).
Zips, D., et al., "New Anticancer Agents: In Vitro and In Vivo Evaluation," in vivo, 19:1-7 (2005).

(56) References Cited

OTHER PUBLICATIONS

Zou et al. Human Glioma-Induced Immunosuppression Involves Soluble Factor(s) That Alters Monocyte Cytokine Profile and Surface Markers. Apr. 15, 1999. vol 162, pp. 4882-4892.
Alizadeh et al., "Distinct types of diffuse large B-cell lymphoma identified by gene expression profiling," Nature, 403:503-511(2000).
Almasri, Nidal M. et al., "Reduced Expression of CD20 Antigen as a Characteristic Marker for Chronic Lymphocytic Leukemia," American Journal of Hematology, vol. 40:259-263 (1992).
Bach, "Immunosuppressive therapy of autoimmune diseases," Immunology Today, 14(6)322-326(1993).
Banerjee, D., et al., "Blocking CD200-CD200 receptor axis augments Nos. 2 expression and aggravates experimental autoimmune uveoretinitis in Lewis rats," Ocular Immunology and Inflammation, 12(2):115-125 (2004).
Barclay and Ward, "Purification and Chemical Characterisation of Membrane Glycoproteins From Rat Thymocytes and Brain, Recognised by Monoclonal Antibody MRC OX2," European J. Biochemistry, 129:447-458(1982).
Barclay et al.,"CD200 and membrane protein interactions in the control of myeloid cells," Trends in Immunology, 23(6): 285-290 (2002).
Barclay, A.N., "Different reticular elements in rat lymphoid tissue identified by localization of Ia, Thy-1 and MRC OX 2 antigens," Immunology, 44:727-736 (1981).
Barclay, A.N., et al., "Neuronal/Lymphoid Membrane Glycoprotein MRC OX-2 is a Member of the Immunoglobulin Superfamily with a Light-Chain-Like Structure," Biochem. Soc. Symp., 51:149-157 (1985).
Bauvois et al., Constitutive expression of CD26/dipeptidylpepidase IV on peripheral blood B lymphocytes of patients with B chronic lymphocytic leukaemia. British Journal of Cancer 1999., vol. 79. p. 1042-1048.
Bello, Celeste et al., "Monoclonal Antibodies for B-Cell Lymphomas: Rituximab and Beyond," Hematology, pp. 233-242 (2007).
Blazer, B.R., et al., "CD28/B7 Interactions Are Required for Sustaining the Graft-Versus_Leukemia Effect of Delayed Post-Bone Marrow Transplantation Splenocyte Infusion in Murine Recipients of Myeloid or Lymphoid Leukemia Cells," J. Immunol., 159:3460-3473 (1997).
Bodey et al. "Human Cancer Detection and Immunotherapy with Conjugated and Non-Conjugated Monoclonal Antibodies" Anticancer Research 16: 661-674 (1996).
Bohen, S.P., "Variation in gene expression patterns in follicular lymphoma and the response to rituximab," PNAS, 100(4):1926-1930(2003).
Boon, Thierry., "Toward a Genetic Analysis of Tumor Rejection Antigens," Advances in Cancer Res., 58:177-210 (1992).
Borriello et al., "MRC OX-2 Defines a Novel T Cell Costimulatory Pathway," J. Immunol., 158:4549-4554(1997).
Borriello, F., et al., "Characterization and localization of Mox2, the gene encoding the murine homolog of the rat MRC OX-2 membrane glycoprotein," Mammalian Genome, 9(2):114-118 (1998).
Broderick et al., "Constitutive Retinal CD200 Expression Regulates Resident Microglia and Activin State of Inflammatory Cells During Experimental Autoimmune Uveoretinitis," Am. J of Pathology, 161(5):1669-1677(2002).
Bruggemann et al., "A Matched Set of Rat/Mouse Chimeric Antibodies: Identification and Biological Properties of Rat H Chain Constant Regions .mu., .gamma.I, .gamma.2a, .gamma.2b, .gamma.2c, .epsilon., and .alpha.1," The Journal of Immunology, vol. 142(9), pp. 3145-3150 (1989).
Bukovsky, A., et al., "Association of lymphoid cell markers with rat ascitic malignant cells," IRCS Med. Sci., 11:866-867 (1983).
Bukovsky, A., et al., "Association of some cell surface antigens of lymphoid cells and cell surface differentiation antigens with early rat pregnancy," Immunology, 52:631-640 (1984).
Bukovsky, A., et al., "Ihe localization of Thy-1.1, MRC OX 2 and Ia antigens in the rat ovary andfollopian tube," Immunology, 48:587-596 (1983).
Bukovsky, A., et al., "The ovarian follicle as a model for the cell-mediated control of tissue growth," Cell Tissue Res., 236:717-724 (1984).
Burge, Daniel J. et al., "Pharmacokinetic and Pharmacodynamic Properties of TRU-015, a CD20-Directed Small Modular Immunopharmaceutical Protein Therapeutic, in Patients with Rheumatoid Arthritis: A Phase I, Open-Label, Dose-Escalation ClinicalStudy," Clinical Therapeutics, vol. 30(10):1806-1816 (2008).
Caldas et al., "Humanization of the anti-CD18 antibody 6.7: an unexpected effect of a framework residue in binding to antigen," Molecular Immunology, 39(15):941-952 (2003).
Chaouat and Clark, FAS/FAS Ligand Interaction at the Placental Interface is not Required for the Success of Allogeneic Pregnancy in Anti-Paternal MHC Preimmunized Mice, Presented at the 6th Congress of the Adria-Alps Soc. of Immunol. of Reprod.,(2000) / Amer. J. of Reprod. Immunol., 45:108-115(2001).
Chaudhary et al., "A recombinant immunotoxin consisting of two antibody variable domains fused to Pseudomonas exotoxin," Nature, vol. 339, 394-397 (1989).
Chen, D., et al., "Discrete Monoclonal Antibodies Define Functionally Important Epitopes in the CD200 Molecule Responsible for Immunosupression Function," Transplantation, 79:282-288 (2005).
Chen, D., et al., "Synthetic peptides from the N-terminal regions of CD200 and CD200R1 modulate immunosupressive and anti-inflammatory effects of CD200-CD200R1 interaction," International Immunology, 17(3):289-296 (2005).
Chen, Z., et al., "Cloning and characterization of the murine homologue of the rat/human MRC OX-2 gene," Database Medline, Biochemica et Biophysica Acta, 1362(1):6-10 (1997).
Cherwinski, H.M., et al., "The CD200 Receptor Is a Novel and Potent Regulator of Murine and Human Mast Cell Function," J. Immunol., 174:1348-1356 (2005).
Chien et al., "Significant structural and functional change of an antigen-binding site by a distant amino acid substitution: proposal of a structural mechanism," Proc. Natl. Acad. Sci. USA 86:5532-5536 (1989).
Chitnis et al., "The Role of CD200 in Immune-Modulation and Neural Protection in EAE," Abstract 12th International Congress of Immunology and 4th Annual Conference of FOCIS, Montreal, Jul. 21, 2004. Abstract Only.
Chitnis, T., et al., "Elevated Neuronal Expression of CD200 Protects Wld.sup.s Mice from Inflammation-Mediated Neurodegeneration," American Journal of Pathology, 170(5):1695-1712 (2007).
Clark et al., "Fg12 prothrombinase expression in mouse trophoblast and decidua triggers abortion but may be countered by OX-2," Mol. Human Reprod., 7:185-194(2001).
Clark et al., "Labile CD200 tolerance signal important in transfusion-related immunomodulation (TRIM) prevention of recurrent miscarriages," Amer. J. Reprod. Immunol., 45:361(2001). Abstract Only.
Clark et al., "Procoagulants in fetus rejection: the role of the OX-2 (CD200) tolerance signal," Seminars in Immunol., 13 (4)255-263(2001).
Clark et al., "The OX-2 Tolerance Signal Molecule at the Fetomaternal Interface Determines Pregnancy Outcome," Amer. Journal of Reprod Immunol., 43:326(2000). Abstract Only.
Clark et al., Amer. Soc. for Reprod. Medicine, 55th Annual Meeting (1999). Abstract Only.
Clark, D.A., "Intralipid as Treatment for Recurrent Unexplained Abortion?", Am. J. of Reprod. Immunol., 32:290-293 (1994).
Clark, M.J., et al., "MRC OX-2 antigen: a lymphoid/neuronal membrane glycoprotein with a structure like a single immunoglobulin light chain," EMBO Journal, 4(1): 113-118 (1985).
Clarke, M.J., "MRC OX-2 lymphoid brain glycoprotein: S1 mapping suggests higher levels of abnormal RNA in the thymus than in the brain," Biochemical Society Transactions, 14:80-81 (1986).
Cochlovius et al., "Cure of Burkitt's Lymphome in Severe Combined Immunodeficiency Mice by T Cells, Tetravalent CD3 .times. CD19 Tandem Diabody, and CD28 Costimulation," Cancer Res. 60:4336-4341 (2000).

(56) References Cited

OTHER PUBLICATIONS

Cohen, P.L., "Systemic Autoimmunity," in Fundamental Immunology, Fourth edition, W.E. Paul, Editor, Lippincott-Raven Publishers, Philadelphia, Ch. 33, p. 1067-1088(1999).
Coles, S.J. et al., "The immunosuppressive ligands PD-L1 and CD200 are linked in AML T-cell immunosuppression: identification of a new immunotherapeutic synapse," Leukemia, vol. 29(9): 1952-1954 (2015).
Cui, Weiguo et al., "CD200 and its receptor, CD200R, modulate bone mass via the differentiation of osteoclasts," PNAS, vol. 104(36):14436-14441 (2007).
Davidson, A., et al. "Autoimmune Diseases," (editors Mackay and Rosen) New England Journal of Medicine, 345 (5):340-350 (2001).
DeNardo et al., "Increased Survival Associated with Radiolabeled Lym-1 Therapy for Non-Hodgkin's Lymphoma and Chronic Lymphocyctic Leukemia." Cancer Supplement (1997) vol. 80, No. 12. pp 2706-2711.
Dennis, C., "Off by a whisker," Nature, 442,:739-741 (2006).
Dick et al., "Control of Myeloid Activity During Retinal Inflammation," J. of Leukocyte Bio., 74:161-166(2003).
Dorai et al., "Aglycosylated Chimeric Mouse/Human IgG1 Antibody Retains Some Effector Function," Hybridoma, vol. 10(2): 211-217 (1991).
Huang, "Structural chemistry and therapeutic intervention of protein-protein interactions in immune response, human immunodeficiency virus entry, and apoptosis," Pharmacol. Therapeutics, 86:201-215(2000).
Hutchings, N.J., et al., "Interactions of Cytoplasmic Region of OX2R Are Consistent with an Inhibitory Function," Annual Congress of the British Society for Immunology, 101 (Supplement 1): 24, Abstract #10.6 (2000).
International Preliminary Report on Patentability, PCT/US2018/052792, dated Mar. 31, 2020, 6 pages.
International Search Report and Written Opinion, PCT/US2018/052792, dated Dec. 7, 2018, 8 pages.
Iwanuma et al., "Antitumor Immune Response of Human Peripheral Blood Lymphocytes Coengrafted with Tumor into Severe Combined Immunodeficient Mice," Cancer Research, 57:2937-2942(1997).
Jain, "The next frontier of molecular medicine: Delivery of therapeutics," Nature Medicine, 4(6):655-657(1998).
Jansky, L., et al., "Dynamics of Cytokine Production in Human Peripheral Blood Mononuclear Cells Stimulated by LPS or Infected by Borrelia," Physiol. Res., 52:593-598 (2003).
Jeurissen, S.H.M., et al., "Characteristics and functional aspects of nonlymphoid cells in rat germinal centers, recognized by two monoclonal antibodies ED5 and ED6," Eur, J. Immunol., 16:562-568 (1986).
Kausar, Fariha et al., "Ocrelizumab: a step forward in the evolution of B-cell therapy," Expert Opin. Biol. Ther., vol. 9 (7):889-895 (2009).
Keil et al., "The Tolerance-Promoting Molecule OX-2 is Expressed in Fetal Trophoblast Cells that Cocoon the 'Fetal Allograft' and May Prevent Pregnancy Loss Caused by Cytokine-Activation of FGL2 Prothrombinase," Amer. J. Reprod. Immunol.,45:343(2001) (abstract).
Kim et al., "Divergent Effects of 4-1BB Antibodies on Antitumor Immunity and on Tumor-reactive T-Cell Generation," Cancer Res., 61:2031-2037(2001).
Kjaergaard et al., "Therapeutic Efficacy of OX-40 Receptor antibody Depends on Tumor Immunogenicity and Anatomic Site of Tumor Growth," Cancer Res. 60:5514-5521(2000).
Kneitz, C., et al., "Inhibition of Tcell/B cell interaction by B-CLL cells," Leukemia, vol. 13, pp. 98-104 (1999).
Kretz-Rommel, "CD200 Expression on Tumor Cells Suppresses Antitumor Immunity: New Approaches to Cancer Immunotherapy," J. Immunol. 178:5595-5605 (2007).
Kretz-Rommel, A., et al., "CD200 Expression on Tumor Cells Suppresses Anti-Tumor Immunity: New Approaches to Cancer Immunotherapy," J. Immunother., 29(6):666 (2006).
Kretz-Rommel, A., et al., "Immune Evasion by CD200: New Approaches to Targeted Therapies for Chronic Lymphocytic Leukemia," J. Immunother., 28(6):650 (2005).
Kretz-Rommel, A., et al., "The Immuno-Regulatory Protein CD200 Is Overexpressed in a Subset of B-Cell Chronic Lymphocytic Leukemias and Plays a Role in Down-Regulatin the TH1 Immune Response," J. Immunother., 27(6):S46 (2004).
Kretz-Rommel, Anke et al., "Blockade of CD200 in the Presence or Absence of Antibody Effector Function: Implications for Anti-CD200 Therapy," The Journal of Immunology, vol. 180:699-705 (2008).
Kroese, F.G.M., et al., "Germinal centre formation and follicular antigen trapping in the spleen of lethally X-irradiated and reconstituted rats," Immunology, 57:99-104 (1986).
Kroese, F.G.M., et al., "The ontogeny of germinal centre forming capacity of neonatal rat spleen," Immunology, 60:597-602 (1987).
Levene, Adam P. et al., "Therapeutic monoclonal antibodies in oncology," J.R. Soc. Med., vol. 98:146-152 (2005).
Liu et al., "Effect of combined T- and B-cell depletion of allogenic HLA-mismatched bone marrow graft on the magnitude and kinetics of Epstein-Barr virus load in the peripheral blood of bone marrow transplant recipients," Clin. Transplant.18:518-524 (2004).
Mariuzza et al., "The Structural Basis of Antigen-Antibody Recognition," Ann. Rev. Biophys. Biophys. Chem. 16:139-159 (1987).
Marsh, M.N., "Functional and Structural Aspects of the Epithelial Lymphocyte, with Implications for Coeliac Disease and Tropical Sprue," Scandinavian Journal of Gastroenterology 114: 55-75 (1985).
Marti, G.E. et al., "CD20 and CD5 Expression in B-Chronic Lymphocytic Leukemia," Annals of the New York Academy of Sciences, vol. 651:480-483 (1992).
Matutes et al. Morphological and Immuniphenotypic Features of Chronic Lymphocytic Leukemia. Rev. Clin. Exp. Hematol. vol. 4.1, Mar. 2000 p. 22-47.
McCaughan et al., "Characterization of the Human Homolog of the Rat MRC OX-2 Membrane Glycoprotein," Immunogenetics, 25:329-335(1987).
McCaughan, G.M., et al., "Identification of the human homologue of the rat lymphoid/brain antigen MRC OX-2," Australian and New Zealand Journal of Medicine 17: 142 (Abstract) (1987).
McCaughan, G.W., et al., "The Gene for MRC OX-2 Membrane Glycoprotein Is Localized on Human Chromosome 3," Immunogenetics, 25:133-135 (1987).
McMaster, W.R., et al., "Identification of la glycoproteins in rat thymus and purification from rat spleen," Eur. J. Immunol., 9:426-433 (1979).
McWhirter et al., Supplemental Materials, "Antibodies selected from combinatorial libraries block a tumor antigen that plays a key role in immunomodulation," PNAS, vol. 103, pp. 1041-1046 (2006).
McWhirter, J.R, et al., "Antibodies selected from combinatorial libraries block a tumor antigen that plays a key role in immunomodulation," PNAS, 103(4): 1041-1046 (2006).
Milani, Cannon et al., "Veltuzumab, an anti-CD20 mAb for the treatment of non-Hodgkin's lymphoma, chronic lymphocytic leukemia and immune thrombocytopenic purpura," Current Opinion in Molecular Therapeutics, vol. 11 (2):200-207 (2009). cited byapplicant.
Mjaaland et al., "Modulation of immune responses with monoclonal antibodies. I. Effects on regional lymph node morphology and on anti-hapten responses to haptenized monoclonal antibodies", Eur. J. Immunol., 20:1457-1461 (1990).
Mjaaland, S., et al., "The Localization of Antigen in Lymph Node Follicles of Congenitally Athymic Nude Rats," Scand. J. Immunol., 26:141-147 (1987).
Mohammad, R.M., et al., "Establishment of a human B-CLL xenograft model: utility as a preclinical therapeutic model," Leukemia, 10:130-137 (1996).
Mori et al., "Establishment of a new anti-cancer drugs-resistant cell line derived from B-chronic lymphocyctic leukemia," Proceedings, Fifty-Ninth Annual Meeting of the Japanese Cancer Association, p. 583, #3788 (Sep. 1, 2000).
Morris, R.J., et al., "Sequential Expression of OX2 and Thy-1 Glycoproteins on the Neuronal Surface during Development," Dev. Neurosci., 9:33-44 (1987).

(56) References Cited

OTHER PUBLICATIONS

Morschhauser, Franck et al., "Humanized Anti-CD20 Antibody, Veltuzumab, in Refractory/Recurrent Non-Hodgkin's Lymphoma: Phase I/II Results," Journal of Clinical Oncology, vol. 27(20):3346-3353 (2009).

Mueller et al., "Aglycosylated chimeric mouse/human IgG1 antibody retains some effector function," Hybridoma, vol. 10 (2), pp. 211-217 (1991).

Mueller et al., "Humanized Porcine VCAM-Specific Monoclonal Antibodies With Chimeric** IgG2/G4 Constant Regions Block Human Leukocyte Binding to Porcine Endothelial Cells," Molecular Immunology, vol. 34(6), pp. 441-452 (1997).

Myers et al., "Characterization of a Peptide Analog of a Determinant of Type II Collagen that Suppresses Collagen-Induced Arthritis," J. of Immunology, 3589-3595(1998).

Nagelkerken L., et al., "Accessory Cell Function of Thoracic Duct Nonlymphoid Cells, Dentritic Cells, and Splenic Adherent Cells in the Brown-Norway Rat," Cellular Immunology, 93:520-531 (1985).

Nathan and Muller, "Putting the Brakes on innate immunity: a regulatory role for CD200?", Nat Immunol., 2(1):17-19 (2001).

Ni et al., "An immunoadhesin incorporating the molecule OX-2 is a potent immunosuppressant which prolongs allograft survival", FASEB Journal 13(5):A983(1999). Abstract Only.

Ohno et al., "Antigen-binding specificities of antibodies are primarily determined by seven residues of VH," Proc. Natl. Acad. Sci., vol. 82, pp. 2945-2949 (1985).

Pakula and Sauer, "Genetic analysis of protein stability and function," Annu. Rev. Genet., vol. 23, pp. 289-310 (1989).

Panka et al., "Variable region framework differences result in decreased or increased affinity of variant anti-digoxin antibodies," Proc, Natl. Acad. Sci. USA, vol. 85:3080-3084 (1988).

Pardoll, Drew., "Therapeutic Vaccination for Cancer," Clin. Immunol., 95(1):S44-S62(2000).

Paterson, D.J., et al., "Antigens of Activated Rat T Lymphocytes Including a Molecule of 50,000 Mr Detected Only on CD4 Positive T Blasts," Molecular Immunology, 24(12):1281-1290 (1987).

\* cited by examiner

Tissue Microarrays and Slides

| identifier | source/vendor | tumor type | | description |
|---|---|---|---|---|
| SO2082a | USBiomax | Rhabdomyosarcoma TMA | Unstained TMA Slides | 104 Cases/208 Cores |
| BS17017b | USBiomax | Brain Tumors TMA | Unstained TMA Slides | 63 Cases/63 Cores |
| NB642 | USBiomax | Neuroblastoma TMA | Unstained TMA Slides | 32 Cases/64 Cores |
| MC809a | USBiomax | Blastoma TMA | Unstained TMA Slides | 80 Cases/80 Cores |
| PC701 | USBiomax | Pediatric Malignant Tumor TMA | Unstained TMA Slides | 70 Cases/70 Cores |
| OS804b | USBiomax | Osteosarcoma TMA | Unstained TMA Slides | 40 Cases/80 Cores |
| 76056T2 (1) | ProteoGenex | Neuroblastoma | Unstained Slides | single patient |
| 76064T2 (2) | ProteoGenex | Neuroblastoma | Unstained Slides | single patient |
| 76072T2 (4) | ProteoGenex | Neuroblastoma | Unstained Slides | single patient |
| 76081T2 (2) | ProteoGenex | Neuroblastoma | Unstained Slides | single patient |
| 67221T6 (2) | ProteoGenex | Osteosarcoma | Unstained Slides | single patient |
| 67158T2 (1) | ProteoGenex | Osteosarcoma | Unstained Slides | single patient |
| 67154T2 (1) | ProteoGenex | Osteosarcoma | Unstained Slides | single patient |
| 24209S2 (2) | ProteoGenex | Embryonal Rhabdomyosarcoma | Unstained Slides | single patient |
| 24086S2 (2) | ProteoGenex | Rhabdomyosarcoma | 8 Unstained Slides | single patient |

FIG. 7

Tissue Samples Analyzed

| tissue | tumor | # pediatric (p) samples | # adult (A) samples |
|---|---|---|---|
| CNS.brain | neuroblastoma | 62 | 14 |
| CNS.brain | astrocytoma | 3 | 26 |
| CNS.brain | glioblastoma multiforme | 7 | 33 |
| CNS.brain | medulloblastoma | 11 | 6 |
| CNS.brain | ependymoblastoma/ependymoma | 2 | 1 |
| CNS.brain | choroid plexus papilloma | 1 | 0 |
| CNS.brain | primitive neuroectodermal tumor | 1 | 0 |
| CNS.brain | retinoblastoma | 5 | 1 |
| CNS.brain | hemangioblastoma | 0 | 6 |
| bone | osteosarcoma | 27 | 54 |
| muscle | rhabdomyosarcoma (embryonal, spindle, pleiomorphic, alveolus) | 37 | 139 |
| muscle | myofibroblastoma | 0 | 5 |
| muscle | leiomyosarcoma | 1 | 0 |
| kidney | nephroblastoma | 34 | 5 |
| kidney | Adrenocortical carcinoma | 1 | 0 |
| reproductive | teratoma, gynandroblastoma, endodermal sinus | 8 | 3 |
| normal brain | N/A | 2 | 8 |
| normal peripheral nerve | N/A | 0 | 9 |
| normal skeletal muscle | N/A | 5 | 10 |
| normal kidney | N/A | 2 | 2 |
| normal reproductive | N/A | 0 | 3 |
| Total number of samples | | 174 | 325 |

FIG. 8

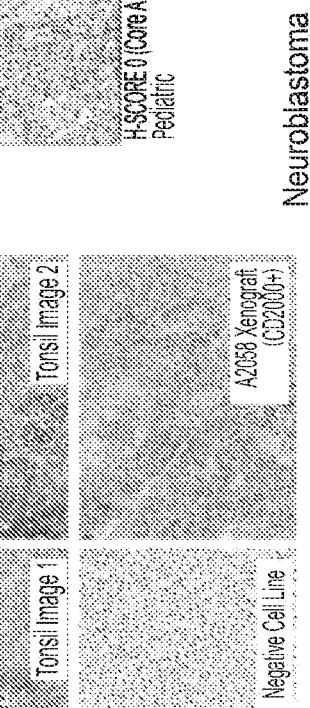

BIOMARKER SIGNATURE FOR PREDICTING TUMOR RESPONSE TO ANTI-CD200 THERAPY

RELATED APPLICATIONS

This application is a 35 U.S.C. 371 national stage filing of International Application No. PCT/US2018/052792, filed on Sep. 26, 2018, which claims priority to U.S. Provisional Application No. 62/578,643, filed on Oct. 30, 2017, and U.S. Provisional Application No. 62/564,052, filed on Sep. 27, 2017. The entire contents of the aforementioned applications is incorporated herein by reference.

SEQUENCE LISTING

The instant application contains a Sequence Listing which has been submitted electronically in ASCII format and is hereby incorporated by reference in its entirety. Said ASCII copy, created on Mar. 18, 2020, is named AXJ-244US_Sequence_Listing txt and is 130,540 bytes in size.

BACKGROUND

The human immune system employs a variety of immune surveillance mechanisms, which can identify malignant cells within a host organism and kill the cells before a cancer develops (see, e.g., Geertsen et al. (1999) *Int J Mol Med* 3(1):49-57; Kerebijn et al. (1999) *Crit. Rev Oncol Hematol* 31(1):31-53; and Pardoll (2003) *Annu Rev Immunol* 21:807-39). However, cancer cells are known to evade detection by the immune system. One potential mechanism by which cancer cells escape immunosurveillance is expression or overexpression of CD200 (OX-2) protein and/or expression or overexpression of CD200 receptor.

CD200 is an immune checkpoint protein expressed by a number of immune cells, including B, T cells and macrophages, as well as non-immune cells, including endothelial cells and neurons. CD200 binds to its receptor (CD200R1), expressed on antigen-presenting cells (APCs) and T cells, and is believed to play an important role in normal immune homeostasis. However, CD200 protein has also been shown to be expressed or overexpressed on a variety of human cancer cells including, e.g., B cell chronic lymphocytic leukemia cells, prostate cancer cells, breast cancer cells, colon cancer cells, and brain cancer cells (see, e.g., Kawasaki et al. (2007) *Biochem Biophys Res Commun* 364(4): 778-782; Kretz-Rommel et al. (2007); and Siva et al. (2008) *Cancer Immunol Immunother* 57(7):987-96). Overexpression of CD200 by tumor cells implicates CD200 in tumor-mediated immunosuppression and regulation of anti-tumor activity and is associated with worse outcomes.

The variable response rates of patients to monoclonal antibody therapies and chemotherapies means that methods are needed for accurately predicting which patients are likely to respond to therapeutic treatment, so that the treatment can be administered to only those patients who are likely to receive benefits that outweigh the financial costs and potential deleterious effects of treatment (including possible damage to the patient due to tumor growth over time during the administration of ineffective treatments). Particular biomarkers or sets of biomarkers (e.g., gene products such as proteins or RNAs) in tumors may be found for which a particular concentration range or expression level for each biomarker (e.g., in the set) correlates with tumor responsiveness to a particular therapy.

Accordingly, the following disclosure provides novel biomarker criteria that allow for optimization of tumor therapy using CD200 inhibitors, improved methods for treating cancer patients, and methods for monitoring the progression and abatement of cancer.

SUMMARY

Provided herein are methods for treating cancer in a patient who has been determined to have positive expression of CD200 receptor (CD200R1) and one or more biomarkers (i.e., Inducible T-cell COStimulator (ICOS), T Cell Immunoreceptor with Ig and ITIM Domains (TIGIT), Tumor Necrosis Factor Receptor Superfamily Member 9 (TNFRSF9), Hepatitis A Virus Cellular Receptor 2 (HAVCR2), and Programmed Cell Death 1 (PDCD1), Fc Fragment Of IgG Receptor IIa (FCGR2A), Fc Fragment Of IgG Receptor Ia (FCGR1A), Cluster of Differentiation 163 (CD163), and/or CD14), by administering to the patient a CD200 inhibitor.

In one embodiment, a method for treating a patient having cancer who has been determined to have positive expression of CD200 receptor (CD200R1) and one or more biomarkers (e.g., two or more, three or more, four or more, five or more, 6 or more, 7 or more, 8 or more, or 9) in a biological sample from the patient is provided, the method comprising administering to the patient a CD200 inhibitor in an amount and with a frequency sufficient to reduce the cancer burden in the patient (e.g., by about 30, 40, 50, 60, 70, 80, 90, or 100%). In one embodiment, the biomarker is ICOS. In another embodiment, the biomarker is TIGIT. In another embodiment, the biomarker is TNFRSF9. In another embodiment, the biomarker is HAVCR2. In another embodiment, the biomarker is PDCD1. In another embodiment, the biomarker is FCGR2A. In another embodiment, the biomarker is FCGR1A. In another embodiment, the biomarker is CD163. In another embodiment, the biomarker is CD14.

In one embodiment, the patient has been determined to have positive expression of CD200R1 and positive expression of two biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of three biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of four biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of five biomarkers selected from the group consisting of ICOS, TIGIT, TNFRSF9, HAVCR2, PDCD1, FCGR2A, FCGR1A, CD163, and CD14. In another embodiment, the patient has been determined to have an positive expression of CD200R1 and positive expression of six biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of seven biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of eight biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1, ICOS, TIGIT, TNFRSF9, HAVCR2, PDCD1, FCGR2A, FCGR1A, CD163, and CD14. The patient can have positive expression of any possible combination of the biomarkers disclosed herein.

In one embodiment, the method includes determining if a patient having cancer has positive expression of CD200 receptor (CD200R1) and one or more biomarkers (i.e., Inducible T-cell COStimulator (ICOS), T Cell Immunoreceptor with Ig and ITIM Domains (TIGIT), Tumor Necrosis Factor Receptor Superfamily Member 9 (TNFRSF9), Hepatitis A Virus Cellular Receptor 2 (HAVCR2), and Programmed Cell Death 1 (PDCD1), Fc Fragment Of IgG Receptor IIa (FCGR2A), Fc Fragment Of IgG Receptor Ia (FCGR1A), Cluster of Differentiation 163 (CD163), and/or CD14) and administering to the patient a CD200 inhibitor if the patient has positive expression of CD200R1 and one or more biomarkers.

In one embodiment, positive expression of CD200R1 in the biological sample is equal to or greater than expression of CD200R1 in a normal biological sample of the same type. In another embodiment, positive expression of the one more biomarkers in the biological sample is equal to or greater than expression of the one or more biomarkers in a normal biological sample of the same type.

Also, provided are methods for monitoring responsiveness of a subject having cancer to treatment with a CD200 inhibitor, the method comprising: determining expression levels of CD200R1 and one or more (e.g., two or more, three or more, four or more, five or more, 6 or more, 7 or more, 8 or more, or 9) biomarkers (i.e., ICOS, TIGIT, TNFRSF9, HAVCR2, PDCD1, FCGR2A, FCGR1A, CD163, and/or CD14) in a biological sample from the patient, wherein increased expression levels of CD200R1 and the one or more biomarkers, as compared to the expression levels in a biological sample of the same type obtained from the subject prior to treatment with the CD200 inhibitor, indicates that the subject is responsive to treatment with the CD200 inhibitor.

In one embodiment, increased expression levels of CD200R1 and one biomarker selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, expression levels of CD200R1 and two biomarkers selected from the group consisting of ICOS, TIGIT, TNFRSF9, HAVCR2, PDCD1, FCGR2A, FCGR1A, CD163, and CD14, compared to the expression levels ncentrations in a biological sample of the same type obtained from the subject prior to treatment with the CD200 inhibitor, indicates that the subject is responsive to treatment with the CD200 inhibitor. In another embodiment, increased expression levels of CD200R1 and three biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and four biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and five biomarkers selected from the group consisting of ICOS, TIGIT, TNFRSF9, HAVCR2, PDCD1, FCGR2A, FCGR1A, CD163, and CD14, compared to expression levels in a biological f the same type obtained from the subject prior to treatment with the CD200 inhibitor, indicates that the subject is responsive to treatment with the CD200 inhibitor. In another embodiment, increased expression levels of CD200R1 and six biomarkers selected from the group consisting of ICOS, TIGIT, TNFRSF9, HAVCR2, PDCD1, FCGR2A, FCGR1A, CD163, and CD14, compared to expression levels in a biological sample of the same type obtained from the subject prior to treatment with the CD200 inhibitor, indicates that the subject is responsive to treatment with the CD200 inhibitor. In another embodiment, increased expression levels of CD200R1 and seven biomarkers selected from the group consisting of ICOS, TIGIT, TNFRSF9, HAVCR2, PDCD1, FCGR2A, FCGR1A, CD163, and CD14, compared to expression levels in a sample of biological the same type obtained from the subject prior to treatment with the CD200 inhibitor, indicates that the subject is responsive to treatment with the CD200 inhibitor. In another embodiment, increased expression levels of CD200R1 and eight biomarkers selected from the group consisting of ICOS, TIGIT, TNFRSF9, HAVCR2, PDCD1, FCGR2A, FCGR1A, CD163, and CD14, compared to expression levels in a biological sample of the same type obtained from the subject prior to treatment with the CD200 inhibitor, indicates that the subject is responsive to treatment with the CD200 inhibitor. In another embodiment, increased expression levels of CD200R1, ICOS, TIGIT, TNFRSF9, HAVCR2, PDCD1, FCGR2A, FCGR1A, CD163, and CD14, compared to expression levels in a sample of biological the same type obtained from the subject prior to treatment with the CD200 inhibitor, indicates that the subject is responsive to treatment with the CD200 inhibitor. The patient can have elevated expression levels of any possible combination of the biomarkers disclosed herein.

Any suitable CD200 inhibitor can be used in the methods described herein. In one embodiment, the CD200 inhibitor is a small molecule. In another embodiment, the CD200 inhibitor is a polypeptide. In another embodiment, the CD200 inhibitor is a polypeptide analog. In another embodiment, the CD200 inhibitor is a peptidomimetic. In another embodiment, the CD200 inhibitor is an aptamer.

In another embodiment, the CD200 inhibitor is an antibody, or an antigen-binding fragment thereof. For example, the antibody, or antigen-binding fragment thereof, can be a humanized antibody, a recombinant antibody, a diabody, a chimerized or chimeric antibody, a monoclonal antibody, a deimmunized antibody, a fully human antibody, a single chain antibody, an $F_v$ fragment, an $F_d$ fragment, an Fab fragment, an Fab' fragment, or an F(ab')$_2$ fragment.

An exemplary anti-CD200 antibody is samalizumab (also known as "ALXN6000").

In one embodiment, the anti-CD200 antibody antigen-binding fragment thereof, comprises a heavy chain variable region CDR1 having the sequence set forth in SEQ ID NO: 7, a heavy chain variable region CDR2 having the sequence set forth in SEQ ID NO: 8, a heavy chain variable region CDR3 having the sequence set forth in SEQ ID NO: 9, a light chain variable region CDR1 having the sequence set forth in SEQ ID NO: 4, a light chain variable region CDR2 having the sequence set forth in SEQ ID NO: 5, and a light chain variable region CDR3 having the sequence set forth in SEQ ID NO: 6.

In another embodiment, the anti-CD200 antibody comprises heavy and light chain variable regions having the sequences set forth in SEQ ID NOs: 13 and 12, respectively.

In another embodiment, the anti-CD200 antibody comprises heavy and light chains having the sequences as set forth in SEQ ID NOs: 11 and 10, respectively.

In another embodiment, the anti-CD200 antibody, or antigen binding fragment thereof, comprises the CDR1, CDR2 and CDR3 domains of a heavy chain variable region having the sequence set forth in SEQ ID NO: 13, and the CDR1, CDR2 and CDR3 domains of a light chain variable region having the sequence set forth in SEQ ID NO: 12.

In another embodiment, the anti-CD200 antibody, or antigen binding fragment thereof, comprising the CDR1, CDR2, and CDR3 domains of a heavy chain region having the sequence set forth in SEQ ID NO: 11, and the CDR1, CDR2, and CDR3 domains of a light chain region having the sequence set forth in SEQ ID NO: 10.

In another embodiment, the anti-CD200 antibody is a human antibody. In another embodiment, a composition of anti-CD200 antibodies, or fragments thereof, is use in the methods described herein, wherein the composition (e.g., a sterile composition) comprises a pharmaceutically acceptable carrier.

In another embodiment, the anti-CD200 antibody or antigen-binding fragment thereof inhibits the interaction between CD200 and CD200R1. In another embodiment, the method of treatment results in a CD200 saturation of at least 60%, 65%, 70%, 75%, 80%, 85%, 86%, 87%, 88%, 89%, 90%, 91%, 92%, 93%, 94%, 95%, 96%, 97%, 98%, or 99%.

In one embodiment, the anti-CD200 antibody is administered at a dose of about 300 mg/m$^2$ to about 600 mg/m$^2$. In another embodiment, the anti-CD200 antibody is administered at a dose of about 300 mg/m$^2$. In another embodiment, the anti-CD200 antibody is administered at a dose of about 400 mg/m$^2$. In another embodiment, the anti-CD200 antibody is administered at a dose of about 500 mg/m$^2$. In another embodiment, the anti-CD200 antibody is administered at a dose of about 600 mg/m$^2$. In another embodiment, the anti-CD200 antibody is administered at a dose of about 700 mg/m$^2$. In another embodiment, the anti-CD200 antibody is administered at a dose of about 300 mg/m$^2$. In another embodiment, the anti-CD200 antibody is administered at a dose of about 800 mg/m$^2$. In another embodiment, the anti-CD200 antibody is administered at a dose of about 900 mg/m$^2$. In another embodiment, the anti-CD200 antibody is administered at a dose of about 1000 mg/m$^2$. In another embodiment, the anti-CD200 antibody is administered at a dose of about 1100 mg/m$^2$.

In another embodiment, the anti-CD200 antibody is administered at a dose of about 5 mg/kg to about 50 mg/kg. In another embodiment, the anti-CD200 antibody is administered at a dose of about 10 mg/kg to about 30 mg/kg. In another embodiment, the anti-CD200 antibody is administered at a dose of about 15 mg/kg to about 25 mg/kg. In another embodiment, the anti-CD200 antibody is administered at a dose of about 10 mg/kg to about 20 mg/kg. In another embodiment, the anti-CD200 antibody is administered at a dose of about 10 mg/kg. In another embodiment, the anti-CD200 antibody is administered at a dose of about 15 mg/kg. In another embodiment, the anti-CD200 antibody is administered at a dose of about 20 mg/kg. In another embodiment, the anti-CD200 antibody is administered at a dose of about 25 mg/kg. In another embodiment, the anti-CD200 antibody is administered at a dose of about 40 mg/kg.

Expression levels CD200R1 and the one or more biomarkers can be measured by quantitation of protein and/or RNA levels in a biological sample from the patient (e.g., tumor tissue, tumor cells, blood, or a blood fraction) using any suitable technique. In one embodiment, expression levels are measured by quantitation of protein and/or RNA levels, using at least one of an immunoassay, immunochemistry assay, immunohistochemistry assay, nucleoprobe assay, in situ hybridization, fluorescent RNA probes, RT-PCR, microarray transcription assay, and/or RNA transcription assay. In another embodiment, expression levels are measured using an immunoassay (e.g., an enzyme-linked immunosorbent assay (ELISA) or a radioimmunoassay (RIA)).

In one embodiment, expression levels of CD200R1 and one or more biomarkers are measured in two or more types of biological samples. In another embodiment, expression levels of CD200R1 and one or more biomarkers are measured in one type of biological sample and levels of a second biomarker are measured in a second type of biological sample.

In one embodiment, positive expression of CD200R1 in the biological sample is equal to or greater than expression of CD200R1 in a normal biological sample of the same type. In another embodiment, positive expression of the one more biomarkers in the biological sample is equal to or greater than expression of the one or more biomarkers in a normal biological sample of the same type.

In one embodiment, the method further comprises measuring CD200 expression in the biological sample and identifying patients with tumors having elevated expression of CD200, wherein the elevated expression of CD200 in the biological sample is greater than median expression levels of CD200 in normal tissue.

In one embodiment, the patient is an adult and the cancer is selected from the group consisting of diffuse large B cell lymphoma (DLBL), lung adenocarcinoma (LUAD), lung squamous cell carcinoma (LUSC), glioblastoma (GBM), low grade glioma (LGG), clear cell RCC (KIRC), chromophobe (KICH), papillary cell RCC (KIRP), melanoma (SKCM), ovarian cancer (OV), colon cancer (COAD), rectum cancer (READ), uterine endometrial cancer (UCEC).

In another embodiment, the patient is a pediatric patient, and the cancer is selected from atypical teratoid rhabdoid tumor (AT/RT), ependymoma, osteosarcoma, rhabdomyosarcoma, Ewing sarcoma, pilocytic astrocytoma, neuroblastoma, and retinoblastoma.

In one embodiment, the treatment produces at least one therapeutic effect, for example, morphologic complete remission, cytogenetic complete remission, morphologic CR with incomplete blood count recovery, partial remission, and/or stable disease.

Other features and advantages of the methods of treatment will be apparent from the following description, the examples, and from the claims. All publications, patent applications, patents, and other references mentioned herein are incorporated by reference in their entirety.

BRIEF DESCRIPTION OF THE DRAWINGS

FIG. 7 shows the tissue microarrays and slides that were used for Example 3.

FIG. 8 shows the tissue samples that were analyzed for Example 3.

FIGS. 9A-9D depict the results of the IHC assay for control tissues (FIG. 9A), rhabdomyosarcoma (FIG. 9B), nephroblastoma (FIG. 9C), and neuroblastoma (FIG. 9D) (Example 3).

DETAILED DESCRIPTION

Figure 1:
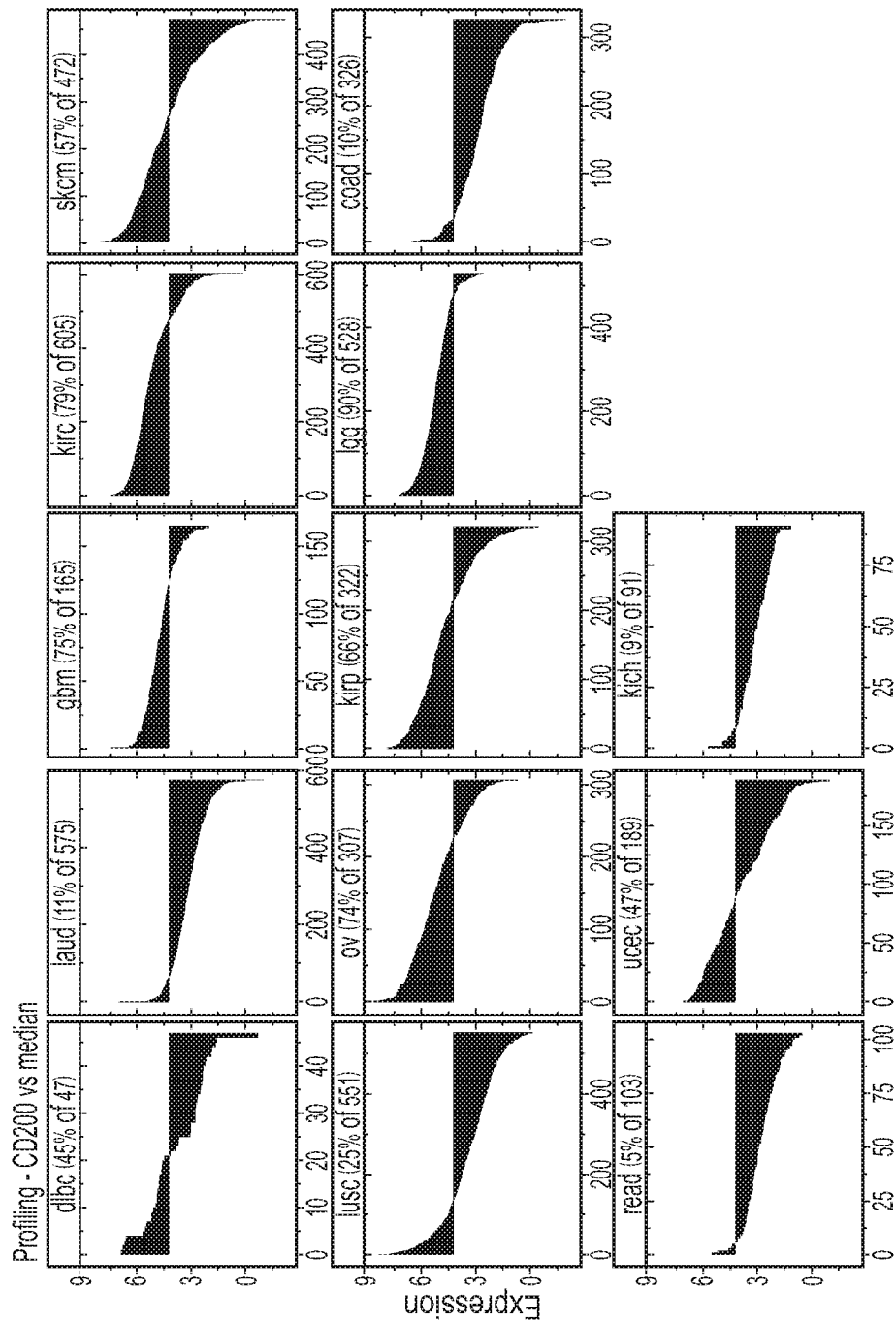
FIG. 1 depicts the results of a gene expression analysis, wherein publically available human tumor gene expression data (TCGA) was mined and analyzed for the expression of CD200 by tumor type.

As described herein and exemplified in the working Examples, the inventors have developed a "samalizumab competent" gene signature from genes which co-correlate with CD200R1 expression across tumor types, which includes biomarkers of T cells and macrophages.

This signature was used to identify tumor types which harbor CD200R1-expressing immune infiltrates that are responsive to CD200 inhibitors, including but not limited to samalizumab. Accordingly, analysis of expression and/or activity levels of these signature biomarkers can be employed to evaluate and/or treat patients having cancer and/or monitor treatment response to a CD200 inhibitor, such as samalizumab.

I. Definitions

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques, and pharmacology are employed.

As used herein, the singular forms "a," "an" and "the" include plural referents unless the context clearly dictates otherwise. The use of "or" or "and" means "and/or" unless stated otherwise. Furthermore, use of the term "including" as well as other forms, such as "include", "includes", and "included," is not limiting.

The term "about" as used herein when referring to a measurable value such as an amount, a temporal duration and the like, is encompasses variations of up to ±10% from the specified value. Unless otherwise indicated, all numbers expressing quantities of ingredients, properties such as molecular weight, reaction conditions, etc., used herein are to be understood as being modified by the term "about".

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream. As used herein, the term includes pre-malignant, as well as malignant cancers.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune response or reaction includes, e.g., activation or inhibition of a T cell, e.g., an effector T cell or a Th cell, such as a CD4+ or CD8+ T cell, or the inhibition of a Treg cell.

"Immunotherapy" refers to the treatment of a subject afflicted with, or at risk of contracting or suffering a recurrence of, a disease by a method comprising inducing, enhancing, suppressing or otherwise modifying an immune response. "Immunostimulating therapy" or "immunostimulatory therapy" refers to a therapy that results in increasing (inducing or enhancing) an immune response in a subject for, e.g., treating cancer. "Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the terms "inhibits" or "blocks" (e.g., referring to inhibition/blocking of activity, function and/or the expression of CD200 and/or its receptor) are used interchangeably and encompass both partial and complete inhibition/blocking.

As used herein, the term "normal," when used to modify the term "individual" or "subject" refers to an individual or group of individuals who does/do not have a particular disease or condition (e.g., cancer) and is also not suspected of having or being at risk for developing the disease or condition. The term "normal" is also used herein to qualify a biological specimen or sample (e.g., a biological fluid) isolated from a normal or healthy individual or subject (or group of such subjects), for example, a "normal control sample" or "normal control biological fluid".

As used herein, the term "positive expression" refers to an expression level of a biomarker in a biological sample that is approximately equal to, or greater than, to the expression of the same biomarker in a normal biological sample of the same type. In this instance, biomarker may refer to the expression of a gene (i.e., RNA) and/or the expression of a peptide.

"Polypeptide," "peptide," and "protein" are used interchangeably and mean any peptide-linked chain of amino acids, regardless of length or post-translational modification. The proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST software. Appropriate parameters for measuring alignment, including any algorithms needed to achieve maximal alignment over the full-length of the sequences being compared can be determined by known methods.

The term "antibody" as used herein refers to polypeptides comprising at least one antibody derived antigen binding site (e.g., $V_H/V_L$ region or $F_v$, or CDR), and includes whole antibodies and any antigen binding fragments (i.e., "antigen-binding portions") or single chains thereof. Antibodies include known forms of antibodies. For example, the antibody can be a human antibody, a humanized antibody, a bispecific antibody, or a chimeric antibody. A whole "antibody" refers to a glycoprotein comprising at least two heavy (H) chains and two light (L) chains inter-connected by disulfide bonds, in which each heavy chain is comprised of a heavy chain variable region (abbreviated herein as $V_H$) and a heavy chain constant region; and each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The exact boundaries of CDRs can be defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In other embodiments, the positions of the CDRs of a light or heavy chain variable region can be as defined by Chothia et al. (1989) *Nature* 342:877-883. Accordingly, these regions can be referred to as "Chothia CDRs" (e.g., "Chothia LCDR2" or "Chothia HCDR3"). In other embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) *Mol Immunol* 33(17/18):1389-1401] exemplifies the identification of CDR boundaries according to Kabat and Chothia definitions. In other embodiments, the positions of the CDRs or framework regions within a light or heavy chain variable domain can be as defined by the international ImMunoGeneTics database (IMGT) standard. Marie-Paule Lefranc et al. [(2003) *Developmental & Comparative Immunology* 27(1):55-77] exemplifies the identification of and CDR boundaries according to IMGT standard. Accordingly, these regions can be referred to as "IMGT CDRs" (e.g., "IMGT-LCDR2" or "IMGT-HCDR3").

The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, and/or conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest, Fifth Edition*, U.S. Department of Health and Human Services, NIH Publication No. 91-3242).

The term "antigen-binding portion" of an antibody (or simply "antibody portion"), as used herein, refers to one or more fragments of an antibody that retain the ability to specifically bind to an antigen (e.g., CD200), e.g., a Fab, Fab'2, ScFv, SMIP, AFFIBODY® antibody mimetic (Affibody AB AKTIEBOLAG, Sweden), nanobody, or a domain antibody. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) *Proc. Natl. Acad. Sci. USA* 90:6444-6448; Poljak, R. J., et al. (1994) *Structure* 2:1121-1123). In one embodiment, the composition contains an antigen-binding portions described in U.S. Pat. Nos. 6,090,382 and 6,258,562, each incorporated by reference herein.

The term "monoclonal antibody," as used herein, includes an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. The monoclonal antibodies to be used in accordance with the formulations disclosed herein may be made by the hybridoma method first described by Kohler, et al., (1975) *Nature* 256: 495 or other methods known in the art. A "polyclonal antibody" is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

An "isolated" antibody or antigen binding fragment is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified to greater than 95% by weight of antibody, and in some embodiments, to greater than 99% by weight of antibody.

The term "pharmaceutical formulation" or "pharmaceutical composition" refers to preparations which are in such form as to permit the biological activity of the active ingredients to be unequivocally effective, and which contain no additional components which are significantly toxic to the subjects to which the formulation would be administered.

As used herein, an "aqueous" pharmaceutical composition is a composition suitable for pharmaceutical use, wherein the aqueous carrier comprises water. A composition suitable for pharmaceutical use may be sterile, homogeneous, and/or isotonic. Aqueous pharmaceutical compositions may be prepared directly in an aqueous form and/or may be reconstituted from a lyophilisate and/or powder form.

A "sterile" composition is aseptic or free or essentially free from all living microorganisms and their spores.

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., recombinant human CD200, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, unless otherwise indicated, an antibody that "specifically binds to human CD200" refers to an antibody that binds to soluble or cell bound human CD200 with a $K_D$ of $10^{-7}$ M or less, such as approximately less than $10^{-8}$ M, $10^{-9}$ M, or $10^{-10}$ M or even lower.

An "epitope" refers to the site on a protein (e.g., a human CD200 protein) that is bound by an antibody. "Overlapping epitopes" include at least one (e.g., two, three, four, five, or six) common amino acid residue(s).

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating cancer in a subject, will be apparent from the following description, the examples, and from the claims.

1. Biomarkers

Biomarkers provided herein can be used as an indicator to, e.g., evaluate whether a patient having cancer will be responsive to treatment with a CD200 inhibitor (including, but not limited to samalizumab) and/or to monitoring response to treatment with a CD200 inhibitor).

A. Signature Biomarkers

The GenBank (National Center for Biotechnology Information (NCBI)) reference numbers for the protein and gene sequences associated with each of the biomarkers described herein are listed below in Tables 1-2, the sequences of which are all expressly incorporated herein by reference. Additionally information regarding the individual biomarkers follows Tables 1-2.

TABLE 1

T Cell Markers

Inducible T-cell COStimulator
(also known as "ICOS", "CD278", "Activation-Inducible Lymphocyte Immunomediatory Molecule", "AILIM", "Inducible T-Cell Co-Stimulator", "Inducible Costimulator", "CD278 Antigen", "CD278", and "CVID1").
NCBI Reference Sequence: NP_036224.1 (SEQ ID NO: 14)
NCBI Reference Sequence: NM_012092.3 (SEQ ID NO: 15)
T Cell Immunoreceptor with Ig and ITIM Domains
(also known as "TIGIT," "WUCAM," "Vstm3," "T-Cell Immunoreceptor With Ig And ITIM Domains V-Set And Immunoglobulin Domain-Containing Protein," "V-Set And Transmembrane Domain-Containing Protein," "V-Set And Immunoglobulin Domain Containing 9", "V-Set And Transmembrane Domain Containing 3," "VSIG9," "VSTM3," "T Cell Immunoreceptor With Ig And ITIM Domains," "Washington University Cell Adhesion Molecule," and "WUCAM")
NCBI Reference Sequence: NP_776160.2 (SEQ ID NO: 16)
NCBI Reference Sequence: NM_173799.3, mRNA (SEQ ID NO: 17)
Tumor Necrosis Factor Receptor Superfamily Member 9
(also known as "TNFRSF9", "CD37", "4-1BB", "induced by lymphocyte activation", "ILA", "TNF Receptor Superfamily Member 9," "T-Cell Antigen 4-1BB Homolog," "4-1BB Ligand Receptor," "CD137 Antigen," "CDw137," "CD137,", "Interleukin-Activated Receptor, Homolog Of Mouse Ly63," "Tumor Necrosis Factor Receptor Superfamily, Member 9," "Tumor Necrosis Factor Receptor Superfamily Member 9," "Homolog Of Mouse 4-1BB," "Receptor Protein 4-1BB," "T Cell Antigen ILA," and "T-Cell Antigen ILA")
NCBI Reference Sequence: NP_001552.2 (SEQ ID NO: 18)
NCBI Reference Sequence: NM_001561.5 (SEQ ID NO: 19)
Hepatitis A Virus Cellular Receptor 2
(also known as "HAVCR2," "T-Cell Immunoglobulin And Mucin Domain-Containing Protein," "T-Cell Immunoglobulin Mucin Family Member," "T-Cell Immunoglobulin Mucin Receptor," "T-Cell Membrane Protein", "HAVcr-2," "TIMD-3", "Tim-3", "TIMD3", "TIM3", "T Cell Immunoglobulin Mucin", "Kidney Injury Molecule-3", "CD366", and "KIM-3")
NCBI Reference Sequence: NP_116171.3 (SEQ ID NO: 20)
NCBI Reference Sequence: NM_032782.4 (SEQ ID NO: 21)
Programmed Cell Death 1
(also known as "PDCD1", "Systemic Lupus Erythematosus Susceptibility", "Protein PD-1", "HPD-1", "PD1", "Programmed Cell Death 1 Protein", "Programmed Cell Death Protein 1", "CD279 Antigen", "CD279", "HPD-L", "HSLE1", "SLEB2", and "PD-1")
NCBI Reference Sequence: NP_005009.2 (SEQ ID NO: 22)
NCBI Reference Sequence: NM_005018.2 (SEQ ID NO: 23)

TABLE 2

Macrophage Markers

Fc Fragment Of IgG Receptor IIa
(also known as "FCGR2A", "Fc Fragment Of IgG, Low Affinity IIa", "Receptor (CD32)", "Immunoglobulin G Fc Receptor II", "IgG Fc Receptor II-A", "Fc-Gamma-RIIa", "FcRII-A", "FCGR2A1", "CDw32", "IGFR2", "FCG2",
"CD32", "Fc Fragment Of IgG, Low Affinity IIa, Receptor For (CD32)", "Low Affinity Immunoglobulin Gamma Fc Region Receptor II-A", "Fc Gamma Receptor IIa," "Fc-Gamma RII-A", "CD32 Antigen", "CD32A" "FCGR2", and "FcGR 3")
NCBI Reference Sequence: NP_001129691.1 (SEQ ID NO: 24) [Isoform 1]
NCBI Reference Sequence: NM_001136219.1 (SEQ ID NO: 25)
NCBI Reference Sequence: NP_067674.2 (SEQ ID NO: 26) [Isoform 2]
NCBI Reference Sequence: NM_021642.3 (SEQ ID NO: 27)
Fc Fragment Of IgG Receptor Ia
(also known as "FCGR1A", "Fc Fragment Of IgG Receptor Ia", "Fc Fragment Of IgG, High Affinity Ia, Receptor For (CD64)", "Fc Fragment Of IgG, High Affinity Ia, Receptor (CD64)", "Fc Gamma Receptor Ia", "IgG Fc Receptor I", "Fc-Gamma RIA", "Fc-Gamma RI", "FcgammaRIa" and "IGFR1")
NCBI Reference Sequence: NP_000557.1 (SEQ ID NO: 28)
NCBI Reference Sequence: NM_000566.3 (SEQ ID NO: 29)
Cluster of Differentiation 163
(also known as "CD163", "CD163 Molecule", "Hemoglobin Scavenger Receptor", "CD163 Antigen", "M130", "Scavenger Receptor Cysteine-Rich Type 1 Protein M130", "Macrophage-Associated Antigen", "SCARI1", and "MM130")
NCBI Reference Sequence: NP_004235.4 (SEQ ID NO: 30)
NCBI Reference Sequence: NM_004244.5 (SEQ ID NO: 31)
NCBI Reference Sequence: NP_981961.2 (SEQ ID NO: 32)
NCBI Reference Sequence: NM_203416.3 (SEQ ID NO: 33)
CD14

TABLE 2-continued

Macrophage Markers (also known as "CD14 Molecule", "CD14 Antigen 2", and "Myeloid Cell-Specific Leucine-Rich Glycoprotein").
NCBI Reference Sequence: NP_000582.1_(SEQ ID NO: 34)
NCBI Reference Sequence: NM_000591.3 (SEQ ID NO: 35)
NCBI Reference Sequence: NP_001035110.1 (SEQ ID NO: 36)
NCBI Reference Sequence: NM_001040021.2 (SEQ ID NO: 37)
NCBI Reference Sequence: NP_001167575.1 (SEQ ID NO: 38)
NCBI Reference Sequence: NM_001174104.1 (SEQ ID NO: 39)
NCBI Reference Sequence: NP_001167576.1 (SEQ ID NO: 40)
NCBI Reference Sequence: NM_001174105.1 (SEQ ID NO: 41)

ICOS is an immune checkpoint protein that in humans is encoded by the ICOS gene (see, e.g., Hutloff A, et al. (January 1999), *Nature* 397 (6716): 263-6; and Yoshinaga et al. (December 1999), *Nature* 402 (6763): 827-32). ICOS is a CD28-superfamily costimulatory molecule that is expressed on activated T cells. It is thought to be important for Th2 cells, in particular (see, e.g., Rudd C E, et al. (July 2003), *Nature Reviews: Immunology* 3 (7): 544-56; and Dong et al. (January 2001), *Nature* 409 (6816): 97-101). It forms homodimers and plays an important role in cell-cell signaling, immune responses and regulation of cell proliferation.

TIGIT is an immune receptor present on some T cells and Natural Killer Cells(NK) (see, e.g., Yu X, et al. (January 2009). *Nat Immunol.* 10 (1): 48-57). TIGIT Binds with high affinity to the poliovirus receptor (PVR), which causes increased secretion of IL10 and decreased secretion of IL12B and suppresses T-cell activation by promoting the generation of mature immunoregulatory dendritic cells.

TNFRSF9 is a member of the tumor necrosis factor (TNF) receptor family (see, e.g., Schwarz H, et al., (1993), *Gene* 134 (2): 295-8). TNFRSF9 can be expressed by activated T cells, but to a larger extent on CD8 than on CD4 T cells. In addition, TNFRSF9 expression is found on dendritic cells, B cells, follicular dendritic cells, natural killer cells, granulocytes, and cells of blood vessel walls at sites of inflammation.

HAVCR2 belongs to the immunoglobulin superfamily, and TIM family of proteins. CD4-positive T helper lymphocytes can be divided into types 1 (Th1) and 2 (Th2) on the basis of their cytokine secretion patterns. Th1 cells are involved in cell-mediated immunity to intracellular pathogens and delayed-type hypersensitivity reactions, whereas, Th2 cells are involved in the control of extracellular helminthic infections and the promotion of atopic and allergic diseases. This protein is a Th1-specific cell surface protein that regulates macrophage activation, and inhibits Th1-mediated auto- and alloimmune responses, and promotes immunological tolerance (see, e.g., Monney L, et al. (February 2002), *Nature* 415 (6871): 536-41).

PDCD1 is a cell surface membrane protein of the immunoglobulin superfamily that plays an important role in down-regulating the immune system and promoting self-tolerance by suppressing T cell inflammatory activity. PDCD1 is an immune checkpoint and guards against autoimmunity through a dual mechanism of promoting apoptosis (programmed cell death) in antigen specific T-cells in lymph nodes while simultaneously reducing apoptosis in regulatory T cells (anti-inflammatory, suppressive T cells) (see, e.g., Francisco L M, et al. (July 2010), *Immunological Reviews* 236: 219-42; and Fife B T, Pauken K E (January 201), *Ann. NY Acad. of Sci.* 1217: 45-59).

Receptors for the Fc portion of IgG, such as FCGR2A, play an essential role in the protection of the organism against foreign antigens by removing antigen-antibody complexes from the circulation (Hibbs, M. et al., *Proc. Nat. Acad. Sci.* 85: 2240-2244, 1988). Receptors are present on monocytes, macrophages, neutrophils, natural killer (NK) cells, and T and B lymphocytes, and they participate in diverse functions such as phagocytosis of immune complexes and modulation of antibody production by B cells. Alternative splicing results in multiple transcript variants.

Fc-gamma receptors (FCGRs), such as FCGR1A, are integral membrane glycoproteins that exhibit complex activation or inhibitory effects on cell functions after aggregation by complexed immunoglobulin G (IgG). FCGR1A is a 72-kD activating FCGR found exclusively on antigen-presenting cells (APCs) of macrophage and dendritic cell (DC) lineages and has a high affinity for monomeric IgG1 (Rodrigo, W., et al, *J. Virol.* 80: 10128-10138, 2006).

CD163 is a protein that in humans is encoded by the CD163 gene. CD163 is the high affinity scavenger receptor for the hemoglobin-haptoglobin complex and in the absence of haptoglobin—with lower affinity—for hemoglobin alone (see, e.g., Schaer D J, et al., *Blood.* 2006 Jan. 1; 107(1): 373-80). It has also been shown to mark cells of monocyte/macrophage lineage (see, e.g., Lau S K, et al., *Am. J. Clin. Path.* 122 (5): 794-801). The receptor was discovered in 1987 (see, e.g., Onofre G, et al., *Acta Medica (Hradec Kralove).* 52 (2): 57-61). CD163 functions as an acute phase-regulated receptor involved in the clearance and endocytosis of hemoglobin/haptoglobin complexes by macrophages, and may thereby protect tissues from free hemoglobin-mediated oxidative damage. This protein may also function as an innate immune sensor for bacteria and inducer of local inflammation. Alternatively spliced transcript variants encoding different isoforms have been described for this gene.

CD14 was first identified on the surface of monocytes and macrophages (see Griffin J D, et al., *J. Clin. Invest.* 1981; 68: 932-41). At the first leucocyte typing workshop in Paris in 1982, several monoclonal antibodies binding to the same epitope on human monocytes were assigned to a provisional CD14 cluster, which was labelled as a leucocyte differentiation antigen. Later, the level of expression of CD14 on these cells was reported to be in the order of 30,000-45,000 copies (see Van Voorhis, et al., *J. Exp. Med.* 1983; 158: 126-45; and Vasselon T, et al., *J. Immunol.* 1997; 159: 4498-505). Another very thorough analysis using both reference beads and Scatchard analysis estimated the number to be greater: approximately 110,000 molecules per monocyte (Antal-Szalmas P, et al. *J. Leukoc. Biol.* 1997; 61: 721-8). Because of its abundance on these cells, CD14 is widely used as a monocyte/macrophage marker in immunohistochemistry as well as in flow cytometry. CD14 is a 55 kDa glycoprotein with multiple leucine-rich repeats (Setoguchi M, et al., *Biochim. Biophys. Acta.* 1989; 1008: 213-22; and Ferrero E, et al., *J. Immunol.* 1990; 145: 331-6). It is encoded on chromosome 5q23-31, together with IL-3, GM-CSF, epidermal growth factor (EGF) receptor, beta2 adrenergic receptor and platelet-derived growth factor (PDGF) (see Goyert S M, et al. *Science* 1988; 239: 497-500). CD14 is attached to the cell membrane via a glycosylphosphatidylinositol (GPI) anchor, which is encoded on the X chromosome (Haziot A, et al., *J. Immunol.* 1988; 141: 547-52; and Takeda J, et al., *Cell* 1993; 73: 703-11).

In some embodiments, CD200R1 expression levels are determined in combination with one or more biomarkers selected from the group consisting of ICOS, TIGIT, TNFRSF9, HAVCR2, PDCD1, FCGR2A, FCGR1A, CD163, and CD14. In some embodiments, at least two, three, four, five, six, seven, eight, or nine, of the biomarker proteins set forth in Tables 1 and 2 can be used in combination as a panel, in addition to CD200R1. The expression levels and/or activity of one or more of the biomarkers in Tables 1 and 2 (or any of the subsets of biomarkers mentioned herein) can be measured in combination with the expression level and/or activity of CD200R1.

B. Biomarker Measurements

Measuring or determining protein expression levels in a biological sample may be performed by any suitable method (see, e.g., Harlow and Lane (1988) "*Antibodies: A Laboratory Manual*," Cold Spring Harbor Laboratory: Cold Spring Harbor, N.Y.).

In general, protein levels are determined by contacting a biological sample obtained from a subject with binding agents for one or more of the biomarker proteins; detecting, in the biological sample the expression level (e.g., levels) of one or more of the biomarker proteins that bind to the binding agents; and comparing the levels of one or more of the biomarker proteins in the sample with the levels of the corresponding protein biomarkers in a control sample (e.g., a normal sample). In certain embodiments, a suitable binding agent is a ribosome, with or without a peptide component, an RNA molecule, or a polypeptide (e.g., a polypeptide that comprises a polypeptide sequence of a protein marker, a peptide variant thereof, or a non-peptide mimetic of such a sequence).

Suitable binding agents also include an antibody specific for a biomarker protein described herein (e.g., an antibody specific for any biomarker listed in Table 1 or Table 2). Suitable antibodies for use in the methods of the present invention include monoclonal and polyclonal antibodies and antigen-binding fragments (e.g., Fab fragments or scFvs) of antibodies. Antibodies, including monoclonal and polyclonal antibodies, fragments and chimeras, may be prepared using methods known in the art (see, for example, Kohler and Milstein (1975) *Nature* 256:495-497; Kozbor et al. (1985) *J Immunol Methods* 81:31-42; Cote et al. (1983) *Proc Natl Acad Sci USA* 80:2026-203; and Zhang et al. (2002) *J Biol Chem* 277:39379-39387). Antibodies to be used in the methods of the invention can be purified by methods well known in the art. Antibodies may also be obtained from commercial sources.

In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or fragment thereof). The detectable agent can be selected such that it generates a signal that can be measured and whose intensity is related (preferably proportional) to the amount of protein marker present in the sample being analyzed. Methods for labeling biological molecules such as polypeptides and antibodies are well-known in the art. Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, e.g., those used in an ELISA, i.e., horseradish peroxidase, beta-galactosidase, luciferase, alkaline phosphatase), colorimetric labels, magnetic labels, and biotin, digoxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose (SEPHAROSE®, Pharmacia), cellulose, nitrocellulose, dextran, cross-linked dextran gel (SEPHADEX®, Pharmacia), liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein expression levels in a biological sample may be determined using immunoassays. Examples of such assays are time resolved fluorescence immunoassays (TR-FIA), radioimmunoassays, enzyme immunoassays (e.g., ELISA), immunofluorescence immunoprecipitation, latex agglutination, hemagglutination, Western blot, and histochemical tests, which are conventional methods well-known in the art. Methods of detection and quantification of the signal generated by the complex formed by binding of the binding agent with the protein marker will depend on the nature of the assay and of the detectable moiety (e.g., fluorescent moiety).

In one example, the presence or amount of protein expression of a gene (e.g., a biomarker protein depicted in Table 1 or Table 2) can be determined using a Western blotting technique. For example, a lysate can be prepared from a biological sample, or the biological sample (e.g., biological fluid) itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a biomarker protein (e.g., one depicted in Table 1 or Table 2). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here, as above, the presence or amount of bound detectably-labeled antibody indicates the presence or amount of protein in the biological sample.

Alternatively, the protein expression levels may be determined using mass spectrometry based methods or image-based methods known in the art for the detection of proteins. Other suitable methods include 2D-gel electrophoresis, proteomics-based methods such as the identification of individual proteins recovered from the gel (e.g., by mass spectrometry or N-terminal sequencing) and/or bioinformatics.

Methods for detecting or measuring protein expression can, optionally, be performed in formats that allow for rapid preparation, processing, and analysis of multiple samples. This can be, for example, in multi-well assay plates (e.g., 96 wells or 386 wells) or arrays (e.g., protein chips). Stock solutions for various reagents can be provided manually or robotically, and subsequent sample preparation, pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize commercially available reader technologies, i.e., ARRAYSCAN™ VTI HCS Reader or KINETIC-ICSCAN® HCS Reader technology (Thermo Fisher Scientific, Waltham, Mass.).

In some embodiments, the protein expression level (or activity) of at least two biomarker proteins (e.g., at least three proteins, at least four proteins, at least five proteins, at least six proteins, at least seven proteins, at least eight proteins, at least nine proteins, or at least 10 proteins) can be assessed and/or measured.

Expression of the biomarker can also be detected at the nucleic acid level (e.g., based on RNA levels). In one embodiment, RNA is detected using an RNA-ISH assay. Another method for determining the level of RNA in a sample involves the process of nucleic acid amplification from homogenized tissue, e.g., by RT-PCR (reverse transcribing the RNA and then, amplifying the resulting cDNA employing PCR or any other nucleic acid amplification method, followed by the detection of the amplified molecules. In another embodiment, RNA expression is assessed by quantitative fluorogenic RT-PCR (qPCR).

In one embodiment, expression levels of CD200R1 and one or more biomarkers are measured in two or more types of biological samples. In another embodiment, expression levels of CD200R1 and one or more biomarkers are measured in one type of biological sample and levels of a second biomarker are measured in a second type of biological sample.

In one embodiment, the methods described herein involve comparing the measured expression level or activity of a biomarker protein (as measured in a biological sample obtained from a subject) to a control sample. In some embodiments, control sample is obtained from the subject prior to administering to the subject the CD200 inhibitor (e.g., samalizumab). In some embodiments, the control sample can be (or can be based on), e.g., a collection of samples obtained from one or more (e.g., two, three, four, five, six, seven, eight, nine, 10, 15, 20, 25, 30, 35, or 40 or more) healthy individuals that have not been administered CD200 inhibitor. In some embodiments, the control sample can be (or can be based on), e.g., a pooled sample obtained from two or more (e.g., two, three, four, five, six, seven, eight, nine, 10, 15, 20, 25, 30, 35, or 40 or more) individuals. In some embodiments of any of the methods described herein, the pooled samples can be from healthy individuals, or at least, individuals who do not have or are not suspected of having cancer. In another embodiment, determining whether the expression level or activity of an biomarker has increased following treatment with a CD200 inhibitor can involve comparing the expression level or activity of the biomarker in a biological sample obtained from a subject prior to treatment to the expression level of the biomarker in a sample of the same biological type obtained from the patient after treatment with the inhibitor (e.g., one day, two days, three days, four days, five days, six days, 1 week, 2 weeks, 3 weeks, a month, 6 weeks, two months, or three months after treatment with the inhibitor).

In some embodiments, determining whether a CD200 inhibitor has produced a desired effect (e.g., a reduction in cancer burden (e.g., by about 30, 40, 50, 60, 70, 80, 90, or 100%)) in a human can be performed by querying whether the post-treatment expression level of the biomarker falls within a predetermined range indicative of responsiveness to a CD200 inhibitor by a human. In some embodiments, determining whether a CD200 inhibitor has produced a desired effect in a human can include querying if the post-treatment expression level or activity of one or more biomarkers falls above or below a predetermined cut-off value. A cut-off value is typically the expression level or activity of a given biomarker in a given biological sample above or below which is considered indicative of a certain phenotype—e.g., responsiveness to therapy with a CD200 inhibitor.

In some embodiments of any of the methods described herein, the same practitioner may administer the CD200 inhibitor to the subject prior to determining whether a change in the expression level or activity of one or more biomarkers has occurred, whereas in some embodiments, the practitioner who administers the inhibitor to the subject is different from the practitioner who determines whether a response has occurred in the subject. In some embodiments, the practitioner may obtain a biological sample from the subject prior to administration of the inhibitor. In some embodiments, the practitioner may obtain a biological sample from the subject following the administration of the inhibitor to the subject. In some embodiments, the post-treatment sample can be obtained from the subject less than 48 (e.g., less than 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, nine, eight, seven, six, five, four, three, two, or even less than one) hour following administration of the inhibitor to the subject. In some embodiments, the post-treatment sample can be obtained from the subject less than 20 (e.g., less than 19, 18, 17, 16, 15, 14, 13, 12, 11, 10, nine, eight, seven, six, five, four, three, two, or one) day(s) after administering to the subject the inhibitor. In some embodiments, the biological sample is obtained from the subject no more than 20 (e.g., no more than 19, 18, 17, 16, 15, 14, 13, 12, 11, 10, nine, eight, seven, six, five, four, three, two, or one) day(s) after the inhibitor is administered to the subject.

In some embodiments, the expression level of CD200R1 and at least one (e.g., at least two, three, four, five, six, seven, eight, or nine) biomarker is increased by at least 5 (e.g., at least 10, 15, 20, 25, 30, 35, 40, 45, 50, 55, 60, 65, or 70) % following administration of the inhibitor.

In some embodiments, the expression level of CD200R1 and at least one (e.g., at least two, three, four, five, six, seven, eight, or nine) biomarkers is increased to within 50 (e.g., 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1) % of the normal expression level of the biomarker following administration of one or more doses of the inhibitor.

In some embodiments of any of the methods described herein, the expression level of ICOS is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of TIGIT is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of TNFRSF9 is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of HAVCR2 is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of PDCD1 is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of FCGR2A is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of FCGR1A is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of CD163 is increased by at least about 40% (e.g., 40, 45, 50, 60, 665, 70, 80, 85, 90, 95, or up to 100%) following administration of a CD200 inhibitor (e.g., samalizumab). In some embodiments of any of the methods described herein, the expression level of CD14 is increased by at least about 40% (e.g., 40, 45, 50, 60, 665, 70, 80, 85, 90, 95, or up to 100%) following administration of a CD200 inhibitor (e.g., samalizumab).

In some embodiments of any of the methods described herein, the expression level of ICOS is increased by at least about 1.5-fold, 2-fold, 2.5-fold, or 3-fold following administration of a CD200 inhibitor (e.g., samalizumab) compared to the expression level of ICOS in a biological sample of the same type obtained from the subject prior to treatment with the CD200 inhibitor. In another embodiment of any of the methods described herein, the expression level of TIGIT is increased by at least about 1.5-fold, 2-fold, 2.5-fold, or 3-fold following administration of a CD200 inhibitor (e.g., samalizumab) compared to the expression level of TIGIT in a biological sample of the same type obtained from the subject prior to treatment with the CD200 inhibitor. In another embodiment of any of the methods described herein, the expression level of TNFRSF9 is increased by at least about 1.5-fold, 2-fold, 2.5-fold, or 3-fold following administration of a CD200 inhibitor (e.g., samalizumab) compared to the expression level of TNFRSF9 in a biological sample of the same type obtained from the subject prior to treatment with the CD200 inhibitor. In another embodiment of any of the methods described herein, the expression level of HAVCR2 is increased by at least about 1.5-fold, 2-fold, 2.5-fold, or 3-fold following administration of a CD200 inhibitor (e.g., samalizumab) compared to the expression level of HAVCR2 in a biological sample of the same type obtained from the subject prior to treatment with the CD200 inhibitor. In another embodiment of any of the methods described herein, the expression level of PDCD1 is increased by at least about 1.5-fold, 2-fold, 2.5-fold, or 3-fold following administration of a CD200 inhibitor (e.g., samalizumab) compared to the expression level of TIGIT in a biological sample of the same type obtained from the subject prior to treatment with the PDCD1 inhibitor. In another embodiment of any of the methods described herein, the expression level of FCGR2A is increased by at least about 1.5-fold, 2-fold, 2.5-fold, or 3-fold following administration of a CD200 inhibitor (e.g., samalizumab) compared to the expression level of FCGR2A in a biological sample of the same type obtained from the subject prior to treatment with the CD200 inhibitor. In another embodiment of any of the methods described herein, the expression level of FCGR1A is increased by at least about 1.5-fold, 2-fold, 2.5-fold, or 3-fold following administration of a CD200 inhibitor (e.g., samalizumab) compared to the expression level of FCGR1A in a biological sample of the same type obtained from the subject prior to treatment with the CD200 inhibitor. In another embodiment of any of the methods described herein, the expression level of CD163 is increased by at least about 1.5-fold, 2-fold, 2.5-fold, or 3-fold following administration of a CD200 inhibitor (e.g., samalizumab) compared to the expression level of CD163 in a biological sample of the same type obtained from the subject prior to treatment with the CD200 inhibitor. In another embodiment of any of the methods described herein, the expression level of CD14 is increased by at least about 1.5-fold, 2-fold, 2.5-fold, or 3-fold following administration of a CD200 inhibitor (e.g., samalizumab) compared to the expression level of CD14 in a biological sample of the same type obtained from the subject prior to treatment with the CD200 inhibitor.

In another embodiment of any of the methods described herein, the expression level of CD200R1 is increased by at least about 1.5-fold, 2-fold, 2.5-fold, or 3-fold following administration of a CD200 inhibitor (e.g., samalizumab) compared to the expression level of CD200R1 in a biological sample of the same type obtained from the subject prior to treatment with the CD200 inhibitor.

2. CD200 Inhibitors

The terms "CD200", "OX-2" and "OX-2/CD200" are used interchangeably herein and refers to the highly conserved type I transmembrane glycoprotein including multiple transcript variants: CD200 isoform a (SEQ ID NO: 1; NCBI Reference Sequence: NP_005935.4), CD200 isoform b (SEQ ID NO:2; NCBI Reference Sequence: NP_001004196.2), CD200 isoform c (SEQ ID NO:3; NCBI Reference Sequence: NP_001305755.1 or NP_001305759.1), CD200 isoform d (SEQ ID NO: 46; NCBI Reference Sequence: NP_001305757.1).

CD200 interacts with the CD200 receptor (also known as "CD200R," "CD200R1," "Cell Surface Glycoprotein OX2 Receptor," "CD200 Cell Surface Glycoprotein Receptor," "MOX2 Receptor," "MOX2R," "OX2R," "Cell Surface Glycoprotein CD200 Receptor," "Cell Surface Glycoprotein Receptor CD200," "HCRTR2," and "CRTR2"), which induces immune suppression by skewing the immune response from a Th1-cytokine producing response, to a response characterized by an increased frequency of immunosuppressive regulatory T cells and suppression of memory T cell function. CD200R1 is restricted to the surfaces of myeloid lineage cells. Alternative splicing of CD200R1 gene results in multiple transcript variants, including CD200R1 isoform a (SEQ ID NO: 42; NCBI Reference Sequence: NP_620161.1), CD200R1 isoform b (SEQ ID NO: 43; NCBI Reference Sequence: NP_620385.1), CD200R1 isoform c (SEQ ID NO: 44; NCBI Reference Sequence: NP_620386.1), and CD200R1 isoform d (SEQ ID NO: 45; NCBI Reference Sequence: NP_740750.1).

The terms "CD200 antagonist" and "CD200 inhibitor" as used herein include any agent that is capable of inhibiting the activity, function and/or the expression of CD200 or its receptor. In certain embodiments, the antagonist disrupts the interaction of CD200 and CD200R1. In other embodiments, the CD200 antagonist is capable of decreasing the immunosuppressive effects of CD200 or are capable of targeting CD200-expressing cells for depletion or elimination.

Any compound which binds to and inhibits, or otherwise inhibits the activity, function and/or the expression of CD200 or its receptor may be utilized in accordance with the present disclosure. For example, an inhibitor of CD200 can be, e.g., a small molecule, a nucleic acid or nucleic acid analog, a peptidomimetic, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA, locked nucleic acid inhibitors, and peptide nucleic acid inhibitors. In some embodiments, a CD200 inhibitor may be a protein or protein fragment.

Other compounds which may be utilized include, but are not limited to, proteins, protein fragments, peptides, small molecules, RNA aptamers, L-RNA aptamers, spiegelmers, antisense compounds, serine protease inhibitors, molecules which may be utilized in RNA interference (RNAi) such as double stranded RNA including small interfering RNA (siRNA), locked nucleic acid (LNA) inhibitors, peptide nucleic acid (PNA) inhibitors, etc.

An inhibitor of CD200 can be, e.g., a small molecule, a polypeptide, a polypeptide analog, a nucleic acid, or a nucleic acid analog.

"Small molecule" as used herein, is meant to refer to an agent, which has a molecular weight preferably of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* (1998) 120:8565-8566). It is within the scope of this application that such a library may be used to screen for agents that bind to a target antigen of interest (e.g., CD200). There are numerous commercially available compound libraries, such as the Chembridge DIVERSet™ diverse screening library. Libraries are also available from academic investigators, such as the Diversity set from the NCI developmental therapeutics program. Rational drug design may also be employed. Rational drug design can also be achieved based on known compounds, e.g., a known inhibitor of CD200 (e.g., an antibody, or antigen-binding fragment thereof, that binds to CD200).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal. It should be noted that peptidomimetics may or may not have similar two-dimensional chemical structures, but share common three-dimensional structural features and geometry. Each peptidomimetic may further have one or more unique additional binding elements.

Nucleic acid inhibitors can be used to bind to and inhibit a target antigen of interest. The nucleic acid antagonist can be, e.g., an aptamer. Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do (see, e.g., Ulrich (2006) *Handb Exp Pharmacol.* 173:305-326).

In some embodiments, the CD200 inhibitor is a non-antibody scaffold protein. These proteins are, generally, obtained through combinatorial chemistry-based adaptation of pre-existing antigen-binding proteins. For example, the binding site of human transferrin for human transferrin receptor can be modified using combinatorial chemistry to create a diverse library of transferrin variants, some of which have acquired affinity for different antigens. Ali et al. (1999) *J Biol Chem* 274:24066-24073. The portion of human transferrin not involved with binding the receptor remains unchanged and serves as a scaffold, like framework regions of antibodies, to present the variant binding sites. The libraries are then screened, as an antibody library is, against a target antigen of interest to identify those variants having optimal selectivity and affinity for the target antigen. Non-antibody scaffold proteins, while similar in function to antibodies, are touted as having a number of advantages as compared to antibodies, which advantages include, among other things, enhanced solubility and tissue penetration, less costly manufacture, and ease of conjugation to other molecules of interest. Hey et al. (2005) *TRENDS Biotechnol* 23(10):514-522.

One of skill in the art would appreciate that the scaffold portion of the non-antibody scaffold protein can include, e.g., all or part of: the Z domain of *S. aureus* protein A, human transferrin, human tenth fibronectin type III domain, Kunitz domain of a human trypsin inhibitor, human CTLA-4, an ankyrin repeat protein, a human lipocalin, human crystallin, human ubiquitin, or a trypsin inhibitor from *E. elaterium*. Hey et al., (2005).

In some embodiments, the CD200 inhibitor is an antibody, or antigen-binding fragment thereof, which binds to CD200 (e.g., an "anti-CD200 antibody.")

In some embodiments, an anti-CD200 antibody described herein binds to an epitope within the extracellular portion of 65 a CD200 protein. For example, in some embodiments, the anti-CD200 antibody can bind to CD200 protein at an epitope within or overlapping with: (i) amino acids 1 to 233 of the amino acid sequence depicted in SEQ ID NO: 1; (ii) amino acids 1 to 258 of the amino acid sequence depicted in SEQ ID NO:2; or amino acids 1 to 229 of the amino acid sequence depicted in SEQ ID NO:3.

In some embodiments, the anti-CD200 antibody binds to an epitope in the human CD200 protein lacking the leader sequence. For example, an anti-CD200 antibody described herein can bind to a CD200 protein at an epitope within or overlapping with amino acids 31 to 233 of the amino acid sequence depicted in SEQ ID NO: 1, which corresponds to the extracellular portion of the mature form of human CD200 isoform A less the amino terminal leader sequence. In some embodiments, an anti-CD200 antibody described herein can bind to a CD200 protein at an epitope within or overlapping with amino acids 56 to 258 of the amino acid sequence depicted in SEQ ID NO: 2, which corresponds to the extracellular portion of the mature form of human CD200 isoform B less the amino terminal leader sequence. In some embodiments, an anti-CD200 antibody described herein can bind to a CD200 protein at an epitope within or overlapping with amino acids 27 to 229 of the amino acid sequence depicted in SEQ ID NO: 3, which corresponds to the extracellular portion of the mature form of human CD200 less the amino terminal leader sequence.

In some embodiments, the anti-CD200 antibody specifically binds to a human CD200 protein (e.g., the human CD200 protein having the amino acid sequence depicted in SEQ ID NO: 1, SEQ ID NO: 2, SEQ ID NO: 3, SEQ ID NO:46 or the extracellular domains of the mature forms of the CD200 proteins). Methods for identifying the epitope to which a particular antibody binds are also know in the art.

Anti-CD200 antibodies for use in the methods provided herein are CD200 antagonists and include whole antibodies, or antibody fragments capable of binding to CD200, particularly anti-CD200 antibodies which disrupt the interaction between CD200 and CD200R1. Exemplary anti-CD200 antibodies, or antigen binding fragments thereof, which can be used in the methods described herein include, but are not limited to, those disclosed in U.S. Pat. Nos. 7,408,041; 8,075,884; and WO 2012/106634 (the contents of each of which are herein incorporated by reference in their entirety).

In one embodiment, the anti-CD200 antibody, or antigen binding fragment thereof, comprises the CDR1, CDR2, and CDR3 domains of a heavy chain variable region having the sequence set forth in SEQ ID NO: 13, and the CDR1, CDR2, and CDR3 domains of a light chain variable region having the sequence set forth in SEQ ID NO: 12.

In another embodiment, the anti-CD200 antibody, or antigen binding fragment thereof, comprising the CDR1, CDR2 and CDR3 domains of a heavy chain region having the sequence set forth in SEQ ID NO: 11, and the CDR1, CDR2 and CDR3 domains of a light chain region having the sequence set forth in SEQ ID NO: 10.

In another embodiment, the anti-CD200 antibody, or antigen binding fragment thereof, comprises: (a) a light chain variable domain that comprises (i) a light chain CDR1 comprising the sequence set forth in SEQ ID NO: 4, (ii) a light chain CDR2 comprising the sequence set forth in SEQ ID NO: 5, and (iii) a light chain CDR3 comprising the sequence set forth in SEQ ID NO: 6; and (b) a heavy chain variable domain comprising (i) a heavy chain CDR1 comprising the sequence set forth in SEQ ID NO: 7, (ii) a heavy chain CDR2 comprising the sequence set forth in SEQ ID NO: 8 and (iii) a heavy chain CDR3 comprising the sequence set forth in SEQ ID NO: 9.

In another embodiment, the antibody comprises a light chain region sequence as set forth in SEQ ID NO: 10 and/or a heavy chain variable region sequence as set forth in SEQ ID NO: 11. In one embodiment, the antibody comprises a light chain sequence as set forth in SEQ ID NO: 12 and/or a heavy chain sequence as set forth in SEQ ID NO: 13. In one embodiment, the anti-CD200 antibody is samalizumab (also known as ALXN6000; Alexion Pharmaceuticals, Inc.).

Antibodies and antigen binding fragments thereof may be obtained according to established hybridoma and recombinant procedures. Suitable methods for producing an antibody (e.g., an anti-CD200 antibody) or antigen-binding fragments thereof may be obtained according to established hybridoma and recombinant procedures as previously disclosed (see, e.g., U.S. Pat. Nos. 7,427,665; 7,435,412; and 7,408,041). For example, a process for the production of an antibody disclosed herein includes culturing a host (e.g., *E. coli* or a mammalian cell), which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria, suitable culture media include, but are not limited to, medium LE, NZCYM, NZYM, NZM, Terrific Broth, SOB, SOC, 2xYT, and/or M9 Minimal Medium. For yeast, suitable culture media include, but are not limited to, medium YPD, YEPD, Minimal Medium, and/or Complete Minimal Dropout Medium.

In vitro production provides relatively pure antibody preparations and allows scale-up to give large amounts of the desired antibodies. Techniques for bacterial cell, yeast, plant, or mammalian cell cultivation are known in the art and include homogeneous suspension culture (e.g., in an airlift reactor or in a continuous stirrer reactor), and immobilized or entrapped cell culture (e.g., in hollow fibers, microcapsules, on agarose microbeads or ceramic cartridges).

Large quantities of the desired antibodies can also be obtained by multiplying mammalian cells in vivo. For this purpose, cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristine. After one to two weeks, ascitic fluid is taken from the animals.

The antibody which is formulated is preferably essentially pure and desirably essentially homogeneous (e.g., free from contaminating proteins, etc.). "Essentially pure" antibody means a composition comprising at least about 90% by weight of the antibody, based on total weight of the composition, preferably at least about 95% by weight of the antibody. "Essentially homogeneous" antibody means a composition comprising at least about 99% by weight of antibody, based on total weight of the composition.

Techniques for purification of therapeutic antibodies to pharmaceutical grade are well known in the art. For example, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g., affinity chromatography with a one or more surface polypeptides derived from a CLL cell line according to this disclosure, or with Protein-A or G.

The foregoing, and other, techniques are discussed in, for example, Kohler and Milstein, (1975) *Nature* 256:495-497; U.S. Pat. No. 4,376,110; Harlow and Lane, *Antibodies: a Laboratory Manual*, (1988) Cold Spring Harbor, the disclosures of which are all incorporated herein by reference. Techniques for the preparation of recombinant antibody molecules is described in the above references and also in, for example WO 97/08320; U.S. Pat. Nos. 5,427,908 and 5,508,717; Smith, 1985, *Science*, Vol. 225, pp 1315-1317; Parmley and Smith 1988, *Gene* 73, pp 305-318; De La Cruz et al, 1988, *J. Biol. Chem.*, 263 pp 4318-4322; U.S. Pat. Nos. 5,403,484; 5,223,409; WO88/06630; WO 92/15679; U.S. Pat. Nos. 5,780,279; 5,571,698; and 6,040,136; Davis et al., *Cancer Metastasis Rev.*, 1999; 18(4):421-5; Taylor, et al., *Nucleic Acids Research* 20 (1992): 6287-6295; and Tomizuka et al., *Proc. Nat. Academy of Sciences USA* 97(2) (2000): 722-727 (the contents of each are incorporated herein by reference).

3. Biological Samples and Sample Collection

Suitable biological samples for use in the methods described herein include whole blood (or a fraction thereof), tumor tissue, or tumor cells. A biological sample can be further fractionated, if desired, to a fraction containing particular analytes (e.g., proteins) of interest. For example, a whole blood sample can be fractionated into serum or into fractions containing particular types of proteins.

Biological samples suitable for the invention may be fresh or frozen samples collected from a subject, or archival samples with known diagnosis, treatment and/or outcome history. The biological samples can be obtained from a subject, e.g., a subject having, suspected of having, or at risk of developing, cancer. Any suitable methods for obtaining the biological samples can be employed, although exemplary methods include, e.g., phlebotomy, swab (e.g., buccal or other swab), lavage, or fine needle aspirate biopsy procedure. Biological samples can also be obtained from bone marrow.

In some embodiments, a protein extract may be prepared from a biological sample. In some embodiments, a protein extract contains the total protein content. Methods of protein extraction are well known in the art. See, e.g., Roe (2001) *Protein Purification Techniques: A Practical Approach*, $2^{nd}$ Edition, Oxford University Press. Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.).

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes (e.g., changes in osmolarity or pH) in protein structure. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of *Methods in Molecular Biology*, Humana Press; Masters (2000) "Animal cell culture: a practical approach," Volume 232 of *Practical Approach Series*, Oxford University Press; and Jones (1996) "Human cell culture protocols," volume 2 of *Methods in Molecular Medicine*, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

4. Methods for Treatment

Also provided herein are methods for treating cancer in a subject (e.g., a human). In one embodiment, the patient is an adult and the cancer is selected from the group consisting of diffuse large B cell lymphoma (DLBL), lung adenocarcinoma (LUAD), lung squamous cell carcinoma (LUSC), glioblastoma (GBM), low grade glioma (LGG), clear cell RCC (KIRC), chromophobe (KICH), papillary cell RCC (KIRP), melanoma (SKCM), ovarian cancer (OV), colon cancer (COAD), rectum cancer (READ), and uterine endometrial cancer (UCEC).

In another embodiment, the patient is a pediatric patient, and the cancer is selected from atypical teratoid rhabdoid tumor (AT/RT), ependymoma, osteosarcoma, rhabdomyosarcoma, Ewing sarcoma, pilocytic astrocytoma, neuroblastoma, and retinoblastoma.

The terms "treat," "treating," and "treatment," as used herein, refer to therapeutic measures described herein. The methods of treatment employ administration to a subject (such as a human) the combination disclosed herein in order to cure, delay, reduce the severity of, or ameliorate one or more symptoms of the disease or disorder or recurring disease or disorder, or in order to prolong the survival of a subject beyond that expected in the absence of such treatment.

The terms "effective amount" or "therapeutically effective amount" are used interchangeably and refer to an amount of formulation or antibody effective to alleviate or ameliorate one or more symptom(s) of cancer or to prolong the survival of the subject being treated. Determination of a therapeutically effective amount is well within the capability of those skilled in the art, especially in light of the detailed disclosure provided herein. Therapeutically effective dosages may be determined by using in vitro and in vivo methods.

In one embodiment, a method for treating a patient having cancer who has been determined to have positive expression of CD200 receptor (CD200R1) and one or more biomarkers (e.g., two or more, three or more, four or more, five or more, 6 or more, 7 or more, 8 or more, or 9) in a biological sample from the patient is provided, the method comprising administering to the patient a CD200 inhibitor in an amount and with a frequency sufficient to reduce the cancer burden in the patient (e.g., by about 30, 40, 50, 60, 70, 80, 90, or 100%). In one embodiment, the biomarker is ICOS. In another embodiment, the biomarker is TIGIT. In another embodiment, the biomarker is TNFRSF9. In another embodiment, the biomarker is HAVCR2. In another embodiment, the biomarker is PDCD1. In another embodiment, the biomarker is FCGR2A. In another embodiment, the biomarker is FCGR1A. In another embodiment, the biomarker is CD163. In another embodiment, the biomarker is CD14.

In one embodiment, the patient has been determined to have positive expression of CD200R1 and positive expression of two biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of three biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of four biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of five biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of six biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of seven biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1 and positive expression of eight biomarkers selected from the group consisting of ICOS, TIGIT, TNFRSF9, HAVCR2, PDCD1, FCGR2A, FCGR1A, CD163, and CD14. In another embodiment, the patient has been determined to have positive expression of CD200R1, ICOS, TIGIT, TNFRSF9, HAVCR2, PDCD1, FCGR2A, FCGR1A, CD163, and CD14. The patient can have positive expression of any possible combination of the biomarkers disclosed herein.

In one embodiment, the method includes determining if a patient having cancer has positive expression of CD200 receptor (CD200R1) and one or more biomarkers (i.e., Inducible T-cell COStimulator (ICOS), T Cell Immunoreceptor with Ig and ITIM Domains (TIGIT), Tumor Necrosis Factor Receptor Superfamily Member 9 (TNFRSF9), Hepatitis A Virus Cellular Receptor 2 (HAVCR2), and Programmed Cell Death 1 (PDCD1), Fc Fragment Of IgG Receptor IIa (FCGR2A), Fc Fragment Of IgG Receptor Ia (FCGR1A), Cluster of Differentiation 163 (CD163), and/or CD14) and administering to the patient a CD200 inhibitor if the patient has an positive expression of CD200R1 and one or more biomarkers.

The CD200 inhibitor can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. patent publication no. 20080241223; U.S. Pat. Nos. 5,501,856; 4,863,457; and 3,710,795; and European patent nos. EP488401 and EP430539, the disclosures of each of which are incorporated herein by reference in their entirety. The composition can be delivered to the subject by way of an implantable device based on, e.g., diffusive, erodible or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

A suitable dose of a CD200 inhibitor (e.g., an anti-CD200 antibody or fragment thereof), which dose is capable of treating cancer in a subject, can depend on a variety of factors including, e.g., the age, sex, and weight of a subject to be treated and the particular inhibitor compound used. For example, a different dose of an siRNA specific for human CD200 may be required to treat a subject with cancer as compared to the dose of an anti-CD200 antibody required to treat the same patient. Other factors affecting the dose administered to the subject include, e.g., the type or severity of the cancer. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

The inhibitor can be administered as a fixed dose, or in a milligram per kilogram "mg/kg" dose. In one embodiment, the CD200 inhibitor is an anti-CD200 antibody administered at a dose of about 300 mg/m² to about 600 mg/m². In another embodiment, the anti-CD200 antibody is administered at a dose of about 300 mg/m². In another embodiment, the anti-CD200 antibody is administered at a dose of about 400 mg/m². In another embodiment, the anti-CD200 antibody is administered at a dose of about 500 mg/m². In another embodiment, the anti-CD200 antibody is administered at a dose of about 600 mg/m². In another embodiment, the anti-CD200 antibody is administered at a dose of about 700 mg/m². In another embodiment, the anti-CD200 antibody is administered at a dose of about 300 mg/m². In another embodiment, the anti-CD200 antibody is administered at a dose of about 800 mg/m². In another embodiment, the anti-CD200 antibody is administered at a dose of about 900 mg/m². In another embodiment, the anti-CD200 antibody is administered at a dose of about 1000 mg/m². In another embodiment, the anti-CD200 antibody is administered at a dose of about 1100 mg/m².

In another embodiment, the anti-CD200 antibody is administered at a dose of about 5 mg/kg to about 50 mg/kg. In another embodiment, the anti-CD200 antibody is administered at a dose of about 10 mg/kg to about 30 mg/kg. In another embodiment, the anti-CD200 antibody is administered at a dose of about 15 mg/kg to about 25 mg/kg. In another embodiment, the anti-CD200 antibody is administered at a dose of about 10 mg/kg to about 20 mg/kg. In another embodiment, the anti-CD200 antibody is administered at a dose of about 10 mg/kg. In another embodiment, the anti-CD200 antibody is administered at a dose of about 15 mg/kg. In another embodiment, the anti-CD200 antibody is administered at a dose of about 20 mg/kg. In another embodiment, the anti-CD200 antibody is administered at a dose of about 25 mg/kg.

A pharmaceutical composition can include a therapeutically effective amount of an inhibitor of CD200 (e.g., an anti-CD200 antibody or antigen-binding fragment thereof). Such effective amounts can be readily determined by one of ordinary skill in the art based, in part, on the effect of the administered inhibitor, or the combinatorial effect of the antibody and one or more additional active agents, if more than one agent is used. A therapeutically effective amount of an inhibitor of a CD200 inhibitor (e.g., such as samalizumab) can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of aHUS. For example, a therapeutically effective amount of a CD200 inhibitor can inhibit (lessen the severity of or eliminate the occurrence of) of any one of the symptoms of cancer. A therapeutically effective amount is also one in which any toxic or detrimental effects of the composition are outweighed by the therapeutically beneficial effects.

Toxicity and therapeutic efficacy of CD200 inhibitors can be determined by known pharmaceutical procedures in cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions, or inhibitors (e.g., anti-CD200 antibodies) of the compositions, that exhibit high therapeutic indices are preferred. While compositions that exhibit toxic side effects may be used, care should be taken to design a delivery system that targets such compounds to the site of affected tissue and to minimize potential damage to normal cells and, thereby, reduce side effects.

In some embodiments, the CD200 inhibitor can be administered to a subject as a monotherapy. Alternatively, as described above, the inhibitor can be administered to a subject as a combination therapy with another treatment, e.g., another treatment for cancer. For example, the combination therapy can include administering to the subject (e.g., a human patient) one or more additional that provide a therapeutic benefit to the subject who has cancer. In one embodiment, the inhibitor is administered first in time and the one or more additional active agents are administered second in time. In some embodiments, the one or more additional active agents are administered first in time and the inhibitor is administered second in time.

5. Methods of Monitoring Responsiveness

Also, provided are methods for monitoring responsiveness of a subject having cancer to treatment with a CD200 inhibitor, the method comprising: determining the expression level of CD200R1 and one or more (e.g., two or more, three or more, four or more, five or more, 6 or more, 7 or more, 8 or more, or 9) biomarkers (i.e., ICOS, TIGIT, TNFRSF9, HAVCR2, PDCD1, FCGR2A, FCGR1A, CD163, and/or CD14) in a biological sample from the patient, wherein increased expression levels of CD200R1 and the one or more biomarkers, as compared to expression levels in a biological sample of the same type obtained from the subject prior to treatment with the CD200 inhibitor, indicates that the subject is responsive to treatment with the CD200 inhibitor.

In one embodiment, increased expression levels of CD200R1 and one biomarker selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and two biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and three biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and four biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and five biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and six biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and seven biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1 and eight biomarkers selected from the group consisting of ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. In another embodiment, increased expression levels of CD200R1, ICOS, TIGIT, TNFRSF9, HAVCR2, PDCD1, FCGR2A, FCGR1A, CD163, and CD14, compared to the expression levels in a biological sample of the same type obtained from the subject prior to treatment with the CD200 inhibitor, indicates that the subject is responsive to treatment with the CD200 inhibitor. The patient can have elevated expression levels) of any possible combination of the biomarkers disclosed herein.

6. Additional Agents/Therapies

The anti-CD200 inhibitors described herein (e.g., samalizumab) can also be used in conjunction with other well-known therapies that are selected for their particular usefulness against the cancer that is being treated. Combinations of the present disclosure may alternatively be used sequentially with known pharmaceutically acceptable agent(s) when inappropriate.

For example, the CD200 inhibitors described herein can further be used in combination (e.g., simultaneously or separately) with an additional treatment, such as irradiation, chemotherapy (e.g., using cytarabine, daunorubicin, camptothecin (CPT-11), 5-fluorouracil (5-FU), cisplatin, doxorubicin, irinotecan, paclitaxel, gemcitabine, cisplatin, paclitaxel, doxorubicin, 5-fu, or camptothecin+apo21/TRAIL (a 6× combo)).

The CD200 inhibitors described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN®), fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): methotrexate, 5-Fluorouracil, floxuridine, cytarabine, 6-Mercaptopurine, 6-Thioguanine, fludarabine phosphate, pentostatine, and gemcitabine.

Suitable anti-proliferative agents for use in the methods of disclosed herein, include, without limitation, taxanes, paclitaxel (paclitaxel is commercially available as TAXOL®) (tamoxifen), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment as described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX® (goserelin acetate), can also be administered to the patient. When employing the methods or compositions of the present disclosure, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

7. Outcomes

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy. In another embodiment, the treatment produces at least one therapeutic effect, for example, morphologic complete remission, cytogenetic complete remission, morphologic CR with incomplete blood count recovery, partial remission, and/or stable disease.

In another embodiment, the patient treated exhibits a complete response, partial response, and/or stable disease. In another embodiment, the patient treated experiences tumor shrinkage and/or decrease in growth rate, i.e., suppression of tumor growth (e.g., by about 30, 40, 50, 60, 70, 80, 90, or 100%). In another embodiment, unwanted cell proliferation is reduced or inhibited (e.g., by about 30, 40, 50, 60, 70, 80, 90, or 100%). In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In another embodiment, the methods of treatment produce a clinical benefit (e.g., Morphologic Complete Remission (Morphologic CR), cytogenetic complete remission (CRc), morphologic CR with incomplete blood count recovery (CRi), or partial remission (PR)).

Morphologic CR requires <5% blasts in bone marrow aspirate, neutrophils ≥1,000/µL, platelets ≥100,000/µL, no extramedullary disease, no blasts with Auer rods detected, and No circulating blasts (rare may be permitted)/No evidence of pre-treatment blast phenotype by flow cytometry (i.e. CD34, CD7 co-expression).

CRc requires <5% blasts in bone marrow aspirate, neutrophils ≥1,000/µL, platelets ≥100,000/µL, no extramedullary disease, no blasts with Auer rods detected, no circulating blasts (rare may be permitted)/no evidence of pre-treatment blast phenotype by flow cytometry (i.e. CD34, CD7 co-expression), and reversion to a normal karyotype.

CRi requires <5% blasts in bone marrow aspirate, neutrophils <1,000/µL or Platelets <100,000/µL, no extramedullary disease, no blasts with Auer rods detected, and no circulating blasts (rare may be permitted)/no evidence of pre-treatment blast phenotype by flow cytometry (i.e. CD34, CD7 co-expression).

PR requires all criteria for CR except for bone marrow blasts, must have greater than 50% decrease in blasts in bone marrow aspirate to a range of 5-25%, neutrophils ≥1,000/µL, platelets ≥100,000/µL, no extramedullary disease, and if Auer rods are detected the blast count in the bone marrow must be ≤5%.

In another aspect, the treatment produces a desired immunomodulatory effect in a human (e.g., a cancer patient). The immunomodulatory effect can be characterized by a change (e.g., an increase) in at least one biomarker, i.e., CD200R1 and one or more of ICOS, TIGIT, TNFRSF9, HAVCR2, PDCD1, FCGR2A, FCGR1A, CD163, and/or CD14. It is understood that any of the methods described herein can involve determining whether there has been a change (e.g., an increase) in one or more (e.g., three, four, five, six, seven, eight, or nine) of the biomarkers described herein. Where interrogation of more than one of the biomarkers is practiced, any combination of two or more (e.g., three, four, five, six, seven, eight, nine, or 10 or more) of the biomarkers can be analyzed.

Methods for determining immune response following treatment with an ani-CD200 antibody, or antigen-binding fragment thereof, are elaborated on in, e.g., U.S. Pat. No. 9,180,186.

8. Kits

Also provided are kits comprising various reagents and materials useful for carrying out the methods described herein. The procedures for measuring, diagnosing, evaluating, and/or assessing described herein may be performed by diagnostic laboratories, experimental laboratories, or individual practitioners. The invention provides kits which can be used in any or all of these settings. In some embodiments, the kits described herein comprise materials and reagents for, among other things, characterizing or processing biological samples (e.g., biological samples), measuring biomarker levels (e.g., protein or nucleic acid levels), monitoring treatment response in a subject according to the methods provided herein. In certain embodiments, an inventive kit comprises at least one or more reagents that specifically detect protein levels of one or more biomarker proteins described herein (e.g., those Tables 1 and 2) and, optionally, instructions for using the kit. The kit can include, e.g., any of the arrays described herein.

In some embodiments, the kits may include suitable control samples (e.g., biological samples from normal healthy individuals or a solution comprising a known, control amount of a particular analyte of interest). In some embodiments, kits of the invention may include instructions for using the kit according to one or more methods described herein and may comprise instructions for processing the biological sample obtained from the subject and/or for performing the test or instructions for interpreting the results.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, or process step or steps, to the objective, spirit and scope of the present disclosure. All such modifications are intended to be within the scope of the disclosure.

The following examples are intended to illustrate, not limit, the invention.

EXAMPLES

Example 1: Immune Effector Cells Signature Development

CD200 (OX-2) is an immune checkpoint protein expressed by a number of immune cells, including B, T cells and macrophages, as well as non-immune cells, including endothelial cells and neurons. CD200 binds to its receptor (CD200R1), expressed on antigen-presenting cells (APCs) and T cells and is believed to play an important role in normal immune homeostasis. However, overexpression of CD200 by tumor cells implicates the CD200 pathway in tumor-mediated immunosuppression and regulation of antitumor activity.

Recent evidence suggests that the presence of immune effector cells within tumors is critical for clinical response to immune checkpoint therapy. Similarly, the expression of the immune modulatory target within the tumor may correlate with response to therapy. The purpose of this study was to identify tumor types which may be most sensitive to samalizumab, based on CD200 expression and the presence of immune effector cell populations within the tumor. To this end, tumor gene expression data was mined to evaluate CD200 pathway expression in multiple tumor types, to develop a gene signature which may correlate with response to samalizumab, as described below. Gene expression values for CD200, CD200R1, and other immune cell marker genes were described as the percentage of samples with expression higher than the median for the set of all tumors. The data and methodology is discussed further below.

1. Data Sources and Description

In the field of cancer research, The Cancer Genome Atlas (TCGA) data portal is the largest and most commonly used public resource, providing somatic mutation, gene expression, gene methylation and copy number variation (CNV) data sets, amongst others, for several thousands of tumor samples from adult cancer patients.

RNA-Seq (RNA sequencing), also called whole transcriptome shotgun sequencing (WTSS), uses next-generation sequencing (NGS) to reveal the presence and quantity of RNA in a biological sample at a given moment in time (see, e.g., Ryan D. Morin, et al., *BioTechniques*. 45 (1): 81-94 (2008); Chu Y, Corey D R (August 2012), *Nucleic Acid Ther.* 22 (4): 271-4; and Wang, Zhong, et al., *Nature Reviews Genetics*. 10 (1): 57-63). RNA-Seq is used to analyze the continually changing cellular transcriptome. Specifically, RNA-Seq facilitates the ability to look at alternative gene spliced transcripts, post-transcriptional modifications, gene fusion, mutations/SNPs and changes in gene expression over time, or differences in gene expression in different groups or treatments (see, e.g., Maher C A, et al. (March 2009), *Nature*. 458 (7234): 97-101). In addition to mRNA transcripts, RNA-Seq can look at different populations of RNA to include total RNA, small RNA, such as miRNA, tRNA, and ribosomal profiling (see, e.g., Ingolia N T, et al. (August 2012), *Nat Protoc*. 7 (8): 1534-50). RNA-Seq can also be used to determine exon/intron boundaries and verify or amend previously annotated 5' and 3' gene boundaries.

Publically available human tumor gene expression data (TCGA) from adult patients was mined and analyzed for the expression of CD200 by tumor type (see FIG. 1). RNAseq expression data was retrieved from the TCGA raw data FTP site. Specifically, expression data was retrieved from tcga-data.nci.nih.gov/tcgafiles/ftp_auth/distro_ftpusers/anonymous/tumor/<disease>/cgcc/unc.edu/illuminahiseq_rnasegv2/rnasegv2/. Clinical data was retrieved from tcga-data.nci.nih.gov/tcgafiles/ftp_auth/distro_ftpusers/anonymous/tumor/disease>/bcr/biotab/clin/.

The retrieved files contained sets of genes, raw read counts (RPKM), scaled estimates ("TPM" or "Transcripts Per Million", see www.ncbi.nlm.nih.gov/pmc/articles/PMC4702907/), and clinical measures for each sample/patient. The data was then reformatted and merged, and saved as a simple raw input data file in TSV format for further processing by R scripts. TPM values were considered continuous data, and were compared using standard R statistical tools.

Tumor types included in the analysis were: diffuse large B cell lymphoma (DLBL), lung adenocarcinoma (LUAD), lung squamous cell carcinoma (LUSC), glioblastoma (GBM), low grade glioma (LGG), clear cell RCC (KIRC), chromophobe (KICH), papillary cell RCC (KIRP), melanoma (SKCM), ovarian cancer (OV), colon cancer (COAD), rectum cancer (READ), uterine endometrial cancer (UCEC). The cutoff date of data download was March 2016.

2. Correlation of Gene Expression in Tumors

Pair-wise correlation of gene expression was evaluated for a list of genes including CD200, CD200R1, and a number of immune cell markers and targets: NT5E, IDO1, LRRC32, CTLA4, TNFRSF9, CD27, CD40, TNFRSF25, TNFRSF18, ICOS, TNFRSF4, PDCD1, CD274, PDCD1LG2, TIGIT, HAVCR2, LAG3, KIR2DL1, KIR2DL2, KIR2DL3, KIR2DS1, CXCR4, FOXP3, CD8B, CD3E, CD4, CD19, NCR1, CD68, CD14, CD163, MRC1, FCGR2A, FCGR1A, FCGR1B, TBX21, GATA3, PTPRC. Pearson correlation coefficients were calculated per tumor type, and per gene pair.

3. Generation of a Signature Indicative of Responsiveness to Anti-CD200 Therapy

Recent literature suggests that the presence of immune effector cells within tumors is critical for clinical response to immunotherapy. To find a tumor indication that may respond to anti-CD200 therapy, it was postulated that tumors with infiltrating effector cells expressing CD200 and/or CD200R1 might be responsive to anti-CD200 therapy. To this end the correlation between immune markers and CD200/CD200R1 were examined.

Figure 3:
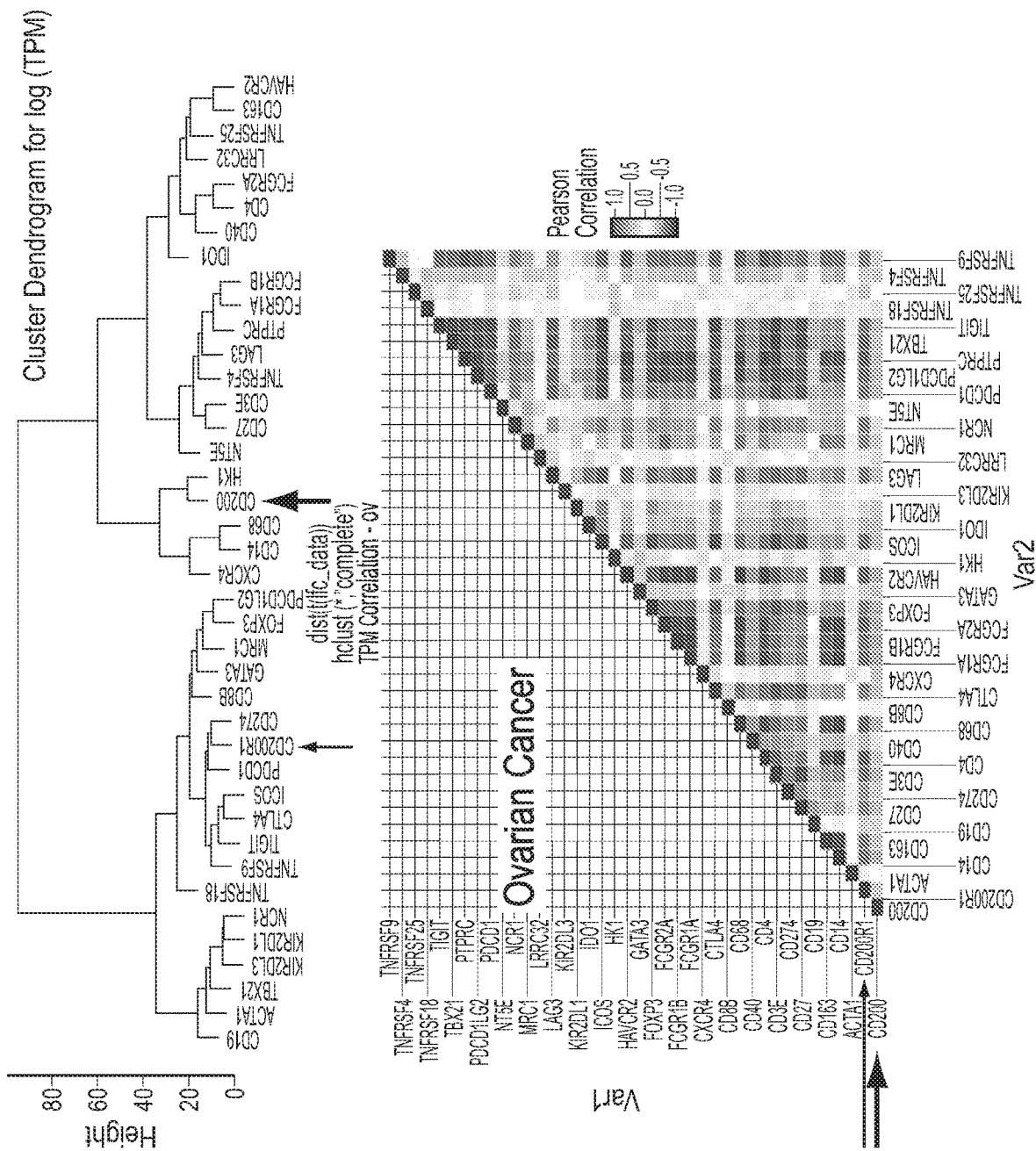
FIG. 3 depicts the Pearson correlation results of the TCGA dataset analysis for ovarian cancer, and shows that CD200R1, but not CD200, significantly correlates with the expression of immune cell markers, across all tumor types examined.

This assessment revealed that CD200R1, but not CD200, is significantly correlated with the expression of immune cell markers, across all tumor types examined (see FIG. 3). CD200 expression is not restricted to immune cells; both tumor cells and infiltrating immune cells contribute to overall expression of CD200 in tumor tissues. However, CD200R1 expression is restricted to immune effector cells (macrophages, monocytes, etc.). This suggested that CD200R1 was a better marker of immune cell infiltration in tumors. In particular, immune markers that exhibited the most significant correlation are markers of T cell and macrophage, two effector cell types known to express CD200R1.

Accordingly, a "samalizumab competent" gene signature was developed from genes which co-correlate with CD200R1 expression across tumor types, and includes markers of T cells and macrophages. This gene expression signature is composed of 10 genes: CD200R1, T cell markers such as ICOS, TIGIT, TNFRSF9, HAVCR2, and PDCD1, and macrophage markers such as FCGR2A, FCGR1A, CD163, and CD14. These T cell and macrophage markers exhibit the most significant correlation with CD200R1. This signature was used to identify tumor types which harbor CD200R1-expressing immune infiltrates that may mediate sensitivity to samalizumab.

Figure 17:
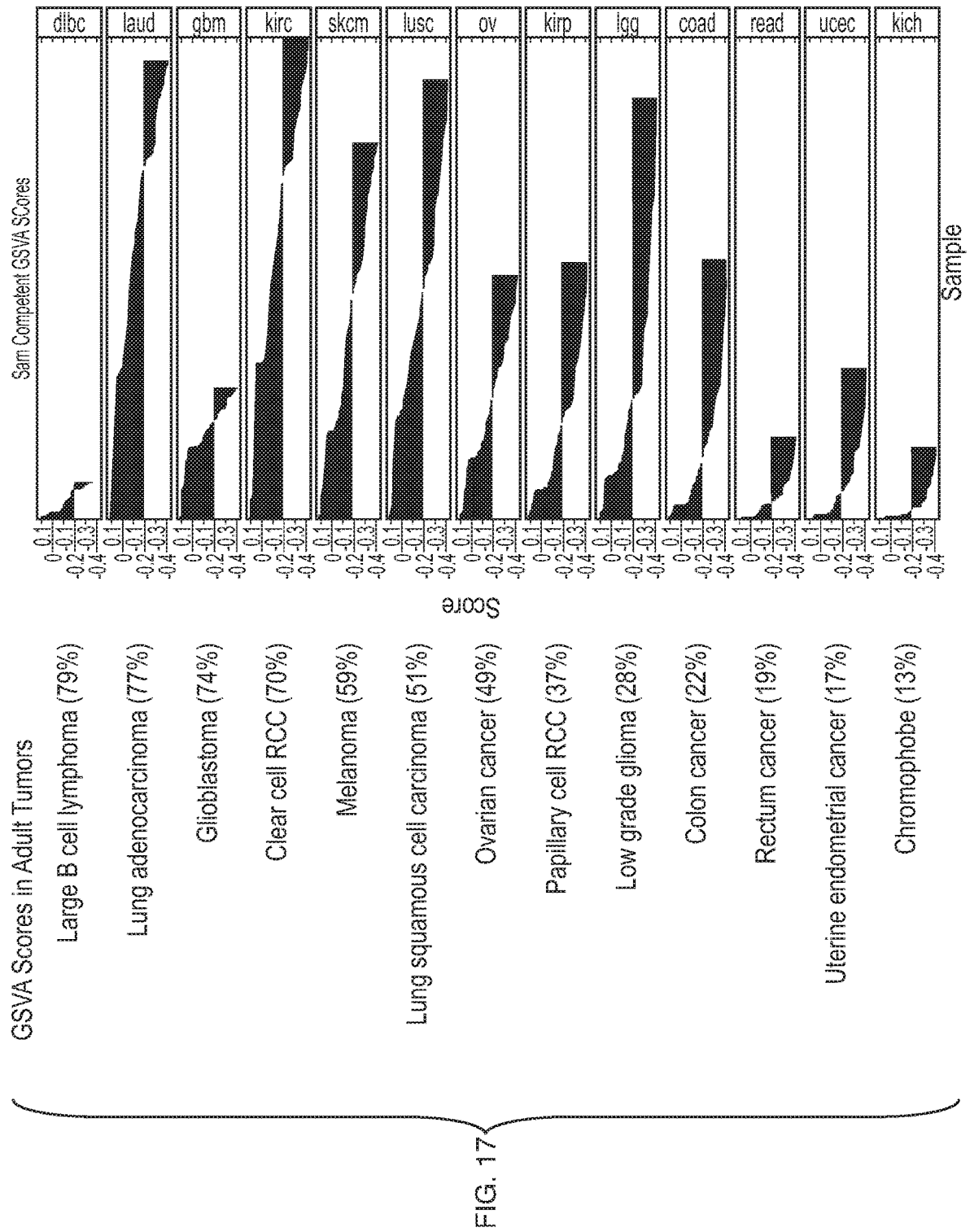
FIG. 17 depicts samalizumab competent signature GSVA scores in adult tumors (Example 1).

The Gene Set Variation Analysis (GSVA) was utilized to calculate sample-wise gene set enrichment scores as a function of genes inside and outside the gene set (i.e. signature), analogously to a competitive gene set test (see, e.g., Hänzelmann, S., et al., *BMC Bioinformatics* 14, 7 (2013). The median signature score across all samples was then calculated. For every tumor type, the percentage of samples with signature scores above the overall median was calculated. Tumor types were then ranked based on the percentage values. As shown in FIG. 17, high samalizumab competent signature scores were found in large B cell lymphoma (79%), lung adenocarcinoma (77%), and glioblastoma (74%). Low signature scores were found in chromophobe (13%), uterine endometrial cancer (17%) and rectum cancer (19%). Immunohistochemistry (see Example 3) and the gene expression data were highly concordant.

The data suggest that tumors having the "samalizumab competent" gene signature will be more likely to respond to treatment with samalizumab or other anti-CD200 therapy than tumors that lack this gene signature.

Example 2: Pediatric Tumor Application

The resulting gene signature from Example 1 was then applied to a pediatric tumor database and the expression levels were evaluated and normalized in pediatric tumors.

1. Data source and processing Possible pediatric tumor expression projects were identified through key words searches in the ArrayExpress and Gene Expression Omnibus (GEO) databases using terms "pediatric tumor" and "pediatric cancer". In order to be able to normalize expression across projects, projects utilizing UniGene Build #133 based arrays (e.g. HG-U133A, HG-U133 plus 2.0, and HG-U133+ PM) were retained for further analysis. The raw data (.CEL files) of the selected projects were downloaded and processed uniformly using the R package oligo::rma with default settings (with quantile normalization and background). Biobase::exprs was used to extract the normalized expression data as a matrix for further processing.

Figure 2:
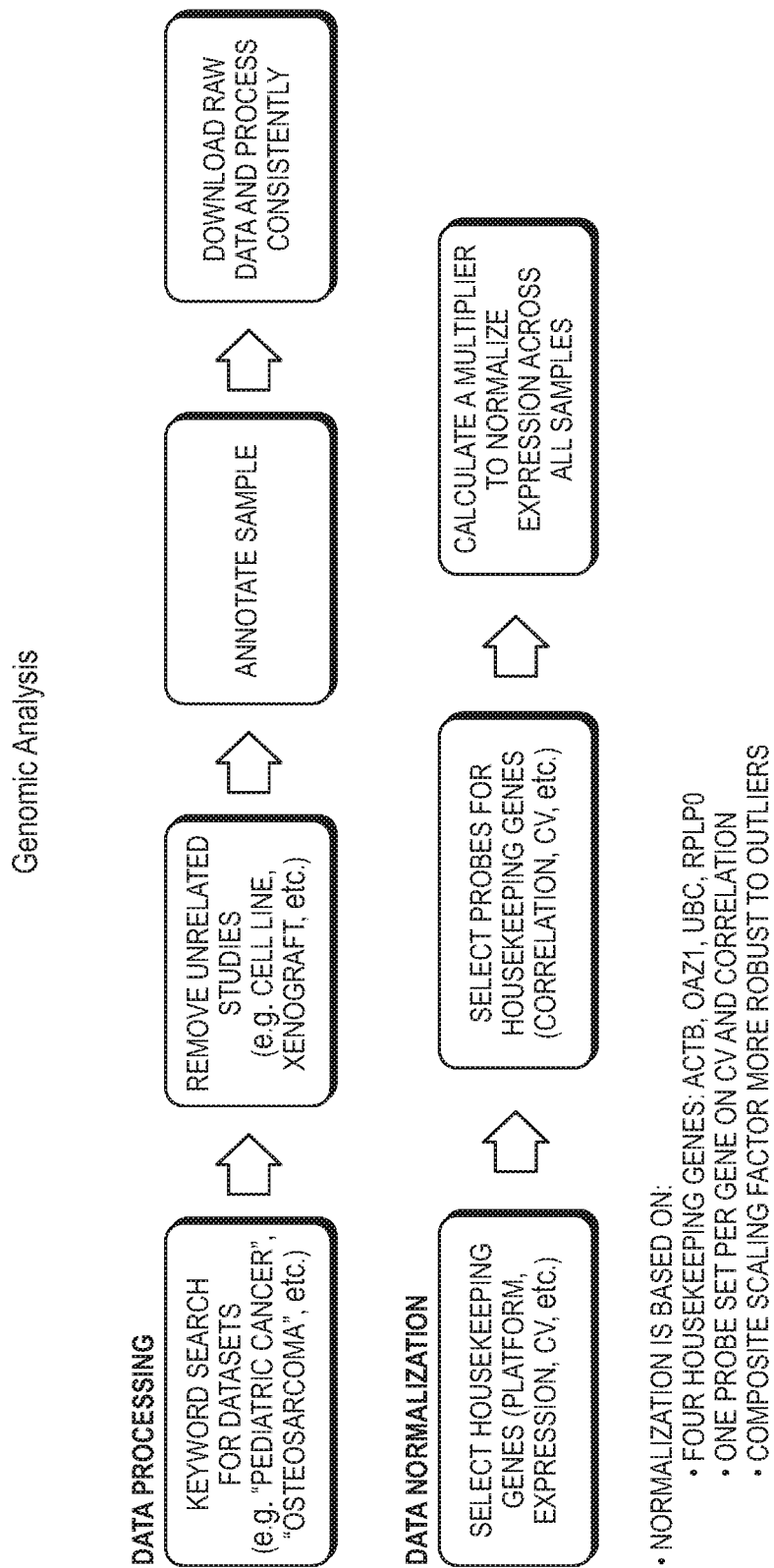
FIG. 2 is a flow chart that outlines the steps of the genomic analysis of Example 2.

Sample annotations were also extracted from the respective databases and used to eliminate non-pediatric samples. Samples were identified as pediatric based on explicit identification as such, an exclusively pediatric tumor type, or patient age under 18. Non-primary human tumor samples such as tumor cell line, xenograft, etc. were excluded entirely. The data was processed and normalized according to the analysis set forth in FIG. 2.

2. Mapping from Probe Set to Gene

A single probe set was selected for each gene. Only probe sets that uniquely identified a gene and were in use across all array types were considered. For each of the housekeeping genes (ACTB, OAZ1, UBC, RPLPO) used for normalization, the probe set with the highest average Spearman correlation with other housekeeping genes across all sample was chosen. For all other genes, the probe set with the highest mean expression across the most projects was chosen. After the mapping, each sample was translated into a list of analyzable genes with expression values for the sample.

3. Data Normalization Across Projects

An intensity multiplier was calculated for each sample based on the expression of four housekeeping genes: actin beta (ACTB), ornithine decarboxylase antizyme 1 (OAZ1), ubiquitin C (UBC), and ribosomal protein lateral stalk subunit P0 (RPLP0). First, for each housekeeping gene, the mean expression across all samples was calculated. Second, for each sample and for each housekeeping gene, a scale factor was calculated by dividing the sample expression value by the mean expression value. Third, for each sample, its intensity multiplier was calculated as the geometric mean of the scale factors of the four housekeeping genes.

For all samples, the gene expression values were normalized by multiplying with the sample intensity multiplier value.

4. Expression and Signature Analyses

Figure 16:
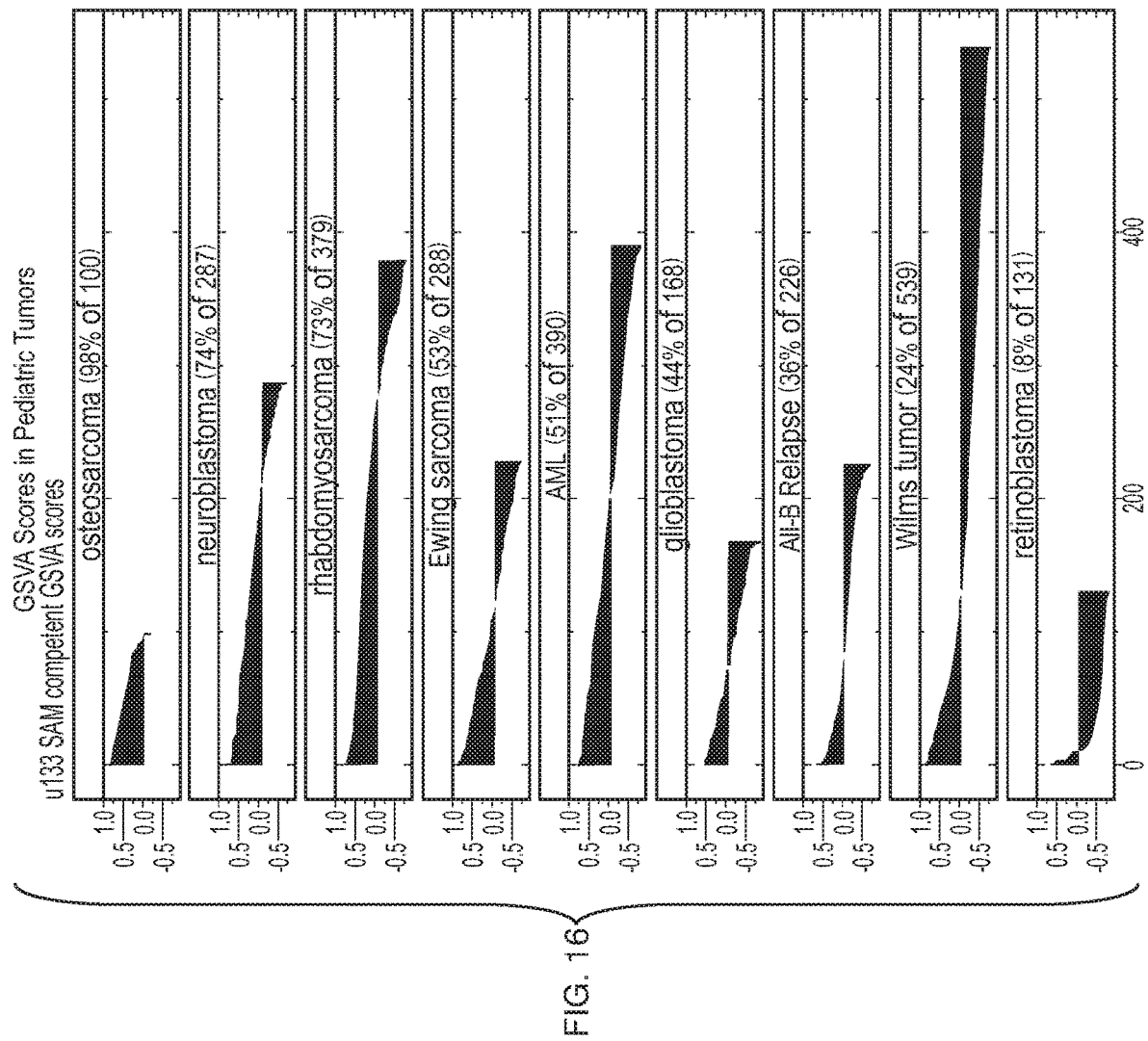
FIG. 16 depicts samalizumab competent signature GSVA scores in pediatric tumors (Example 2).

Because of array coverages, six (ICOS, TNFRSF9, FCGR2A, PDCD1, CD163, CD14) out of the ten genes were used in this signature analysis. The Gene Set Variation Analysis (GSVA) was utilized to calculate sample-wise gene set enrichment scores as a function of genes inside and outside the gene set (i.e. signature), analogously to a competitive gene set test (see, e.g., Hänzelmann, S., et al., BMC Bioinformatics 14, 7 (2013). The median signature score across all samples was then calculated. For every tumor type, the percentage of samples with signature scores above the overall median was calculated. Tumor types were then ranked based on the percentage values. As shown in FIG. 16, high samalizumab scores were found in osteosarcoma (98%), neuroblastoma (74%), and rhabdomyosarcoma (73%). Low signature scores were found in retinoblastoma (8%), Wilms tumor (24%), and ALL B relapse (36%). Immunohistochemistry (see Example 3) and the gene expression data were highly concordant.

For each individual gene of interest, the median value of expression for that gene across all samples was first calculated. For every tumor type, the percentage of samples with the individual gene of interest with expression above the overall median was calculated.

Figure 4:
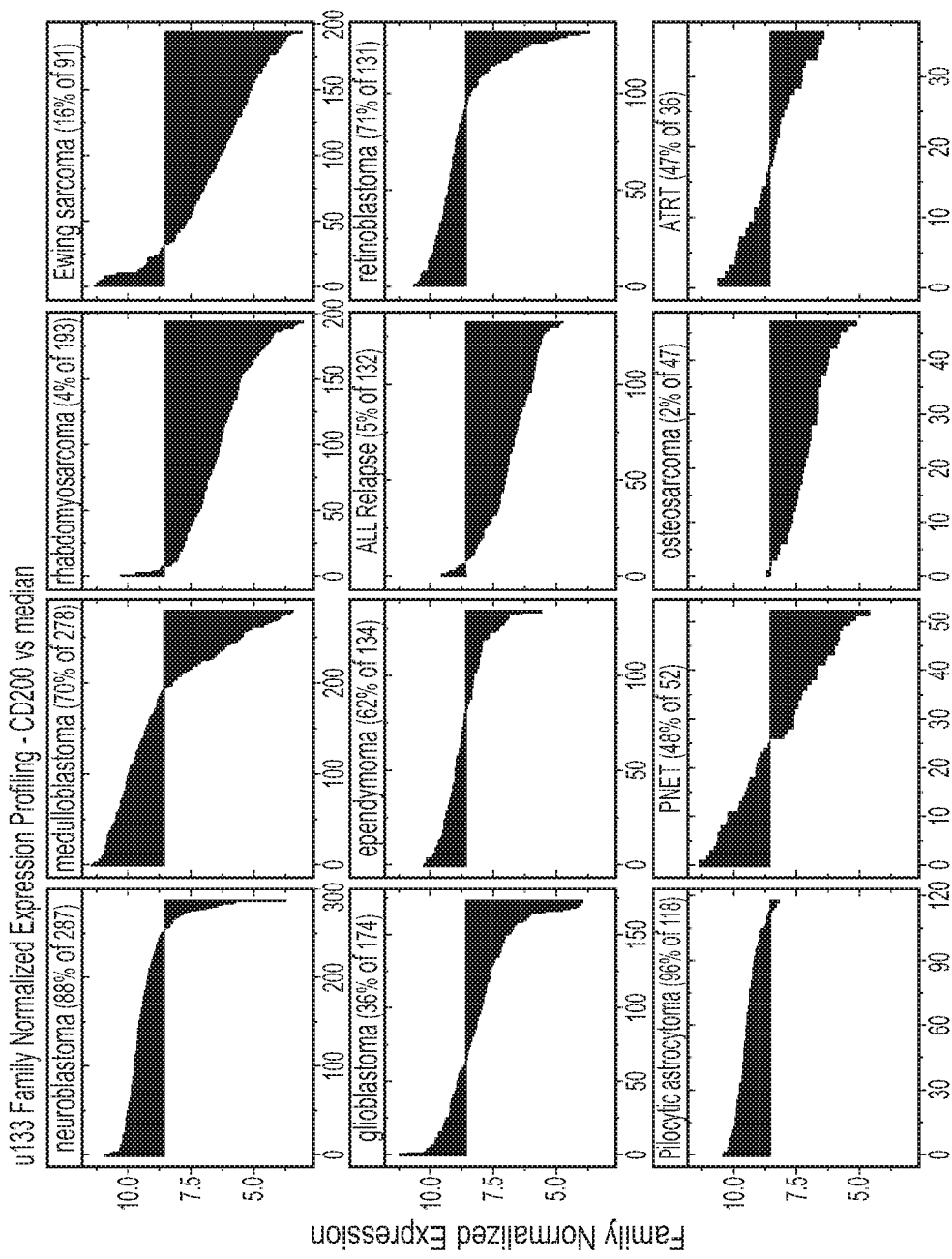
FIG. 4 depicts normalized CD200 expression in pediatric tumors.
Figure 5A:
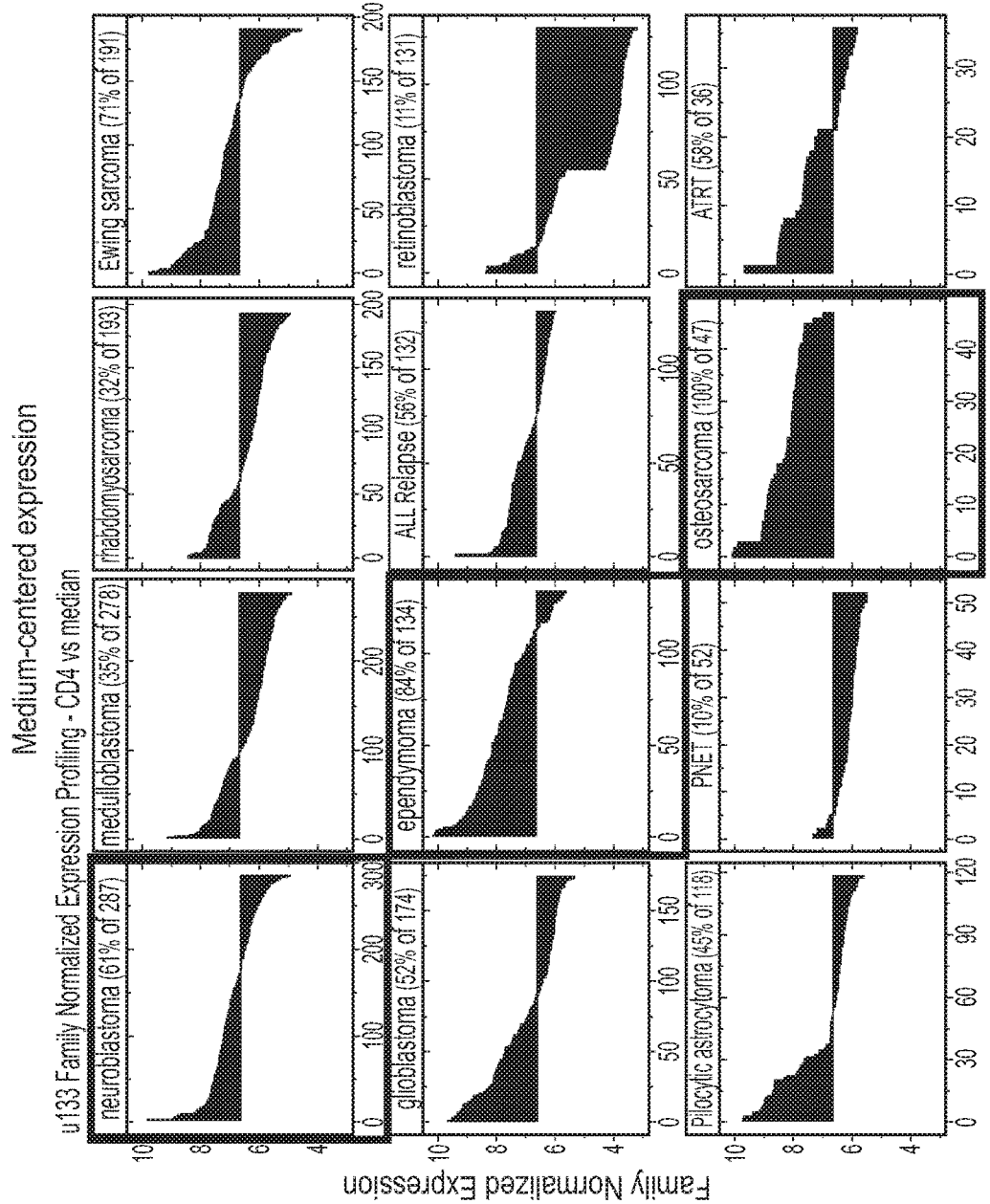
FIGS. 5A and 5B depict CD4 medium-centered expression and correlation with CD200 in pediatric tumors.
Figure 5B:
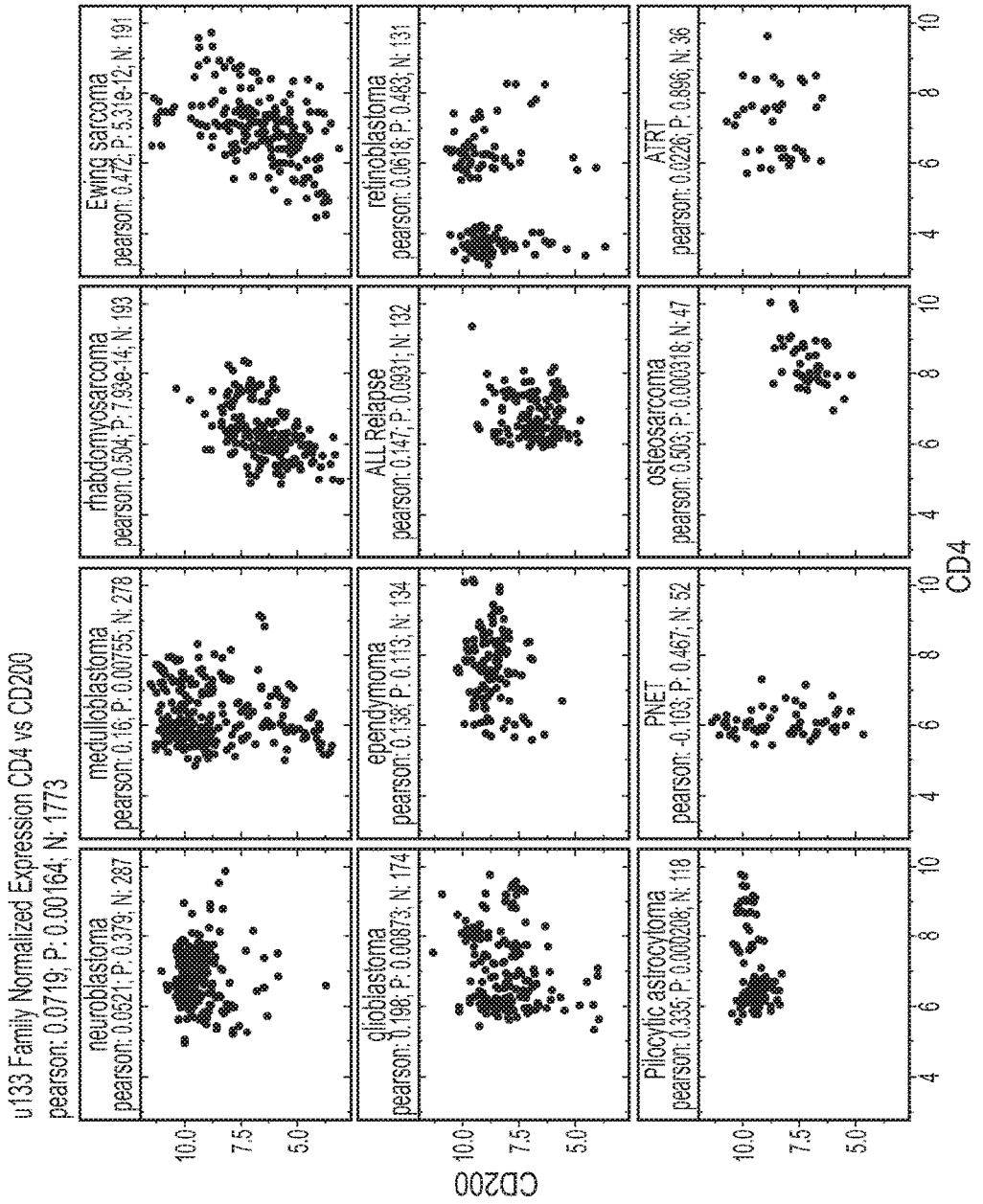
Figure 6A:
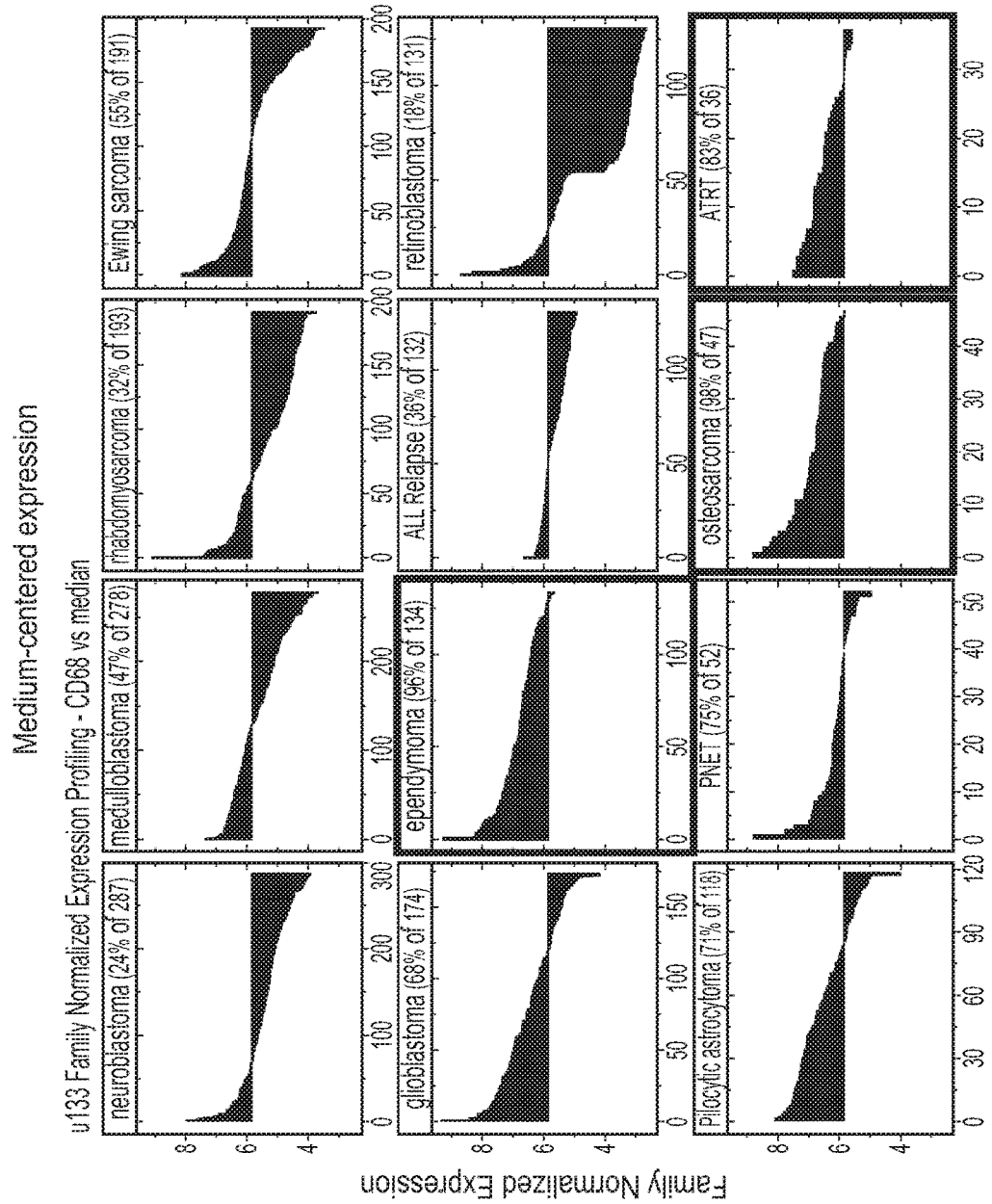
FIGS. 6A and 6B depict CD68 medium-centered expression and correlation with CD200 in pediatric tumors.
Figure 6B:
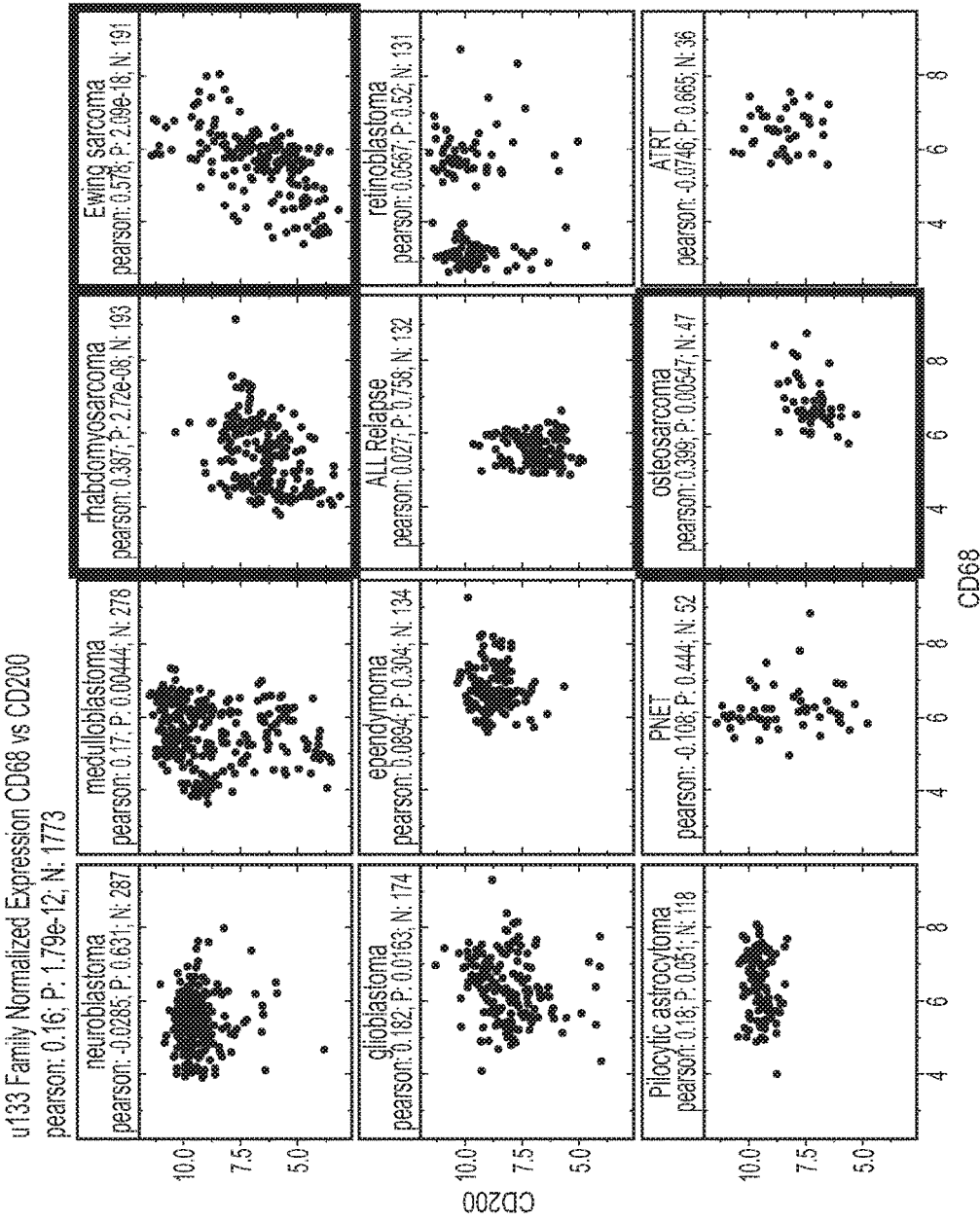

Additionally, CD200 expression levels were measured. As shown in FIG. 4, high CD200 expression levels were found in Pilocytic Astrocytoma (96%), Neuroblastoma (88%), and Retinoblastoma (71%). Low expression levels were found in Osteosarcoma (2%), Rhabdomyosarcoma (4%), and ALL Relapse (5%). CD4 (T cell marker) medium-centered expression and its correlation with CD200 (see FIGS. 5A and 5B), as well as CD68 (macrophage marker) medium centered expression and its correlation with CD200 (see FIGS. 6A and 6B), were also measured. Cancer responsiveness may correlate with CD200 expression in addition to the gene signature.

Example 3: Immunohistochemistry Analysis of Adult and Pediatric Tumors

To confirm the gene expression data, a series of adult and pediatric tumor sections were analyzed by immunohistochemistry for expression of CD200 and infiltration of immune cells. A CD200 Immunohistochemistry (IHC) assay was developed for the analysis of patient biopsies in samalizumab clinical trials. Immune marker IHC assays were commercially available (Table 3). Commercially available tissue microarrays and slides encompassing both adult and pediatric tumor tissues were analyzed for tumor CD200 expression and the presence of the following select immune cell infiltrates by immunohistochemistry:

TABLE 3

| Tissue Marker | Population |
| --- | --- |
| CD200 | Tumor/immune cells |
| CD3 | T-cells |
| CD8 | Cytoxic T-cells |
| CD68 | Monocytes/macrophages |
| FoxP3 | Regulatory T cells |

The tissue microarrays and slides utilized are shown in FIG. 7 and the analyzed tissue samples are shown in FIG. 8.

The results of the IHC assay for control tissues (FIG. 9A), Rhabdomyosarcoma (FIG. 9B), Nephroblastoma (FIG. 9C), and Neuroblastoma (FIG. 9D) are shown in FIGS. 9A-9D.

Figure 10:
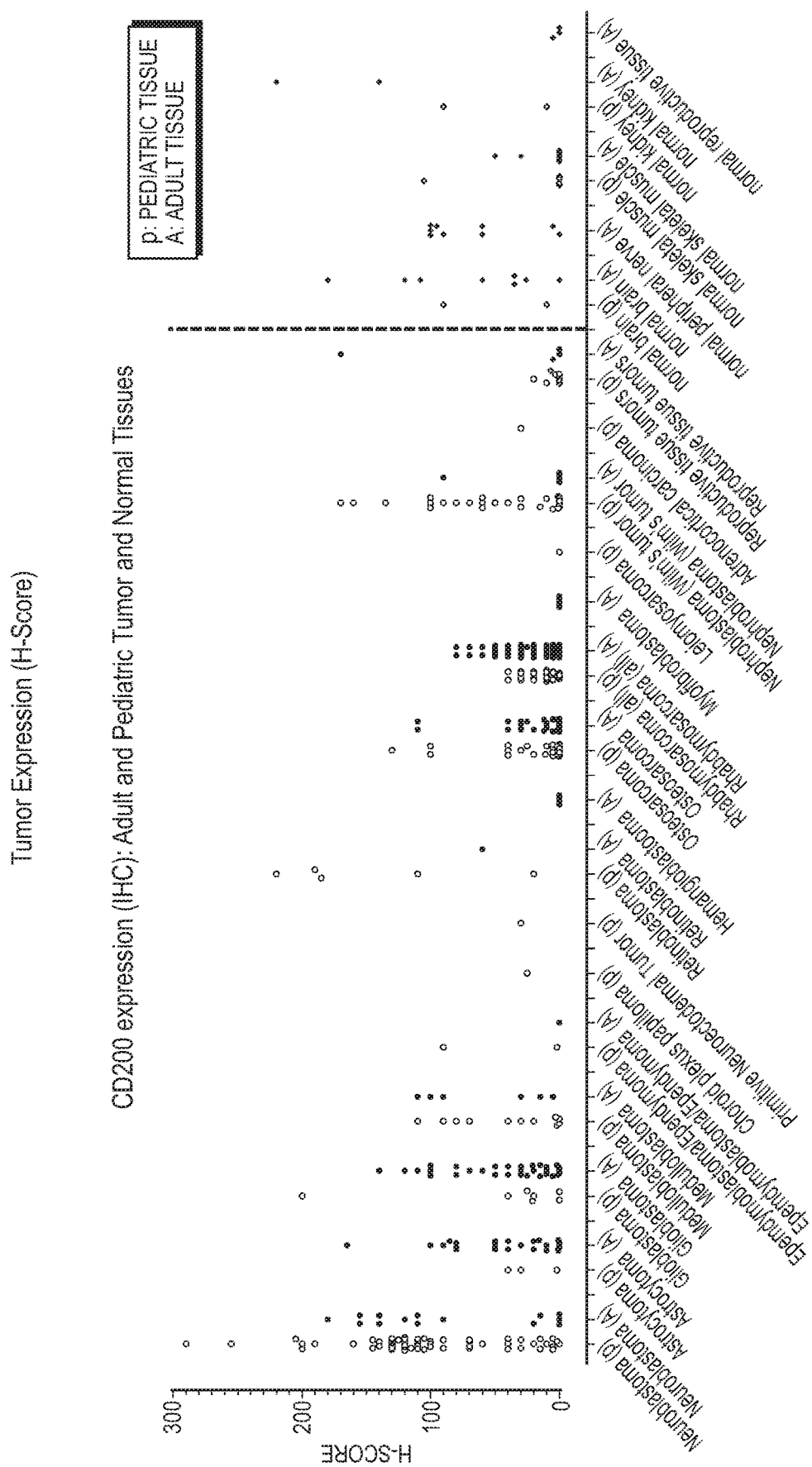
FIG. 10 depicts tumor CD200 expression as assessed by IHC (Example 3).
Figure 11:
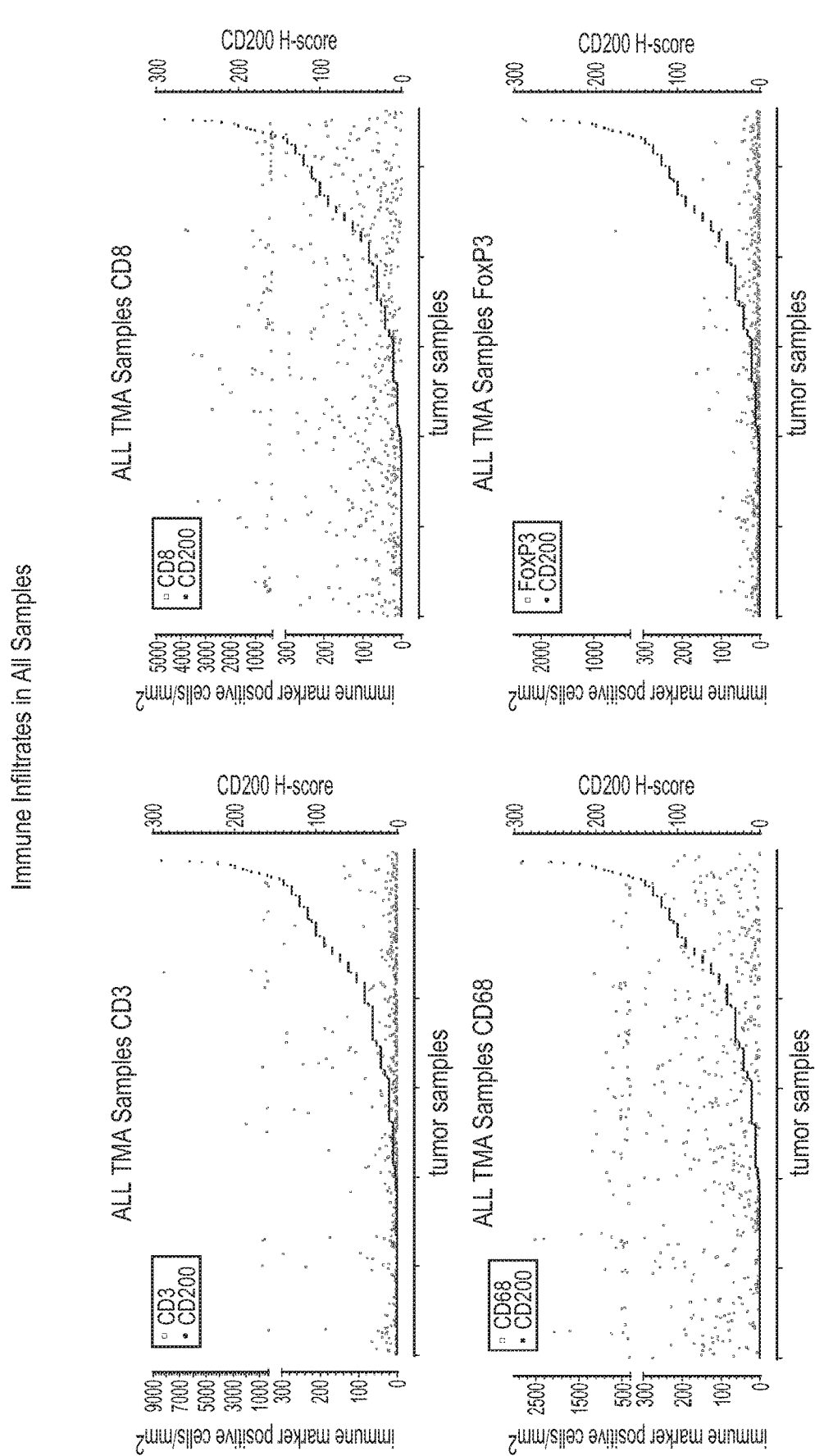
FIG. 11 depicts tumor infiltrates in all samples as shown by IHC (Example 3).
Figure 12:
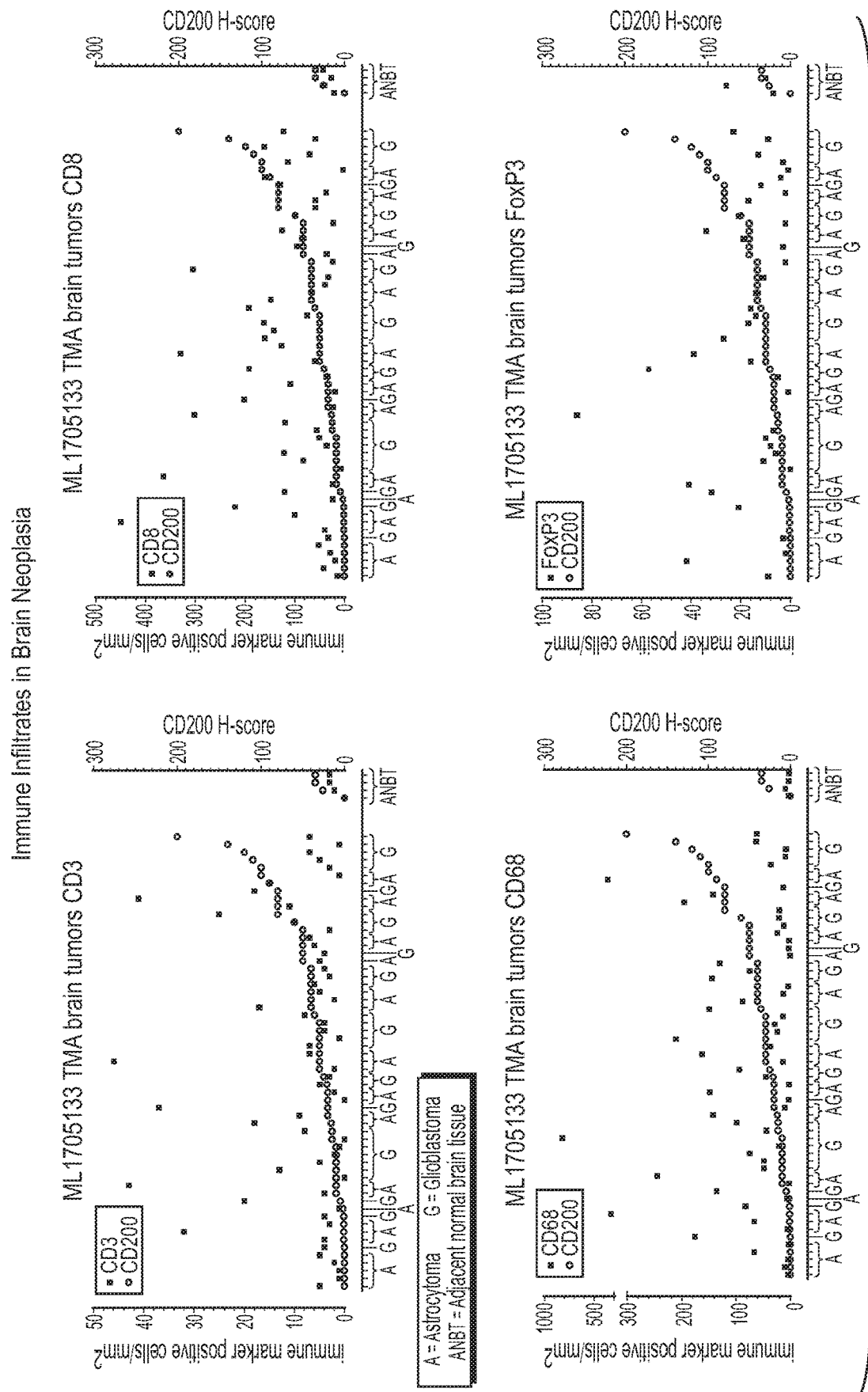
FIG. 12 depicts levels of immune infiltrates in brain neoplasia as shown by IHC (Example 3).
Figure 13:
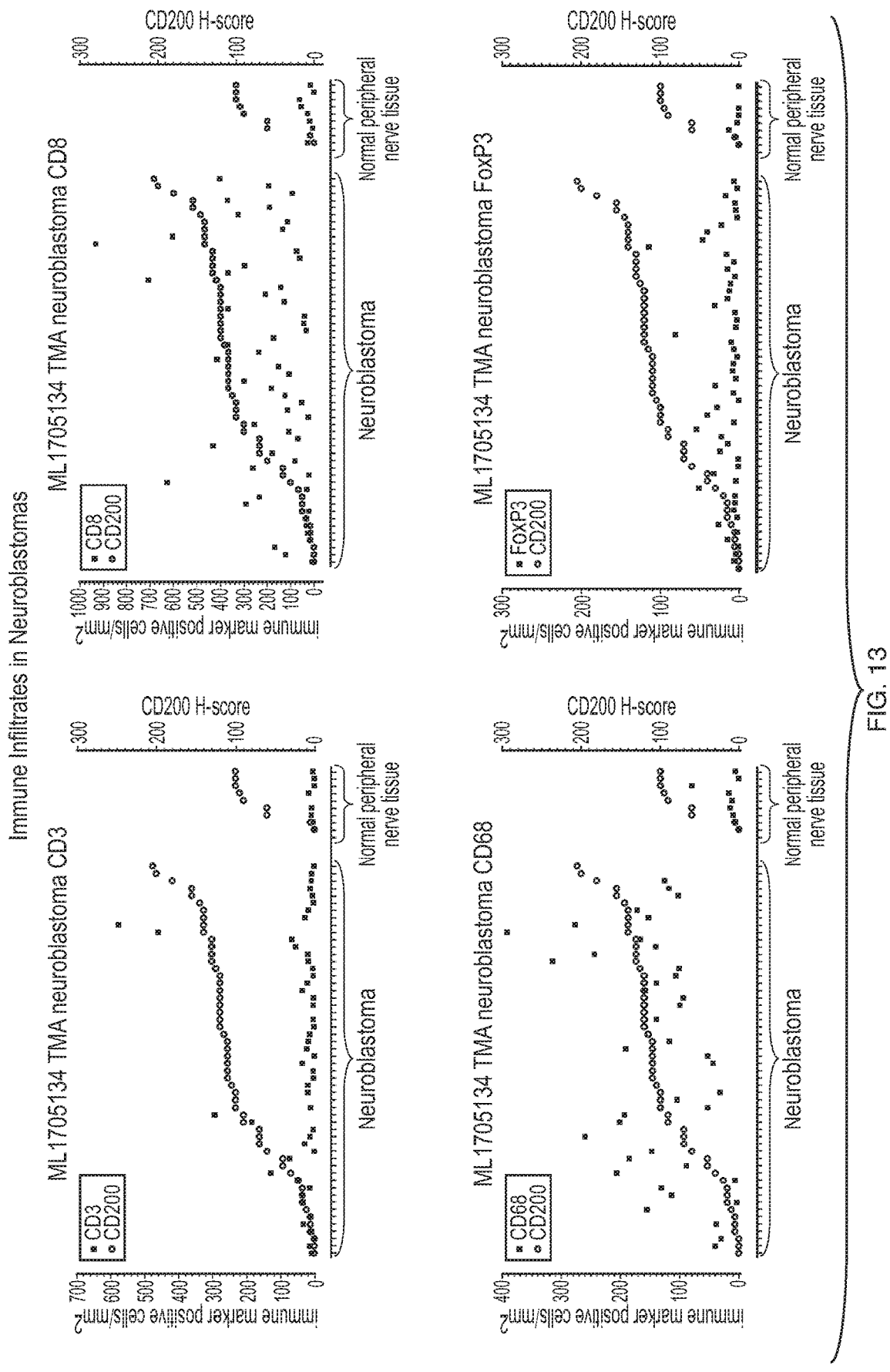
FIG. 13 depicts levels of immune infiltrates neuroblastomas as shown by IHC (Example 3).
Figure 14A:
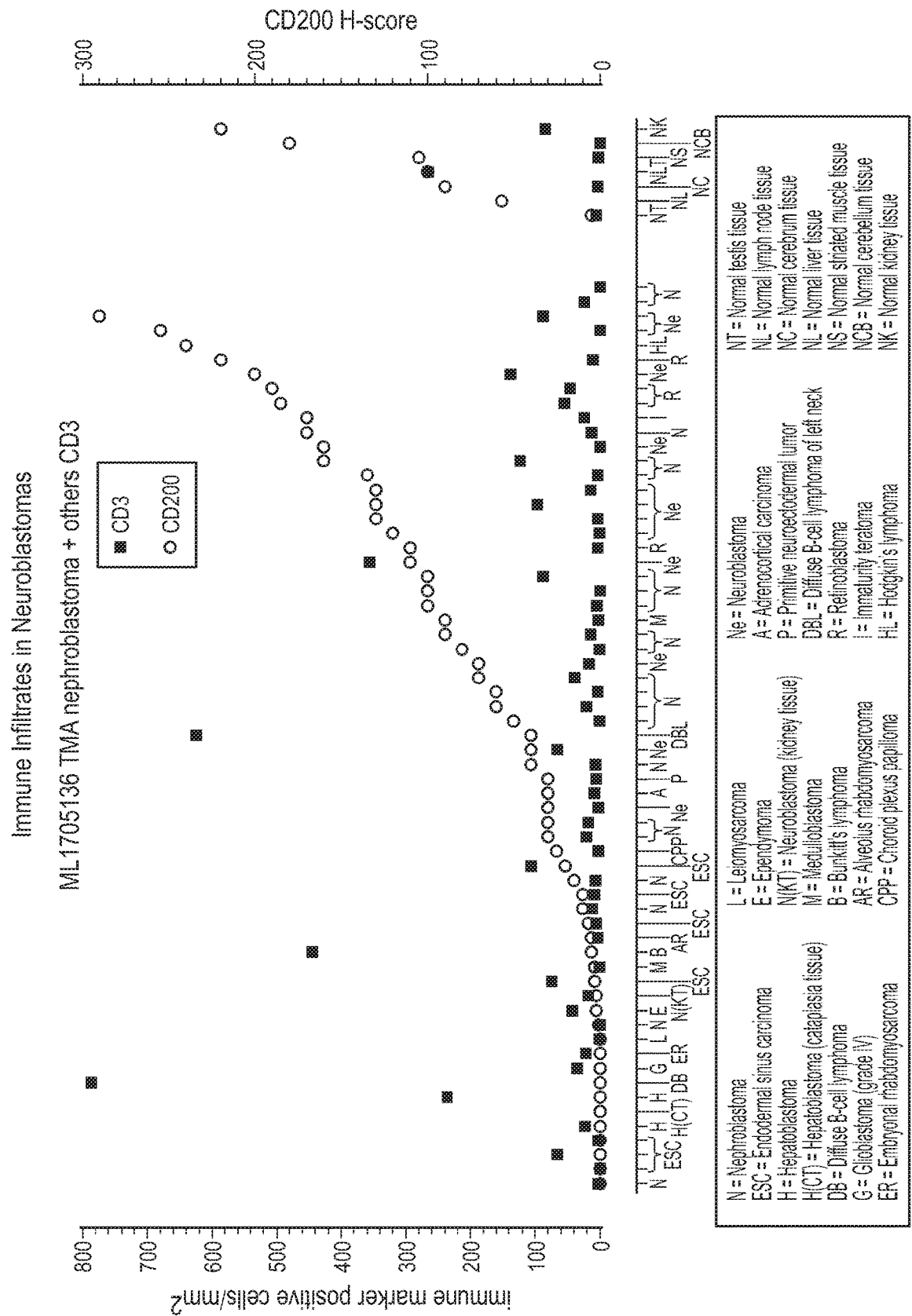
FIGS. 14A-14D depict levels of immune infiltrates nephroblastomas as shown by IHC (Example 3).
Figure 14B:
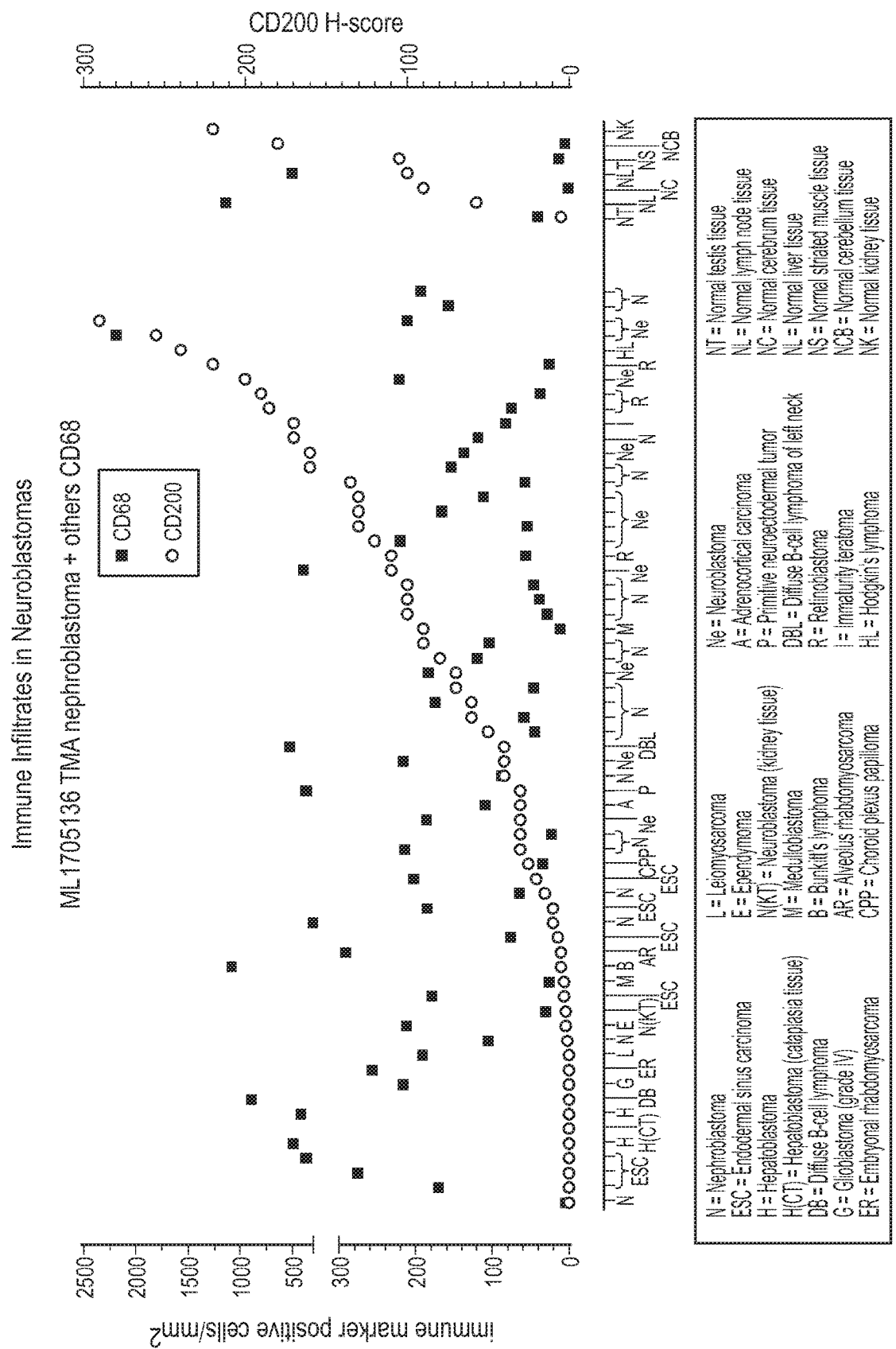
Figure 14C:
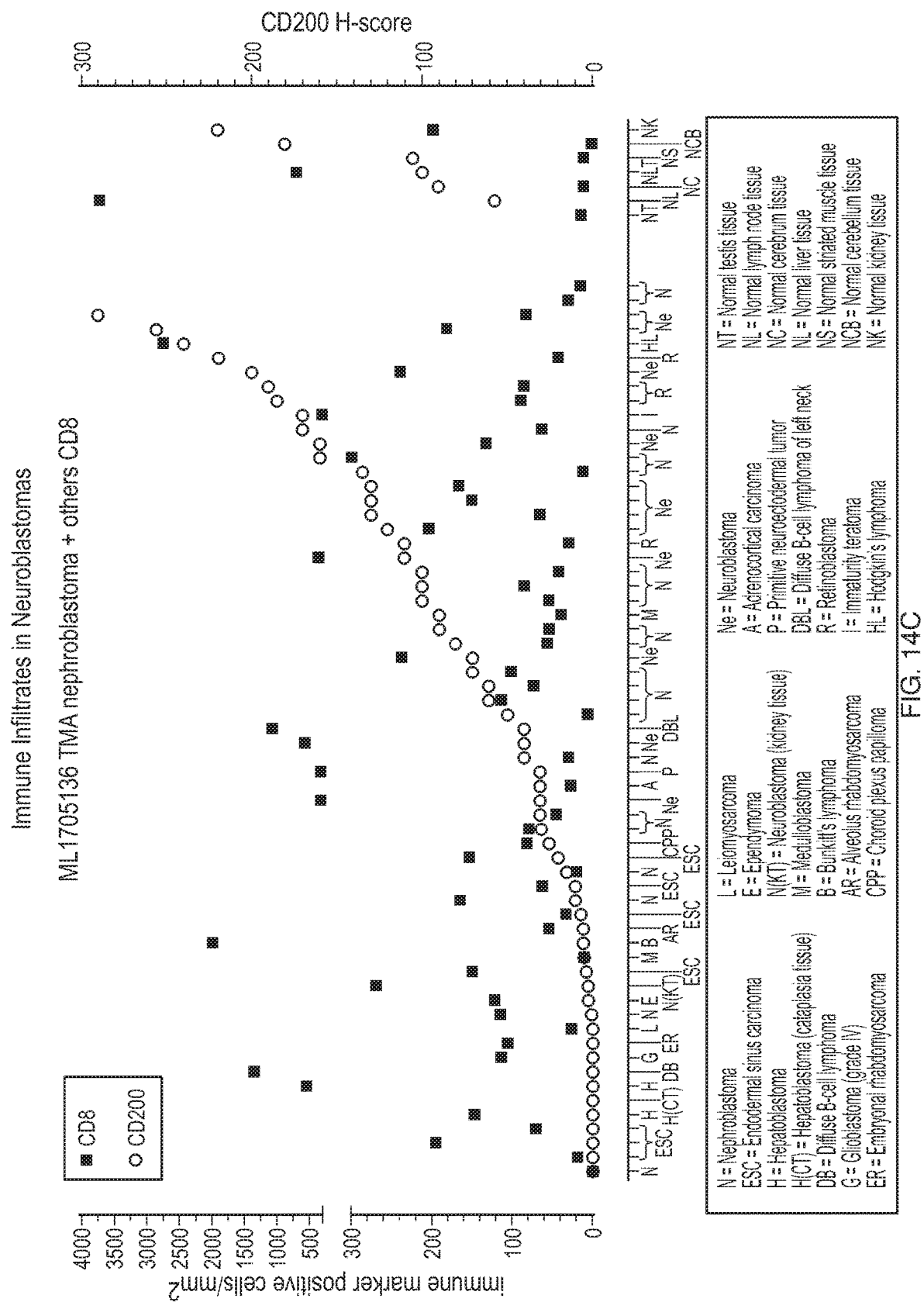
Figure 14D:
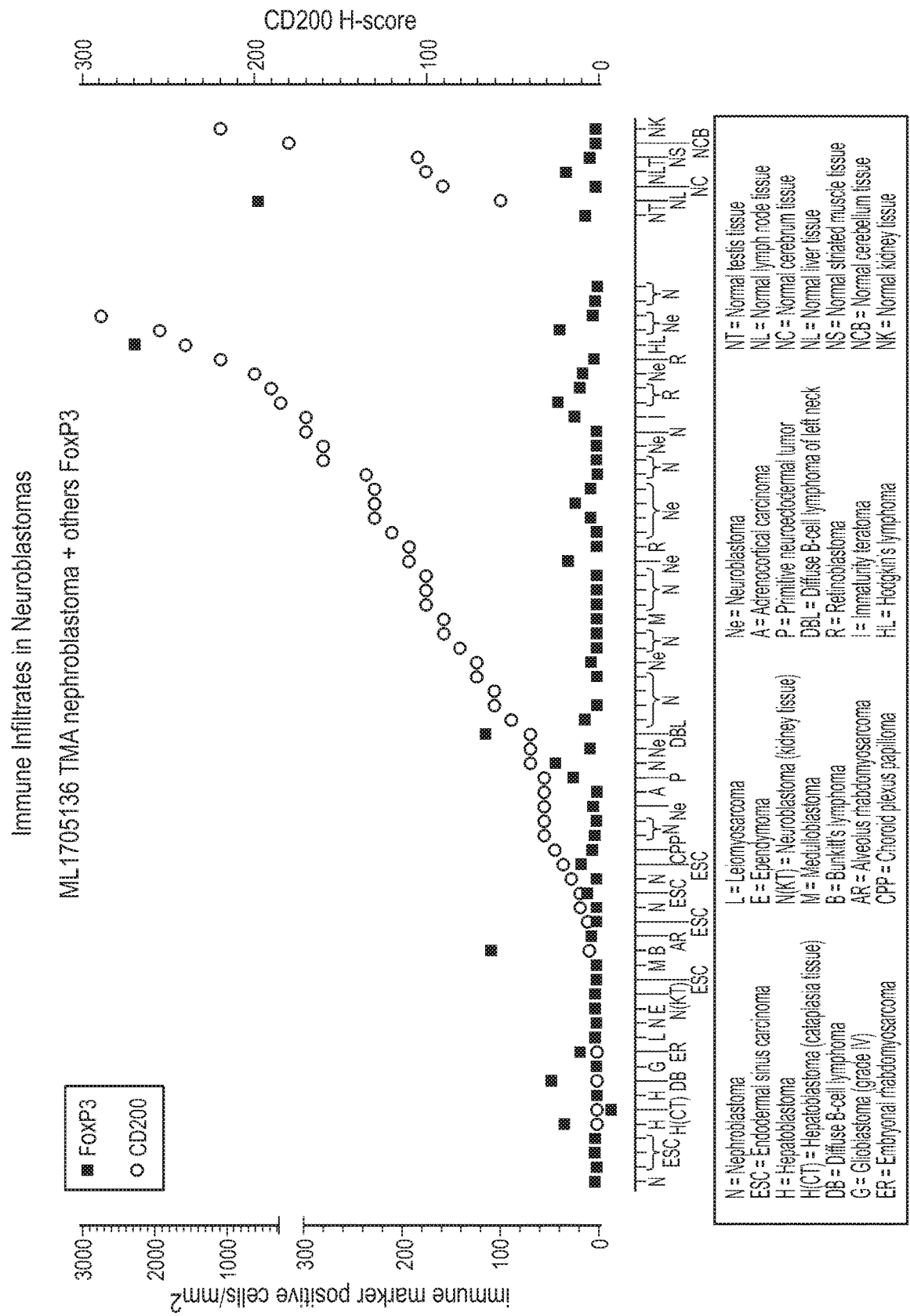
Figure 15A:
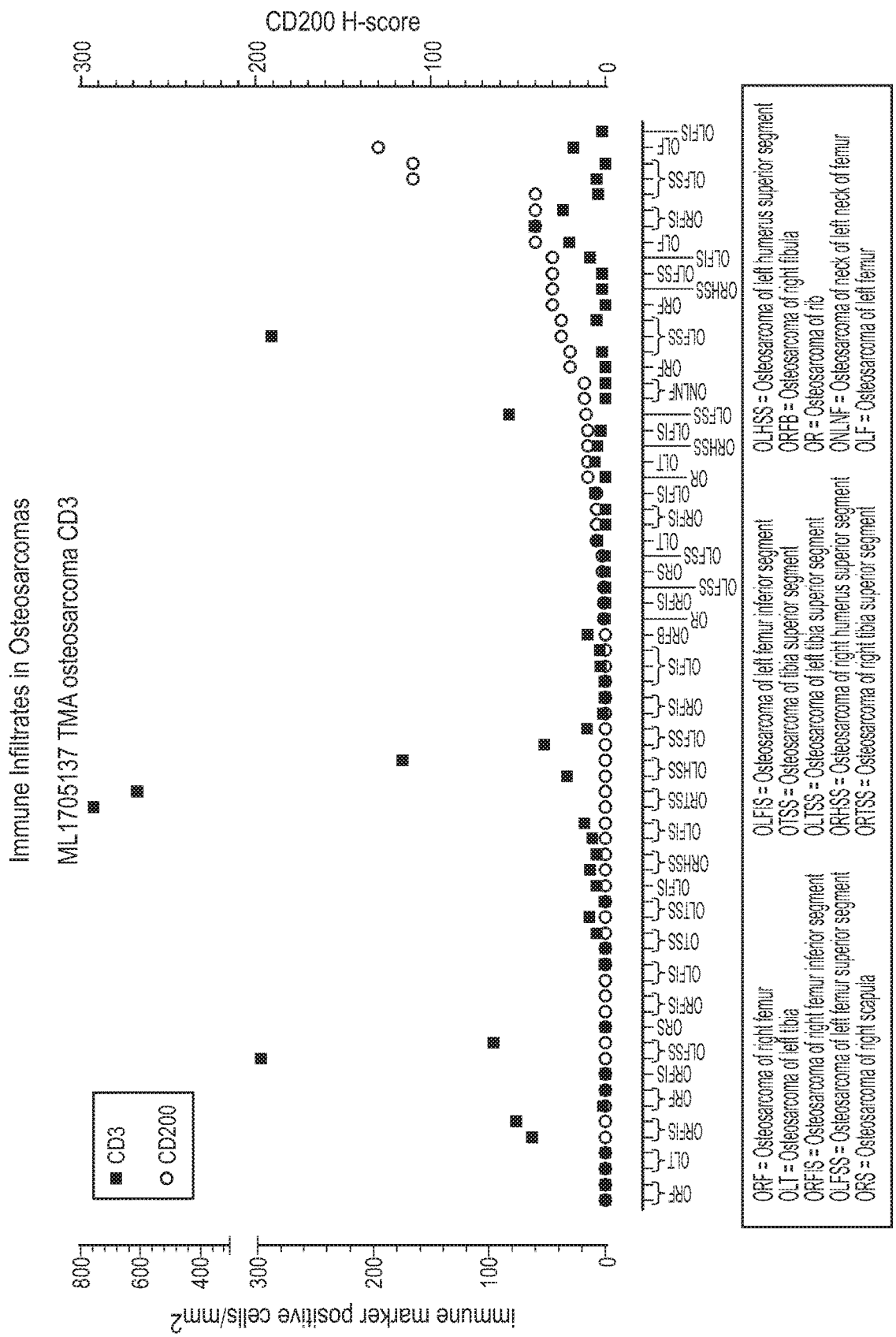
FIGS. 15A-15D depict levels of immune infiltrates osteosarcomas as shown by IHC (Example 3).
Figure 15B:
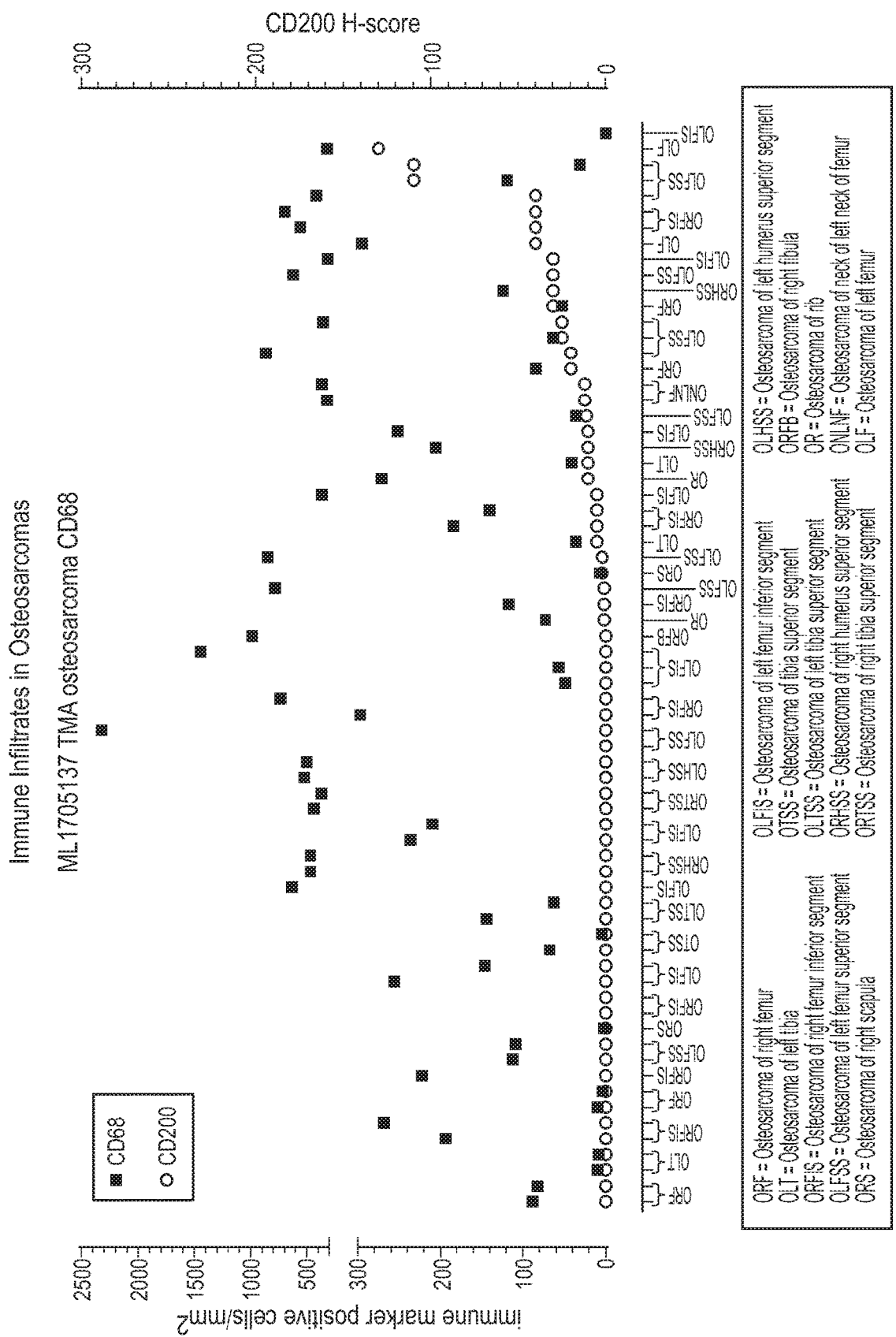
Figure 15C:
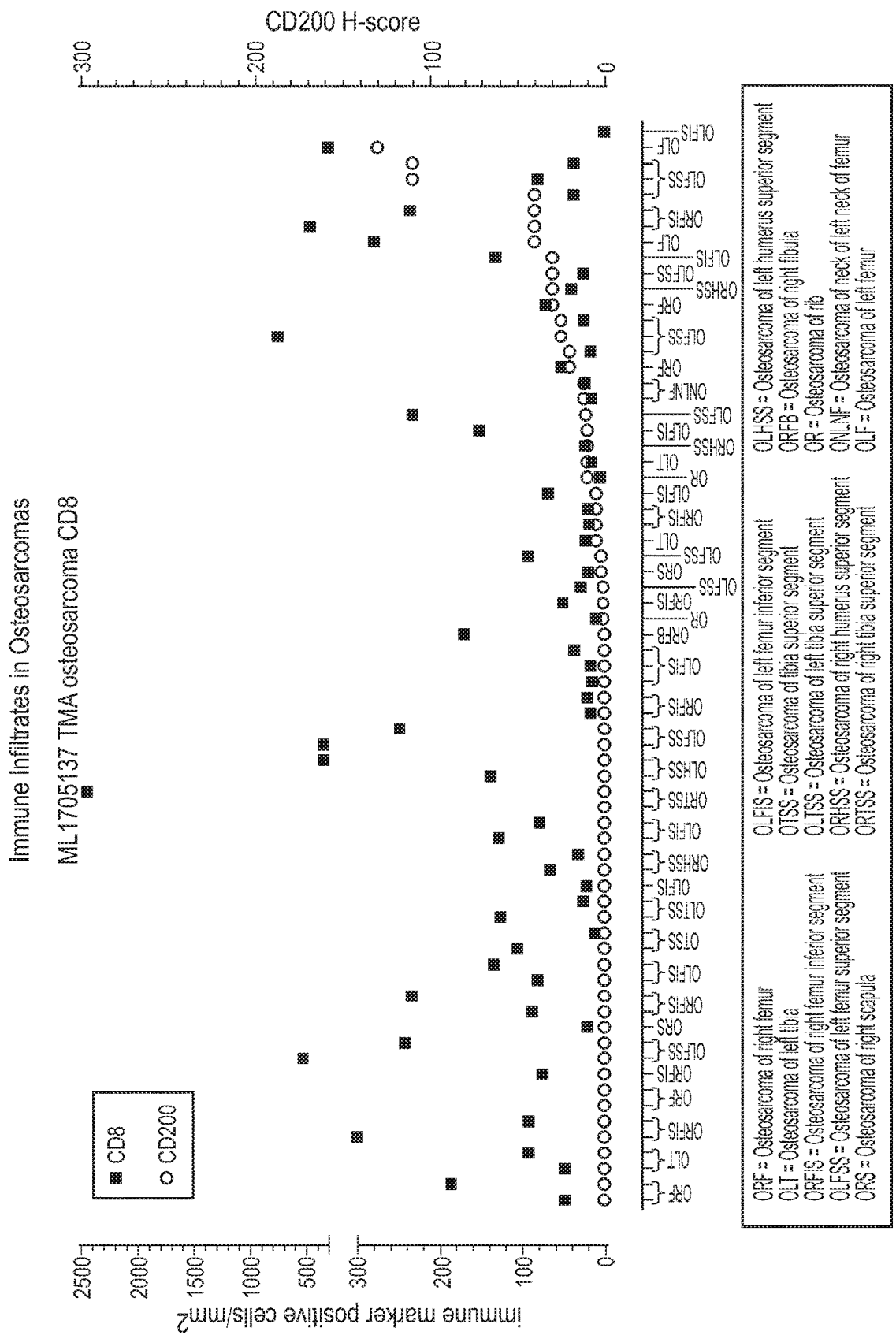
Figure 15D:
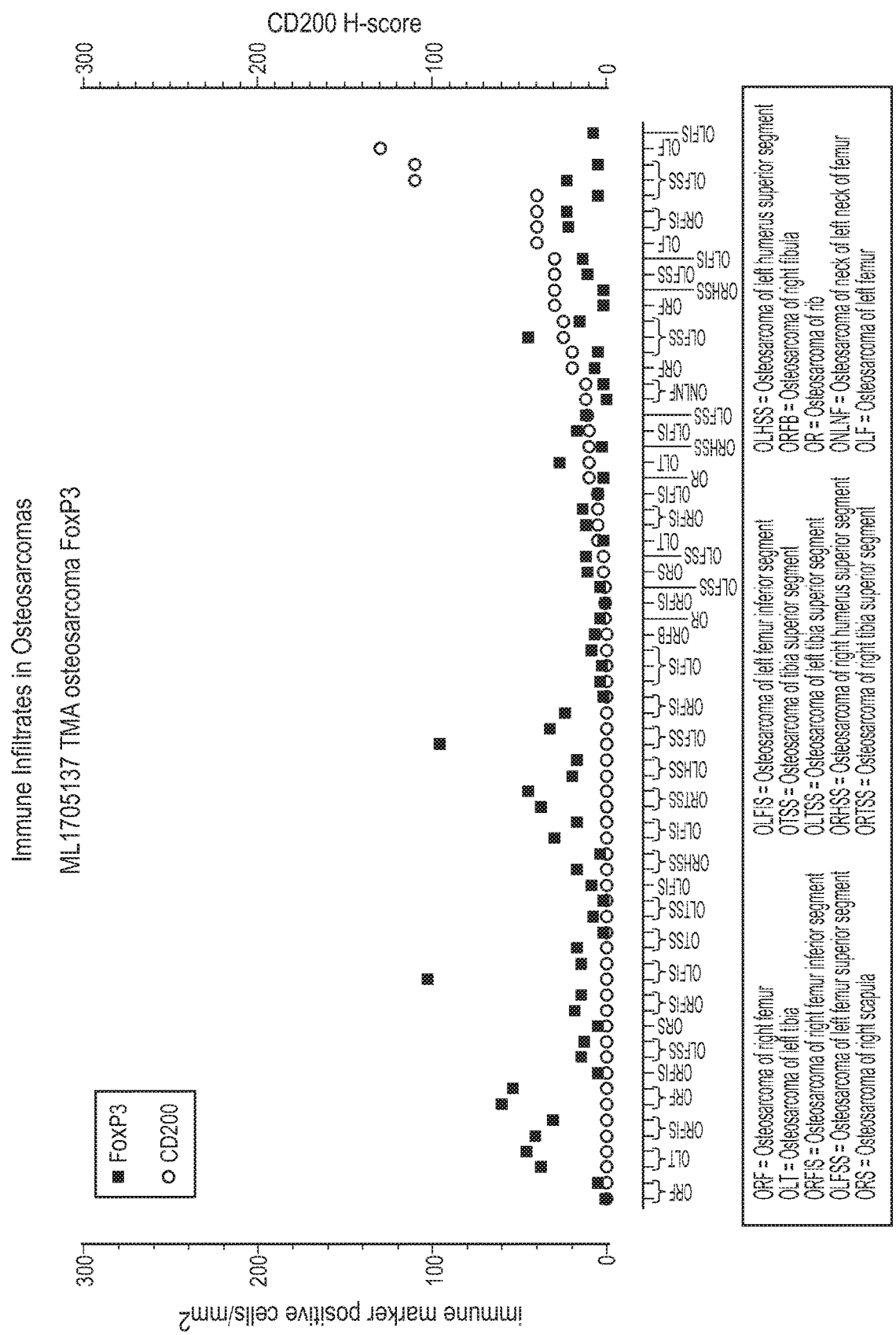

Tumor CD200 expression as assessed by IHC is set forth in FIG. 10. FIG. 11 depicts tumor infiltrates in all samples. Levels of immune infiltrates in brain neoplasia (FIG. 12), neuroblastomas (FIG. 13), nephroblastomas (FIGS. 14A-14D), and osteosarcomas (FIGS. 15A-15D) are also provided. The presence of immune effector cells in these CD200+ human tumors is supportive of targeting CD200 in these populations.

SEQUENCE LISTING SUMMARY

| DESIGNATION | SEQUENCE |
|---|---|
| SEQ ID NO: 1<br>CD200 isoform A<br>NCBI Reference<br>Sequence:<br>NP_005935.4 | MERLVIRMPF SHLSTYSLVW VMAAVVLCTA QVQVVTQDER EQLYTPA<br>SLK CSLQNAQEAL IVTWQKKKAV SPENMVTFSE NHGVVIQPAY<br>KDKINITQLG LQNSTITFWN ITLEDEGCYM CLFNTFGFGK ISGTACLTV<br>Y VQPIVSLHYK FSEDHLNITC SATARPAPMV FWKVPRSGIE NSTVTL<br>SHPN GTTSVTSILH IKDPKNQVGK EVICQVLHLG TVTDFKQTVN<br>KGYWFSVPLLLSIVSLVILL VLISILLYWK RHRNQDREP |
| SEQ ID NO: 2<br>CD200 isoform B<br>NCBI Reference<br>Sequence:<br>NP_001004196.2 | MERLTLTRTI GGPLLTATLL GKTTINDYQV IRMPFSHLST YSLVW<br>VMAAV VLCTAQVQVVTQDEREQLYT PASLKCSLQN AQEALIVTW<br>Q KKKAVSPENM VTFSENHGVV IQPAYKDKINITQLGLQNST ITFW<br>NITLED EGCYMCLFNT FGFGKISGTA CLTVYVQPIV SLHYKFSEDH<br>LNITCSATAR PAPMVFWKVP RSGIENSTVT LSHPNGTTSV TSILHIK<br>DPK NQVGKEVICQVLHLGTVTDF KQTVNKGYWF SVPLLLSIVS<br>LVILLVLISI LLYWKRHRNQ DREP |
| SEQ ID NO: 3<br>CD200 isoform c<br>NCBI Reference<br>Sequence:<br>NP_001305755.1/<br>NP_001305759.1 | MKGVTCVSSI PLVLGRSQER PASPSMPIVS LHYKFSEDHL NITCSA<br>TARP APMVFWKVPRSGIENSTVTL SHPNGTTSVT SILHIKDPKN<br>QVGKEVICQV LHLGTVTDFK QTVNKGYWFSVPLLLSIVSL VILLV<br>LISIL LYWKRHRNQD REP |
| SEQ ID NO: 4<br>Samalizumab<br>Light Chain<br>CDR1 | KASQDINSYLS |
| SEQ ID NO: 5<br>Samalizumab<br>Light Chain<br>CDR2 | RANRLVD |
| SEQ ID NO: 6<br>Samalizumab<br>Light Chain<br>CDR3 | LQYDEFPYT |
| SEQ ID NO: 7<br>Samalizumab<br>Heavy Chain<br>CDR1 | GYSFTDYIIL |
| SEQ ID NO: 8<br>Samalizumab<br>Heavy Chain<br>CDR2 | HIDPYYGSSNYNLKFKG |
| SEQ ID NO: 9<br>Samalizumab<br>Heavy Chain<br>CDR3 | SKRDYFDY |
| SEQ ID NO: 10<br>Samalizumab<br>Light Chain | DIQMTQSPSS LSASIGDRVT ITCKASQDIN SYLSWFQQKP GKAPKLLIYR<br>ANRLVDGVPS RFSGSGSGTD YTLTISSLQP EDFAVYYCLQ<br>YDEFPYTFGG GTKLEIKRTV AAPSVFIFPP SDEQLKSGTA<br>SVVCLLNNFY PREAKVQWKV DNALQSGNSQ ESVTEQDSKD<br>STYSLSSTLTLSKADYEKHK VYACEVTHQ GLSSPVTKSF NRGEC |
| SEQ ID NO: 11<br>Samalizumab<br>Heavy Chain | QVQLQQSGSE LKKPGASVKI SCKASGYSFT DYIILWVRQN<br>PGKGLEWIGH IDPYYGSSNY NLKFKGRVTI TADQSTTTAY<br>MELSSLRSED TAVYYCGRSK RDYFDYWGQG TTLTVSSAST<br>KGPSVFPLAP CSRSTSESTA ALGCLVKDYF PEPVTVSWNS<br>GALTSGVHTF PAVLQSSGLYSLSSVVTVPS SNFGTQTYTC<br>NVDHKPSNTK VDKTVERKCC VECPPCPAPP VAGPSVFLFP<br>PKPKDTLMIS RTPEVTCVVV DVSQEDPEVQ FNWYVDGVEV<br>HNAKTKPREE QFNSTYRVVSVLTVLHQDWL NGKEYKCKVS<br>NKGLPSSIEK TISKAKGQPR EPQVYTLPPS QEEMTKNQVS<br>LTCLVKGFYP SDIAVEWESN GQPENNYKTT PPVLDSDGSF<br>FLYSRLTVDK SRWQEGNVFS CSVMHEALHN HYTQKSLSLS LGK |
| SEQ ID NO: 12<br>Samalizumab<br>Light Chain<br>Variable Region | DIQMTQSP SSLSASIGDR VTITCKASQD INSYLSWFQQ KPGKAPKLLI<br>YRANRLVDGV PSRFSGSGSG TDYTLTISSL QPEDFAVYYC<br>LQYDEFPYTF GGGTKLEIKR |

-continued

| SEQUENCE LISTING SUMMARY | |
|---|---|
| DESIGNATION | SEQUENCE |
| SEQ ID NO: 13<br>Samalizumab<br>Heavy Chain<br>Variable Region | QVQLQQSGS ELKKPGASVK ISCKASGYSF TDYIILWVRQ<br>NPGKGLEWIG HIDPYYGSSN YNLKFKGRVT ITADQSTTTA<br>YMELSSLRSE DTAVYYCGRS KRDYFDYWGQ GTTLTVSS |
| SEQ ID NO: 14<br>ICOS precursor;<br>NP_036224.1<br>sapiens | MKSGLWYFFL FCLRIKVLTG EINGSANYEM FIFHNGGVQI<br>LCKYPDIVQQ FKMQLLKGGQ ILCDLTKTKG SGNTVSIKSL<br>KFCHSQLSNN SVSFFLYNLD HSHANYYFCN LSIFDPPPFK<br>VTLTGGYLHI YESQLCCQLK FWLPIGCAAF VVVCILGCIL<br>ICWLTKKKYS SSVHDPNGEY MFMRAVNTAK KSRLTDVTL |
| SEQ ID NO: 15<br>*Homo sapiens*<br>inducible T-cell<br>costimulator<br>(ICOS)<br>NM_012092.3,<br>mRNA | cgagagcctg aattcactgt cagctttgaa cactgaacgc gaggactgtt aactgtttct<br>ggcaaacatg aagtcaggcc tctggtattt ctttctcttc tgcttgcgca ttaaagtttt<br>aacaggagaa atcaatggtt ctgccaatta tgagatgttt atatttcaca acggaggtgt<br>acaaatttta tgcaaatatc ctgacattgt ccagcaattt aaaatgcagt tgctgaaagg<br>ggggcaaata ctctgcgatc tcactaagac aaaaggaagt ggaaacacag tgtccattaa<br>gagtctgaaa ttctgccatt ctcagttatc caacaacagt gtctcttttt ttctatacaa<br>cttggaccat tctcatgcca actattactt ctgcaaccta tcaatttttg atcctcctcc<br>tttttaaagta actcttacag gaggatattt gcatatttat gaatcacaac tttgttgcca<br>gctgaagttc tggttaccca taggatgtgc agcctttgtt gtagtctgca ttttgggatg<br>catacttatt tgttggctta caaaaaagaa gtattcatcc agtgtgcacg accctaacgg<br>tgaatacatg ttcatgagag cagtgaacac agccaaaaaa tctagactca cagatgtgac<br>cctataatat ggaactctgg cacccaggca tgaagcacgt tggccagttt tcctcaactt<br>gaagtgcaag attctcttat ttccgggacc acggagagtc tgacttaact acatacatct<br>tctgctgtg ttttgttcaa tctggaagaa tgactgtatc agtcaatggg gattttaaca<br>gactgccttg gtactgccga gtcctctcaa aacaaacacc ctcttgcaac cagcttttgga<br>gaaagcccag ctcctgtgtg ctcactggga gtggaatccc tgtctccaca tctgctccta<br>gcagtgcatc agccagtaaa acaaacacat ttacaagaaa aatgttttaa agatgccagg<br>ggtactgaat ctgcaaagca aatgagcagc caaggaccag catctgtccg catttcacta<br>tcatactacc tcttcttttct gtagggatga gaattcctcc tttaatcagt caagggagat<br>gcttcaaagc tggagctatt ttatttctga gatgttgatg tgaactgtac attagtacat<br>actcagtact ctccttcaat tgctgaaccc cagttgacca ttttaccaag actttagatg<br>cttcttgtg ccctcaattt tcttttttaaa aatacttcta catgactgct tgacagccca<br>acagccactc tcaatagaga gctatgtctt acattctttc ctctgctgct caatagtttt<br>atatatctat gcatacatat atacacacat atgtatataa aattcataat gaatatattt<br>gcctatattc tccctacaag aatatttttg ctccagaaag acatgttctt ttctcaaatt<br>cagttaaaat ggtttacttt gttcaagtta gtggtaggaa acattgcccg gaattgaaag<br>caaatttatt ttattatcct attttctacc attatctatg ttttcatggt gctattaatt<br>acaagtttag ttcttttttg agatcatatt aaaattgcaa acaaaatcat ctttaatggg<br>ccagcattct catggggtag agcagaatat tcatttagcc tgaaagctgc agttactata<br>ggttgctgtc agactatacc catggtgcct ctgggcttga caggtcaaaa tggtccccat<br>cagcctggag cagccctcca gacctgggtg gaattccagg gttgagagac tccctgagc<br>cagaggccac taggtattct tgctcccaga ggctgaagtc accctgggaa tcacagtggt<br>ctacctgcat tcataattcc aggatctgtg aagagcacat atgtgtcagg gcacaattcc<br>ctctcataaa accacacag cctggaaatt ggcctggcc cttcaagata gccttcttta<br>gaatatgatt tggctagaaa gattcttaaa tatgtggaat atgattattc ttagctgaaa<br>tattttctct acttcctgtc tgcatgccca aggcttctga agcagccaat gtcgatgcaa<br>caacatttgt aactttaggt aaactgggat tatgttgtag tttaacattt tgtaactgtg<br>tgcttatagt ttacaagtga gacccgatat gtcattatgc atacttatat tatcttaagc<br>atgtgtaatg ctggatgtgt acagtacagt actgaacttg taatttgaat ctagtatggt<br>gttctgtttt cagctgactt ggacaacctg actggctttg cacaggtgtt ccctgagttg<br>tttgcaggtt tctgtgtgtg gggtggggta tggggaggag aaccttcatg gtggcccacc<br>tggcctggtt gtccaagctg tgcctcgaca catcctcatc cccagcatgg gacacctcaa<br>gatgaataat aaattcacaa atttctgtga aatcaaatcc agttttaaga ggagccactt<br>atcaaagaga ttttaacagt agtaagaagg caaagaataa acatttgata ttcagcaact<br>gaaaaaaaaa aa |
| SEQ ID NO: 16<br>T-cell<br>immunoreceptor<br>with Ig and ITIM<br>domain precursor<br>[*Homo sapiens*]<br>NP_776160.2 | MRWCLLLIWA QGLRQAPLAS GMMTGTIETT GNISAEKGGS<br>IILQCHLSST TAQVTQVNWE QQDQLLAICN ADLGWHISPS<br>FKDRVAPGPG LGLTLQSLTV NDTGEYFCIY HTYPDGTYTG<br>RIFLEVLESS VAEHGARFQI PLLGAMAATL VVICTAVIVV<br>VALTRKKKAL RIHSVEGDLR RKSAGQEEWS PSAPSPPGSC<br>VQAEAAPAGL CGEQRGEDCA ELHDYFNVLS YRSLGNCSFF<br>TETG |
| SEQ ID NO: 17<br>*Homo sapiens* T-<br>cell<br>immunoreceptor<br>with Ig and ITIM<br>domains (TIGIT),<br>mRNA,<br>NM_173799.3 | cgtcctatct gcagtcggct actttcagtg gcagaagagg ccacatctgc ttcctgtaggccctctgggc<br>agaagcatgc gctggtgtct cctcctgatc tgggcccagg gctgaggca ggctcccctc gcctcaggaa<br>tgatgacagg cacaatagaa caacgggga acattctgca gagaaaggt ggctctatca tcttacaatg<br>tcacctctcc tccaccacgg cacaagtgac ccaggtcaac tgggagcagc aggaccagct tctggccatt<br>tgtaatgctg acttggggtggcagcatctc ccatcctca aggatcgagt ggcccaggt cccggcctgg<br>gcctcaccct ccagtcgctg accgtgaacg atacagggga gtacttctgc atctatcaca<br>cctacccgat gggacgtac actgggagaa tcttcctgga ggtcctagaa agctcagtgg ctgagcacgg<br>tgccaggttc cagattccat gcttggagc catggccgcg acgctggtgg tcatctgcac agcagtcatc<br>gtggtggtcg cgttgactag aaagaagaaa gccctcagaa tccattctgt ggaaggtgac ctcaggagaa<br>aatcagctgg acaggaggaa tggagcccca gtgctccctc accccagga agctgtgtcc aggcagaagc |

SEQUENCE LISTING SUMMARY

| DESIGNATION | SEQUENCE |
|---|---|
| | tgcacctgct gggctctgtg gagagcagcg gggagaggac tgtgccgagc tgcatgacta cttcaatgtc ctgagttaca gaagcctggg taactgcagc ttcttcacag agactggtta gcaaccagag gcatcttctg gaagatacac ttttgtcttt gctattatag atgaatatat aagcagctgt actctccatc agtgctgcgt gtgtgtgtgt gtgtgtatgt gtgtgtgtgt tcagttgagt gaataaatgt catcctcttc tccatcttca tttccttggc cttttcgttc tattccattt tgcattatgg caggcctaggg tgagtaacg tggatcttga tcataaatgc aaaattaaaa aatatcttga cctggtttta aatctggcag tttgagcaga tcctatgtct ctgagagaca cattcctcat aatggccagc attttgggct acaaggtttt gtggttgatg atgaggatgg catgactgca gagccatcct catctcattt tttcacgtca ttttcagtaa cttttcactca ttcaaaggca ggttataagt aagtcctggt agcagcctct atggggagat ttgagagtga ctaaatcttg gtatctgccc tcaagaactt acagttaaat gggagacaa tgttgtcatg aaaaggtatt atagtaaggagagaaggaga catacacagg ccttcaggaa gagacgacag tttggggtga ggtagttggc ataggcttat ctgtgatgaa gtggcctggg agcaccaagg ggatgttgag gctagtctgg gaggagcagg agtttttgtct agggaacttg taggaaattc ttggagctga aagtcccaca aagaaggccc tggcaccaag ggagtcagca aacttcagat tttattctct gggcaggcatt tcaagatc cttttgctgt gacatactca tccattagac agcctgatac aggcctgtag cctcttccgg ccgtgtgtgc tggggaagcc ccaggaaacg cacatgccca cacagggagc caagtcgtag catttgggcc ttgatctacc ttttctgcat caatacactc ttgagccttt gaaaaaagaa cgtttcccac taaaaagaaa atgtggattt ttaaaatagg gactcttcct aggggaaaaa gggggggctgg gagtgataga gggtttaaaa aataaacacc ttcaaactaa cttcttcgaa cccttttatt cactccctga cgactttgtg ctgggggttg ggtaactgaa ccgcttattt ctgtttaatt gcattcaggc tggatcttag aagactttta tccttccacc atctctctca gaggaatgag cggggaggtt ggattactg tgactgatt ttctttcatg ggccaaggaa ctgaaagaga atgtgaagca aggttgtgtc ttgcgcatgg ttaaaaataa agcattgtcc tgcttcctaa gacttagact ggggttgaca attgttttag caacaagaca attcaactat ttctcctagg attttttatta ttatttttt ttcactttttc taccaaatgg gttacatagg aagaatgaac tgaaatctgt ccagagctcc aagtcctttg gaagaaagat tagatgaacg taaaaatgtt gttgttttgct gtggcagttt aagcattt tcttgcaaaa ttgtcaaa tctgttggaa ataagaacaca attcacaaat tggaagtgaa ctaaaatgtaa tgacgaaaa gggagtagtg ttttgatttg gaggaggtgt atattcggca gaggttggac tgagagttgg gtgttattta acataattat ggtaattggg aaacatttat aaacactattg ggatggtga taaatacaa aagggcctat agatgttaga aatgggtcag gttactgaaa tgggattcaa tttgaaaaaa attttttttaa ataaactca ctgaactaga ttctcctctga gaaccagag aagaccattt catgttgga ttcctggaga tatgcgctat ccaccacgta gccactttcc acatgtggcc atcaaccact taagatggg ttagttaaa tcaagatgtg ctgttataat tggtataagc ataaatcac actagattct ggagatttaa tatgaataat aagaatacta tttcagtagt tttggtatat tgtgtgtcaa aatgataat attttggatg tattgggtga aataaatat taacattaaa aaaaaaaa |
| SEQ ID NO: 18 tumor necrosis factor receptor superfamily member 9 precursor [Homo sapiens] NP_001552.2 | MGNSCYNIVA TLLLVLNFER TRSLQDPCSN CPAGTFCDNN RNQICSPCPP NSFSSAGGQRTCDICRQCKG VFRTRKECSS TSNAECDCTP GFHCLGAGCS MCEQDCKQGQ ELTKKGCKDC CFGTFNDQKR GICRPWTNCS LDGKSVLVNG TKERDVVCGP SPADLSPGAS SVTPPAPAREPGHSPQIISF FLALTSTALL FLLFFLTLRF SVVKRGRKKL LYIFKQPFMR PVQTTQEEDGCSCRFPEEEE GGCEL |
| SEQ ID NO: 19 Homo sapiens TNF receptor superfamily member 9 (TNFRSF9), mRNA, NM_001561.5 | caaggaggga tcccacagat gtcacagggc tgtcacagag ctgtggtggg aatttcccatg agaccccgc ccctggctga gtcaccgcac tcctgtgttt gacctgaagt cctctcgagc tgcagaagcc tgaagaccaa ggagtggaaa gttctccggc agccctgaga tctcaagagt gacatttgtg agaccagcta atttgattaa aattctcttg gaatcagctt tgctagtatc ataccctgtgc cagatttcat catgggaaac agctgttaca acatagtagc cactctgttg ctggtcctca actttgagag gacaagatca ttgcaggatc cttgtagtaa ctgcccagct ggtacattct gtgataataa caggaatcag atttgcagtc cctgtcctcc aaatagtttc tccagcgcag gtggacaaag gacctgtgac atatgcaggc agtgtaaagg tgttttcagg accaggaagg agtgttcctc caccagcaat gcagagtgtg actgcactcc agggtttcactgcctggggg caggatgcag catgtgtgaa caggattgta aacaaggtca agaactgaca aaaaaaggtt gtaaagactg ttgcttttggg acatttaacg atcagaaacg tggcatctgtcgaccctgga caactgttc tttgatgga agtctgtgc ttgtgaatgg gacgaaggag agggacgttg tctgtggacc atctccagcc gacctctctc cgggagcatc ctctgtgaccccgcctgccc ctgcgagaga gccaggacac tctccgcaga tcatctcctt cttcttgcg ctgacgtcga ctgcgttgct cttcctgctg ttcttcctca cgctccgttt ctctgttgtta aacggggca gaaagaaact cctgtatata ttcaaacaac catttatgag accagtacaa actactcaag aggaagatgg ctgtagctgc cgatttccag aagaagaaga aggaggatgt gaactgtgaa atgaagtca ataggggtgt tgggactttc ttgaaaagaa gcaaggaaat atgagtcatc cgctatcaca gctttcaaaa gcaagaacac catcctacat aatcccaggat tccccaa cacacgttct tttctaaatg ccaatgagtt ggcctttaaa aatgcaccac ttttttttttt ttttgacag ggtctcactc tgtcacccag gctggagtgc agtggcacca ccatggctct ctgcagcctt gacctctggg agctcaagtg atcctcctgc ctcagtctcc tgagtagctg gaactacaag gaagggccac cacacctgac taacttttt gtttttttgttg ggtaaagat ggcatttcac catgttgtac aggctggtct caaactccta ggttcacttt ggcctcccaa agtgctggga ttacagacat gaactgccag gcccggccaa aataatgcac cacttttaac agaacagaca gatgaggaca gagctggtga taaaaaaaa aaaaaaaag catttctag ataccactta acaggtttga gctagttttt ttgaaatcca aagaaattatg tttaat tcaattacat agtccagtgg tccaactata attataatca aaatcaatgc aggtttgttt ttggtgcta atatgacata tgacaataag ccacgaggtg cagtaagtac ccgactaaag tttccgtggg ttctgtcatg taacacgaca tgctccaccg tcagggggga gtatgagcag agtgcctgag tttagggtca aggacaaaaa acctcaggcc tggaggaagt ttttggaaaga gttcaagtgt ctgtatatcc tatggtcttc tccatcctca caccttctgc ctttgtcctg ctcccttttta agcaggtta cattctaaaa attcttaact tttaacataa tatttatac caaagccaat aaatgaactg catatgatag |

| SEQUENCE LISTING SUMMARY | |
|---|---|
| DESIGNATION | SEQUENCE |
| | gtatgaagta cagtgagaaa attaacacct gtgagctcat tgtcctacca<br>cagcactaga gtgggggccg ccaaactccc atggccaaac ctggtgcacc atttgccttt gtttgtctgt<br>tggtttgctt gagacagtct tgctctgttg cccaggctgg aatggagtgg ctattcacag gcacaatcat<br>agcacacttt agccttaaac tcctgggctc aagtgatcca cccgcctcag tctcccaagt agctgggatt<br>acaggtgcaa acctggcatg cctgccattg tttggcttat gatctaagga tagcttttta aattttattc<br>atttttatttt tttttgagac agtgtctcac<br>tctgtctccc aggctgagt acagtggtac aatcttggat caccgcctcc<br>cagtttcaag tgatctccct gcctcagcct cctaagtagc tgggactaca ggtatgtgcc accacgcctg<br>gctaattttt atatttttag tagagacggg gtttcaccat gttgtccagg ctggtctcaa actcctgacc<br>tcaggtgatc tgcccacctc tgcctcccaa agtgctggga ttacaggcat gagccaccat gcctggccat<br>ttcttacact tttgtatgac atgcctattg caagctgcg tgcctctgtc ccatgttattt tactctgggg<br>atttaggtgg agggagcagc ttctatttgg aacattggcc atcgcatggc aaatgggtat ctgtcacttc<br>tgctcctatt tagttggttc tactataacc tttagagcaa atcctgcagc caagccaggc atcaataggg<br>cagaaaagta tattctgtaa ataggggtga ggagaagata tttctgaaca atagtctact gcagtaccaa<br>attgcttttc aaagtgctgt tcaatgta ctcccgtcag tcatataagt gtcatgtaag tatcccattg<br>atccacatcc ttgctacccc ctggtactat caggtgccct aatttgcc aagccagtgg<br>gtatagaatgagatctcact gtggtcttag tttgcatttg cttggttact gatgagcacc ttgtcaaata<br>tttatatacc atttgtgttt attttttttaa ataaaatgct tgctcatgct tttttgcccatttgcaaaaa<br>aacttgggc cgggtgcagt ggctcatgcc<br>tgtagtccca gctctttggg aggccaaggt gggcagatcg cttgagccca<br>ggagttcgag accagccttg gcaacatggc gaaaccctgt ctttacaaaa aatacaaaaa ttagccgggt<br>gtggtggtgt gcacctgaag tcccagctac tcagtaggtt ctgggaggca gaggttgcag<br>tgagctgggaccgcatcact acacttcagc ctgggcaaca gagaaaaacc ttttctcaga aacaaacaaa<br>cccaaatgtg gttgtttgtc ctgattccta aaaggtctt atgtattcta gataataatctttggtcagt<br>tatatgtgtt aaaaaatatc ttctttgtgg<br>ccaggcacgg tagctcacac ctgtaatccc agcactttgc ggggctgagg<br>tgggtggatc atctgaggtc aagagttcaa gatcagcctg gccaacacag tgaaacccca tctctactaa<br>acatgtacaa aacttagctg gtatggtgg cgggtgcctg taacccagc tgctccagag gctgtggcag<br>aagaatcgctt gaacccagg aggcagaggt tgcagcgagc caagattgtg ccattgcact ccagactggg<br>tgacaagagt gaaattctgc ctatctatct atctatctat ctatatctat atatatatatatatatcc<br>tttgtaattt attttttccct tttttaaaatt<br>ttttataaaa ttcctttttta ttttttatttt tagcagaggt gaggtttctg aggtttcatt<br>atgttgccca ggctggtctt gaactcctga gctcaagtga tcctcccacc tcagccttcc aaagtgctgg<br>aattgcagac atgagccacc gcgcccctcc tgttttctc taattaatgg tgtcttttctt<br>tgtcttttctggtaataagca aaaagttctt catttgattt ggttaaattt ataactgttt tctcatatgg<br>ttaacattttt ttcttgcctg gctaaagaaa tccttttctg cccaatacta taaagaggttt gcccacatt<br>ttattccaaa agttttaagt tttgtctttc atcttgaagt ctaatgtatc aggaactggc ttttgtgcct<br>gttgggaggt agtgatccaa ttccatgtct tgcatgtaggt aaccactgg tccctgcgcc atgtattcaa<br>tacgtcgtct ttctcctgcg ggtctgcaat ctcacctacc atccatcaag tttccatagg gccatgggtc<br>tgcttctggg ctccctgttctgttccattg tcaatttgtc tatcctgtgc cagtatcaca ctgtgtttat<br>tacaatagct ttgtaacagc tctcgatatc cggtaggaca tctccctcca ccttctttt<br>ctacttcagaagtgtcttag ctaggtcagg cacggtggct cacgcctgta atcccagcac tttgggaggc<br>cgacgcggat ggatcacctg aggtcaggag tttttgaaca gcctggccaa catggtgaaaccccatctct<br>actaaaaaat acaaaaatta gtcaggcatg gtggcatgtg cctgtaatcc cagctatttg ggaggctgag<br>gccggagaat tgcttgaacc cggggggcgg aggttgcagtgagccgagat cgtaccattg cactccagcc<br>tgggtgacag agcgaaactc tgtctcagga aaaaaagaa aagagatgtc ttggttattc ttggttcttt<br>attattcaat ataaattttagaagctgaat ttgaacaagat ttggattgga atttcattaa atctacaggt<br>caatttaggg agagttgata attttacaga attgagtcat ctggtgttcc aataagaata<br>agagaacaattattggctgt acaattcttg ccaaatagta ggcaaagcaa agcttaggaa gtatactggt<br>gccatttcag gaacaaagct aggtgcgaat atttttgtct ttctgaatca tgatgctgtaagttctaaag<br>tgatttctcc tcttggcttt ggacacatgg tgttaatta cctactgctg actatccaca aacagaaaga<br>gactggtcat gcccccacagg gttggggtat ccaagataatggagcgaggc tctcatgtgt cctaggttac<br>acaccgaaaa tccacagttt attctgtgaa<br>gaaaggaggc tatgtttatg atacagactg tgatattttt atcatagcct attctggtatcatgtgcaaa<br>agctataaat gaaaaacaca ggaacttggc atgtagtca ttgctccccc taaatgacaa ttaataagga<br>aggaacattg agacagaata aaatgatccc cttctgggtttaatttagaa agttccataa ttaggtttaa<br>tagaaataaa tgtaaatttc tatgattaaa aataaattag cacatttagg gatacacaaa ttataaatca<br>ttttctaaat gctaaaaacaagctcaggtt ttttttcagaa gaaagttttaa atttttttttc tttagtggaa<br>gatatcactc tgaccggaaag ttttgatgtg<br>agggccggat gactataaag tgggcatctt ccccccacaggaagatgtttc<br>catctgtggg tgagaggtgc ccaccgcagc tagggcaggt tacatgtgcc ctgtgtgtgg taggacttgg<br>agagtgatct ttatcaacgt tttatttttaa aagactatctaataaaacac aaaaactatga tgttcacagg<br>aaaaaaagaa taagaaaaaa agaaaaaaaaa |
| SEQ ID NO: 20<br>hepatitis A virus<br>cellular 1<br>receptor (HAVCR2)<br>[Homo sapiens]<br>NP_116171.3 | MFSHLPFDCV LLLLLLLLTR SSEVEYRAEV GQNAYLPCFY<br>TPAAPGNLVP VCWGKGACPV FECGNVVLRT DERDVNYWTS<br>RYWLNGDFRK GDVSLTIENV TLADSGIYCC RIQIPGIMND<br>EKFNLKLVIK PAKVTPAPTR QRDFTAAFPR MLTTRGHGPA<br>ETQTLGSLPD INLTQISTLANELRDSRLAN DLRDSGATIR IGIYIGAGIC<br>AGLALALIFG ALIFKWYSHS KEKIQNLSLISLANLPPSGL ANAVAEGIRS<br>EENIYTIEEN VYEVEEPNEY YCYVSSRQQP SQPLGCRFAMP |
| SEQ ID NO: 21<br>hepatitis A virus<br>cellular 1 | agaacactta caggatgtgt gtagtgtggc atgacagaga actttggttt cctttaatgt<br>gactgtagac ctggcagtgt tactataaga atcactggca atcagacacc cggtgtgct<br>gagctagcac tcagtggggg cggctactgc tcatgtgatt gtggagtaga cagttggaag |

SEQUENCE LISTING SUMMARY

| DESIGNATION | SEQUENCE |
|---|---|
| receptor (HAVCR2) [Homo sapiens] NM_032782.4 | aagtacccag tccatttgga gagttaaaac tgtgcctaac agaggtgtcc tctgactttt<br>cttctgcaag ctccatgttt tcacatcttc cctttgactg tgtcctgctg ctgctgctgc<br>tactacttac aaggtcctca gaagtggaat acagagcgga ggtcggtcag aatgcctatc<br>tgccctgctt ctacacccca gccgcccag ggaacctcgt gcccgtctgc tggggcaaag<br>gagcctgtcc tgtgtttgaa tgtggcaacg tggtgctcag gactgatgaa agggatgtga<br>attattggac atccagatac tggctaaatg gggatttccg caaaggagat gtgtccctga<br>ccatagaaa tgtgactcta gcagacagtg ggatctactg ctgccggatc caaatcccag<br>gcataatgaa tgatgaaaaa tttaacctga agttggtcat caaaccagcc aaggtcaccc<br>ctgcaccgac tcggcagaga gacttcactg cagcctttcc aaggatgctt accaccaggg<br>gacatggccc agcagagaca cagacactgg ggagcctccc tgatataaat ctaacacaaa<br>tatccacatt ggccaatgag ttacgggact ctagattggc caatgacttc cgggactctg<br>gagcaaccat cagaataggc atctacatcg gagcagggat ctgtgctggg ctggctctgg<br>ctcttatctt cggcgcttta attttcaaat ggtattctca tagcaaagag aagatacaga<br>atttaagcct catctctttg gccaacctcc ctccctcagg attggcaaat ggagtagcag<br>agggaattcg ctcagaagaa aacatctata ccattgaaga gaacgtatat gaagtggagg<br>agcccaatga gtattattgc tatgtcagca gcaggcagca accctcacaa cctttgggtt<br>gtcgctttgc aatgccatag atccaaccac cttatttttg agcttggtgt tttgtctttt<br>tcagaaacta tgagctgtgt cacctgactg gttttggagg ttctgtccac tgctatggag<br>cagagttttc ccatttcag aagataatga ctcacatggg aattgaactg ggacctgcac<br>tgaacttaaa caggcatgtc attgcctctg tatttaagcc aacagagtta cccaacccag<br>agactgttaa tcatggatgt tagagctcaa acgggcttt atatacacta ggaattcttg<br>acgtggggtc tctggagctc caggaaattc gggcacatca tatgtccatg aaacttcaga<br>taaactaggg aaaactgggt gctgaggtga aagcataact ttttggcac agaaagtcta<br>aagggccac tgattttcaa agagatctgt gatccctttt tgttttttgt ttttgagatg<br>gagtcttgct ctgttgccca ggctggagtg caatggcaca atctcggctc actgcaagct<br>ccgcctcctg ggttcaagcg attctcctgc ctcagcctcc tgagtggctg ggattacagg<br>catgcaccac catgcccagc taatttgttg tatttttagt agagacaggg tttcaccatg<br>ttggccagtg tggtctcaaa ctcctgacct catgatttgc ctgcctcggc ctcccaaagc<br>actgggatta caggcgtgag ccaccacatc cagccagtga tccttaaaag attaagagat<br>gactggacca ggtctacctt gatcttgaag attcccttgg aatgttgaga tttaggctta<br>tttgagcact gcctgcccaa ctgtcagtgc cagtgcatag cccttctttt gtctcccta<br>tgaagactgc cctgcagggc tgagatgtgg caggagctcc cagggaaaaa cgaagtgcat<br>ttgattggtg tgtattggcc aagttttgct tgttgtgtgc ttgaaagaaa atatctctga<br>ccaacttctg tattcgtgga ccaaactgaa gctatatttt tcacagaaga agaagcagtg<br>acggggacac aaattctgtt gcctggtgga aagaaggcaa aggccttcag caatctatat<br>taccagcgct ggatcctttg acagagagtg gtccctaaac ttaaatttca agacggtata<br>ggcttgatct gtcttgctta ttgttgcccc ctgcgcctag cacaattctg acacacaatt<br>ggaacttact aaaaattttt ttttactgtt aaaaaaaaaa aaaaaaa |
| SEQ ID NO: 22 Homo sapiens programmed cell death 1 precursor (PDCD1), NP_005009.2[] | MQIPQAPWPV VWAVLQLGWR PGWFLDSPDR PWNPPTFSPA<br>LLVVTEGDNA TFTCSFSNTSESFVLNWYRM SPSNQTDKLA<br>AFPEDRSQPG QDCRFRVTQL PNGRDFHMSV VRARRNDSGT<br>YLCGAISLAP KAQIKESLRA ELRVTERRAE VPTAHPSPSP<br>RPAGQFQTLV VGVVGGLLGSLVLLVWVLAV ICSRAARGTI<br>GARRTGQPLK EDPSAVPVFS VDYGELDFQW REKTPEPPVP<br>CVPEQTEYAT IVFPSGMGTS SPARRGSADG PRSAQPLRPE DGHCSWPL |
| SEQ ID NO: 23 Homo sapiens programmed cell death 1 (PDCD1), mRNA NM_005018.2 | agtttccctt ccgctcacct ccgcctgagc agtggagaag gcggcactct ggtggggctgctccaggcat<br>gcagatccca caggcgccct ggccagtcgt ctgggcggtg ctacaactgg gctggcggcc aggatggttc<br>ttagactccc cagacaggcc ctgaaccccc ccaccttctccccagccct gctcgtggtg accgaagggg<br>acaacgccac cttcacctgc agcttctcca acacatcgga gagcttcgtg ctaaactggt accgcatgag<br>ccccagcaac cagacggaca agctggccgc cttccccgag gaccgcagcc agcccggcca<br>cacaactgcc aacgggcgt gacttccaca tgagcgtggt cagggcccgg cgcaatgaca<br>gcggcaccta cctctgtggg gccatctccc tggccccaa ggcgcagatc aaagagagcctgcgggcaga<br>gctcagggtg acagagagaa gggcagaagt gcccacagcc caccccaggc cctcacccag<br>gccagccggc cagttccaaa ccctggtggt tggtgtcgtg gcggcctgctgggcagcct ggtgctgcta<br>gtctgggtcc tggccgtcat ctgctcccgg gccgcacgag ggacaatagg agccaggcgc<br>accggccagc ccctgaagga ggacccctca gccgtgcctgtgttctctgt ggactatggg gagctggatt<br>tccagtggcg agagaagacc ccggagcccc ccgtgccctg tgtccctgag cagacggagt atgccaccat<br>gtctttcct agcggaatgggcacctcatc ccccgcccgc aggggctcag ctgcagccc tcgagtgcc<br>cagccactga ggcctgagga tggacactgc tcttgcccc tctgaccgg ttccttggcc<br>accagtgttctgcagaccct ccaccatgag cccgggtcag cgcatttcct caggagaagc aggcagggtg<br>caggccattg caggccgtcc aggggctgag ctgcctgggg gcgaccgggg<br>ctccagcctgcacctgcacc aggcacagca ccaccacagg actcatgtct caatgccac agtgagccca<br>ggcagcaggt gtcaccgtcc cctacaggga gggccagatg cagtcactgc ttcaggtcctgccagcacag<br>agctgcctgc gtccagctcc ctgaatctct gctgctgctg ctgctgctgc tgctgctgcc tgcggcccgg<br>ggctgaaggc gccgtggccc tgcctgacgc cccggagcctcctgcctgaa cttgggggct ggttggagat<br>ggccttggag cagccaaggt gcccctggca gtggcatccc gaaacgccct ggacgcaggg<br>cccaagactg gcacagagag tgggaggtacatgggctgg ggactcccca ggagttatct gctccctgca<br>ggcctagaga agtttcaggg aaggtcagaa gagctcctgg ctgtggtggg caggcagga aaccccctcca<br>cctttacacatgcccaggca gcacctcagg ccctttgtgg ggcagggaag ctgaggcagt aagcgggcag<br>gcagagctgg aggcttttca ggcccagcca gcactctggc ctcctgccgc cgcattccacccagccct<br>cacaccactc gggagaggga catcctacgg tcccaaggtc aggagggcag ggctgggtt<br>gactcaggcc cctcccagct gtggccacct gggtgttggg agggcagaagtgcaggcacc tagggcccc<br>catgtgccca ccctgggagc tctccttgga acccattcct gaaattattt aagggggttg gccgggctcc |

| DESIGNATION | SEQUENCE |
|---|---|
| | caccagggcc tgggtgggaa ggtacaggcg ttcccccggg gcctagtacc cccgccgtgg cctatccact<br>cctcacatcc acacactgca cccccactcc tggggcaggg ccaccagcat ccaggcggcc<br>agcaggcacc tgagtggctg ggacaaggga tccccttcc ctgtggttct attatattat aattataatt<br>aaatatgaga gcatgctaag gaaaa |
| SEQ ID NO: 24<br>low affinity<br>immunoglobulin<br>gamma Fc region<br>receptor II-a<br>isoform 1<br>precursor [Homo<br>sapiens]<br>NP_001129691.1 | MTMETQMSQN VCPRNLWLLQ PLTVLLLLAS ADSQAAPPK<br>AVLKLEPPWI NVLQEDSVTLTCQGARSPES DSIQWFHNGN<br>LIPTHTQPSY RFKANNNDSG EYTCQTGQTS LSDPVHLTVL<br>SEWLVLQTPH LEFQEGETIM LRCHSWKDKP LVKVTFFQNG<br>KSQKFSHLDP TFSIPQANHSHSGDYHCTGN IGYTLFSSKP<br>VTITVQVPSM GSSSPMGIIV AVVIATAVAA IVAAVVALIY<br>CRKKRISANS TDPVKAAQFE PPGRQMIAIR KRQLEETNND<br>YETADGGYMT LNPRAPTDDDKNIYLTLPPN DHVNSNN |
| SEQ ID NO: 25<br>low affinity<br>immunoglobulin<br>gamma Fc region<br>receptor II-a<br>isoform 1<br>precursor<br>(FCGR2A) [Homo<br>sapiens] mRNA<br>NM_001136219.1 | ctcttttcta agcttgtctc ttaaaaccca ctggacgttg gcacagtgct gggatgacta<br>tggagaccca aatgtctcag aatgtatgtc ccagaaacct gtggctgctt caaccattga<br>cagttttgct gctgctggct tctgcagaca gtcaagctgc agctccccca aaggctgtgc<br>tgaaacttga gcccccgtgg atcaacgtgc tccaggagga ctctgtgact ctgacatgcc<br>aggggctcg cagccctgag agcgactcca ttcagtggtt ccacaatggg aatctcattc<br>ccacccacac gcagcccagc tacaggttca aggccaacaa caatgacagc ggggagtaca<br>cgtgccagac tggccagace agcctcagcg accctgtca tctgactgtg ctttccgaat<br>ggctggtgct ccagacccct cacctggagt tccaggaggg agaaaccatc atgctgaggt<br>gccacagctg gaaggacaag cctctggtca aggtcacatt cttccagaat ggaaaatccc<br>agaaattctc ccatttggat cccaccttct ccatcccaca gcaaaccac agtcacagtg<br>gtgattacca ctgcacagga aacataggct acacgctgtt ctcatccaag cctgtgacca<br>tcactgtcca agtgcccagc atgggcagct cttcaccaat ggggatcatt gtggctgtgg<br>tcattgcgac tgctgtagca gccattgttg ctgctgtagt ggccttgatc tactgcagga<br>aaaagcggat ttcagccaat tccactgatc ctgtgaaggc tgcccaattt gagccacctg<br>gacgtcaaat gattgccatc agaaagagac aacttgaaga aaccaacaat gactatgaaa<br>cagctgacgg cggctacatg actctgaacc ccagggcacc tactgacgat gataaaaaca<br>tctacctgac tcttcctccc aacgaccatg tcaacagtaa taactaaaga gtaacgttat<br>gccatgtggt catactctca gcttgctgag tggatgacaa aagaggggga attgttaaag<br>gaaaatttaa atggagactg gaaaaatcct gagcaaaacaa accaactgg ccctagaaa<br>tagcttta ac tttgcttaaa ctacaaacac aagcaaaact tcacggggtc atactacata<br>caagcataag caaaacttaa cttggatcat ttctggtaaa tgcttatgtt agaaataaga<br>caacccccagc caatcacaag cagcctacta acatataatt aggtgactag ggactttcta<br>agaagatacc taccccccaaa aaacaattat gtaattgaaa ccaaccgat tgcctttatt<br>ttgcttccac attttcccaa taaatacttg cctgtgacat tttgccactg gaacactaaa<br>cttcatgaat tgcgcctcag atttttcctt taacatcttt tttttttttg acagagtctc<br>aatctgttac ccaggctgga gtgcagtggt gctatcttgg ctcactgcaa acccgcctcc<br>caggtttaag cgattctcat gcctcagcct cccagtagct gggattagag gcatgtgcca<br>tcatacccag ctaatttttg tatttttat tttttttat tagtagagac aggttttcgc<br>aatgttggcc aggccgatct cgaacttctg gcctctagcg atctgcccgc ctcggcctcc<br>caaagtgctg ggatgaccag catcagcccc aatgtccagc ctctttaaca tcttcttcc<br>tatgccctct ctgtggatcc ctactgctgg tttctgcctt ctccatgctg agaacaaaat<br>cacctattca tgcttatgc agtcggaagc tccagaagaa caaagagccc aattaccaga<br>accacattaa gtctccattg ttttgccttg ggatttgaga agaattag agaggtgagg<br>atctggtatt tcctggacta aattcccctt ggggaagacg aagggatgct gcagttccaa<br>aagagaagga ctcttccaga gtcatctacc tgagtcccaa agctccctgt cctgaaagcc<br>acagacaata tggtcccaaa tgactgactg caccttctgt gcctcagccg ttcttgacat<br>caagaatctt ctgttccaca tccacacagc aatacaatt agtcaaacca ctgttattaa<br>cagatgtagc aacatgagaa acgcttatgt tacaggttac atgagagcaa tcatgtaagt<br>ctatatgact tcagaaatgt taaatagac taacctcaa aacaaatta aaagtgattg<br>tttcaaggtg atgcaattat tgatgaccta ttttatttt ctataatgat catatattac<br>ctttgtaata aaacattata accaaaaca |
| SEQ ID NO: 26<br>low affinity<br>immunoglobulin<br>gamma Fc region<br>receptor II-a<br>isoform 2<br>precursor [Homo<br>sapiens]<br>NP_067674.2 | MTMETQMSQN VCPRNLWLLQ PLTVLLLLAS ADSQAAPPKA<br>VLKLEPPWIN VLQEDSVTLTCQGARSPESD SIQWFHNGNL<br>IPTHTQPSYR FKANNNDSGE YTCQTGQTSL SDPVHLTVLS<br>EWLVLQTPHL EFQEGETIML RCHSWKDKPL VKVTFFQNGK<br>SQKFSHLDPT FSIPQANHSHSGDYHCTGNI GYTLFSSKPV<br>TITVQVPSMG SSSPMGIIVA VVIATAVAAI VAAVVALIYC<br>RKKRISANST DPVKAAQFEP PGRQMIAIRK RQLEETNNDY<br>ETADGGYMTL NPRAPTDDDKNIYLTLPPND HVNSNN |
| SEQ ID NO: 27<br>low affinity<br>immunoglobulin<br>gamma Fc region<br>receptor II-a<br>isoform 2<br>precursor<br>(FCGR2A) [Homo | ctcttttcta agcttgtctc ttaaaaccca ctggacgttg gcacagtgct gggatgacta<br>tggagaccca aatgtctcag aatgtatgtc ccagaaacct gtggctgctt caaccattga<br>cagttttgct gctgctggct tctgcagaca gtcaagctgc tccccccaaag gctgtgctga<br>aacttgagcc cccgtggatc aacgtgctcc aggaggactc tgtgactctg acatgccagg<br>gggctcgcag ccctgagagc gactccattc agtggttcca caatgggaat ctcattcca<br>cccacacgca gcccagctac aggttcaagg ccaacaacaa tgacagcggg gagtacacgt<br>gccagactgg ccagaccagc ctcagcgacc ctgtgcatct gactgtgctt tccgaatggc<br>tggtgctcca gacccctcac ctggagttcc aggagggaga accatcatg ctgaggtgcc |

| DESIGNATION | SEQUENCE |
|---|---|
| sapiens] mRNA NM_021642.3 | acagctggaa ggacaagcct ctggtcaagg tcacattctt ccagaatgga aaatcccaga<br>aattctccca tttggatccc accttctcca tcccacaagc aaaccacagt cacagtggtg<br>attaccactg cacaggaaac ataggctaca cgctgttctc atccaagcct gtgaccatca<br>ctgtccaagt gcccagcatg ggcagctctt caccaatggg gatcattgtg gctgtggtca<br>ttgcgactgc tgtagcagcc attgttgctg ctgtagtggc cttgatctac tgcaggaaaa<br>agcggatttc agccaattcc actgatcctg tgaaggctgc ccaatttgag ccacctggac<br>gtcaaatgat tgccatcaga aagagacaac ttgaagaaac caacaatgac tatgaaacag<br>ctgacggcgg ctacatgact ctgaacccca gggcacctac tgacgatgat aaaaacatct<br>acctgactct tcctcccaac gaccatgtca acagtaataa ctaaagagta acgttatgcc<br>atgtggtcat actctcagct tgctgagtgg atgacaaaaa gagggaatt gttaaaggaa<br>aatttaaatg gagactggaa aaatcctgag caaacaaaac cacctggccc ttagaaatag<br>ctttaacttt gcttaaacta caaacacaag caaaacttca cggggtcata ctacatacaa<br>gcataagcaa aacttaactt ggatcatttc tggtaaatgc ttatgttaga aataagacaa<br>cccagccaa tcacaagcag cctactaaca tataattagg tgactaggga ctttctaaga<br>agatacctac ccccaaaaaa caattatgta attgaaaacc aaccgattgc ctttattttg<br>cttccacatt ttcccaataa atacttgcct gtgacatttt gccactggaa cactaaactt<br>catgaattgc gcctcagatt tttcctttaa catcttttt tttttgaca gagtctcaat<br>ctgttaccca ggctggagtg cagtggtgct atcttggctc actgcaaacc cgcctcccag<br>gtttaagcga ttctcatgcc tcagcctccc agtagctggg attagaggca tgtgccatca<br>tacccagcta attttgtat tttttatttt tttttttag tagagacagg gtttcgcaat<br>gttggccagg ccgatctcga acttctggcc tctagcgatc tgcccgcctc ggcctcccaa<br>agtgctggga tgaccagcat cagccccaat gtccagcctc tttaacatct tctttcctat<br>gccctctctg tggatcccca ctgctggttt ctgccttctc catgctgaga acaaaatcac<br>ctattcactg cttatgcagt cggaagctcc agaagaacaa agagcccaat taccagaacc<br>acattaagtc tccattgttt tgccttggga tttgagaaga gaattagaga ggtgaggatc<br>tggtatttcc tggactaaat tccccttggg gaagacgaag ggatgctgca gttccaaaag<br>agaaggactc ttccagagtc atctacctga gtcccaaagc tccctgtcct gaaagccaca<br>gacaatatgg tcccaaatga ctgactgcac cttctgtgcc tcagccgttc ttgacatcaa<br>gaatcttctg ttccacatcc acacagccaa tacaattagt caaaccactg ttattaacag<br>atgtagcaac atgagaaacg cttatgttac aggttacatg agagcaatca tgtaagtcta<br>tatgacttca gaaatgttaa aatagactaa cctctaacaa caaattaaaa gtgattgttt<br>caaggtgatg caattattga tgacctattt tattttcta taatgatcat atattccctt<br>tgtaataaaa cattataacc aaaaca |
| SEQ ID NO: 28 high affinity immunoglobulin gamma Fc receptor I precursor [Homo sapiens] NP_000557.1 | MWFLTTLLLW VPVDGQVDTT KAVITLQPPW VSVFQEETVT<br>LHCEVLHLPG SSSTQWFLNGTATQTSTPSY RITSASVNDS<br>GEYRCQRGLS GRSDPIQLEI HRGWLLLQVS SRVFTEGEPL<br>ALRCHAWKDK LVYNVLYYRN GKAFKFFHWN SNLTILKTNI<br>SHNGTYHCSG MGKHRYTSAGI SVTVKELFP APVLNASVTS<br>PLLEGNLVTL SCETKLLLQR PGLQLYFSFY MGSKTLRGRN<br>TSSEYQILTA RREDSGLYWC EAATEDGNVL KRSPELELQV<br>LGLQLPTPVW FHVLFYLAVGIMFLVNTVLW VTIRKELKRK<br>KKWDLEISLD SGHEKKVISS LQEDRHLEEE LKCQEQKEEQ<br>LQEGVHRKEP QGAT |
| SEQ ID NO: 29 high affinity immunoglobulin gamma Fc receptor I precursor (FCGR1A) [Homo sapiens] mRNA NM_000566.3 | aatatcttgc atgttacaga tttcactgct cccaccagct tggagacaac atgtggttct<br>tgacaactct gctcctttgg gttccagttg atgggcaagt ggacaccaca aaggcagtga<br>tcactttgca gcctccatgg gtcagcgtgt tccaagagga aaccgtaacc ttgcactgtg<br>aggtgctcca tctgcctggg agcagctcta cacagtggtt tctcaatggc acagccactc<br>agacctcgac ccccagctac agaatcacct ctgccagtgt caatgacagt ggtgaataca<br>ggtgccagag aggtctctca gggcgaagtg acccccataca gctggaaatc cacagaggct<br>ggctactact gcaggtctcc agcagagtct tcacggaagg agaacctctg gccttgaggt<br>gtcatgcctg aaggataag ctggtgtaca atgtgcttta ctatcgaaat ggcaaagcct<br>ttaagttttt ccactggaat tctaacctca ccattctgaa aaccaacata agtcacaatg<br>gcacctacca ttgctcagc atgggaaagc atcgctacac atcagcagga atatctgtca<br>ctgtgaaaga gctatttcca gctccagtgc tgaatgcatc tgtgactcc ccactcctgg<br>aggggaatct ggtcaccctg agctgtgaaa caagttgct cttgcagagg cctggttgc<br>agctttactt ctccttctac atgggcagca gaccctgcg aggcaggaac acatcctctg<br>aataccaaat actaactgct agaagagaag actctgggtt atactggtgc gaggctgcca<br>cagaggatgg aaatgtcctt aagcgcagcc ctgagttgga gcttcaagtg cttggcctcc<br>agttaccaac tcctgtctgg tttcatgtcc ttttctatct ggcagtggga ataatgtttt<br>tagtgaacac tgttctctgg gtgacaatac gtaaagaact gaaaagaaag aaaaagtggg<br>atttagaaat ctctttggat tctggtcatg agaagaaggt aatttccagc cttcaagaag<br>acagacattt agaagagag ctgaaatgtc aggaacaaaa agaagaacag ctgcaggaag<br>gggtgcaccg gaaggagccc caggggggca cgtagcagcg gctcagtggg tggccatcga<br>tctggaccgt ccctgcca cttgctcccc gtgagcactg cgtacaaaca tccaaaagtt<br>caacaacacc agaactgtgt gtctcatggt atgtaactct taagcaaat aaatgaactg<br>acttcaactg ggatacattt ggaaatgtgg tcatcaaaga tgacttgaaa tgaggcctac<br>tctaaagaat tcttgaaaaa cttacaagtc aagcctagcc tgataatcct attacatagt<br>ttgaaaaata gtatttatt tctcagaaca aggtaaaaag tgagtgggt gcatatgtca<br>agaagattaa gacagagaaa cagacagaaa gagacacaca cacagccagg agtgggtaga<br>tttcaggag acaagaggga atagtataga caataaggaa ggaaatagta cttacaaatg<br>actcctaagg gactgtgaga ctgagagggc tcacgcctct gtgttcagga tacttagttc<br>atggctttc tctttgactt tactaaaaga gaatgtctcc atacgcgttc taggcataca<br>aggggtaac tcatgatgag aaatggatgt gttattcttg ccctctcttt tgaggctctc |

| DESIGNATION | SEQUENCE |
|---|---|
| | tcataacccc tctatttcta gagacaacaa aaatgctgcc agtcctaggc ccctgccctg<br>taggaaggca gaatgtaact gttctgtttg tttaacgatt aagtccaaat ctccaagtgc<br>ggcactgcaa agagacgctt caagtgggga gaagcggcga taccatagag tccagatctt<br>gcctccagag atttgcttta ccttcctgat tttctggtta ctaattagct tcaggatacg<br>ctgctctcat acttgggctg tagtttggag acaaaatatt ttcctgccac tgtgtaacat<br>agctgaggta aaaactgaac tatgtaaatg actctactaa aagtttaggg aaaaaaaaca<br>ggaggagtat gacacaaaaa aaaaaaaaaa aaaaaaaaaa aaaaaaaaaa aaaaaaaaaa<br>aaaaaaaaaa aaaaaaaaaa aaaaaaaaaa aaaaaaaaaa aaaaaaaa |
| SEQ ID NO: 30<br>CD163 [Homo sapiens]<br>NP_004235.4 | MSKLRMVLLE DSGSADFRRH FVNLSPFTIT VVLLLSACFV<br>TSSLGGTDKE LRLVDGENKCSGRVEVKVQE EWGTVCNNGW<br>SMEAVSVICN QLGCPTAIKA PGWANSSAGS GRIWMDHVSC<br>RGNESALWDC KHDGWGKHSN CTHQQDAGVT CSDGSNLEMR<br>LTRGGNMCSG RIEIKFQGRWGTVCDDNFNI DHASVICRQL<br>ECGSAVSFSG SSNFGEGSGP IWFDDLICNG NESALWNCKH<br>QGWGKHNCDH AEDAGVICSK GADLSLRLVD GVTECSGRLE<br>VRFQGEWGTI CDDGWDSYDAAVACKQLGCP TAVTAIGRVN<br>ASKGFGHIWL DSVSCQGHEP AIWQCKHHEW GKHYCNHNED<br>AGVTCSDGSD LELRLRGGGS RCAGTVEVEI QRLLGKVCDR<br>GWGLKEADVV CRQLGCGSALKTSYQVYSKI QATNTWLFLS<br>SCNGNETSLW DCKNWQWGGL TCDHYEEAKI TCSAHREPRL<br>VGGDIPCSGR VEVKHGDTWG SICDSDFSLE AASVLCRELQ<br>CGTVVSILGG AHFGEGNGQIWAEEFQCEGH ESHLSLCPVA<br>PRPEGTCSHS RDVGVVCSRY TEIRLVNGKT PCEGRVELKT<br>LGAWGSLCNS HWDIEDAHVL CQQLKCGVAL STPGGARFGK<br>GNGQIWRHMF HCTGTEQHMGDCPVTALGAS LCPSEQVASV<br>ICSGNQSQTL SSCNSSSLGP TRPTIPEESA VACIESGQLR<br>LVNGGGRCAG RVEIYHEGSW GTICDDSWDL SDAHVVCRQL<br>GCGEAINATG SAHFGEGTGPIWLDEMKCNG KESRIWQCHS<br>HGWGQQNCRH KEDAGVICSE FMSLRLTSEA SREACAGRLE<br>VFYNGAWGTV GKSSMSETTV GVVCRQLGCA DKGKINPASL<br>DKAMSIPMWV DNVQCPKGPDTLWQCPSSPW EKRLASPSEE<br>TWITCDNKIR LQEGPTSCSG RVEIWHGGSW GTVCDDSWDL<br>DDAQVVCQQL GCGPALKAFK EAEFGQGTGP IWLNEVKCKG<br>NESSLWDCPA RRWGHSECGHKEDAAVNCTD ISVQKTPQKA<br>TTGRSSRQSS FIAVGILGVV LLAIFVALFF LTKKRRQRQR<br>LAVSSRGENL VHQIQYREMN SCLNADDLDL MNSSENSHES<br>ADFSAAELIS VSKFLPISGMEKEAILSHTE KENGNL |
| SEQ ID NO: 31<br>Homo sapiens<br>CD163 mRNA, complete cds<br>mRNA<br>NM_004244.5 | atatgtagcc ttttcatttt catgaaagtg aagtgatttt tagaattctt agttgttttc<br>tttagaagaa catttctagg gaataataca agaagattta ggaatcattg aagttataaa<br>tctttggaat gagcaaactc agaatggtgc tacttgaaga ctctggatct gctgacttca<br>gaagacattt tgtcaactta agtcccttca ccattactgt ggtcttactt ctcagtgcct<br>gttttgtcac cagttctctt ggaggaacag acaaggagct gaggctagtg gatggtgaaa<br>acaagtgtag cgggagagtg gaagtgaaag tccaggagga gtggggaacg tgtgtaata<br>atggctggag catggaagcg gtctctgtga tttgtaacca gctgggatgt ccaactgcta<br>tcaaagcccc tggatgggct aattccagtg caggttctgg acgcatttgg atggatcatg<br>tttcttgtcg tgggaatgag tcagctcttt gggattgcaa acatgatgga tggggaaagc<br>atagtaactg tactcaccaa caagatgctg gagtgacctg ctcagatgga tccaatttgg<br>aaatgaggct gacgcgtgga gggaatatgt gttctggaag aatagagatc aaattccaag<br>gacggtgggg aacagtgtgt gatgataact tcaacataga tcatgcatct gtcatttgta<br>gacaacttga atgtggaagt gctgtcagtt tctctggttc atctaatttt ggagaaggct<br>ctggaccaat ctggtttgat gatcttatat gcaacggaaa tgagtcagct ctctggaact<br>gcaaacatca aggatgggga aagcataact gtgatcatgc tgaggatgct ggagtgattt<br>gctcaaaggg agcagatctg agcctgagac tggtagatgg agtcactgaa tgttcaggaa<br>gattagaagt gagattccaa ggagaatggg gacaatatg tgatgacggc tgggacagtt<br>acgatgctgc tgtggcatgc aagcaactgg gatgtccaac tgccgtcaca gccattggtc<br>gagttaacgc cagtaaggga tttggacaca tctgcttga cagcgtttct tgccagggac<br>atgaacctgc tatctggcaa tgtaaacacc atgaatgggg aaagcattat tgcaatcaca<br>atgagatgc tggcgtgaca tgttctgatg gatcagatct ggagctaaga cttagaggtg<br>gaggcagccg ctgtgctggg acagttgagg tggagattca gagactgtta gggaaggtgt<br>gtgacagagg ctggggactg aaagaagctg atgtggtttg caggcagctg ggatgtggat<br>ctgcactcaa aacatcttat caagtgtact ccaaaatcca ggcaacaaac acatggctgt<br>ttctaagtag ctgtaacgga aatgaaactt ctctttggga ctgcaaagac tggcaatggg<br>gtggacttac ctgtgatcac tatgaagaag ccaaaattac ctgctcagcc cacagggaac<br>ccagactggt tggaggggac attccctgtt ctggacgtgt tgaagtgaag catggtgaca<br>cgtgggggctc catctgtgat tcggacttct ctctggaagc tgccagcgtt ctatgcaggg<br>aattacagtg tggcacagtt gtctctatcc tggggggagc tcactttgga gagggaaatg<br>gacagatctg ggctgaagaa ttccagtgtg agggacatga gtcccatctt tcactctgcc<br>cagtagcacc ccgcccagaa ggaacttgta gccacgacag ggatgttgga gtagtctgct<br>caagatacac agaaattcgc ttggtgaatg gcaagacccc gtgtgagggc agagtggagc<br>tcaaaacgct tggtgcctgg ggatccctct gtaactctca ctgggacata aagatgccc<br>atgttctttg ccagcagctt aaatgtggag ttgccctttc taccccagga ggagcacgtt<br>ttggaaaagg aaatggtcag atctggaggc atatgtttca ctgcactggg actgagcagc<br>acatgggaga ttgtcctgta actgctctag gtgcttcatt atgtccttca gagcaagtgg |

| DESIGNATION | SEQUENCE |
|---|---|
| | cctctgtaat ctgctcagga aaccagtccc aaacactgtc ctcgtgcaat tcatcgtctt<br>tgggcccaac aaggcctacc attccagaag aaagtgctgt ggcctgcata gagagtggtc<br>aacttcgcct ggtaaatgga ggaggtcgct gtgctgggag agtagagatc tatcatgagg<br>gctcctgggg caccatctgt gatgacagct gggacctgag tgatgcccac gtggtttgca<br>gacagctggg ctgtggagag gccattaatg ccactggttc tgctcatttt ggggaaggaa<br>cagggcccat ctggctggat gagatgaaat gcaatggaaa agaatcccgc atttggcagt<br>gccattcaca cggctggggg cagcaaaatt gcaggcacaa ggaggatgcg ggagttatct<br>gctcagaatt catgtctctg agactgacca gtgaagccag cagagaggcc tgtgcagggc<br>gtctggaagt ttttacaat ggagcttggg gcactgttgg caagagtagc atgtctgaaa<br>ccactgtggg tgtggtgtgc aggcagctgg gctgtgcaga caaagggaaa atcaaccctg<br>catctttaga caaggccatg tccattccca tgtgggtgga caatgttcag tgtccaaaag<br>gacctgacac gctgtggcag tgcccatcat ctccatggga aagagactg gccagcccct<br>cggaggagac ctggatcaca tgtgacaaca agataagact tcaggaagga cccacttcct<br>gttctggacg tgtggagatc tggcatggag gttcctgggg gacagtgtgt gatgactctt<br>gggacttgga cgatgctcag gtggtgtgtc aacaacttgg ctgtggtcca gctttgaaag<br>cattcaaaga agcagagttt ggtcagggga ctggaccgat atggctcaat gaagtgaagt<br>gcaaaggaa tgagtcttcc ttgtgggatt gtcctgccag acgctgggc catagtgagt<br>gtgggcacaa ggaagacgct gcagtgaatt gcacagatat ttcagtgcag aaaacccac<br>aaaaagccac aacaggtcgc tcatcccgtc agtcatcctt tattgcagtc gggatccttg<br>gggttgttct gttggccatt ttcgtcgcat tattcttctt gactaaaaag cgaagacaga<br>gacagcggct tgcagtttc tcaagaggag agaacttagt ccaccaaatt caataccggg<br>agatgaattc ttgcctgaat gcagatgatc tggactaat gaattcctca gaaaattccc<br>atgagtcagc tgatttcagt gctgctgaac taatttctgt gtctaaattt cttcctattt<br>ctggaatgga aaaggaggcc attctgagcc acactgaaaa ggaaaatggg aatttataac<br>ccagtgagtt cagccttaa gataccttga tgaagacctg gactattgaa tggagcagaa<br>attcacctct ctcactgact attacagttg cattttag gagttcact tctcctagga<br>ttcctaagac tgctgctgaa tttataaaaa ttaagtttgt gaatgtgact acttagtggt<br>gtatatgaga ctttcaaggg aattaaataa ataaataaga atgttattga tttgagtttg<br>cttttaattac ttgtccttaa ttctattaat ttctaaatgg cttcctaat tttttgtaga<br>gtttcctaga tgtattataa tgtgttttat ttgacagtgt ttcaatttgc atatacagta<br>ctgtatattt tttcttattt ggttttgaata attttcctat taccaaataa aaataaattt<br>attttttactt tagtttttct aagacaggaa aagttaatga tattgaaggg tctgtaaata<br>atatatggct aactttata ggcatgactc acaacgattc tttaactgct ttttgttact<br>gtaattctgt tcactagaat aaaatgcaga gccacacctg gtgagggcac |
| SEQ ID NO: 32<br>CD163<br>NCBI Reference<br>Sequence:<br>NP_981961.2: | MSKLRMVLLE DSGSADFRRH FVNLSPFTIT VVLLLSACFV<br>TSSLGGTDKE LRLVDGENKCSGRVEVKVQE EWGTVCNNGW<br>SMEAVSVICN QLGCPTAIKA PGWANSSAGS GRIWMDHVSC<br>RGNESALWDC KHDGWGKHSN CTHQQDAGVT CSDGSNLEMR<br>LTRGGNMCSG RIEIKFQGRWGTVCDDNFNI DHASVICRQL<br>ECGSAVSFSG SSNFGEGSGP IWFDDLICNG NESALWNCKH<br>QGWGKHNCDH AEDAGVICSK GADLSLRLVD GVTECSGRLE<br>VRFQGEWGTI CDDGWDSYDAAVACKQLGCP TAVTAIGRVN<br>ASKGFGHIWL DSVSCQGHEP AIWQCKHHEW GKHYCNHNED<br>AGVTCSDGSD LELRLRGGGS RCAGTVEVEI QRLLGKVCDR<br>GWGLKEADVV CRQLGCGSALKTSYQVYSKI QATNTWLFLS<br>SCNGNETSLW DCKNWQWGGL TCDHYEEAKI TCSAHREPRL<br>VGGDIPCSGR VEVKHGDTWG SICDSDFSLE AASVLCRELQ<br>CGTVVSILGG AHFGEGNGQIWAEEFQCEGH ESHLSLCPVA<br>PRPEGTCSHS RDVGVVCSRY TEIRLVNGKT PCEGRVELKT<br>LGAWGSLCNS HWDIEDAHVL CQQLKCGVAL STPGGARFGK<br>GNGGQIWRHMF HCTGTEQHMGDCPVTALGAS LCPSEQVASV<br>ICSGNQSQTL SSCNSSSLGP TRPTIPEESA VACIESGQLR<br>LVNGGGRCAG RVEIYHEGSW GTICDDSWDL SDAHVVCRQL<br>GCGEAINATG SAHFGEGTGPIWLDEMKCNG KESRIWQCHS<br>HGWGQQNCRH KEDAGVICSE FMSLRLTSEA SREACAGRLE<br>VFYNGAWGTV GKSSMSETTV GVVCRQLGCA DKGKINPASL<br>DKAMSIPMWV DNVQCPKGPDTLWQCPSSPW EKRLASPSEE<br>TWITCDNKIR LQEGPTSCSG RVEIWHGGSW GTVCDDSWDL<br>DDAQVVCQQL GCGPALKAFK EAEFGQGTGP IWLNEVKCKG<br>NESSLWDCPA RRWGHSECGHKEDAAVNCTD ISVQKTPQKA<br>TTGRSSRQSS FIAVGILGVV LLAIFVALFF LAVSSRGENL<br>VHQIQYREMN SCLNADDLDL MNSSGGHSEP H |
| SEQ ID NO: 33<br>CD163<br>NCBI Reference<br>Sequence:<br>NM_203416.3: | atatgtagcc ttttcatttt catgaaagtg aagtgatttt tagaattctt agttgttttc<br>tttagaagaa catttctagg gaataataca agaagattta ggaatcattg aagttataaa<br>tctttggaat gagcaaactc agaatggtgc tacttgaaga ctctggatct gctgacttca<br>gaagacattt tgtcaacttg agtcccttca ccattactgt ggtcttactc tcagtgcct<br>gttttgtcac cagttctctt ggaggaacag acaaggagct gaggctagtg gatggtgaaa<br>acaagtgtag cggagagtg gaagtgaaag tccaggagga gtggggaacg gtgtgtaata<br>atggctggag catggaagcg gtctctgtga tttgtaacca gctgggatgt ccaactgcta<br>tcaaagcccc tggatgggct aattccagtg caggttctgg acgcatttgg atggatcatg<br>tttcttgtcg tgggaatgag tcagctcttt ggattgcaa acatgatgaa tggggaaagc<br>atagtaactg tactcaccaa caagatgctg gagtgacctg ctcagatgga tccaatttgg<br>aaatgaggct gacgcgtgga gggaatatgt gttctggaag aatagagatc aaattccaag |

| DESIGNATION | SEQUENCE |
|---|---|
| | gacggtgggg aacagtgtgt gatgataact tcaacataga tcatgcatct gtcatttgta |
| | gacaacttga atgtggaagt gctgtcagtt tctctggttc atctaatttt ggagaaggct |
| | ctggaccaat ctggtttgat gatcttatat gcaacggaaa tgagtcagct ctctggaact |
| | gcaaacatca aggatgggga agcataact gtgatcatgc tgaggatgct ggagtgattt |
| | gctcaaaggg agcagatctg agcctgagac tggtagatgg agtcactgaa tgttcaggaa |
| | gattagaagt gagattccaa ggagaatggg ggacaatatg tgatgacggc tgggacagtt |
| | acgatgctgc tgtggcatgc aagcaactgg gatgtccaac tgccgtcaca gccattggtc |
| | gagttaacgc cagtaaggga tttggacaca tctggcttga cagcgtttct tgccagggac |
| | atgaacctgc tatctggcaa tgtaaacacc atgaatgggg aaagcattat tgcaatcaca |
| | atgaagatgc tggcgtgaca tgttctgatg gatcagatct ggagctaaga cttagaggtg |
| | gaggcagccg ctgtgctggg acagttgagg tggagattca gagactgtta gggaaggtgt |
| | gtgacagagg ctggggactg aaagaagctg atgtggtttg caggcagctg ggatgtggat |
| | ctgcactcaa aacatcttat caagtgtact ccaaaatcca ggcaacaaac acatggctgt |
| | ttctaagtag ctgtaacgaa aatgaaactt ctctttggga ctgcaagaac tggcaatggg |
| | gtggacttac ctgtgatcac tatgaagaag ccaaaattac ctgctcagcc cacagggaac |
| | ccagactggt tggaggggac attccctgtt ctggacgtgt gaagtgaag catggtgaca |
| | cgtggggctc catctgtgat tcggacttct ctctggaagc tgccagcgtt ctatgcaggg |
| | aattacagtg tggcacagtt gtctctatcc tgggggagg tcacttgtgg gagggaaatg |
| | gacagatctg ggctgaagaa ttccagtgtg agggacatga gtcccatctt tcactctgcc |
| | cagtagcacc ccgcccagaa ggaacttgta gccacagcag ggatgttgga gtagtctgct |
| | caagatacac agaaattcgc ttggtgaatg gcaagacccc gtgtgagggc agagtggagc |
| | tcaaaacgct tggtgcctgg ggatccctct gtaactctca ctgggacata gaagatgcct |
| | atgttctttg ccagcagctt aaatgtggag ttgccctttc tacccagga ggagcacgtt |
| | ttggaaaagg aaatggtcag atctggaggc atatgtttca ctgcactggg actgagcagc |
| | acatgggaga ttgtcctgta actgctctag gtgcttcatt atgtccttca agcaagtgg |
| | cctctgtaat ctgctcagga aaccagtccc taaacactgtc ctcgtgcaat tcatcgtctt |
| | tgggcccaac aaggcctacc attccagaag aaagtgctgt ggcctgcata gagagtggtc |
| | aacttcgcct ggtaaatgga ggaggtcgct gtgctgggag agtagagatc tatcatgagg |
| | gctcctgggg caccatctgt gatgacagct gggacctgag tgatgcccac gtggtttgca |
| | gacagctggg ctgtggagag gccattaatg ccactggttc tgctcattt ggggaaggaa |
| | cagggcccat ctggctggat gcaatggaaa gaatcccgc atttggcagt |
| | gccattcaca cggctggggg cagcaaaatt gcaggcacaa ggaggatgcg ggagttatct |
| | gctcagaatt catgtctctg agactgacca gtgaagccag cagagaggcc tgtgcagggc |
| | gtctggaagt ttttacaat ggagcttggg gcactgttgg caagagtagc atgtctgaaa |
| | ccactgtggg tgtggtgtgc aggcagctgg gctgtgcaga caagggaaa atcaaccctg |
| | catctttaga caaggccatg tccattccca tgtgggtgga caatgttcag tgtccaaaag |
| | gacctgacac gctgtgcagt gcccatcat ctccatggga aagagactg gccagcccct |
| | cggaggagac ctggatcaca tgtgacaaca agataagact tcaggaagga cccacttcct |
| | gttctggacg tgtggagatc tggcatggag gttcctgggg gacagtgtgt gatgactctt |
| | gggacttgga cgatgctcag gtggtgtgtc aacaactggg ctgtggtcca gctttgaaag |
| | cattcaaaga agcagagttt ggtcagggga ctggaccgat atggctcaat gaagtgaagt |
| | gcaaagggaa tgagtcttcc ttgtgggatt gtcctgccag acgctgggc catagtgagt |
| | gtgggcacaa ggaagacgct gcagtgaatt tcagtgcag aaaaccccac |
| | aaaaagccaa acaggtcgc tcatcccgtc agtcatcctt tattgcagtc gggatccttg |
| | gggttgttct gttggccatt tcgtcgcat tattcttctt gactaaaaag cgaagacaga |
| | gacagcggct tgcagttttc tcaagaggag agaacttagt ccaccaaatt caataccggg |
| | agatgaattc ttgcctgaat gcagatgatc tggacctaat gaattcctca ggaggccatt |
| | ctgagccaca ctgaaaagga aaatgggaat ttataaccca gtgagttcag cctttaagat |
| | accttgatga agacctggac tattgaatgg agcagaaatt cacctctctc actgactatt |
| | acagttgcat ttttatggag ttcttcttct cctaggattc taagactgc tgctgaattt |
| | ataaaaatta agtttgtgaa tgtgactact tagtggtgta tatgagactt tcaagggaat |
| | taaataaata aataagaatg ttattgattt gagtttgctt taattacttg tccttaattc |
| | tattaatttc taaatgggct tcctaatttt ttgtagagtt tcctagatgt attataatgt |
| | gttttatttg acagtgtttc aatttgcata tacagtactg tatattttt cttatttggt |
| | ttgaataatt ttcctattac caaataaaaa taaatttatt ttttactttag ttttctaag |
| | acaggaaaag ttaatgatat tgaagggtct gtaaataata tatggctaac tttataaggc |
| | atgactcaca acgattcttt aactgctttt tgttactgta attctgttca ctagaataaa |
| | atgcagagcc acacctggtg agggcac |
| SEQ ID NO: 34<br>CD14<br>NCBI Reference Sequence:<br>NP_000582.1 | MERASCLLLL LLPLVHVSAT TPEPCELDDE DFRCVCNFSE<br>PQPDWSEAFQ CVSAVEVEIH AGGLNLEPFL KRVDADADPR<br>QYADTVKALR VRRLTVGAAQ VPAQLLVGAL RVLAYSRLKE<br>LTLEDLKITG TMPPLPLEAT GLALSSLRLR NVSWATGRSW<br>LAELQQWLKP GLKVLSIAQA HSPAFSCEQV RAFPALTSLD<br>LSDNPGLGER GLMAALCPHK FPAIQNLALR NTGMETPTGV<br>CAALAAAGVQ PHSLDLSHNS LRATVNPSAP RCMWSSALNS<br>LNLSFAGLEQ VPKGLPAKLR VLDLSCNRLN RAPQPDELPE<br>VDNLTLDGNP FLVPGTALPH EGSMNSGVVP ACARSTLSVG<br>VSGTLVLLQG ARGFA |
| SEQ ID NO: 35<br>CD14<br>NCBI Reference Sequence:<br>NM_000591.3 | cagagaaggc ttaggctccc gagtcaacag ggcattcacc gcctgggcg cctgagtcat<br>caggacactg ccaggagaca cagaaccta gatgcctgc agaatcttc ctgttacggt<br>cccctcctt gaaacatcct tcattgcaat atttccagga aaggaagggg gctggctcgg<br>aggaagagag gtggggaggt gatcagggtt cacagaggag ggaactgaat gacatcccag<br>gattacataa actgtcagag gcagccgaag agttcacaag tgtgaagcct ggaagccggc |

| DESIGNATION | SEQUENCE |
|---|---|
| | gggtgccgct gtgtaggaaa gaagctaaag cacttccaga gcctgtccgg agctcagagg<br>ttcggaagac ttatcgacca tggagcgcgc gtcctgcttg ttgctgctgc tgctgccgct<br>ggtgcacgtc tctgcgacca cgccagaacc ttgtgagctg acgatgaag atttccgctg<br>cgtctgcaac ttctccgaac ctcagcccga ctggtccgaa gccttccagt gtgtgtctgc<br>agtagaggtg gagatccatg ccggcggtct caacctagag ccgtttctaa agcgcgtcga<br>tgcggacgcc gacccgcggc agtatgctga cacggtcaag gctctccgcg tgcggcggct<br>cacagtggga gccgcacagg ttcctgctca gctactggta ggcgccctgc gtgtgctagc<br>gtactcccgc ctcaaggaac tgacgctcga ggacctaaag ataaccggca ccatgcctcc<br>gctgcctctg gaagccacag gacttgcact ttccagcttg cgcctacgca acgtgtcgtg<br>ggcgacaggg cgttcttggc tcgccgagct gcagcaggtg ctcaagccag gcctcaaggt<br>actgagcatt gcccaagcac actcgcctgc cttttcctgc gaacaggttc gcgccttccc<br>ggcccttacc agcctagacc tgtctgacaa tcctggactg ggcgaacgcg gactgatggc<br>ggctctctgt ccccacaagt tcccggccat ccagaatcta gcgctgcgca acacaggaat<br>ggagacgccc acaggcgtgt gcgccgcact ggcggcggca ggtgtgcagc cccagcct<br>agacctcagc cacaactcgc tgcgcgccac cgtaaaccct agcgctccga gatgcatgtg<br>gtccagcgcc ctgaactccc tcaatctgtc gttcgctggg ctggaacagg tgcctaaagg<br>actgccagcc aagctcagag tgctcgatct cagctgcaac agactgaaca gggcgccgca<br>gcctgacgag ctgcccgagg tggataaccT gacactggac gggaatcct tcctggtccc<br>tggaactgcc ctcccccacg agggctcaat gaactccggc gtggtcccag cctgtgcacg<br>ttcgaccctg tcggtggggg tgtcgggaac cctggtgctg ctccaagggg ccgggggctt<br>tgcctaagat ccaagacaga ataatgaatg gactcaaact gccttggctt caggggagtc<br>ccgtcaggac gttgaggact tttcgaccaa tcaacccctt tgccccacct ttattaaaat<br>cttaaacaac gggtcaaaaa aaaaaaaa |
| SEQ ID NO: 36<br>CD14<br>NCBI Reference Sequence:<br>NP_001035110.1 | MERASCLLLL LLPLVHVSAT TPEPCELDDE DFRCVCNFSE<br>PQPDWSEAFQ CVSAVEVEIH AGGLNLEPFL KRVDADADPR<br>QYADTVKALR VRRLTVGAAQ VPAQLLVGAL RVLAYSRLKE<br>LTLEDLKITG TMPPLPLEAT GLALSSLRLR NVSWATGRSW<br>LAELQQWLKP GLKVLSIAQA HSPAFSCEQV RAFPALTSLD<br>LSDNPGLGER GLMAALCPHK FPAIQNLALR NTGMETPTGV<br>CAALAAAGVQ PHSLDLSHNS LRATVNPSAP RCMWSSALNS<br>LNLSFAGLEQ VPKGLPAKLR VLDLSCNRLN RAPQPDELPE<br>VDNLTLDGNP FLVPGTALPH EGSMNSGVVP ACARSTLSVG<br>VSGTLVLLQG ARGFA |
| SEQ ID NO: 37<br>CD14<br>NCBI Reference Sequence:<br>NM_001040021.2 | ttaaatatct gaggatattc agggacttgg atttggtggc aggagatcaa cataaaccaa<br>gacaaggaag aagtcaaaga aatgaatcaa gtagattctc tgggatataa gaggcagccg<br>aagagttcac aagtgtgaag cctggaagcc ggcgggtgcc gctgtgtagg aaagaagcta<br>aagcacttcc agagcctgtc cggagctcag aggttcggaa gacttatcga ccatggagcg<br>cgcgtcctgc ttgttgctgc tgctgctgcc gctggtgcac gtctctgcga ccacgccaga<br>accttgtgag ctggacgatg aagatttccg ctgcgtctgc aacttctccg aacctcagcc<br>cgactggtcc gaagccttcc agtgtgtgtc tgcagtagag gtggagatcc atgccggcgg<br>tctcaaccta gagccgtttc taaagcgcgt cgatgcggac gccgacccgc ggcagtatgc<br>tgacacggtc aaggctctcc gcgtgcggcg gctcacagtg ggagccgcac aggttcctgc<br>tcagctactg gtaggcgccc tgcgtgtgct agcgtactcc cgcctcaagg aactgacgct<br>cgaggaccta aagataaccg gcaccatgcc tccgctgcct ctggaagcca caggacttgc<br>actttccagc ttgcgcctac gcaacgtgtc gtgggcgaca gggcgttctt ggctcgccga<br>gctgcagcag tggctcaagc caggcctcaa ggtactgagc attgcccaag cacactcgcc<br>tgccttttcc tgcgaacagg ttcgcgcctt cccggccctt accagcctag acctgtctga<br>caatcctgga ctgggcgaac gcggactgat ggcggctctc tgtccccaca gttcccggcc<br>atccagaat ctagcgctgc gcaacacagg aatggagacg cccacaggcg tgtgcgccgc<br>actggcggcg gcaggtgtgc agccccacag tgccacaact cgctgcgccg<br>caccgtaaac cctagcgctc cgagatgcat gtggtccagc gccctgaact ccctcaatct<br>gtcgttcgct gggctgaac aggtgcctaa aggactgcca gccaagctca gagtgctcga<br>tctcagctgc aacagactga acagggcgcc gcagcctgac gagctgcccg aggtggataa<br>cctgacactg gacgggaatc ccttcctggt ccctggaact gccctccccc acgagggctc<br>aatgaactcc ggcgtggtcc cagcctgtgc acgttcgacc ctgtcggtgg gggtgtcggg<br>aaccctggtg ctgctccaa ggggccgggg ctttgcctaa gatccaagac agaataatga<br>atggactcaa actgccttgg cttcagggga gtcccgtcag gacgttgagg actttcgac<br>caattcaacc ctttgcccca cctttattaa aatcttaaac aacgggtcaa aaaaaaaaa<br>a |
| SEQ ID NO: 38<br>CD14<br>NCBI Reference Sequence:<br>NP_001167575.1 | MERASCLLLL LLPLVHVSAT TPEPCELDDE DFRCVCNFSE<br>PQPDWSEAFQ CVSAVEVEIH AGGLNLEPFL KRVDADADPR<br>QYADTVKALR VRRLTVGAAQ VPAQLLVGAL RVLAYSRLKE<br>LTLEDLKITG TMPPLPLEAT GLALSSLRLR NVSWATGRSW<br>LAELQQWLKP GLKVLSIAQA HSPAFSCEQV RAFPALTSLD<br>LSDNPGLGER GLMAALCPHK FPAIQNLALR NTGMETPTGV<br>CAALAAAGVQ PHSLDLSHNS LRATVNPSAP RCMWSSALNS<br>LNLSFAGLEQ VPKGLPAKLR VLDLSCNRLN RAPQPDELPE<br>VDNLTLDGNP FLVPGTALPH EGSMNSGVVP ACARSTLSVG<br>VSGTLVLLQG ARGFA |

SEQUENCE LISTING SUMMARY

| DESIGNATION | SEQUENCE |
| --- | --- |
| SEQ ID NO: 39<br>CD14<br>NCBI Reference<br>Sequence:<br>NM_001174104.1 | aattctaccc cccttggtgc caacagatga ggttcacaat ctcttccaca aaacatgcag<br>ttaaatatct gaggatattc agggacttgg atttggtggc aggagatcaa cataaaccaa<br>gacaaggaag aagtcaaaga aatgaatcaa gtagattctc tgggatataa ggaaaggaag<br>ggggctggct cggaggaaga gaggtgggga ggtgatcagg gttcacagag agggaactg<br>aatgacatcc caggattaca taaactgtca gaggcagccg aagagttcac aagtgtgaag<br>cctggaagcc ggcgggtgcc gctgtgtagg aaagaagcta aagcacttcc agagcctgtc<br>cggagctcag aggttcggaa gacttatcga ccatggagcg cgcgtcctgc ttgttgctgc<br>tgctgctgcc gctggtgcac gtctctgcga ccacgccaga accttgtgag ctggacgatg<br>aagatttccg ctgcgtctgc aacttctccg aacctcagcc cgactggtcc gaagccttcc<br>agtgtgtgtc tgcagtagag gtggagatcc atgccggcgg tctcaaccta agccgtttc<br>taaagcgcgt cgatgcggac gccgacccgc ggcagtatgc tgacacggtc aaggctctcc<br>gcgtgcggcg gctcacagtg ggagccgcac aggttcctgc tcagctactg gtaggcgccc<br>tgcgtgtgct agcgtactcc cgcctcaagg aactgacgct cgaggaccta agataaccg<br>gcaccatgcc tccgctgcct ctggaagcca caggacttgc acttccagc ttgcgcctac<br>gcaacgtgtc gtgggcgaca gggcgttctt ggctcgccga gctgcagcag tggctcaagc<br>caggcctcaa ggtactgagc attgcccaag cacactcgcc tgccttttcc tgcgaacagg<br>ttcgcgcctt cccgccctt accagcctag acctgtctga caatcctgga ctgggcgaac<br>gcggactgat ggcggctctc tgtccccaca gttcccggcc catccagaat ctagcgctgc<br>gcaacacagg aatggagacg cccacaggcg tgtgcgccgc actggcggcg caggtgtgc<br>agccccacag cctagacctc agccacaact cgctgcgcgc caccgtaaac cctagcgctc<br>cgagatgcat gtggtccagc ccctgaact ccctcaatct gtcgttcgct gggctggaac<br>aggtgcctaa aggactgcca gccaagctca ggctgtcga tctcagctgc aacagactga<br>acagggcgcc gcagcctgac gagctgcccg aggtggataa cctgacactg gacgggaatc<br>ccttcctggt ccctggaact gccctccccc acgagggctc aatgaactcc ggcgtggtcc<br>cagcctgtgc acgttcgacc ctgtcggtgg ggtgtcggga accctggtg ctgctccaag<br>gggcccgggg cttttgcctaa gatccaagac agaataatga atggactcaa actgccttgg<br>cttcagggga gtcccgtcag gacgttgagg acttttcgac caattcaacc ctttgcccca<br>cctttattaa aatcttaaac aacgggtcaa aaaaaaaaa a |
| SEQ ID NO: 40<br>CD14<br>NCBI Reference<br>Sequence:<br>NP_001167576.1 | MERASCLLLL LLPLVHVSAT TPEPCELDDE DFRCVCNFSE<br>PQPDWSEAFQ CVSAVEVEIH AGGLNLEPFL KRVDADADPR<br>QYADTVKALR VRRLTVGAAQ VPAQLLVGAL RVLAYSRLKE<br>LTLEDLKITG TMPPLPLEAT GLALSSLRLR NVSWATGRSW<br>LAELQQWLKP GLKVLSIAQA HSPAFSCEQV RAFPALTSLD<br>LSDNPGLGER GLMAALCPHK FPAIQNLALR NTGMETPTGV<br>CAALAAAGVQ PHSLDLSHNS LRATVNPSAP RCMWSSALNS<br>LNLSFAGLEQ VPKGLPAKLR VLDLSCNRLN RAPQPDELPE<br>VDNLTLDGNP FLVPGTALPH EGSMNSGVVP ACARSTLSVG<br>VSGTLVLLQG ARGFA |
| SEQ ID NO: 41<br>CD14<br>NCBI Reference<br>Sequence:<br>NM_001174105.1 | aattctaccc cccttggtgc caacagatga ggttcacaat ctcttccaca aaacatgcag<br>ttaaatatct gaggatattc agggacttgg atttggtggc aggagatcaa cataaaccaa<br>gacaaggaag aagtcaaaga aatgaatcaa gtagattctc tgggatataa ggaaaggaag<br>gacaaggaag aagtcaaaga aatgaatcaa ggcagccga agagttcaca agtgtgaagc<br>ctggaagccg gcgggtgccg ctgtgtagga aagaagctaa agcacttcca gagcctgtcc<br>ggagctcaga ggttcggaaa acttatcgac catggagcgc gcgtcctgct tgttgctgct<br>gctgctgccg ctggtgcacg tctctgcgac cacgccagaa ccttgtgagc tggacgatga<br>agatttccgc tgcgtctgca acttctccga acctcagccc gactggtccg aagccttcca<br>gtgtgtgtct gcagtagagg tggagatcca tgccggcggt ctcaacctag agccgtttct<br>aaagcgcgtc gatgcggacg ccgacccgcg gcagtatgct gacacggtca aggctctccg<br>cgtgcggcgg ctcacagtgg gagccgcaca ggttcctgct cagctactgg taggcgccct<br>gcgtgtgcta gcgtactccc gcctcaagga actgacgctc gaggacctaa agataaccgg<br>caccatgcct ccgctgcctc tggaagccac aggacttgca cttccagct gcgcctacg<br>caacgtgtcg tgggcgacag gcgttcttg gctcgccgag ctgcagcagt ggctcaagcc<br>aggcctcaag gtactgagca ttgcccaagc acactcgcct gccttttcct gcgaacaggt<br>tcgcgccttc ccggccctta ccagcctaga cctgtctgac aatcctggac tgggcgaacg<br>cggactgatg gcggctctct gtccccacaa gttcccggcc atccagaatc tagcgctgcg<br>caacacagga atggagacgc ccacaggcgt gtgcgccgca ctggcggcgg caggtgtgca<br>gccccacagc ctagacctca gccacaactc gctgcgcgcc accgtaaacc ctagcgctcc<br>gagatgcatg tggtccagcc cctgaactc ctcaatctg tcgttcgctg ggctggaaca<br>ggtgcctaaa ggactgccaa ccaagctgca gtgctcgat ctcagctgca acagactgaa<br>cagggcgccg cagcctgacg agctgcccga ggtggataac ctgacactgg acgggaatcc<br>cttcctgtc cctggaactg ccctccccca gagggctca atgaactccg gcgtggtccc<br>agcctgtgca cgttcgaccc tgtcggtggg gtgtcggga accctggtgc tgctccaagg<br>ggcccggggc ttttgcctaag atccaagaca gaataatgaa tggactcaaa ctgccttggc<br>ttcagggag tcccgtcagg acgttgagga cttttcgac aattcaaccc tttgccccac<br>ctttattaaa atcttaaaca acgggtcaaa aaaaaaaaa |
| SEQ ID NO: 42<br>cell surface<br>glycoprotein<br>CD200 receptor 1<br>isoform a<br>precursor [*Homo<br>sapiens*]<br>NCBI Reference | MLCPWRTANL GLLLILTIFL VAEAEGAAQP NNSLMLQTSK<br>ENHALASSSL CMDEKQITQN YSKVLAEVNT SWPVKMATNA<br>VLCCPPIALR NLIIITWEII LRGQPSCTKA YKKETNETKE<br>TNCTDERITW VSRPDQNSDL QIRTVAITHD GYYRCIMVTP<br>DGNFHRGYHL QVLVTPEVTL FQNRNRTAVC KAVAGKPAAH<br>ISWIPEGDCA TKQEYWSNGT TVVKSTCHWE VHNVSTVTCH<br>VSHLTGNKSL YIELLPVPGA KKSAKLYIPY IILTIIILTI VGFIWLLKVN<br>GCRKYKLNKT ESTPVVEEDE MQPYASYTEK NNPLYDTTNK |

SEQUENCE LISTING SUMMARY

| DESIGNATION | SEQUENCE |
|---|---|
| Sequence: NP_620161.1 | VKASEALQSE VDTDLHTL |
| SEQ ID NO: 43 cell surface glycoprotein CD200 receptor 1 isoform b precursor [Homo sapiens] NCBI Reference Sequence: NP_620385.1 | MLCPWRTANL GLLLILTIFL VAEAEGAAQP NNSLMLQTSK ENHALASSSL CMDEKQITQN YSKVLAEVNT SWPVKMATNA VLCCPPIALR NLIIITWEII LRGQPSCTKA YKKETNETKE TNCTDERITW VSRPDQNSDL QIRTVAITHD GYYRCIMVTP DGNFHRGYHL QVLGKEHHILRYFTSPDL |
| SEQ ID NO: 44 cell surface glycoprotein CD200 receptor 1 isoform c precursor [Homo sapiens] NCBI Reference Sequence: NP_620386.1 | MLCPWRTANL GLLLILTIFL VAASSSLCMD EKQITQNYSK VLAEVNTSWP VKMATNAVLC CPPIALRNLI IITWEIILRG QPSCTKAYKK ETNETKETNC TDERITWVSR PDQNSDLQIR TVAITHDGYY RCIMVTPDGN FHRGYHLQVL GKEHHILRYF TSPDL |
| SEQ ID NO: 45 cell surface glycoprotein CD200 receptor 1 isoform d precursor [Homo sapiens] NCBI Reference Sequence: NP_740750.1 | MLCPWRTANL GLLLILTIFL VAASSSLCMD EKQITQNYSK VLAEVNTSWP VKMATNAVLCCPPIALRNLI IITWEIILRG QPSCTKAYKK ETNETKETNC TDERITWVSR PDQNSDLQIR TVAITHDGYY RCIMVTPDGN FHRGYHLQVL VTPEVTLFQN RNRTAVCKAV AGKPAAHISWIPEGDCATKQ EYWSNGTVTV KSTCHWEVHN VSTVTCHVSH LTGNKSLYIE LLPVPGAKKS AKLYIPYIIL TIIILTIVGF IWLLKVNGCR KYKLNKTEST PVVE EDEMQP YASYTEKNNPLYDTTNKVKA SEALQSEVDT DLHTL |
| SEQ ID NO: 46 CD200 isoform d NCBI Reference Sequence: NP_001305757.1 | MVTFSENHGV VIQPAYKDKI NITQLGLQNS TITFWNITLE DEGCYMC TFGFGKISGTACLTVYVQPI VSLHYKFSED HLNITCSATA RPAPMVFW PRSGIENSTV TLSHPNGTTSVTSILHIKDP KNQVGKEVIC QVLHLGTVT FKQTVNKGYW FSVPLLLSIV SLVILLVLISILLYWKRHRN QDREP |

What is claimed is:

1. A method for treating a patient having cancer who has been determined to have positive expression of CD200 receptor (CD200R1) and one or more biomarkers in a biological sample from the patient, the method comprising administering to the patient a CD200 inhibitor in an amount and with a frequency sufficient to reduce the cancer burden in the patient, compared to the cancer burden in the patient prior to treatment with the CD200 inhibitor, wherein the one or more biomarkers are selected from the group consisting of Inducible T-cell COStimulator (ICOS), T Cell Immunoreceptor with Ig and ITIM Domains (TIGIT), Tumor Necrosis Factor Receptor Superfamily Member 9 (TNFRSP9), Hepatitis A Virus Cellular Receptor 2 (HAVCR2), Programmed Cell Death 1 (PDCD1), Fc Fragment Of IgG Receptor IIa (FCGR2A), Fc Fragment Of IgG Receptor Ia (FCGR1A), Cluster of Differentiation 163 (CD163), and Cluster of Differentiation 14 (CD14).

2. The method of claim 1, wherein the CD200 inhibitor is selected from the group consisting of a small molecule, a polypeptide, a polypeptide analog, a peptidomimetic, and an aptamer.

3. The method of claim 1, wherein the CD200 inhibitor is an antibody, or an antigen-binding fragment thereof.

4. The method of claim 3, wherein the antibody, or antigen-binding fragment thereof, is selected from the group consisting of a humanized antibody, a recombinant antibody, a diabody, a chimerized or chimeric antibody, a monoclonal antibody, a deimmunized antibody, a fully human antibody, a single chain antibody, an $F_v$ fragment, an $F_d$ fragment, an Fab fragment, an Fab' fragment, and an $F(ab')_2$ fragment.

5. The method of claim 3, wherein the antibody comprises a heavy chain variable region CDR1 having the sequence set forth in SEQ ID NO: 7, a heavy chain variable region CDR2 having the sequence set forth in SEQ ID NO: 8, a heavy chain variable region CDR3 having the sequence set forth in SEQ ID NO: 9, a light chain variable region CDR1 having the sequence set forth in SEQ ID NO: 4, a light chain variable region CDR2 having the sequence set forth in SEQ ID NO: 5, and a light chain variable region CDR3 having the sequence set forth in SEQ ID NO: 6.

6. The method of claim 3, wherein the antibody comprises a heavy chain variable region comprising SEQ ID NO: 13 and a light chain variable region comprising SEQ ID NO: 12.

7. The method of claim 3, wherein the antibody is samalizumab or a variant of samalizumab.

8. The method of claim 3, wherein the antibody or an antigen-binding fragment thereof, is administered at a dose of about 5 mg/kg to about 50 mg/kg.

9. The method of claim 3, wherein the antibody is administered at a dose of about 1 mg/kg to about 20 mg/kg.

10. The method of claim 3, wherein the antibody is administered at a dose of about 10 mg/kg, about 15 mg/kg, about 20 mg/kg, or about 40 mg/kg.

11. The method of claim 1, wherein expression levels of CD200R1 and the one or more biomarkers are measured by quantitation of protein and/or RNA levels, using at least one of an immunoassay, immunochemistry assay, immunohistochemistry assay, nucleoprobe assay, in situ hybridization, fluorescent RNA probes, RT-PCR, microarray transcription assay, and RNA transcription assay.

12. The method of claim 11, wherein the immunoassay is an enzyme-linked immunosorbent assay (ELISA) or a radioimmunoassay (MA).

13. The method of claim 1, wherein the biological sample is at least one of tumor tissue, tumor cells, blood, and a blood fraction.

14. The method of claim 1, wherein: (i) expression levels of CD200R1 and of one or more biomarkers are measured in two or more types of biological samples; or (ii) expression levels of CD200R1 and of one or more biomarkers are measured in one type of biological sample and levels of a second biomarker are measured in a second type of biological sample.

15. The method of claim 1, wherein the positive expression of CD200R1 in the biological sample is equal to or greater than expression of CD200R1 in a normal biological sample of the same type.

16. The method of claim 1, wherein the positive expression of the one more biomarkers in the biological sample is equal to or greater than expression of the one or more biomarkers in a normal biological sample of the same type.

17. The method of claim 1, further comprising measuring CD200 expression in the biological sample and identifying patients with tumors having elevated expression of CD200, wherein the elevated expression of CD200 in the biological sample is greater than median expression levels of CD200 in normal tissue.

18. The method of claim 1, wherein the patient has been determined to have elevated expression levels of CD200R1 and at least one biomarker selected from the group consisting of ICOS, TIGIT, TNFRSF9, HAVCR2, PDCD1, FCGR2A, FCGRIA, CD163, and CD14.

19. The method of claim 1, wherein the patient is an adult and the cancer is selected from the group consisting of diffuse large B cell lymphoma (DLBL), lung adenocarcinoma (LUAD), lung squamous cell carcinoma (LUSC), glioblastoma (GBM), low grade glioma (LGG), clear cell RCC (KIRC), chromophobe (KICH), papillary cell RCC (KIRP), melanoma (SKCM), ovarian cancer (OV), colon cancer (COAD), rectum cancer (READ), uterine endometrial cancer (UCEC).

20. The method of claim 1, wherein the patient is a pediatric patient, and the cancer is selected from atypical teratoid rhabdoid tumor (AT/RT), ependymoma, osteosarcoma, rhabdomyosarcoma, Ewing sarcoma, pilocytic astrocytoma, neuroblastoma, and retinoblastoma.

21. The method of claim 19, wherein the cancer is DLBL, LUAD, or GBM.

* * * * *

SEQUENCE LISTING

<160> NUMBER OF SEQ ID NOS: 46

<210> SEQ ID NO 1
<211> LENGTH: 269
<212> TYPE: PRT
<213> ORGANISM: Homo sapiens

<400> SEQUENCE: 1

```
Met Glu Arg Leu Val Ile Arg Met Pro Phe Ser His Leu Ser Thr Tyr
1               5                   10                  15
Ser Leu Val Trp Val Met Ala Ala Val Val Leu Cys Thr Ala Gln Val
            20                  25                  30
Gln Val Val Thr Gln Asp Glu Arg Glu Gln Leu Tyr Thr Pro Ala Ser
        35                  40                  45
Leu Lys Cys Ser Leu Gln Asn Ala Gln Glu Ala Leu Ile Val Thr Trp
    50                  55                  60
Gln Lys Lys Lys Ala Val Ser Pro Glu Asn Met Val Thr Phe Ser Glu
65                  70                  75                  80
Asn His Gly Val Val Ile Gln Pro Ala Tyr Lys Asp Lys Ile Asn Ile
                85                  90                  95
```

-continued

```
Thr Gln Leu Gly Leu Gln Asn Ser Thr Ile Thr Phe Trp Asn Ile Thr
            100                 105                 110
Leu Glu Asp Glu Gly Cys Tyr Met Cys Leu Phe Asn Thr Phe Gly Phe
        115                 120                 125
Gly Lys Ile Ser Gly Thr Ala Cys Leu Thr Val Tyr Val Gln Pro Ile
    130                 135                 140
Val Ser Leu His Tyr Lys Phe Ser Glu Asp His Leu Asn Ile Thr Cys
145                 150                 155                 160
Ser Ala Thr Ala Arg Pro Ala Pro Met Val Phe Trp Lys Val Pro Arg
                165                 170                 175
Ser Gly Ile Glu Asn Ser Thr Val Thr Leu Ser His Pro Asn Gly Thr
            180                 185                 190
Thr Ser Val Thr Ser Ile Leu His Ile Lys Asp Pro Lys Asn Gln Val
        195                 200                 205
Gly Lys Glu Val Ile Cys Gln Val Leu His Leu Gly Thr Val Thr Asp
    210                 215                 220
Phe Lys Gln Thr Val Asn Lys Gly Tyr Trp Phe Ser Val Pro Leu Leu
225                 230                 235                 240
Leu Ser Ile Val Ser Leu Val Ile Leu Val Leu Ile Ser Ile Leu
                245                 250                 255
Leu Tyr Trp Lys Arg His Arg Asn Gln Asp Arg Glu Pro
            260                 265

<210> SEQ ID NO 2
<211> LENGTH: 294
<212> TYPE: PRT
<213> ORGANISM: Homo sapiens

<400> SEQUENCE: 2

Met Glu Arg Leu Thr Leu Thr Arg Thr Ile Gly Gly Pro Leu Leu Thr
1               5                   10                  15
Ala Thr Leu Leu Gly Lys Thr Thr Ile Asn Asp Tyr Gln Val Ile Arg
            20                  25                  30
Met Pro Phe Ser His Leu Ser Thr Tyr Ser Leu Val Trp Val Met Ala
        35                  40                  45
Ala Val Val Leu Cys Thr Ala Gln Val Gln Val Val Thr Gln Asp Glu
    50                  55                  60
Arg Glu Gln Leu Tyr Thr Pro Ala Ser Leu Lys Cys Ser Leu Gln Asn
65                  70                  75                  80
Ala Gln Glu Ala Leu Ile Val Thr Trp Gln Lys Lys Lys Ala Val Ser
                85                  90                  95
Pro Glu Asn Met Val Thr Phe Ser Glu Asn His Gly Val Val Ile Gln
            100                 105                 110
Pro Ala Tyr Lys Asp Lys Ile Asn Ile Thr Gln Leu Gly Leu Gln Asn
        115                 120                 125
Ser Thr Ile Thr Phe Trp Asn Ile Thr Leu Glu Asp Glu Gly Cys Tyr
    130                 135                 140
Met Cys Leu Phe Asn Thr Phe Gly Phe Gly Lys Ile Ser Gly Thr Ala
145                 150                 155                 160
Cys Leu Thr Val Tyr Val Gln Pro Ile Val Ser Leu His Tyr Lys Phe
                165                 170                 175
Ser Glu Asp His Leu Asn Ile Thr Cys Ser Ala Thr Ala Arg Pro Ala
            180                 185                 190
Pro Met Val Phe Trp Lys Val Pro Arg Ser Gly Ile Glu Asn Ser Thr
        195                 200                 205
```

```
Val Thr Leu Ser His Pro Asn Gly Thr Thr Ser Val Thr Ser Ile Leu
    210                 215                 220

His Ile Lys Asp Pro Lys Asn Gln Val Gly Lys Glu Val Ile Cys Gln
225                 230                 235                 240

Val Leu His Leu Gly Thr Val Thr Asp Phe Lys Gln Thr Val Asn Lys
                245                 250                 255

Gly Tyr Trp Phe Ser Val Pro Leu Leu Leu Ser Ile Val Ser Leu Val
            260                 265                 270

Ile Leu Leu Val Leu Ile Ser Ile Leu Leu Tyr Trp Lys Arg His Arg
        275                 280                 285

Asn Gln Asp Arg Glu Pro
    290

<210> SEQ ID NO 3
<211> LENGTH: 153
<212> TYPE: PRT
<213> ORGANISM: Homo sapiens

<400> SEQUENCE: 3

Met Lys Gly Val Thr Cys Val Ser Ser Ile Pro Leu Val Leu Gly Arg
1               5                   10                  15

Ser Gln Glu Arg Pro Ala Ser Pro Ser Met Pro Ile Val Ser Leu His
                20                  25                  30

Tyr Lys Phe Ser Glu Asp His Leu Asn Ile Thr Cys Ser Ala Thr Ala
            35                  40                  45

Arg Pro Ala Pro Met Val Phe Trp Lys Val Pro Arg Ser Gly Ile Glu
        50                  55                  60

Asn Ser Thr Val Thr Leu Ser His Pro Asn Gly Thr Thr Ser Val Thr
65                  70                  75                  80

Ser Ile Leu His Ile Lys Asp Pro Lys Asn Gln Val Gly Lys Glu Val
                85                  90                  95

Ile Cys Gln Val Leu His Leu Gly Thr Val Thr Asp Phe Lys Gln Thr
            100                 105                 110

Val Asn Lys Gly Tyr Trp Phe Ser Val Pro Leu Leu Leu Ser Ile Val
        115                 120                 125

Ser Leu Val Ile Leu Leu Val Leu Ile Ser Ile Leu Leu Tyr Trp Lys
    130                 135                 140

Arg His Arg Asn Gln Asp Arg Glu Pro
145                 150

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Lys Ala Ser Gln Asp Ile Asn Ser Tyr Leu Ser
1               5                   10

<210> SEQ ID NO 5
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 5

Arg Ala Asn Arg Leu Val Asp
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Leu Gln Tyr Asp Glu Phe Pro Tyr Thr
1               5

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Tyr Ser Phe Thr Asp Tyr Ile Ile Leu
1               5                   10

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

His Ile Asp Pro Tyr Tyr Gly Ser Ser Asn Tyr Asn Leu Lys Phe Lys
1               5                   10                  15

Gly

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Lys Arg Asp Tyr Phe Asp Tyr
1               5

<210> SEQ ID NO 10
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 10

Asp Ile Gln Met Thr Gln Ser Pro Ser Ser Leu Ser Ala Ser Ile Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Ser Phe Thr Asp Tyr
            20                  25                  30

Ile Ile Leu Trp Val Arg Gln Asn Pro Gly Lys Gly Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Ala Asp Gln Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Thr
            100                 105                 110

Leu Thr Val Ser Ser Ala Ser Thr Lys Gly Pro Ser Val Phe Pro Leu
```

```
            115                 120                 125
Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 12
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Gln Met Thr Gln Ser Pro Ser Ser Leu Ser Ala Ser Ile Gly
1               5                   10                  15

Asp Arg Val Thr Ile Thr Cys Lys Ala Ser Gln Asp Ile Asn Ser Tyr
            20                  25                  30
```

```
Leu Ser Trp Phe Gln Gln Lys Pro Gly Lys Ala Pro Lys Leu Leu Ile
                35                  40                  45

Tyr Arg Ala Asn Arg Leu Val Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Val Tyr Tyr Cys Leu Gln Tyr Asp Glu Phe Pro Tyr
                 85                  90                  95

Thr Phe Gly Gly Gly Thr Lys Leu Glu Ile Lys Arg
                100                 105
```

<210> SEQ ID NO 13
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

```
Gln Val Gln Leu Gln Gln Ser Gly Ser Glu Leu Lys Lys Pro Gly Ala
 1               5                  10                  15

Ser Val Lys Ile Ser Cys Lys Ala Ser Gly Tyr Ser Phe Thr Asp Tyr
                 20                  25                  30

Ile Ile Leu Trp Val Arg Gln Asn Pro Gly Lys Gly Leu Glu Trp Ile
                35                  40                  45

Gly His Ile Asp Pro Tyr Tyr Gly Ser Ser Asn Tyr Asn Leu Lys Phe
 50                  55                  60

Lys Gly Arg Val Thr Ile Thr Ala Asp Gln Ser Thr Thr Thr Ala Tyr
 65                  70                  75                  80

Met Glu Leu Ser Ser Leu Arg Ser Glu Asp Thr Ala Val Tyr Tyr Cys
                 85                  90                  95

Gly Arg Ser Lys Arg Asp Tyr Phe Asp Tyr Trp Gly Gln Gly Thr Thr
                100                 105                 110

Leu Thr Val Ser Ser
            115
```

<210> SEQ ID NO 14
<211> LENGTH: 199
<212> TYPE: PRT
<213> ORGANISM: Homo sapiens

<400> SEQUENCE: 14

```
Met Lys Ser Gly Leu Trp Tyr Phe Phe Leu Phe Cys Leu Arg Ile Lys
 1               5                  10                  15

Val Leu Thr Gly Glu Ile Asn Gly Ser Ala Asn Tyr Glu Met Phe Ile
                 20                  25                  30

Phe His Asn Gly Gly Val Gln Ile Leu Cys Lys Tyr Pro Asp Ile Val
                35                  40                  45

Gln Gln Phe Lys Met Gln Leu Leu Lys Gly Gly Gln Ile Leu Cys Asp
 50                  55                  60

Leu Thr Lys Thr Lys Gly Ser Gly Asn Thr Val Ser Ile Lys Ser Leu
 65                  70                  75                  80

Lys Phe Cys His Ser Gln Leu Ser Asn Asn Ser Val Ser Phe Phe Leu
                 85                  90                  95

Tyr Asn Leu Asp His Ser His Ala Asn Tyr Tyr Phe Cys Asn Leu Ser
```

```
                    100                 105                 110
Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
            130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 15
<211> LENGTH: 2652
<212> TYPE: DNA
<213> ORGANISM: Homo sapiens

<400> SEQUENCE: 15
cgagagcctg aattcactgt cagctttgaa cactgaacgc gaggactgtt aactgtttct      60
ggcaaacatg aagtcaggcc tctggtattt ctttctcttc tgcttgcgca ttaaagtttt     120
aacaggagaa atcaatggtt ctgccaatta tgagatgttg tatttcaca acggaggtgt     180 acaaatttta tgcaaatatc ctgacattgt ccagcaattt aaaatgcagt tgctgaaagg     240
ggggcaaata ctctgcgatc tcactaagac aaaaggaagt ggaaacacag tgtccattaa     300
gagtctgaaa ttctgccatt ctcagttatc caacaacagt gtctcttttt ttctatacaa     360
cttggaccat tctcatgcca actattactt ctgcaaccta tcaatttttg atcctcctcc     420 tttttaaagta actcttacag gaggatattt gcatatttat gaatcacaac tttgttgcca     480
gctgaagttc tggttaccca taggatgtgc agcctttgtt gtagtctgca tttttgggatg     540 catacttatt tgttggctta caaaaaagaa gtattcatcc agtgtgcacg accctaacgg     600
tgaatacatg ttcatgagag cagtgaacac agccaaaaaa tctagactca cagatgtgac     660
cctataatat ggaactctgg cacccaggca tgaagcacgt tggccagttt tcctcaactt     720
gaagtgcaag attctcttat ttccgggacc acggagagtc tgacttaact acatacatct     780
tctgctggtg ttttgttcaa tctggaagaa tgactgtatc agtcaatggg attttaaca     840 gactgccttg gtactgccga gtcctctcaa aacaaacacc ctcttgcaac cagctttgga     900
gaaagcccag ctcctgtgtg ctcactggga gtggaatccc tgtctccaca tctgctccta     960
gcagtgcatc agccagtaaa acaaacacat ttacaagaaa aatgttttaa agatgccagg    1020
ggtactgaat ctgcaaagca atgagcagc caaggaccag catctgtccg catttcacta    1080
tcatactacc tcttctttct gtagggatga gaattcctct tttaatcagt caagggagat    1140
gcttcaaagc tggagctatt ttatttctga tgttgatg tgaactgtac attagtacat     1200
actcagtact ctccttcaat tgctgaaccc cagttgacca ttttaccaag actttagatg    1260
ctttcttgtg ccctcaattt tcttttaaa aatacttcta catgactgct tgacagccca    1320
acagccactc tcaatagaga gctatgtctt acattctttc ctctgctgct caatagtttt    1380
atatatctat gcatacatat atacacacat atgtatataa aattcataat gaatatattt    1440
gcctatattc tccctacaag aatattttg ctccagaaag acatgttctt ttctcaaatt    1500
cagttaaaat ggtttacttt gttcaagtta gtggtaggaa acattgcccg gaattgaaag    1560
```

-continued

```
caaatttatt ttattatcct attttctacc attatctatg ttttcatggt gctattaatt    1620
acaagtttag ttcttttgt agatcatatt aaaattgcaa acaaaatcat ctttaatggg    1680
ccagcattct catggggtag agcagaatat tcatttagcc tgaaagctgc agttactata    1740
ggttgctgtc agactatacc catggtgcct ctgggcttga caggtcaaaa tggtccccat    1800
cagcctggag cagccctcca gacctgggtg gaattccagg gttgagagac tccctgagc    1860 cagaggccac taggtattct tgctcccaga ggctgaagtc accctgggaa tcacagtggt    1920
ctacctgcat tcataattcc aggatctgtg aagagcacat atgtgtcagg gcacaattcc    1980
ctctcataaa aaccacacag cctggaaatt ggccctggcc cttcaagata gccttcttta    2040
gaatatgatt tggctagaaa gattcttaaa tatgtggaat atgattattc ttagctggaa    2100
tattttctct acttcctgtc tgcatgccca aggcttctga agcagccaat gtcgatgcaa    2160
caacatttgt aactttaggt aaactgggat tatgttgtag tttaacatt tgtaactgtg    2220 tgcttatagt ttacaagtga gacccgatat gtcattatgc atacttatat tatcttaagc    2280
atgtgtaatg ctggatgtgt acagtacagt actgaacttg taatttgaat ctagtatggt    2340
gttctgtttt cagctgactt ggacaacctg actggctttg cacaggtgtt ccctgagttg    2400
tttgcaggtt tctgtgtgtg gggtggggta tggggaggag aaccttcatg gtggcccacc    2460
tggcctggtt gtccaagctg tgcctcgaca catcctcatc cccagcatgg gacacctcaa    2520
gatgaataat aattcacaaa atttctgtga aatcaaatcc agttttaaga ggagccactt    2580
atcaaagaga ttttaacagt agtaagaagg caaagaataa acatttgata ttcagcaact    2640
gaaaaaaaaa aa    2652
```

<210> SEQ ID NO 16
<211> LENGTH: 244
<212> TYPE: PRT
<213> ORGANISM: Homo sapiens

<400> SEQUENCE: 16

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175
```

```
Gly Asp Leu Arg Arg Lys Ser Ala Gly Gln Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 17
<211> LENGTH: 2978
<212> TYPE: DNA
<213> ORGANISM: Homo sapiens

<400> SEQUENCE: 17
```

| | | | | |
|---|---|---|---|---|
| cgtcctatct | gcagtcggct | actttcagtg | gcagaagagg | ccacatctgc | ttcctgtagg | 60 |
| ccctctgggc | agaagcatgc | gctggtgtct | cctcctgatc | tgggcccagg | ggctgaggca | 120 |
| ggctcccctc | gcctcaggaa | tgatgacagg | cacaatagaa | acaacgggga | acatttctgc | 180 |
| agagaaaggt | ggctctatca | tcttacaatg | tcacctctcc | tccaccacgg | cacaagtgac | 240 |
| ccaggtcaac | tgggagcagc | aggaccagct | tctggccatt | tgtaatgctg | acttggggtg | 300 |
| gcacatctcc | ccatccttca | aggatcgagt | ggccccaggt | cccggcctgg | gcctcaccct | 360 |
| ccagtcgctg | accgtgaacg | atacagggga | gtacttctgc | atctatcaca | cctaccctga | 420 |
| tgggacgtac | actgggagaa | tcttcctgga | ggtcctagaa | agctcagtgg | ctgagcacgg | 480 |
| tgccaggttc | cagattccat | tgcttggagc | catggccgcg | acgctggtgg | tcatctgcac | 540 |
| agcagtcatc | gtggtggtcg | cgttgactag | aaagaagaaa | gccctcagaa | tccattctgt | 600 |
| ggaaggtgac | ctcaggagaa | aatcagctgg | acaggaggaa | tggagcccca | gtgctccctc | 660 |
| acccccagga | agctgtgtcc | aggcagaagc | tgcacctgct | gggctctgtg | gagagcagcg | 720 |
| gggagaggac | tgtgccgagc | tgcatgacta | cttcaatgtc | ctgagttaca | gaagcctggg | 780 |
| taactgcagc | ttcttcacag | agactggtta | gcaaccagag | gcatcttctg | gaagatacac | 840 |
| ttttgtcttt | gctattatag | atgaatatat | aagcagctgt | actctccatc | agtgctgcgt | 900 |
| gtgtgtgtgt | gtgtgtatgt | gtgtgtgtgt | tcagttgagt | gaataaatgt | catcctcttc | 960 |
| tccatcttca | tttccttggc | cttttcgttc | tattccattt | tgcattatgg | caggcctagg | 1020 |
| gtgagtaacg | tggatcttga | tcataaatgc | aaaattaaaa | aatatcttga | cctggtttta | 1080 |
| aatctggcag | tttgagcaga | tcctatgtct | ctgagagaca | cattcctcat | aatggccagc | 1140 |
| attttgggct | acaaggtttt | gtggttgatg | atgaggatgg | catgactgca | gagccatcct | 1200 |
| catctcattt | tttcacgtca | ttttcagtaa | cttttcactca | ttcaaaggca | ggttataagt | 1260 |
| aagtcctggt | agcagcctct | atggggagat | ttgagagtga | ctaaatcttg | gtatctgccc | 1320 |
| tcaagaactt | acagttaaat | ggggagacaa | tgttgtcatg | aaaaggtatt | atagtaagga | 1380 |
| gagaaggaga | catacacagg | ccttcaggaa | gagacgacag | tttggggtga | ggtagttggc | 1440 |
| ataggcttat | ctgtgatgaa | gtggcctggg | agcaccaagg | ggatgttgag | gctagtctgg | 1500 |
| gaggagcagg | agttttgtct | agggaacttg | taggaaattc | ttggagctga | agtccccaca | 1560 |
| aagaaggccc | tggcaccaag | ggagtcagca | aacttcagat | tttattctct | gggcaggcat | 1620 |
| ttcaagtttc | cttttgctgt | gacatactca | tccattagac | agcctgatac | aggcctgtag | 1680 |

```
cctcttccgg ccgtgtgtgc tggggaagcc ccaggaaacg cacatgccca cacagggagc    1740
caagtcgtag catttgggcc ttgatctacc ttttctgcat caatacactc ttgagccttt    1800 gaaaaagaa cgtttcccac taaaaagaaa atgtggattt ttaaaatagg gactcttcct    1860
aggggaaaaa ggggggctgg gagtgataga gggtttaaaa aataaacacc ttcaaactaa    1920
cttcttcgaa cccttttatt cactccctga cgactttgtg ctggggttgg ggtaactgaa    1980
ccgcttattt ctgtttaatt gcattcaggc tggatcttag aagacttta tccttccacc     2040 atctctctca gaggaatgag cggggaggtt ggatttactg gtgactgatt ttctttcatg    2100
ggccaaggaa ctgaaagaga atgtgaagca aggttgtgtc ttgcgcatgg ttaaaaataa    2160
agcattgtcc tgcttcctaa gacttagact ggggttgaca attgttttag caacaagaca    2220
attcaactat ttctcctagg attttttatta ttattatttt ttcactttttc taccaaatgg   2280 gttacatagg aagaatgaac tgaaatctgt ccagagctcc aagtcctttg gaagaaagat    2340
tagatgaacg taaaaatgtt gttgtttgct gtggcagttt acagcatttt tcttgcaaaa    2400
ttagtgcaaa tctgttggaa atagaacaca attcacaaat tggaagtgaa ctaaaatgta    2460
atgacgaaaa gggagtagtg ttttgatttg gaggaggtgt atattcggca gaggttggac    2520
tgagagttgg gtgttattta acataattat ggtaattggg aaacatttat aaacactatt    2580
gggatggtga taaaatacaa aagggcctat agatgttaga atgggtcag gttactgaaa    2640 tgggattcaa tttgaaaaaa attttttaa atagaactca ctgaactaga ttctcctctg    2700
agaaccagag aagaccattt catagttgga ttcctggaga catgcgctat ccaccacgta    2760
gccactttcc acatgtggcc atcaaccact aagatgggg ttagtttaaa tcaagatgtg    2820
ctgttataat tggtataagc ataaaatcac actagattct ggagatttaa tatgaataat    2880
aagaatacta tttcagtagt tttggtatat tgtgtgtcaa aaatgataat attttggatg    2940
tattgggtga aataaaatat taacattaaa aaaaaaaa                            2978
```

<210> SEQ ID NO 18
<211> LENGTH: 255
<212> TYPE: PRT
<213> ORGANISM: Homo sapiens

<400> SEQUENCE: 18

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140
```

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
            165                 170                 175

Pro Ala Arg Glu Pro Gly His Ser Pro Gln Ile Ile Ser Phe Phe Leu
        180                 185                 190

Ala Leu Thr Ser Thr Ala Leu Leu Phe Leu Leu Phe Phe Leu Thr Leu
    195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 19
<211> LENGTH: 6001
<212> TYPE: DNA
<213> ORGANISM: Homo sapiens

<400> SEQUENCE: 19
caaggaggga tcccacagat gtcacagggc tgtcacagag ctgtggtggg aatttcccat      60
gagaccccgc ccctggctga gtcaccgcac tcctgtgttt gacctgaagt cctctcgagc    120
tgcagaagcc tgaagaccaa ggagtggaaa gttctccggc agccctgaga tctcaagagt    180
gacatttgtg agaccagcta atttgattaa aattctcttg gaatcagctt tgctagtatc    240
atacctgtgc cagatttcat catgggaaac agctgttaca acatagtagc cactctgttg    300
ctggtcctca actttgagag acaagatca ttgcaggatc cttgtagtaa ctgcccagct    360
ggtacattct gtgataataa caggaatcag atttgcagtc cctgtcctcc aaatagtttc    420
tccagcgcag gtggacaaag gacctgtgac atatgcaggc agtgtaaagg tgttttcagg    480
accaggaagg agtgttcctc caccagcaat gcagagtgtg actgcactcc agggtttcac    540
tgcctggggg caggatgcag catgtgtgaa caggattgta acaaggtca agaactgaca    600 aaaaaaggtt gtaaagactg ttgctttggg acatttaacg atcagaaacg tggcatctgt    660
cgaccctgga caaactgttc ttttgatgga aagtctgtgc ttgtgaatgg gacgaaggag    720
agggacgtgg tctgtggacc atctccagcc gacctctctc cgggagcatc ctctgtgacc    780
ccgcctgccc ctgcgagaga gccaggacac tctccgcaga tcatctcctt ctttcttgcg    840
ctgacgtcga ctgcgttgct cttcctgctg ttcttcctca cgctccgttt ctctgttgtt    900
aaacggggca gaaagaaact cctgtatata ttcaaacaac catttatgag accagtacaa    960
actactcaag aggaagatgg ctgtagctgc cgatttccag aagaagaaga aggaggatgt   1020
gaactgtgaa atggaagtca atagggctgt tgggactttc ttgaaaagaa gcaaggaaat   1080
atgagtcatc cgctatcaca gctttcaaaa gcaagaacac catcctacat aatacccagg   1140
attcccccaa cacacgttct tttctaaatg ccaatgagtt ggcctttaaa aatgcaccac   1200
tttttttttt ttttttgacag ggtctcactc tgtcacccag gctggagtgc agtggcacca   1260
ccatggctct ctgcagcctt gacctctggg agctcaagtg atcctcctgc ctcagtctcc   1320
tgagtagctg gaactacaag gaagggccac cacacctgac taactttttt gtttttttgtt   1380 tggtaaagat ggcatttcac catgttgtac aggctggtct caaactccta ggttcacttt   1440
ggcctcccaa agtgctggga ttacagacat gaactgccag gcccggccaa aataatgcac   1500

```
cacttttaac agaacagaca gatgaggaca gagctggtga taaaaaaaaa aaaaaaaaag    1560
cattttctag ataccactta acaggtttga gctagttttt ttgaaatcca agaaaatta     1620 tagtttaaat tcaattacat agtccagtgg tccaactata attataatca aaatcaatgc    1680
aggtttgttt tttggtgcta atatgacata tgacaataag ccacgaggtg cagtaagtac    1740
ccgactaaag tttccgtggg ttctgtcatg taacacgaca tgctccaccg tcagggggga    1800
gtatgagcag agtgcctgag tttagggtca aggacaaaaa acctcaggcc tggaggaagt    1860
tttggaaaga gttcaagtgt ctgtatatcc tatggtcttc tccatcctca caccttctgc    1920
ctttgtcctg ctccctttta agccaggtta cattctaaaa attcttaact tttaacataa    1980
tattttatac caaagccaat aaatgaactg catatgatag gtatgaagta cagtgagaaa    2040
attaacacct gtgagctcat tgtcctacca cagcactaga gtgggggccg ccaaactccc    2100
atggccaaac ctggtgcacc atttgccttt gtttgtctgt tggtttgctt gagacagtct    2160
tgctctgttg cccaggctgg aatggagtgg ctattcacag gcacaatcat agcacacttt    2220
agccttaaac tcctgggctc aagtgatcca cccgcctcag tctcccaagt agctgggatt    2280
acaggtgcaa acctggcatg cctgccattg tttggcttat gatctaagga tagcttttta    2340
aattttattc attttatttt tttttgagac agtgtctcac tctgtctccc aggctggagt    2400
acagtggtac aatcttggat caccgcctcc cagtttcaag tgatctccct gcctcagcct    2460
cctaagtagc tgggactaca ggtatgtgcc accacgcctg gctaatttt atattttag      2520 tagagacggg gtttcaccat gttgtccagg ctggtctcaa actcctgacc tcaggtgatc    2580
tgcccacctc tgcctcccaa agtgctggga ttacaggcat gagccaccat gcctggccat    2640
ttcttacact tttgtatgac atgcctattg caagcttgcg tgcctctgtc ccatgttatt    2700
ttactctggg atttaggtgg agggagcagc ttctatttgg aacattggcc atcgcatggc    2760
aaatgggtat ctgtcacttc tgctcctatt tagttggttc tactataacc tttagagcaa    2820
atcctgcagc caagccaggc atcaataggg cagaaaagta tattctgtaa atagggggtga   2880 ggagaagata tttctgaaca atagtctact gcagtaccaa attgcttttc aaagtggctg    2940
ttctaatgta ctcccgtcag tcatataagt gtcatgtaag tatcccattg atccacatcc    3000
ttgctaccct ctggtactat caggtgccct taattttgcc aagccagtgg gtatagaatg    3060
agatctcact gtggtcttag tttgcatttg cttggttact gatgagcacc ttgtcaaata    3120
tttatatacc atttgtgttt atttttttaa ataaaatgct tgctcatgct tttttgccca    3180
tttgcaaaaa aacttggggc cgggtgcagt ggctcatgcc tgtagtccca gctctttggg    3240
aggccaaggt gggcagatcg cttgagccca ggagttcgag accagccttg caacatggc     3300 gaaaccctgt ctttacaaaa aatacaaaaa ttagccgggt gtggtggtgt gcacctgaag    3360
tcccagctac tcagtaggtt cgctttgagc ctggaggca gaggttgcag tgagctggga     3420
ccgcatcact acacttcagc ctgggcaaca gagaaaaacc ttttctcaga aacaaacaaa    3480
cccaaatgtg gttgtttgtc ctgattccta aaaggtcttt atgtattcta gataataatc    3540
tttggtcagt tatatgtgtt aaaaaatatc ttctttgtgg ccaggcacgg tagctcacac    3600
ctgtaatccc agcactttgc ggggctgagg tgggtggatc atctgaggtc aagagttcaa    3660
gatcagcctg gccaacacag tgaaacccca tctctactaa acatgtacaa aacttagctg    3720
ggtatggtgg cgggtgcctg taaccccagc tgctccagag gctgtggcag aagaatcgct    3780
tgaacccagg aggcagaggt tgcagcgagc caagattgtg ccattgcact ccagactggg    3840
tgacaagagt gaaattctgc ctatctatct atctatctat ctatatctat atatatat      3900
```

```
atatatatcc tttgtaattt attttccct ttttaaaatt ttttataaaa ttctttttta    3960
tttttatttt tagcagaggt gaggtttctg aggtttcatt atgttgccca ggctggtctt    4020
gaactcctga gctcaagtga tcctcccacc tcagccttcc aaagtgctgg aattgcagac    4080
atgagccacc gcgcccctcc tgttttctc taattaatgg tgtctttctt tgtctttctg    4140
gtaataagca aaaagttctt catttgattt ggttaaattt ataactgttt tctcatatgg    4200
ttaacatttt ttcttgcctg gctaaagaaa tccttttctg cccaatacta taaagaggtt    4260
tgcccacatt ttattccaaa agtttaagt tttgtctttc atcttgaagt ctaatgtatc    4320
aggaactggc ttttgtgcct gttgggaggt agtgatccaa ttccatgtct tgcatgtagg    4380
taaccactgg tccctgcgcc atgtattcaa tacgtcgtct ttctcctgcg ggtctgcaat    4440
ctcacctacc atccatcaag tttccatagg gccatgggtc tgcttctggg ctccctgttc    4500
tgttccattg tcaatttgtc tatcctgtgc cagtatcaca ctgtgtttat tacaatagct    4560
ttgtaacagc tctcgatatc cggtaggaca tctccctcca ccttctttt ctacttcaga    4620 agtgtcttag ctaggtcagg cacggtggct cacgcctgta atcccagcac tttgggaggc    4680
cgacgcggat ggatcacctg aggtcaggag ttttgagaca gcctggccaa catggtgaaa    4740
ccccatctct actaaaaaat acaaaaatta gtcaggcatg gtggcatgtg cctgtaatcc    4800
cagctatttg ggaggctgag gccggagaat tgcttgaacc cggggggcgg aggttgcagt    4860
gagccgagat cgtaccattg cactccagcc tgggtgacag agcgaaactc tgtctcagga    4920 aaaaaagaa aagagatgtc ttggttattc ttggttcttt attattcaat ataaatttta    4980
gaagctgaat ttgaaaagat ttggattgga atttcattaa atctacaggt caatttaggg    5040
agagttgata attttacaga attgagtcat ctggtgttcc aataagaata agagaacaat    5100
tattggctgt acaattcttg ccaaatagta ggcaaagcaa agcttaggaa gtatactggt    5160
gccatttcag gaacaaagct aggtgcgaat atttttgtct ttctgaatca tgatgctgta    5220
agttctaaag tgatttctcc tcttggcttt ggacacatgg tgtttaatta cctactgctg    5280
actatccaca aacagaaaga gactggtcat gccccacagg gttggggtat ccaagataat    5340
ggagcgaggc tctcatgtgt cctaggttac acaccgaaaa tccacagttt attctgtgaa    5400
gaaaggaggc tatgtttatg atacagactg tgatatttt atcatagcct attctggtat    5460
catgtgcaaa agctataaat gaaaacaca ggaacttggc atgtgagtca ttgctccccc    5520
taaatgacaa ttaataagga aggaacattg agacagaata aaatgatccc cttctgggtt    5580
taatttagaa agttccataa ttaggtttaa tagaaataaa tgtaaatttc tatgattaaa    5640 aataaaattag cacatttagg gatacacaaa ttataaatca ttttctaaat gctaaaaaca    5700
agctcaggtt ttttcagaa gaaagtttta atttttttc tttagtggaa gatatcactc    5760
tgacggaaag ttttgatgtg aggggcggat gactataaag tgggcatctt cccccacagg    5820
aagatgtttc catctgtggg tgagaggtgc ccaccgcagc tagggcaggt tacatgtgcc    5880
ctgtgtgtgg taggacttgg agagtgatct ttatcaacgt ttttatttaa aagactatct    5940
aataaaacac aaaactatga tgttcacagg aaaaaagaa taagaaaaaa agaaaaaaaa    6000
a                                                                    6001
```

<210> SEQ ID NO 20
<211> LENGTH: 301
<212> TYPE: PRT
<213> ORGANISM: Homo sapiens

<400> SEQUENCE: 20

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
290                 295                 300

<210> SEQ ID NO 21
<211> LENGTH: 2448
<212> TYPE: DNA
<213> ORGANISM: Homo sapiens

<400> SEQUENCE: 21
agaacactta caggatgtgt gtagtgtggc atgacagaga actttggttt cctttaatgt      60
gactgtagac ctggcagtgt tactataaga atcactggca atcagacacc cgggtgtgct     120
gagctagcac tcagtggggg cggctactgc tcatgtgatt gtggagtaga cagttggaag     180
aagtacccag tccatttgga gagttaaaac tgtgcctaac agaggtgtcc tctgactttt     240
cttctgcaag ctccatgttt tcacatcttc cctttgactg tgtcctgctg ctgctgctgc     300
tactacttac aaggtcctca gaagtggaat acagagcgga ggtcggtcag aatgcctatc     360

| | |
|---|---|
| tgccctgctt ctacacccca gccgcccag ggaacctcgt gcccgtctgc tggggcaaag | 420 |
| gagcctgtcc tgtgtttgaa tgtgcaacg tggtgctcag gactgatgaa agggatgtga | 480 |
| attattggac atccagatac tggctaaatg gggatttccg caaggagat gtgtccctga | 540 |
| ccatagagaa tgtgactcta gcagacagtg ggatctactg ctgccggatc caaatcccag | 600 |
| gcataatgaa tgatgaaaaa tttaacctga agttggtcat caaaccagcc aaggtcaccc | 660 |
| ctgcaccgac tcggcagaga gacttcactg cagccttttcc aaggatgctt accaccaggg | 720 |
| gacatggccc agcagagaca cagacactgg ggagcctccc tgatataaat ctaacacaaa | 780 |
| tatccacatt ggccaatgag ttacgggact ctagattggc caatgactta cgggactctg | 840 |
| gagcaaccat cagaataggc atctacatcg agcagggat ctgtgctggg ctggctctgg | 900 |
| ctcttatctt cggcgcttta attttcaaat ggtattctca tagcaaagag aagatacaga | 960 |
| atttaagcct catctctttg gccaacctcc ctccctcagg attggcaaat gcagtagcag | 1020 |
| agggaattcg ctcagaagaa acatctata ccattgaaga aacgtatat gaagtggagg | 1080 |
| agcccaatga gtattattgc tatgtcagca gcaggcagca accctcacaa cctttgggtt | 1140 |
| gtcgctttgc aatgccatag atccaaccac cttatttttg agcttggtgt tttgtctttt | 1200 |
| tcagaaacta tgagctgtgt cacctgactg gttttggagg ttctgtccac tgctatggag | 1260 |
| cagagttttc ccattttcag aagataatga ctcacatggg aattgaactg ggacctgcac | 1320 |
| tgaacttaaa caggcatgtc attgcctctg tatttaagcc aacagagtta cccaacccag | 1380 |
| agactgttaa tcatggatgt tagagctcaa acgggctttt atatacacta ggaattcttg | 1440 |
| acgtggggtc tctggagctc caggaaattc gggcacatca tatgtccatg aaacttcaga | 1500 |
| taaactaggg aaaactgggt gctgaggtga agcataact tttttggcac agaaagtcta | 1560 |
| aaggggccac tgattttcaa agagatctgt gatcccttt tgtttttttgt ttttgagatg | 1620 |
| gagtcttgct ctgttgccca ggctggagtg caatggcaca atctcggctc actgcaagct | 1680 |
| ccgcctcctg ggttcaagcg attctcctgc ctcagcctcc tgagtggctg ggattacagg | 1740 |
| catgcaccac catgcccagc taatttgttg tattttttagt agagacaggg tttcaccatg | 1800 |
| ttggccagtg tggtctcaaa ctcctgacct catgatttgc ctgcctcggc ctcccaaagc | 1860 |
| actgggatta caggcgtgag ccaccacatc cagccagtga tccttaaaag attaagagat | 1920 |
| gactggacca ggtctacctt gatcttgaag attcccttgg aatgttgaga tttaggctta | 1980 |
| tttgagcact gcctgcccaa ctgtcagtgc cagtgcatag cccttctttt gtctccctta | 2040 |
| tgaagactgc cctgcagggc tgagatgtgg caggagctcc cagggaaaaa cgaagtgcat | 2100 |
| ttgattggtg tgtattggcc aagtttttgct tgttgtgtgc ttgaaagaaa atatctctga | 2160 |
| ccaacttctg tattcgtgga ccaaactgaa gctatatttt tcacagaaga agaagcagtg | 2220 |
| acggggacac aaattctgtt gcctggtgga agaaggcaa aggccttcag caatctatat | 2280 |
| taccagcgct ggatcctttg acagagagtg gtccctaaac ttaaatttca agacggtata | 2340 |
| ggcttgatct gtcttgctta ttgttgcccc ctgcgcctag cacaattctg acacacaatt | 2400 |
| ggaacttact aaaaatttttt ttttactgtt aaaaaaaaaa aaaaaaa | 2448 |

<210> SEQ ID NO 22
<211> LENGTH: 288
<212> TYPE: PRT
<213> ORGANISM: Homo sapiens

<400> SEQUENCE: 22

Met Gln Ile Pro Gln Ala Pro Trp Pro Val Val Trp Ala Val Leu Gln

```
1               5                   10                  15
Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 23
<211> LENGTH: 2095
<212> TYPE: DNA
<213> ORGANISM: Homo sapiens

<400> SEQUENCE: 23
agtttccctt ccgctcacct ccgcctgagc agtggagaag gcggcactct ggtgggctg    60 ctccaggcat gcagatccca caggcgccct ggccagtcgt ctgggcggtg ctacaactgg   120
gctggcggcc aggatggttc ttagactccc agacaggcc ctggaacccc ccaccttct   180 ccccagccct gctcgtggtg accgaagggg acaacgccac cttcacctgc agcttctcca   240
acacatcgga gagcttcgtg ctaaactggt accgcatgag ccccagcaac cagacggaca   300
agctggccgc cttccccgag gaccgcagcc agcccggcca cagactgcc aacgggcgt   360 gacttccaca tgagcgtggt cagggcccgg cgcaatgaca gcggcaccta cctctgtggg   420
gccatctccc tggccccaa ggcgcagatc aaagagagcc tgcgggcaga gctcagggtg   480
acagagagaa gggcagaagt gcccacagcc accccagcc cctcacccag gccagccggc   540
```

| | | |
|---|---|---|
| cagttccaaa ccctggtggt tggtgtcgtg ggcggcctgc tgggcagcct ggtgctgcta | 600 | |
| gtctgggtcc tggccgtcat ctgctcccgg gccgcacgag ggacaatagg agccaggcgc | 660 | |
| accggccagc ccctgaagga ggaccccctca gccgtgcctg tgttctctgt ggactatggg | 720 | |
| gagctggatt ccagtggcg agagaagacc ccggagcccc ccgtgccctg tgtccctgag | 780 | |
| cagacggagt atgccaccat tgtctttcct agcggaatgg gcacctcatc cccgcccgc | 840 | |
| aggggctcag ctgacggccc tcggagtgcc cagccactga ggcctgagga tggacactgc | 900 | |
| tcttggcccc tctgaccggc ttccttggcc accagtgttc tgcagaccct ccaccatgag | 960 | |
| cccgggtcag cgcatttcct caggagaagc aggcagggtg caggccattg caggccgtcc | 1020 | |
| aggggctgag ctgcctgggg gcgaccgggg ctccagcctg cacctgcacc aggcacagcc | 1080 | |
| ccaccacagg actcatgtct caatgcccac agtgagccca ggcagcaggt gtcaccgtcc | 1140 | |
| cctacaggga gggccagatg cagtcactgc ttcaggtcct gccagcacag agctgcctgc | 1200 | |
| gtccagctcc ctgaatctct gctgctgctg ctgctgctgc tgctgctgcc tgcggcccgg | 1260 | |
| ggctgaaggc gccgtggccc tgcctgacgc cccggagccc cctgcctgaa cttgggggct | 1320 | |
| ggttggagat ggccttggag cagccaaggt gcccctggca gtggcatccc gaaacgccct | 1380 | |
| ggacgcaggg cccaagactg gcacaggag tgggaggtac atggggctgg ggactcccca | 1440 | |
| ggagttatct gctccctgca ggcctagaga gtttcaggg aaggtcagaa gagctcctgg | 1500 | |
| ctgtggtggg cagggcagga aaccccctcca cctttacaca tgcccaggca gcacctcagg | 1560 | |
| cccctttgtgg ggcagggaag ctgaggcagt aagcgggcag gcagagctgg aggcctttca | 1620 | |
| ggcccagcca gcactctggc ctcctgccgc cgcattccac cccagcccct cacaccactc | 1680 | |
| gggagaggga catcctacgg tcccaaggtc aggagggcag gctggggtt gactcaggcc | 1740 | |
| cctcccagct gtggccacct gggtgttggg agggcagaag tgcaggcacc tagggccccc | 1800 | |
| catgtgccca ccctgggagc tctccttgga acccattcct gaaattattt aaaggggttg | 1860 | |
| gccgggctcc caccagggcc tgggtgggaa ggtacaggcg ttcccccggg gcctagtacc | 1920 | |
| cccgccgtgg cctatccact cctcacatcc acacactgca cccccactcc tggggcaggg | 1980 | |
| ccaccagcat ccaggcggcc agcaggcacc tgagtggctg gacaaggga tccccccttcc | 2040 | |
| ctgtggttct attatattat aattataatt aaatatgaga gcatgctaag gaaaa | 2095 | |

<210> SEQ ID NO 24
<211> LENGTH: 317
<212> TYPE: PRT
<213> ORGANISM: Homo sapiens

<400> SEQUENCE: 24

Met Thr Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
            20                  25                  30

Ser Gln Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser

| | | | | | | | | | | |
|---|---|---|---|---|---|---|---|---|---|---|
| | | | 100 | | | 105 | | | 110 | |
| Asp | Pro | Val | His | Leu | Thr | Val | Leu | Ser | Glu | Trp | Leu | Val | Leu | Gln | Thr |
| | | | 115 | | | | | 120 | | | | | 125 | | |
| Pro | His | Leu | Glu | Phe | Gln | Glu | Gly | Glu | Thr | Ile | Met | Leu | Arg | Cys | His |
| | 130 | | | | | 135 | | | | | 140 | | | | |
| Ser | Trp | Lys | Asp | Lys | Pro | Leu | Val | Lys | Val | Thr | Phe | Phe | Gln | Asn | Gly |
| 145 | | | | | 150 | | | | | 155 | | | | | 160 |
| Lys | Ser | Gln | Lys | Phe | Ser | His | Leu | Asp | Pro | Thr | Phe | Ser | Ile | Pro | Gln |
| | | | | 165 | | | | | 170 | | | | | 175 | |
| Ala | Asn | His | Ser | His | Ser | Gly | Asp | Tyr | His | Cys | Thr | Gly | Asn | Ile | Gly |
| | | | 180 | | | | | 185 | | | | | 190 | | |
| Tyr | Thr | Leu | Phe | Ser | Ser | Lys | Pro | Val | Thr | Ile | Thr | Val | Gln | Val | Pro |
| | | 195 | | | | | 200 | | | | | 205 | | | |
| Ser | Met | Gly | Ser | Ser | Pro | Met | Gly | Ile | Ile | Val | Ala | Val | Val | Ile |
| | 210 | | | | | 215 | | | | | 220 | | | | |
| Ala | Thr | Ala | Val | Ala | Ala | Ile | Val | Ala | Ala | Val | Val | Ala | Leu | Ile | Tyr |
| 225 | | | | | 230 | | | | | 235 | | | | | 240 |
| Cys | Arg | Lys | Lys | Arg | Ile | Ser | Ala | Asn | Ser | Thr | Asp | Pro | Val | Lys | Ala |
| | | | | 245 | | | | | 250 | | | | | 255 | |
| Ala | Gln | Phe | Glu | Pro | Pro | Gly | Arg | Gln | Met | Ile | Ala | Ile | Arg | Lys | Arg |
| | | | 260 | | | | | 265 | | | | | 270 | | |
| Gln | Leu | Glu | Glu | Thr | Asn | Asn | Asp | Tyr | Glu | Thr | Ala | Asp | Gly | Gly | Tyr |
| | | 275 | | | | | 280 | | | | | 285 | | | |
| Met | Thr | Leu | Asn | Pro | Arg | Ala | Pro | Thr | Asp | Asp | Lys | Asn | Ile | Tyr |
| | 290 | | | | | 295 | | | | | 300 | | | | |
| Leu | Thr | Leu | Pro | Pro | Asn | Asp | His | Val | Asn | Ser | Asn | Asn |
| 305 | | | | | 310 | | | | | 315 | | |

<210> SEQ ID NO 25
<211> LENGTH: 2429
<212> TYPE: DNA
<213> ORGANISM: Homo sapiens

<400> SEQUENCE: 25

```
ctctttctcta agcttgtctc ttaaaaccca ctggacgttg cacagtgct gggatgacta      60
tggagaccca aatgtctcag aatgtatgtc ccagaaacct gtggctgctt caaccattga     120
cagttttgct gctgctggct tctgcagaca gtcaagctgc agctccccca aaggctgtgc     180
tgaaacttga gccccgtgg atcaacgtgc tccaggagga ctctgtgact ctgacatgcc     240
agggggctcg cagccctgag agcgactcca ttcagtggtt ccacaatggg aatctcattc     300
ccacccacac gcagcccagc tacaggttca aggccaacaa caatgacagc ggggagtaca     360
cgtgccagac tggccagacc agcctcagcg accctgtgca tctgactgtg ctttccgaat     420
ggctggtgct ccagacccct cacctggagt tccaggaggg agaaaccatc atgctgaggt     480
gccacagctg gaaggacaag cctctggtca aggtcacatt cttccagaat ggaaaatccc     540
agaaattctc ccatttggat cccaccttct ccatcccaca agcaaaccac agtcacagtg     600
gtgattacca ctgcacagga acataggct acacgctgtt ctcatccaag cctgtgacca     660
tcactgtcca agtgcccagc atgggcagct cttcaccaat ggggatcatt gtggctgtgg     720
tcattgcgac tgctgtagca gccattgttg ctgctgtagt ggccttgatc tactgcagga     780
aaaagcggat ttcagccaat tccactgatc ctgtgaaggc tgcccaattt gagccacctg     840
gacgtcaaat gattgccatc agaaagagac aacttgaaga aaccaacaat gactatgaaa     900
```

```
cagctgacgg cggctacatg actctgaacc ccagggcacc tactgacgat gataaaaaca    960
tctacctgac tcttcctccc aacgaccatg tcaacagtaa taactaaaga gtaacgttat   1020
gccatgtggt catactctca gcttgctgag tggatgacaa aagagggga attgttaaag    1080
gaaaatttaa atggagactg gaaaaatcct gagcaaacaa aaccacctgg cccttagaaa   1140
tagctttaac tttgcttaaa ctacaaacac aagcaaaact tcacggggtc atactacata   1200
caagcataag caaaacttaa cttggatcat ttctggtaaa tgcttatgtt agaaataaga   1260
caaccccagc caatcacaag cagcctacta acatataatt aggtgactag ggactttcta   1320
agaagatacc tacccccaaa aaacaattat gtaattgaaa accaaccgat tgcctttatt   1380
ttgcttccac attttcccaa taaatacttg cctgtgacat tttgccactg gaacactaaa   1440
cttcatgaat tgcgcctcag attttttcctt taacatcttt tttttttttg acagagtctc   1500
aatctgttac ccaggctgga gtgcagtggt gctatcttgg ctcactgcaa acccgcctcc   1560
caggtttaag cgattctcat gcctcagcct cccagtagct gggattagag gcatgtgcca   1620
tcatacccag ctaattttg tatttttat ttttttttt tagtagagac agggtttcgc     1680
aatgttggcc aggccgatct cgaacttctg gcctctagcg atctgcccgc ctcggcctcc   1740
caaagtgctg ggatgaccag catcagcccc aatgtccagc tctttaaca tcttctttcc    1800
tatgccctct ctgtggatcc ctactgctgg tttctgcctt ctccatgctg agaacaaaat   1860
cacctattca ctgcttatgc agtcggaagc tccagaagaa caaagagccc aattaccaga   1920
accacattaa gtctccattg ttttgccttg ggatttgaga agagaattag agaggtgagg   1980
atctggtatt tcctggacta aattccccctt ggggaagacg aagggatgct gcagttccaa   2040
aagagaagga ctcttccaga gtcatctacc tgagtcccaa agctccctgt cctgaaagcc   2100
acagacaata tggtcccaaa tgactgactg caccttctgt gcctcagccg ttcttgacat   2160
caagaatctt ctgttccaca tccacacagc caatacaatt agtcaaacca ctgttattaa   2220
cagatgtagc aacatgagaa acgcttatgt tacaggttac atgagagcaa tcatgtaagt   2280
ctatatgact tcagaaatgt taaaatagac taacctctaa caacaaatta aaagtgattg   2340
tttcaaggtg atgcaattat tgatgaccta ttttatttt ctataatgat catatattac    2400
ctttgtaata aaacattata accaaaaca                                     2429
```

<210> SEQ ID NO 26
<211> LENGTH: 316
<212> TYPE: PRT
<213> ORGANISM: Homo sapiens

<400> SEQUENCE: 26

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
                20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
```

```
              100                 105                 110
Pro Val His Leu Thr Val Leu Ser Glu Trp Leu Val Leu Gln Thr Pro
            115                 120                 125

His Leu Glu Phe Gln Glu Gly Glu Thr Ile Met Leu Arg Cys His Ser
        130                 135                 140

Trp Lys Asp Lys Pro Leu Val Lys Val Thr Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Ile Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 27
<211> LENGTH: 2426
<212> TYPE: DNA
<213> ORGANISM: Homo sapiens

<400> SEQUENCE: 27 ctctttttcta agcttgtctc ttaaaaccca ctggacgttg cacagtgct gggatgacta      60 tggagaccca aatgtctcag aatgtatgtc ccagaaacct gtggctgctt caaccattga    120
cagttttgct gctgctggct tctgcagaca gtcaagctgc tcccccaaag gctgtgctga    180
aacttgagcc cccgtggatc aacgtgctcc aggaggactc tgtgactctg acatgccagg    240
gggctcgcag ccctgagagc gactccattc agtggttcca caatgggaat ctcattccca    300
cccacacgca gcccagctac aggttcaagg ccaacaacaa tgacagcggg gagtacacgt    360
gccagactgg ccagaccagc ctcagcgacc ctgtgcatct gactgtgctt tccgaatggc    420
tggtgctcca gacccctcac ctggagttcc aggagggaga accatcatg ctgaggtgcc     480 acagctggaa ggacaagcct ctggtcaagg tcacattctt ccagaatgga aatcccaga    540 aattctccca tttggatccc accttctcca tcccacaagc aaaccacagt cacagtggtg    600
attaccactg cacaggaaac ataggctaca cgctgttctc atccaagcct gtgaccatca    660
ctgtccaagt gccagcatg ggcagctctt caccaatggg gatcattgtg ctgtggtca     720 ttgcgactgc tgtagcagcc attgttgctg ctgtagtggc cttgatctac tgcaggaaaa    780
agcggatttc agccaattcc actgatcctg tgaaggctgc ccaatttgag ccacctggac    840
gtcaaatgat tgccatcaga aagagacaac ttgaagaaac caacaatgac tatgaaacag    900
```

```
ctgacggcgg ctacatgact ctgaacccca gggcacctac tgacgatgat aaaaacatct    960
acctgactct tcctcccaac gaccatgtca acagtaataa ctaaagagta acgttatgcc   1020
atgtggtcat actctcagct tgctgagtgg atgacaaaaa gaggggaatt gttaaaggaa   1080
aatttaaatg gagactggaa aaatcctgag caaacaaaac cacctggccc ttagaaatag   1140
ctttaacttt gcttaaacta caaacacaag caaaacttca cggggtcata ctacatacaa   1200
gcataagcaa aacttaactt ggatcatttc tggtaaatgc ttatgttaga aataagacaa   1260
ccccagccaa tcacaagcag cctactaaca tataattagg tgactaggga ctttctaaga   1320
agatacctac ccccaaaaaa caattatgta attgaaaacc aaccgattgc ctttattttg   1380
cttccacatt ttcccaataa atacttgcct gtgacatttt gccactggaa cactaaactt   1440
catgaattgc gcctcagatt tttcctttaa catctttttt tttttttgaca gagtctcaat   1500
ctgttaccca ggctggagtg cagtggtgct atcttggctc actgcaaacc cgcctcccag   1560
gtttaagcga ttctcatgcc tcagcctccc agtagctggg attagaggca tgtgccatca   1620
tacccagcta attttgtat tttttatttt tttttttag tagagacagg gtttcgcaat    1680
gttggccagg ccgatctcga acttctggcc tctagcgatc tgcccgcctc ggcctcccaa   1740
agtgctggga tgaccagcat cagccccaat gtccagcctc tttaacatct tctttcctat   1800
gccctctctg tggatcccta ctgctggttt ctgccttctc catgctgaga acaaaatcac   1860
ctattcactg cttatgcagt cggaagctcc agaagaacaa agagcccaat taccagaacc   1920
acattaagtc tccattgttt tgccttggga tttgagaaga gaattagaga ggtgaggatc   1980
tggtatttcc tggactaaat tcccttgggg aagacgaag ggatgctgca gttccaaaag    2040
agaaggactc ttccagagtc atctacctga gtcccaaagc tccctgtcct gaaagccaca   2100
gacaatatgg tcccaaatga ctgactgcac cttctgtgcc tcagccgttc ttgacatcaa   2160
gaatcttctg ttccacatcc acacagccaa tacaattagt caaaccactg ttattaacag   2220
atgtagcaac atgagaaacg cttatgttac aggttacatg agagcaatca tgtaagtcta   2280
tatgacttca gaaatgttaa aatagactaa cctctaacaa caaattaaaa gtgattgttt   2340
caaggtgatg caattattga tgacctattt tattttcta taatgatcat atattacctt    2400
tgtaataaaa cattataacc aaaaca                                         2426
```

<210> SEQ ID NO 28
<211> LENGTH: 374
<212> TYPE: PRT
<213> ORGANISM: Homo sapiens

<400> SEQUENCE: 28

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
```

|           | 100       |           |           |           | 105       |           |           |           | 110       |           |
|-----------|-----------|-----------|-----------|-----------|-----------|-----------|-----------|-----------|-----------|-----------|

Val Phe Thr Glu Gly Glu Pro Leu Ala Leu Arg Cys His Ala Trp Lys
            115                      120                      125

Asp Lys Leu Val Tyr Asn Val Leu Tyr Tyr Arg Asn Gly Lys Ala Phe
 130                     135                      140

Lys Phe Phe His Trp Asn Ser Asn Leu Thr Ile Leu Lys Thr Asn Ile
145                     150                      155                      160

Ser His Asn Gly Thr Tyr His Cys Ser Gly Met Gly Lys His Arg Tyr
                165                      170                      175

Thr Ser Ala Gly Ile Ser Val Thr Val Lys Glu Leu Phe Pro Ala Pro
            180                      185                      190

Val Leu Asn Ala Ser Val Thr Ser Pro Leu Leu Glu Gly Asn Leu Val
          195                      200                      205

Thr Leu Ser Cys Glu Thr Lys Leu Leu Leu Gln Arg Pro Gly Leu Gln
 210                     215                      220

Leu Tyr Phe Ser Phe Tyr Met Gly Ser Lys Thr Leu Arg Gly Arg Asn
225                     230                      235                      240

Thr Ser Ser Glu Tyr Gln Ile Leu Thr Ala Arg Arg Glu Asp Ser Gly
                245                      250                      255

Leu Tyr Trp Cys Glu Ala Ala Thr Glu Asp Gly Asn Val Leu Lys Arg
            260                      265                      270

Ser Pro Glu Leu Glu Leu Gln Val Leu Gly Leu Gln Leu Pro Thr Pro
          275                      280                      285

Val Trp Phe His Val Leu Phe Tyr Leu Ala Val Gly Ile Met Phe Leu
 290                     295                      300

Val Asn Thr Val Leu Trp Val Thr Ile Arg Lys Glu Leu Lys Arg Lys
305                     310                      315                      320

Lys Lys Trp Asp Leu Glu Ile Ser Leu Asp Ser Gly His Glu Lys Lys
                325                      330                      335

Val Ile Ser Ser Leu Gln Glu Asp Arg His Leu Glu Glu Glu Leu Lys
            340                      345                      350

Cys Gln Glu Gln Lys Glu Glu Gln Leu Gln Glu Gly Val His Arg Lys
          355                      360                      365

Glu Pro Gln Gly Ala Thr
     370

<210> SEQ ID NO 29
<211> LENGTH: 2268
<212> TYPE: DNA
<213> ORGANISM: Homo sapiens

<400> SEQUENCE: 29

```
aatatcttgc atgttacaga tttcactgct cccaccagct tggagacaac atgtggttct    60
tgacaactct gctcctttgg gttccagttg atgggcaagt ggacaccaca aaggcagtga   120
tcactttgca gcctccatgg gtcagcgtgt ccaagagga aaccgtaacc ttgcactgtg    180
aggtgctcca tctgcctggg agcagctcta cacagtggtt tctcaatggc acagccactc    240
agacctcgac ccccagctac agaatcaccT ctgccagtgt caatgacagt ggtgaataca    300
ggtgccagag aggtctctca gggcgaagtg accccataca gctggaaatc acagaggct    360 ggctactact gcaggtctcc agcagagtct tcacggaagg agaacctctg gccttgaggt    420
gtcatgcgtg gaaggataag ctggtgtaca atgtgcttta ctatcgaaat ggcaaagcct    480
ttaagttttt ccactggaat tctaacctca ccattctgaa aaccaacata agtcacaatg    540
```

-continued

| | |
|---|---|
| gcacctacca ttgctcaggc atgggaaagc atcgctacac atcagcagga atatctgtca | 600 |
| ctgtgaaaga gctatttcca gctccagtgc tgaatgcatc tgtgacatcc ccactcctgg | 660 |
| aggggaatct ggtcaccctg agctgtgaaa caaagttgct cttgcagagg cctggtttgc | 720 |
| agctttactt ctccttctac atgggcagca agaccctgcg aggcaggaac acatcctctg | 780 |
| aataccaaat actaactgct agaagagaag actctgggtt atactggtgc gaggctgcca | 840 |
| cagaggatgg aaatgtcctt aagcgcagcc tgagttgga gcttcaagtg cttgcctcc | 900 |
| agttaccaac tcctgtctgg tttcatgtcc ttttctatct ggcagtggga ataatgtttt | 960 |
| tagtgaacac tgttctctgg gtgacaatac gtaaagaact gaaagaaag aaaaagtggg | 1020 |
| atttagaaat ctctttggat tctggtcatg agaagaaggt aatttccagc cttcaagaag | 1080 |
| acagacattt agaagaagag ctgaaatgtc aggaacaaaa agaagaacag ctgcaggaag | 1140 |
| gggtgcaccg gaaggagccc caggggggcca cgtagcagcg gctcagtggg tggccatcga | 1200 |
| tctggaccgt cccctgccca cttgctcccc gtgagcactg cgtacaaaca tccaaaagtt | 1260 |
| caacaacacc agaactgtgt gtctcatggt atgtaactct taaagcaaat aaatgaactg | 1320 |
| acttcaactg ggatacattt ggaaatgtgg tcatcaaaga tgacttgaaa tgaggcctac | 1380 |
| tctaaagaat tcttgaaaaa cttacaagtc aagcctagcc tgataatcct attacatagt | 1440 |
| ttgaaaaata gtattttatt tctcagaaca aggtaaaaag gtgagtgggt gcatatgtac | 1500 |
| agaagattaa gacagagaaa cagacagaaa gagacacaca cacagccagg agtgggtaga | 1560 |
| tttcagggag acaagaggga atagtataga caataaggaa ggaaatagta cttacaaatg | 1620 |
| actcctaagg gactgtgaga ctgagagggc tcacgcctct gtgttcagga tacttagttc | 1680 |
| atggcttttc tctttgactt tactaaaaga gaatgtctcc atacgcgttc taggcataca | 1740 |
| agggggtaac tcatgatgag aaatggatgt gttattcttg ccctctcttt tgaggctctc | 1800 |
| tcataacccc tctatttcta gagacaacaa aaatgctgcc agtcctaggc ccctgccctg | 1860 |
| taggaaggca gaatgtaact gttctgtttg tttaacgatt aagtccaaat ctccaagtgc | 1920 |
| ggcactgcaa agagacgctt caagtgggga gaagcggcga taccatagag tccagatctt | 1980 |
| gcctccagag atttgctta ccttcctgat tttctggtta ctaattagct tcaggatacg | 2040 |
| ctgctctcat acttgggctg tagtttggag acaaaatatt ttcctgccac tgtgtaacat | 2100 |
| agctgaggta aaaactgaac tatgtaaatg actctactaa aagtttaggg aaaaaaaaca | 2160 |
| ggaggagtat gacacaaaaa aaaaaaaaaa aaaaaaaaa aaaaaaaaa aaaaaaaaa | 2220 |
| aaaaaaaaa aaaaaaaaa aaaaaaaaa aaaaaaaaa aaaaaaaa | 2268 |

<210> SEQ ID NO 30
<211> LENGTH: 1156
<212> TYPE: PRT
<213> ORGANISM: Homo sapiens

<400> SEQUENCE: 30

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
    50                  55                  60

Glu Val Lys Val Gln Glu Glu Trp Gly Thr Val Cys Asn Asn Gly Trp

-continued

```
                65                  70                  75                  80
Ser Met Glu Ala Val Ser Val Ile Cys Asn Gln Leu Gly Cys Pro Thr
                    85                  90                  95
Ala Ile Lys Ala Pro Gly Trp Ala Asn Ser Ala Gly Ser Gly Arg
                100                 105                 110
Ile Trp Met Asp His Val Ser Cys Arg Gly Asn Glu Ser Ala Leu Trp
                    115                 120                 125
Asp Cys Lys His Asp Gly Trp Gly Lys His Ser Asn Cys Thr His Gln
130                 135                 140
Gln Asp Ala Gly Val Thr Cys Ser Asp Gly Ser Asn Leu Glu Met Arg
145                 150                 155                 160
Leu Thr Arg Gly Gly Asn Met Cys Ser Gly Arg Ile Glu Ile Lys Phe
                    165                 170                 175
Gln Gly Arg Trp Gly Thr Val Cys Asp Asp Asn Phe Asn Ile Asp His
                180                 185                 190
Ala Ser Val Ile Cys Arg Gln Leu Glu Cys Gly Ser Ala Val Ser Phe
                195                 200                 205
Ser Gly Ser Ser Asn Phe Gly Glu Gly Ser Gly Pro Ile Trp Phe Asp
            210                 215                 220
Asp Leu Ile Cys Asn Gly Asn Glu Ser Ala Leu Trp Asn Cys Lys His
225                 230                 235                 240
Gln Gly Trp Gly Lys His Asn Cys Asp His Ala Glu Asp Ala Gly Val
                    245                 250                 255
Ile Cys Ser Lys Gly Ala Asp Leu Ser Leu Arg Leu Val Asp Gly Val
                260                 265                 270
Thr Glu Cys Ser Gly Arg Leu Glu Val Arg Phe Gln Gly Glu Trp Gly
            275                 280                 285
Thr Ile Cys Asp Asp Gly Trp Asp Ser Tyr Asp Ala Ala Val Ala Cys
            290                 295                 300
Lys Gln Leu Gly Cys Pro Thr Ala Val Thr Ala Ile Gly Arg Val Asn
305                 310                 315                 320
Ala Ser Lys Gly Phe Gly His Ile Trp Leu Asp Ser Val Ser Cys Gln
                    325                 330                 335
Gly His Glu Pro Ala Ile Trp Gln Cys Lys His His Glu Trp Gly Lys
                340                 345                 350
His Tyr Cys Asn His Asn Glu Asp Ala Gly Val Thr Cys Ser Asp Gly
            355                 360                 365
Ser Asp Leu Glu Leu Arg Leu Arg Gly Gly Gly Ser Arg Cys Ala Gly
370                 375                 380
Thr Val Glu Val Glu Ile Gln Arg Leu Leu Gly Lys Val Cys Asp Arg
385                 390                 395                 400
Gly Trp Gly Leu Lys Glu Ala Asp Val Val Cys Arg Gln Leu Gly Cys
                    405                 410                 415
Gly Ser Ala Leu Lys Thr Ser Tyr Gln Val Tyr Ser Lys Ile Gln Ala
                420                 425                 430
Thr Asn Thr Trp Leu Phe Leu Ser Ser Cys Asn Gly Asn Glu Thr Ser
                    435                 440                 445
Leu Trp Asp Cys Lys Asn Trp Gln Trp Gly Gly Leu Thr Cys Asp His
                450                 455                 460
Tyr Glu Glu Ala Lys Ile Thr Cys Ser Ala His Arg Glu Pro Arg Leu
465                 470                 475                 480
Val Gly Gly Asp Ile Pro Cys Ser Gly Arg Val Glu Val Lys His Gly
                    485                 490                 495
```

```
Asp Thr Trp Gly Ser Ile Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Gly Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Glu Gln Val Ala Ser Val Ile Cys Ser Gly Asn Gln Ser Gln
        675                 680                 685

Thr Leu Ser Ser Cys Asn Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Thr Val Gly Lys Ser Ser Met Ser Glu Thr Thr Val Gly Val Val Cys
    850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910
```

Arg Leu Ala Ser Pro Ser Glu Glu Thr Trp Ile Thr Cys Asp Asn Lys
            915                 920                 925

Ile Arg Leu Gln Glu Gly Pro Thr Ser Cys Ser Gly Arg Val Glu Ile
        930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
            965                 970                 975

Lys Ala Phe Lys Glu Ala Glu Phe Gln Gly Thr Gly Pro Ile Trp
        980                 985                 990

Leu Asn Glu Val Lys Cys Lys Gly Asn Glu Ser Ser Leu Trp Asp Cys
        995                 1000                1005

Pro Ala Arg Arg Trp Gly His Ser Glu Cys Gly His Lys Glu Asp
    1010                1015                1020

Ala Ala Val Asn Cys Thr Asp Ile Ser Val Gln Lys Thr Pro Gln
    1025                1030                1035

Lys Ala Thr Thr Gly Arg Ser Ser Arg Gln Ser Ser Phe Ile Ala
    1040                1045                1050

Val Gly Ile Leu Gly Val Val Leu Leu Ala Ile Phe Val Ala Leu
    1055                1060                1065

Phe Phe Leu Thr Lys Lys Arg Arg Gln Arg Gln Arg Leu Ala Val
    1070                1075                1080

Ser Ser Arg Gly Glu Asn Leu Val His Gln Ile Gln Tyr Arg Glu
    1085                1090                1095

Met Asn Ser Cys Leu Asn Ala Asp Asp Leu Asp Leu Met Asn Ser
    1100                1105                1110

Ser Glu Asn Ser His Glu Ser Ala Asp Phe Ser Ala Ala Glu Leu
    1115                1120                1125

Ile Ser Val Ser Lys Phe Leu Pro Ile Ser Gly Met Glu Lys Glu
    1130                1135                1140

Ala Ile Leu Ser His Thr Glu Lys Glu Asn Gly Asn Leu
    1145                1150                1155

<210> SEQ ID NO 31
<211> LENGTH: 4190
<212> TYPE: DNA
<213> ORGANISM: Homo sapiens

<400> SEQUENCE: 31
atatgtagcc ttttcatttt catgaaagtg aagtgatttt tagaattctt agttgttttc    60
tttagaagaa catttctagg gaataataca agaagattta ggaatcattg aagttataaa   120
tctttggaat gagcaaactc agaatggtgc tacttgaaga ctctggatct gctgacttca   180
gaagacattt tgtcaacttg agtcccttca ccattactgt ggtcttactt ctcagtgcct   240
gttttgtcac cagttctctt ggaggaacag acaaggagct gaggctagtg gatggtgaaa   300
acaagtgtag cgggagagtg gaagtgaaag tccaggagga gtgggaacg gtgtgtaata   360 atggctggag catggaagcg gtctctgtga tttgtaacca gctgggatgt ccaactgcta   420
tcaaagcccc tggatgggct aattccagtg caggttctgg acgcatttgg atggatcatg   480
tttcttgtcg tgggaatgag tcagctcttt gggattgcaa acatgatgga tggggaaagc   540
atagtaactg tactcaccaa caagatgctg gagtgacctg ctcagatgga tccaatttgg   600
aaatgaggct gacgcgtgga gggaatatgt gttctggaag aatagagatc aaattccaag   660
gacggtgggg aacagtgtgt gatgataact tcaacataga tcatgcatct gtcatttgta   720

```
gacaacttga atgtggaagt gctgtcagtt tctctggttc atctaatttt ggagaaggct      780
ctggaccaat ctggtttgat gatcttatat gcaacggaaa tgagtcagct ctctggaact      840
gcaaacatca aggatgggga aagcataact gtgatcatgc tgaggatgct ggagtgattt      900
gctcaaaggg agcagatctg agcctgagac tggtagatgg agtcactgaa tgttcaggaa      960
gattagaagt gagattccaa ggagaatggg ggacaatatg tgatgacggc tgggacagtt     1020
acgatgctgc tgtggcatgc aagcaactgg gatgtccaac tgccgtcaca gccattggtc     1080
gagttaacgc cagtaaggga tttggacaca tctggcttga cagcgtttct tgccagggac     1140
atgaacctgc tatctggcaa tgtaaacacc atgaatgggg aaagcattat tgcaatcaca     1200
atgaagatgc tggcgtgaca tgttctgatg gatcagatct ggagctaaga cttagaggtg     1260
gaggcagccg ctgtgctggg acagttgagg tggagattca gagactgtta gggaaggtgt     1320
gtgacagagg ctggggactg aaagaagctg atgtggtttg caggcagctg ggatgtggat     1380
ctgcactcaa aacatcttat caagtgtact ccaaaatcca ggcaacaaac acatggctgt     1440
ttctaagtag ctgtaacgga aatgaaactt ctctttggga ctgcaagaac tggcaatggg     1500
gtggacttac ctgtgatcac tatgaagaag ccaaaattac ctgctcagcc cacagggaac     1560
ccagactggt tggaggggac attccctgtt ctggacgtgt tgaagtgaag catggtgaca     1620 cgtgggctc catctgtgat tcggacttct ctctggaagc tgccagcgtt ctatgcaggg     1680
aattacagtg tggcacagtt gtctctatcc tgggggagc tcactttgga gagggaaatg     1740
gacagatctg ggctgaagaa ttccagtgtg agggacatga gtcccatctt tcactctgcc     1800
cagtagcacc ccgcccagaa ggaacttgta gccacagcag ggatgttgga gtagtctgct     1860
caagatacac agaaattcgc ttggtgaatg gcaagacccc gtgtgagggc agagtggagc     1920
tcaaaacgct tggtgcctgg ggatccctct gtaactctca ctgggacata aagatgccc      1980 atgttctttg ccagcagctt aaatgtggag ttgccctttc tacccagga ggagcacgtt      2040 ttggaaaagg aaatggtcag atctggaggc atatgtttca ctgcactggg actgagcagc     2100
acatgggaga ttgtcctgta actgctctag gtgcttcatt atgtccttca gagcaagtgg     2160
cctctgtaat ctgctcagga aaccagtccc aaacactgtc ctcgtgcaat tcatcgtctt     2220
tgggcccaac aaggcctacc attccagaag aaagtgctgt ggcctgcata gagagtggtc     2280
aacttcgcct ggtaaatgga ggaggtcgct gtgctgggag agtagagatc tatcatgagg     2340
gctcctgggg caccatctgt gatgacagct gggacctgag tgatgcccac gtggtttgca     2400
gacagctggg ctgtggagag gccattaatg ccactggttc tgctcatttt ggggaaggaa     2460
cagggcccat ctggctggat gagatgaaat gcaatggaaa agaatcccgc atttggcagt     2520
gccattcaca cggctggggg cagcaaaatt gcaggcacaa ggaggatgcg ggagttatct     2580
gctcagaatt catgtctctg agactgacca gtgaagccag cagagaggcc tgtgcagggc     2640
gtctggaagt ttttacaat ggagcttggg gcactgttgg caagagtagc atgtctgaaa     2700
ccactgtggg tgtggtgtgc aggcagctgg gctgtgcaga caaagggaaa atcaaccctg     2760
catctttaga caaggccatg tccattccca tgtgggtgga caatgttcag tgtccaaaag     2820
gacctgacac gctgtggcag tgcccatcat ctccatggga agagactg gccagcccct      2880 cggaggagac ctggatcaca tgtgacaaca agataagact tcaggaagga cccacttcct     2940
gttctggacg tgtggagatc tggcatggag gttcctgggg acagtgtgt gatgactctt      3000 gggacttgga cgatgctcag gtggtgtgtc aacaacttgg ctgtggtcca gctttgaaag     3060
```

-continued

```
cattcaaaga agcagagttt ggtcagggga ctggaccgat atggctcaat gaagtgaagt    3120
gcaaagggaa tgagtcttcc ttgtgggatt gtcctgccag acgctggggc catagtgagt    3180
gtgggcacaa ggaagacgct gcagtgaatt gcacagatat ttcagtgcag aaaccccac    3240 aaaaagccac aacaggtcgc tcatcccgtc agtcatcctt tattgcagtc gggatccttg    3300
gggttgttct gttggccatt tcgtcgcat tattcttctt gactaaaaag cgaagacaga    3360
gacagcggct tgcagtttcc tcaagaggag agaacttagt ccaccaaatt caataccggg    3420
agatgaattc ttgcctgaat gcagatgatc tggacctaat gaattcctca gaaaattccc    3480
atgagtcagc tgatttcagt gctgctgaac taatttctgt gtctaaattt cttcctattt    3540
ctggaatgga aaaggaggcc attctgagcc acactgaaaa ggaaaatggg aatttataac    3600
ccagtgagtt cagcctttaa gataccttga tgaagacctg gactattgaa tggagcagaa    3660
attcacctct ctcactgact attacagttg catttttatg gagttcttct tctcctagga    3720
ttcctaagac tgctgctgaa tttataaaaa ttaagtttgt gaatgtgact acttagtggt    3780
gtatatgaga ctttcaaggg aattaaataa ataaataaga atgttattga tttgagtttg    3840
ctttaattac ttgtccttaa ttctattaat ttctaaatgg gcttcctaat tttttgtaga    3900
gtttcctaga tgtattataa tgtgttttat ttgacagtgt ttcaatttgc atatacagta    3960
ctgtatattt tttcttattt ggtttgaata attttcctat taccaaataa aaataaattt    4020 attttactt tagttttttct aagacaggaa aagttaatga tattgaaggg tctgtaaata    4080
atatatggct aactttataa ggcatgactc acaacgattc tttaactgct ttttgttact    4140
gtaattctgt tcactagaat aaaatgcaga gccacacctg gtgagggcac               4190
```

<210> SEQ ID NO 32
<211> LENGTH: 1111
<212> TYPE: PRT
<213> ORGANISM: Homo sapiens

<400> SEQUENCE: 32

```
Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
    50                  55                  60

Glu Val Lys Val Gln Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175
```

-continued

```
Gln Gly Arg Trp Gly Thr Val Cys Asp Asp Asn Phe Asn Ile Asp His
            180                 185                 190
Ala Ser Val Ile Cys Arg Gln Leu Glu Cys Gly Ser Ala Val Ser Phe
        195                 200                 205
Ser Gly Ser Ser Asn Phe Gly Glu Gly Ser Gly Pro Ile Trp Phe Asp
    210                 215                 220
Asp Leu Ile Cys Asn Gly Asn Glu Ser Ala Leu Trp Asn Cys Lys His
225                 230                 235                 240
Gln Gly Trp Gly Lys His Asn Cys Asp His Ala Glu Asp Ala Gly Val
            245                 250                 255
Ile Cys Ser Lys Gly Ala Asp Leu Ser Leu Arg Leu Val Asp Gly Val
        260                 265                 270
Thr Glu Cys Ser Gly Arg Leu Glu Val Arg Phe Gln Gly Glu Trp Gly
    275                 280                 285
Thr Ile Cys Asp Asp Gly Trp Asp Ser Tyr Asp Ala Ala Val Ala Cys
290                 295                 300
Lys Gln Leu Gly Cys Pro Thr Ala Val Thr Ala Ile Gly Arg Val Asn
305                 310                 315                 320
Ala Ser Lys Gly Phe Gly His Ile Trp Leu Asp Ser Val Ser Cys Gln
            325                 330                 335
Gly His Glu Pro Ala Ile Trp Gln Cys Lys His His Glu Trp Gly Lys
        340                 345                 350
His Tyr Cys Asn His Asn Glu Asp Ala Gly Val Thr Cys Ser Asp Gly
    355                 360                 365
Ser Asp Leu Glu Leu Arg Leu Arg Gly Gly Ser Arg Cys Ala Gly
370                 375                 380
Thr Val Glu Val Glu Ile Gln Arg Leu Leu Gly Lys Val Cys Asp Arg
385                 390                 395                 400
Gly Trp Gly Leu Lys Glu Ala Asp Val Val Cys Arg Gln Leu Gly Cys
            405                 410                 415
Gly Ser Ala Leu Lys Thr Ser Tyr Gln Val Tyr Ser Lys Ile Gln Ala
        420                 425                 430
Thr Asn Thr Trp Leu Phe Leu Ser Ser Cys Asn Gly Asn Glu Thr Ser
    435                 440                 445
Leu Trp Asp Cys Lys Asn Trp Gln Trp Gly Gly Leu Thr Cys Asp His
450                 455                 460
Tyr Glu Glu Ala Lys Ile Thr Cys Ser Ala His Arg Glu Pro Arg Leu
465                 470                 475                 480
Val Gly Gly Asp Ile Pro Cys Ser Gly Arg Val Glu Val Lys His Gly
            485                 490                 495
Asp Thr Trp Gly Ser Ile Cys Asp Ser Asp Phe Ser Leu Glu Ala Ala
        500                 505                 510
Ser Val Leu Cys Arg Glu Leu Gln Cys Gly Thr Val Val Ser Ile Leu
    515                 520                 525
Gly Gly Ala His Phe Gly Glu Gly Asn Gly Gln Ile Trp Ala Glu Glu
530                 535                 540
Phe Gln Cys Glu Gly His Glu Ser His Leu Ser Leu Cys Pro Val Ala
545                 550                 555                 560
Pro Arg Pro Glu Gly Thr Cys Ser His Ser Arg Asp Val Gly Val Val
            565                 570                 575
Cys Ser Arg Tyr Thr Glu Ile Arg Leu Val Asn Gly Lys Thr Pro Cys
        580                 585                 590
Glu Gly Arg Val Glu Leu Lys Thr Leu Gly Ala Trp Gly Ser Leu Cys
```

-continued

```
            595                 600                 605
Asn Ser His Trp Asp Ile Glu Asp Ala His Val Leu Cys Gln Gln Leu
    610                 615                 620
Lys Cys Gly Val Ala Leu Ser Thr Pro Gly Gly Ala Arg Phe Gly Lys
625                 630                 635                 640
Gly Asn Gly Gln Ile Trp Arg His Met Phe His Cys Thr Gly Thr Glu
                645                 650                 655
Gln His Met Gly Asp Cys Pro Val Thr Ala Leu Gly Ala Ser Leu Cys
                660                 665                 670
Pro Ser Glu Gln Val Ala Ser Val Ile Cys Ser Gly Asn Gln Ser Gln
                675                 680                 685
Thr Leu Ser Ser Cys Asn Ser Ser Leu Gly Pro Thr Arg Pro Thr
    690                 695                 700
Ile Pro Glu Glu Ser Ala Val Ala Cys Ile Glu Ser Gly Gln Leu Arg
705                 710                 715                 720
Leu Val Asn Gly Gly Gly Arg Cys Ala Gly Arg Val Glu Ile Tyr His
                725                 730                 735
Glu Gly Ser Trp Gly Thr Ile Cys Asp Asp Ser Trp Asp Leu Ser Asp
                740                 745                 750
Ala His Val Val Cys Arg Gln Leu Gly Cys Gly Glu Ala Ile Asn Ala
                755                 760                 765
Thr Gly Ser Ala His Phe Gly Glu Gly Thr Gly Pro Ile Trp Leu Asp
    770                 775                 780
Glu Met Lys Cys Asn Gly Lys Glu Ser Arg Ile Trp Gln Cys His Ser
785                 790                 795                 800
His Gly Trp Gly Gln Gln Asn Cys Arg His Lys Glu Asp Ala Gly Val
                805                 810                 815
Ile Cys Ser Glu Phe Met Ser Leu Arg Leu Thr Ser Glu Ala Ser Arg
                820                 825                 830
Glu Ala Cys Ala Gly Arg Leu Glu Val Phe Tyr Asn Gly Ala Trp Gly
                835                 840                 845
Thr Val Gly Lys Ser Ser Met Ser Glu Thr Thr Val Gly Val Val Cys
    850                 855                 860
Arg Gln Leu Gly Cys Ala Asp Lys Gly Lys Ile Asn Pro Ala Ser Leu
865                 870                 875                 880
Asp Lys Ala Met Ser Ile Pro Met Trp Val Asp Asn Val Gln Cys Pro
                885                 890                 895
Lys Gly Pro Asp Thr Leu Trp Gln Cys Pro Ser Ser Pro Trp Glu Lys
                900                 905                 910
Arg Leu Ala Ser Pro Ser Glu Glu Thr Trp Ile Thr Cys Asp Asn Lys
    915                 920                 925
Ile Arg Leu Gln Glu Gly Pro Thr Ser Cys Ser Gly Arg Val Glu Ile
    930                 935                 940
Trp His Gly Gly Ser Trp Gly Thr Val Cys Asp Asp Ser Trp Asp Leu
945                 950                 955                 960
Asp Asp Ala Gln Val Val Cys Gln Gln Leu Gly Cys Gly Pro Ala Leu
                965                 970                 975
Lys Ala Phe Lys Glu Ala Glu Phe Gly Gln Gly Thr Gly Pro Ile Trp
                980                 985                 990
Leu Asn Glu Val Lys Cys Lys Gly Asn Glu Ser Ser Leu Trp Asp Cys
    995                 1000                1005
Pro Ala Arg Arg Trp Gly His Ser Glu Cys Gly His Lys Glu Asp
    1010                1015                1020
```

| Ala | Ala | Val | Asn | Cys | Thr | Asp | Ile | Ser | Val | Gln | Lys | Thr | Pro | Gln |
|---|---|---|---|---|---|---|---|---|---|---|---|---|---|---|
| 1025 | | | | 1030 | | | | | 1035 | | | | | |

| Lys | Ala | Thr | Thr | Gly | Arg | Ser | Ser | Arg | Gln | Ser | Ser | Phe | Ile | Ala |
|---|---|---|---|---|---|---|---|---|---|---|---|---|---|---|
| 1040 | | | | | 1045 | | | | | 1050 | | | | |

| Val | Gly | Ile | Leu | Gly | Val | Val | Leu | Leu | Ala | Ile | Phe | Val | Ala | Leu |
|---|---|---|---|---|---|---|---|---|---|---|---|---|---|---|
| 1055 | | | | | 1060 | | | | | 1065 | | | | |

| Phe | Phe | Leu | Ala | Val | Ser | Ser | Arg | Gly | Glu | Asn | Leu | Val | His | Gln |
|---|---|---|---|---|---|---|---|---|---|---|---|---|---|---|
| 1070 | | | | | 1075 | | | | | 1080 | | | | |

| Ile | Gln | Tyr | Arg | Glu | Met | Asn | Ser | Cys | Leu | Asn | Ala | Asp | Asp | Leu |
|---|---|---|---|---|---|---|---|---|---|---|---|---|---|---|
| 1085 | | | | | 1090 | | | | | 1095 | | | | |

| Asp | Leu | Met | Asn | Ser | Ser | Gly | Gly | His | Ser | Glu | Pro | His |
|---|---|---|---|---|---|---|---|---|---|---|---|---|
| 1100 | | | | | 1105 | | | | | 1110 | | |

```
<210> SEQ ID NO 33
<211> LENGTH: 4107
<212> TYPE: DNA
<213> ORGANISM: Homo sapiens

<400> SEQUENCE: 33
atatgtagcc ttttcatttt catgaaagtg aagtgatttt tagaattctt agttgttttc      60
tttagaagaa catttctagg gaataataca agaagattta ggaatcattg aagttataaa     120
tctttggaat gagcaaactc agaatggtgc tacttgaaga ctctggatct gctgacttca     180
gaagacattt tgtcaacttg agtcccttca ccattactgt ggtcttactt ctcagtgcct     240
gttttgtcac cagttctctt ggaggaacag acaaggagct gaggctagtg atggtgaaa      300
acaagtgtag cgggagagtg gaagtgaaag tccaggagga gtggggaacg gtgtgtaata     360
atggctggag catggaagcg gtctctgtga tttgtaacca gctgggatgt ccaactgcta     420
tcaaagcccc tggatgggct aattccagtg caggttctgg acgcatttgg atggatcatg     480
tttcttgtcg tgggaatgag tcagctcttt gggattgcaa acatgatgga tggggaaagc     540
atagtaactg tactcaccaa caagatgctg gagtgacctg ctcagatgga tccaatttgg     600
aaatgaggct gacgcgtgga gggaatatgt gttctggaag aatagagatc aaattccaag     660
gacggtgggg aacagtgtgt gatgataact tcaacataga tcatgcatct gtcatttgta     720
gacaacttga atgtgaagt gctgtcagtt tctctggttc atctaatttt ggagaaggct      780
ctggaccaat ctggtttgat gatcttatat gcaacgaaa tgagtcagct ctctggaact      840
gcaaacatca aggatgggga aagcataact gtgatcatgc tgaggatgct ggagtgattt     900
gctcaaaggg agcagatctg agcctgagac tggtagatgg agtcactgaa tgttcaggaa     960
gattagaagt gagattccaa ggagaatggg ggacaatatg tgatgacggc tgggacagtt    1020
acgatgctgc tgtggcatgc aagcaactgg gatgtccaac tgccgtcaca gccattggtc    1080
gagttaacgc cagtaaggga tttggacaca tctggcttga cagcgtttct tgccagggac    1140
atgaacctgc tatctggcaa tgtaaacacc atgaatgggg aaagcattat tgcaatcaca    1200
atgaagatgc tggcgtgaca tgttctgatg gatcagatct ggagctaaga cttagaggtg    1260
gaggcagccg ctgtgctggg acagttgagg tggagattca gagactgtta gggaaggtgt    1320
gtgacagagg ctgggactg aaagaagctg atgtggtttg caggcagctg gatgtggat     1380
ctgcactcaa aacatcttat caagtgtact ccaaaatcca ggcaacaaac acatggctgt    1440
ttctaagtag ctgtaacgga aatgaaactt ctctttggga ctgcaagaac tggcaatggg    1500
gtggacttac ctgtgatcac tatgaagaag ccaaaattac ctgctcagcc cacagggaac    1560
```

| | |
|---|---|
| ccagactggt tggaggggac attccctgtt ctggacgtgt tgaagtgaag catggtgaca | 1620 |
| cgtggggctc catctgtgat tcggacttct ctctggaagc tgccagcgtt ctatgcaggg | 1680 |
| aattacagtg tggcacagtt gtctctatcc tggggggagc tcactttgga gagggaaatg | 1740 |
| gacagatctg ggctgaagaa ttccagtgtg agggacatga gtcccatctt tcactctgcc | 1800 |
| cagtagcacc ccgcccagaa ggaacttgta gccacagcag ggatgttgga gtagtctgct | 1860 |
| caagatacac agaaattcgc ttggtgaatg caagacccc gtgtgagggc agagtggagc | 1920 |
| tcaaaacgct tggtgcctgg ggatccctct gtaactctca ctgggacata aagatgccc | 1980 |
| atgttctttg ccagcagctt aaatgtggag ttgccctttc taccccagga ggagcacgtt | 2040 |
| ttggaaaagg aaatggtcag atctggaggc atatgtttca ctgcactggg actgagcagc | 2100 |
| acatgggaga ttgtcctgta actgctctag gtgcttcatt atgtccttca gagcaagtgg | 2160 |
| cctctgtaat ctgctcagga aaccagtccc aaacactgtc ctcgtgcaat tcatcgtctt | 2220 |
| tgggcccaac aaggcctacc attccagaag aaagtgctgt ggcctgcata gagagtggtc | 2280 |
| aacttcgcct ggtaaatgga ggaggtcgct gtgctgggag agtagagatc tatcatgagg | 2340 |
| gctcctgggg caccatctgt gatgacagct gggacctgag tgatgcccac gtggtttgca | 2400 |
| gacagctggg ctgtggagag gccattaatg ccactggttc tgctcatttt ggggaaggaa | 2460 |
| cagggcccat ctggctggat gagatgaaat gcaatggaaa agaatcccgc atttggcagt | 2520 |
| gccattcaca cggctggggg cagcaaaatt gcaggcacaa ggaggatgcg ggagttatct | 2580 |
| gctcagaatt catgtctctg agactgacca gtgaagccag cagagaggcc tgtgcagggc | 2640 |
| gtctggaagt tttttacaat ggagcttggg gcactgttgg caagagtagc atgtctgaaa | 2700 |
| ccactgtggg tgtggtgtgc aggcagctgg gctgtgcaga caagggaaa atcaaccctg | 2760 |
| catctttaga caaggccatg tccattccca tgtgggtgga caatgttcag tgtccaaaag | 2820 |
| gacctgacac gctgtggcag tgcccatcat ctccatggga aagagactg ccagcccct | 2880 |
| cggaggagac ctggatcaca tgtgacaaca agataagact tcaggaagga cccacttcct | 2940 |
| gttctggacg tgtggagatc tggcatggag gttcctgggg acagtgtgt gatgactctt | 3000 |
| gggacttgga cgatgctcag gtggtgtgtc aacaacttgg ctgtggtcca gctttgaaag | 3060 |
| cattcaaaga agcagagttt ggtcagggga ctggaccgat atggctcaat gaagtgaagt | 3120 |
| gcaaagggaa tgagtcttcc ttgtgggatt gtcctgccag acgctgggc catagtgagt | 3180 |
| gtgggcacaa ggaagacgct gcagtgaatt gcacagatat ttcagtgcag aaaaccccac | 3240 |
| aaaaagccac aacaggtcgc tcatcccgtc agtcatcctt tattgcagtc gggatccttg | 3300 |
| gggttgttct gttggccatt ttcgtcgcat tattcttctt gactaaaaag cgaagacaga | 3360 |
| gacagcggct tgcagtttcc tcaagaggag agaacttagt ccaccaaatt caataccggg | 3420 |
| agatgaattc ttgcctgaat gcagatgatc tggacctaat gaattcctca ggaggccatt | 3480 |
| ctgagccaca ctgaaaagga aaatgggaat ttataaccca gtgagttcag cctttaagat | 3540 |
| accttgatga agacctggac tattgaatgg agcagaaatt caccctctctc actgactatt | 3600 |
| acagttgcat ttttatggag ttcttcttct cctaggattc ctaagactgc tgctgaattt | 3660 |
| ataaaaatta agtttgtgaa tgtgactact tagtggtgta tatgagactt tcaagggaat | 3720 |
| taaataaata aataagaatg ttattgattt gagtttgctt taattacttg tccttaattc | 3780 |
| tattaatttc taaatgggct tcctaatttt ttgtagagtt tcctagatgt attataatgt | 3840 |
| gttttatttg acagtgtttc aatttgcata tacagtactg tatattttt cttatttggt | 3900 |
| ttgaataatt ttcctattac caaataaaaa taaatttatt tttactttag tttttctaag | 3960 |

-continued

```
acaggaaaag ttaatgatat tgaagggtct gtaaataata tatggctaac tttataaggc    4020
atgactcaca acgattcttt aactgctttt tgttactgta attctgttca ctagaataaa    4080
atgcagagcc acacctggtg agggcac                                        4107
```

<210> SEQ ID NO 34
<211> LENGTH: 375
<212> TYPE: PRT
<213> ORGANISM: Homo sapiens

<400> SEQUENCE: 34

| Met | Glu | Arg | Ala | Ser | Cys | Leu | Leu | Leu | Leu | Leu | Pro | Leu | Val | His |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Val | Ser | Ala | Thr | Thr | Pro | Glu | Pro | Cys | Glu | Leu | Asp | Asp | Glu | Asp |  Phe |
|-----|-----|-----|-----|-----|-----|-----|-----|-----|-----|-----|-----|-----|-----|-----|------|
|     |     |     | 20  |     |     |     |     | 25  |     |     |     |     | 30  |     |      |

Arg Cys Val Cys Asn Phe Ser Glu Pro Gln Pro Asp Trp Ser Glu Ala
            35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
            100                 105                 110

Leu Ala Tyr Ser Arg Leu Lys Glu Leu Thr Leu Glu Asp Leu Lys Ile
        115                 120                 125

Thr Gly Thr Met Pro Pro Leu Pro Leu Glu Ala Thr Gly Leu Ala Leu
    130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
    210                 215                 220

Gln Asn Leu Ala Leu Arg Asn Thr Gly Met Glu Thr Pro Thr Gly Val
225                 230                 235                 240

Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys 340                 345                 350
Ala Arg Ser Thr Leu Ser Val Gly Val Ser Gly Thr Leu Val Leu Leu
            355                 360                 365

Gln Gly Ala Arg Gly Phe Ala
        370                 375

<210> SEQ ID NO 35
<211> LENGTH: 1648
<212> TYPE: DNA
<213> ORGANISM: Homo sapiens

<400> SEQUENCE: 35

| | | | | | |
|---|---|---|---|---|---|
| cagagaaggc | ttaggctccc | gagtcaacag | ggcattcacc | gcctggggcg | cctgagtcat | 60 |
| caggacactg | ccaggagaca | cagaacccta | gatgccctgc | agaatccttc | ctgttacggt | 120 |
| ccccctccct | gaaacatcct | tcattgcaat | atttccagga | aggaagggg | gctggctcgg | 180 |
| aggaagagag | gtggggaggt | gatcagggtt | cacagaggag | ggaactgaat | gacatcccag | 240 |
| gattacataa | actgtcagag | gcagccgaag | agttcacaag | tgtgaagcct | ggaagccggc | 300 |
| gggtgccgct | gtgtaggaaa | gaagctaaag | cacttccaga | gcctgtccgg | agctcagagg | 360 |
| ttcgaaagac | ttatcgacca | tggagcgcgc | gtcctgcttg | ttgctgctgc | tgctgccgct | 420 |
| ggtgcacgtc | tctgcgacca | cgccagaacc | ttgtgagctg | gacgatgaag | atttccgctg | 480 |
| cgtctgcaac | ttctccgaac | tcagcccga | ctggtccgaa | gccttccagt | gtgtgtctgc | 540 |
| agtagaggtg | gagatccatg | ccggcggtct | caacctagag | ccgtttctaa | agcgcgtcga | 600 |
| tgcggacgcc | gacccgcggc | agtatgctga | cacggtcaag | gctctccgcg | tgcggcggct | 660 |
| cacagtggga | gccgcacagg | ttcctgctca | gctactggta | ggcgccctgc | gtgtgctagc | 720 |
| gtactcccgc | ctcaaggaac | tgacgctcga | ggacctaaag | ataaccggca | ccatgcctcc | 780 |
| gctgcctctg | gaagccacag | gacttgcact | tccagcttg | cgcctacgca | acgtgtcgtg | 840 |
| ggcgacaggg | cgttcttggc | tcgccgagct | gcagcagtgg | ctcaagccag | gcctcaaggt | 900 |
| actgagcatt | gcccaagcac | actcgcctgc | cttttcctgc | gaacaggttc | gcgccttccc | 960 |
| ggcccttacc | agcctagacc | tgtctgacaa | tcctggactg | ggcgaacgcg | gactgatggc | 1020 |
| ggctctctgt | ccccacaagt | tcccggccat | ccagaatcta | gcgctgcgca | acacaggaat | 1080 |
| ggagacgccc | acaggcgtgt | gcgccgcact | ggcggcggca | ggtgtgcagc | cccacagcct | 1140 |
| agacctcagc | cacaactcgc | tgcgcgccac | cgtaaaccct | agcgctccga | gatgcatgtg | 1200 |
| gtccagcgcc | ctgaactccc | tcaatctgtc | gttcgctggg | ctggaacagg | tgcctaaagg | 1260 |
| actgccagcc | aagctcagag | tgctcgatct | cagctgcaac | agactgaaca | gggcgccgca | 1320 |
| gcctgacgag | ctgcccgagg | tggataacct | gacactggac | gggaatccct | tcctggtccc | 1380 |
| tggaactgcc | ctcccccacg | agggctcaat | gaactccggc | gtggtcccag | cctgtgcacg | 1440 |
| ttcgaccctg | tcggtggggg | tgtcgggaac | cctggtgctg | ctccaagggg | cccggggctt | 1500 |
| tgcctaagat | ccaagacaga | ataatgaatg | gactcaaact | gccttggctt | caggggagtc | 1560 |
| ccgtcaggac | gttgaggact | tttcgaccaa | ttcaacccct | tgccccacct | ttattaaaat | 1620 |
| cttaaacaac | gggtcaaaaa | aaaaaaaa | | | | 1648 |

<210> SEQ ID NO 36
<211> LENGTH: 375
<212> TYPE: PRT
<213> ORGANISM: Homo sapiens

<400> SEQUENCE: 36

```
Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
                35                  40                  45

Phe Gln Cys Val Ser Ala Val Glu Val Glu Ile His Ala Gly Gly Leu
50                      55                      60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
                100                 105                 110

Leu Ala Tyr Ser Arg Leu Lys Glu Leu Thr Leu Glu Asp Leu Lys Ile
            115                 120                 125

Thr Gly Thr Met Pro Pro Leu Pro Leu Glu Ala Thr Gly Leu Ala Leu
130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
                180                 185                 190

Phe Pro Ala Leu Thr Ser Leu Asp Leu Ser Asp Asn Pro Gly Leu Gly
            195                 200                 205

Glu Arg Gly Leu Met Ala Ala Leu Cys Pro His Lys Phe Pro Ala Ile
210                 215                 220

Gln Asn Leu Ala Leu Arg Asn Thr Gly Met Glu Thr Pro Thr Gly Val
225                 230                 235                 240

Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
                260                 265                 270

Met Trp Ser Ser Ala Leu Asn Ser Leu Asn Leu Ser Phe Ala Gly Leu
            275                 280                 285

Glu Gln Val Pro Lys Gly Leu Pro Ala Lys Leu Arg Val Leu Asp Leu
290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
                340                 345                 350

Ala Arg Ser Thr Leu Ser Val Gly Val Ser Gly Thr Leu Val Leu Leu
            355                 360                 365

Gln Gly Ala Arg Gly Phe Ala
370                 375

<210> SEQ ID NO 37
<211> LENGTH: 1501
<212> TYPE: DNA
<213> ORGANISM: Homo sapiens
```

<400> SEQUENCE: 37

```
ttaaatatct gaggatattc agggacttgg atttggtggc aggagatcaa cataaaccaa      60
gacaaggaag aagtcaaaga aatgaatcaa gtagattctc tgggatataa gaggcagccg     120
aagagttcac aagtgtgaag cctggaagcc ggcgggtgcc gctgtgtagg aaagaagcta     180
aagcacttcc agagcctgtc cggagctcag aggttcggaa gacttatcga ccatggagcg     240
cgcgtcctgc ttgttgctgc tgctgctgcc gctggtgcac gtctctgcga ccacgccaga     300
accttgtgag ctggacgatg aagatttccg ctgcgtctgc aacttctccg aacctcagcc     360
cgactggtcc gaagccttcc agtgtgtgtc tgcagtagag gtggagatcc atgccggcgg     420
tctcaaccta gagccgtttc taaagcgcgt cgatgcggac gccgacccgc ggcagtatgc     480
tgacacggtc aaggctctcc gcgtgcggcg gctcacagtg ggagccgcac aggttcctgc     540
tcagctactg gtaggcgccc tgcgtgtgct agcgtactcc cgcctcaagg aactgacgct     600
cgaggaccta aagataaccg gcaccatgcc tccgctgcct ctggaagcca caggacttgc     660
actttccagc ttgcgcctac gcaacgtgtc gtgggcgaca gggcgttctt ggctcgccga     720
gctgcagcag tggctcaagc caggcctcaa ggtactgagc attgcccaag cacactcgcc     780
tgccttttcc tgcgaacagg ttcgcgcctt cccggccctt accagcctag acctgtctga     840
caatcctgga ctgggcgaac gcggactgat ggcggctctc tgtccccaca gttcccggc     900
catccagaat ctagcgctgc gcaacacagg aatggagacg cccacaggcg tgtgcgccgc     960
actggcggcg gcaggtgtgc agccccacag cctagacctc agccacaact cgctgcgcgc    1020
caccgtaaac cctagcgctc cgagatgcat gtggtccagc gccctgaact ccctcaatct    1080
gtcgttcgct gggctggaac aggtgcctaa aggactgcca gccaagctca gagtgctcga    1140
tctcagctgc aacagactga acaggggcgcc gcagcctgac gagctgcccg aggtggataa    1200
cctgacactg gacgggaatc ccttcctggt ccctggaact gccctccccc acgagggctc    1260
aatgaactcc ggcgtggtcc cagcctgtgc acgttcgacc ctgtcggtgg gggtgtcggg    1320
aaccctggtg ctgctccaag gggcccgggg ctttgcctaa gatccaagac agaataatga    1380
atggactcaa actgccttgg cttcagggga gtcccgtcag gacgttgagg acttttcgac    1440
caattcaacc ctttgcccca cctttattaa aatcttaaac aacgggtcaa aaaaaaaaa    1500
a                                                                   1501
```

<210> SEQ ID NO 38
<211> LENGTH: 375
<212> TYPE: PRT
<213> ORGANISM: Homo sapiens

<400> SEQUENCE: 38

```
Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
        35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95
```

Gly Ala Ala Gln Val Pro Ala Gln Leu Leu Val Gly Ala Leu Arg Val
                100                 105                 110

Leu Ala Tyr Ser Arg Leu Lys Glu Leu Thr Leu Glu Asp Leu Lys Ile
            115                 120                 125

Thr Gly Thr Met Pro Pro Leu Pro Leu Glu Ala Thr Gly Leu Ala Leu
        130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
210                 215                 220

Gln Asn Leu Ala Leu Arg Asn Thr Gly Met Glu Thr Pro Thr Gly Val
225                 230                 235                 240

Cys Ala Ala Leu Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
                290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
        355                 360                 365

Gln Gly Ala Arg Gly Phe Ala
    370                 375

<210> SEQ ID NO 39
<211> LENGTH: 1661
<212> TYPE: DNA
<213> ORGANISM: Homo sapiens

<400> SEQUENCE: 39
aattctaccc cccttggtgc aacagatga ggttcacaat ctcttccaca aaacatgcag    60
ttaaatatct gaggatattc agggacttgg atttggtggc aggagatcaa cataaaccaa   120
gacaaggaag aagtcaaaga atgaatcaa gtagattctc tgggatataa ggaaaggaag   180
ggggctggct cggaggaaga gaggtgggga ggtgatcagg gttcacagag gagggaactg   240
aatgacatcc caggattaca taaactgtca gaggcagccg aagagttcac aagtgtgaag   300
cctggaagcc ggcgggtgcc gctgtgtagg aaagaagcta agcacttcc agagcctgtc   360 cggagctcag aggttcggaa gacttatcga ccatggagcg cgcgtcctgc ttgttgctgc   420
tgctgctgcc gctggtgcac gtctctgcga ccacgccaga accttgtgag ctggacgatg   480

-continued

```
aagatttccg ctgcgtctgc aacttctccg aacctcagcc cgactggtcc gaagccttcc    540
agtgtgtgtc tgcagtagag gtggagatcc atgccggcgg tctcaaccta gagccgtttc    600
taaagcgcgt cgatgcggac gccgacccgc ggcagtatgc tgacacggtc aaggctctcc    660
gcgtgcggcg gctcacagtg ggagccgcac aggttcctgc tcagctactg gtaggcgccc    720
tgcgtgtgct agcgtactcc cgcctcaagg aactgacgct cgaggaccta agataaccg     780
gcaccatgcc tccgctgcct ctggaagcca caggacttgc actttccagc ttgcgcctac    840
gcaacgtgtc gtgggcgaca gggcgttctt ggctcgccga gctgcagcag tggctcaagc    900
caggcctcaa ggtactgagc attgcccaag cacactcgcc tgccttttcc tgcgaacagg    960
ttcgcgcctt cccggcccctt accagcctag acctgtctga caatcctgga ctgggcgaac   1020
gcggactgat ggcggctctc tgtccccaca agttcccggc catccagaat ctagcgctgc    1080
gcaacacagg aatggagacg cccacaggcg tgtgcgccgc actggcggcg caggtgtgc     1140
agccccacag cctagacctc agccacaact cgctgcgcgc caccgtaaac cctagcgctc    1200
cgagatgcat gtggtccagc gccctgaact ccctcaatct gtcgttcgct gggctggaac    1260
aggtgcctaa aggactgcca gccaagctca gagtgctcga tctcagctgc aacagactga    1320
acagggcgcc gcagcctgac gagctgcccg aggtggataa cctgacactg gacgggaatc    1380
ccttcctggt ccctggaact gccctccccc acgagggctc aatgaactcc ggcgtggtcc    1440
cagcctgtgc acgttcgacc ctgtcgtggg gggtgtcggg aaccctggtg ctgctccaag    1500
gggcccgggg ctttgcctaa gatccaagac agaataatga atggactcaa actgccttgg    1560
cttcagggga gtcccgtcag gacgttgagg acttttcgac caattcaacc ctttgcccca    1620
cctttattaa aatcttaaac aacgggtcaa aaaaaaaaa a                         1661
```

<210> SEQ ID NO 40
<211> LENGTH: 375
<212> TYPE: PRT
<213> ORGANISM: Homo sapiens

<400> SEQUENCE: 40

Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
        35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
            100                 105                 110

Leu Ala Tyr Ser Arg Leu Lys Glu Leu Thr Leu Glu Asp Leu Lys Ile
        115                 120                 125

Thr Gly Thr Met Pro Pro Leu Pro Leu Glu Ala Thr Gly Leu Ala Leu
    130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser

|  | 165 |  |  |  | 170 |  |  |  | 175 |  |  |
|---|---|---|---|---|---|---|---|---|---|---|---|

Ile Ala Gln Ala His Ser Pro Ala Phe Ser Cys Glu Gln Val Arg Ala
        180                     185                     190

Phe Pro Ala Leu Thr Ser Leu Asp Leu Ser Asp Asn Pro Gly Leu Gly
        195                     200                     205

Glu Arg Gly Leu Met Ala Ala Leu Cys Pro His Lys Phe Pro Ala Ile
210                     215                     220

Gln Asn Leu Ala Leu Arg Asn Thr Gly Met Glu Thr Pro Thr Gly Val
225                     230                     235                     240

Cys Ala Ala Leu Ala Ala Gly Val Gln Pro His Ser Leu Asp Leu
            245                     250                     255

Ser His Asn Ser Leu Arg Ala Thr Val Asn Pro Ser Ala Pro Arg Cys
            260                     265                     270

Met Trp Ser Ser Ala Leu Asn Ser Leu Asn Leu Ser Phe Ala Gly Leu
            275                     280                     285

Glu Gln Val Pro Lys Gly Leu Pro Ala Lys Leu Arg Val Leu Asp Leu
290                     295                     300

Ser Cys Asn Arg Leu Asn Arg Ala Pro Gln Pro Asp Glu Leu Pro Glu
305                     310                     315                     320

Val Asp Asn Leu Thr Leu Asp Gly Asn Pro Phe Leu Val Pro Gly Thr
                325                     330                     335

Ala Leu Pro His Glu Gly Ser Met Asn Ser Gly Val Val Pro Ala Cys
            340                     345                     350

Ala Arg Ser Thr Leu Ser Val Gly Val Ser Gly Thr Leu Val Leu Leu
            355                     360                     365

Gln Gly Ala Arg Gly Phe Ala
370                     375

<210> SEQ ID NO 41
<211> LENGTH: 1540
<212> TYPE: DNA
<213> ORGANISM: Homo sapiens

<400> SEQUENCE: 41

| aattctaccc | cccttggtgc | caacagatga | ggttcacaat | ctcttccaca | aaacatgcag | 60 |
| ttaaatatct | gaggatattc | agggacttgg | atttggtggc | aggagatcaa | cataaaccaa | 120 |
| gacaaggaag | aagtcaaaga | aatgaatcaa | aggcagccga | agagttcaca | agtgtgaagc | 180 |
| ctggaagccg | gcgggtgccg | ctgtgtagga | aagaagctaa | agcacttcca | gagcctgtcc | 240 |
| ggagctcaga | ggttcggaag | acttatcgac | catggagcgc | gcgtcctgct | tgttgctgct | 300 |
| gctgctgccg | ctggtgcacg | tctctgcgac | cacgccagaa | ccttgtgagc | tggacgatga | 360 |
| agatttccgc | tgcgtctgca | acttctccga | acctcagccc | gactggtccg | aagccttcca | 420 |
| gtgtgtgtct | gcagtagagg | tggagatcca | tgccggcggt | ctcaacctag | agccgtttct | 480 |
| aaagcgcgtc | gatgcggacg | ccgacccgcg | gcagtatgct | gacacggtca | aggctctccg | 540 |
| cgtgcggcgg | ctcacagtgg | gagccgcaca | ggttcctgct | cagctactgg | taggcgccct | 600 |
| gcgtgtgcta | gcgtactccc | gcctcaagga | actgacgctc | gaggacctaa | agataaccgg | 660 |
| caccatgcct | ccgctgcctc | tggaagccac | aggacttgca | ctttccagct | tgcgcctacg | 720 |
| caacgtgtcg | tgggcgacag | ggcgttcttg | gctcgccgag | ctgcagcagt | ggctcaagcc | 780 |
| aggcctcaag | gtactgagca | ttgcccaagc | acactcgcct | gccttttcct | gcgaacaggt | 840 |
| tcgcgccttc | ccggccctta | ccagcctaga | cctgtctgac | aatcctggac | tgggcgaacg | 900 |

```
cggactgatg gcggctctct gtccccacaa gttcccggcc atccagaatc tagcgctgcg      960
caacacagga atgagacgc ccacaggcgt gtgcgccgca ctggcggcgg caggtgtgca      1020
gccccacagc ctagacctca gccacaactc gctgcgcgcc accgtaaacc ctagcgctcc      1080
gagatgcatg tggtccagcg ccctgaactc cctcaatctg tcgttcgctg ggctggaaca      1140
ggtgcctaaa ggactgccag ccaagctcag agtgctcgat ctcagctgca acagactgaa      1200
cagggcgccg cagcctgacg agctgcccga ggtggataac ctgacactgg acggaatcc      1260 cttcctggtc cctggaactg ccctccccca cgagggctca atgaactccg gcgtggtccc      1320
agcctgtgca cgttcgaccc tgtcggtggg ggtgtcggga accctggtgc tgctccaagg      1380
ggcccggggc tttgcctaag atccaagaca gaataatgaa tggactcaaa ctgccttggc      1440
ttcaggggag tcccgtcagg acgttgagga cttttcgacc aattcaaccc tttgccccac      1500
ctttattaaa atcttaaaca acgggtcaaa aaaaaaaaa                            1540
```

<210> SEQ ID NO 42
<211> LENGTH: 348
<212> TYPE: PRT
<213> ORGANISM: Homo sapiens

<400> SEQUENCE: 42

```
Met Leu Cys Pro Trp Arg Thr Ala Asn Leu Gly Leu Leu Ile Leu
1               5                   10                  15

Thr Ile Phe Leu Val Ala Glu Ala Glu Gly Ala Ala Gln Pro Asn Asn
            20                  25                  30

Ser Leu Met Leu Gln Thr Ser Lys Glu Asn His Ala Leu Ala Ser Ser
        35                  40                  45

Ser Leu Cys Met Asp Glu Lys Gln Ile Thr Gln Asn Tyr Ser Lys Val
    50                  55                  60

Leu Ala Glu Val Asn Thr Ser Trp Pro Val Lys Met Ala Thr Asn Ala
65                  70                  75                  80

Val Leu Cys Cys Pro Pro Ile Ala Leu Arg Asn Leu Ile Ile Ile Thr
                85                  90                  95

Trp Glu Ile Ile Leu Arg Gly Gln Pro Ser Cys Thr Lys Ala Tyr Lys
            100                 105                 110

Lys Glu Thr Asn Glu Thr Lys Glu Thr Asn Cys Thr Asp Glu Arg Ile
        115                 120                 125

Thr Trp Val Ser Arg Pro Asp Gln Asn Ser Asp Leu Gln Ile Arg Thr
    130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Val Thr Leu Phe Gln Asn Arg Asn Arg Thr Ala Val Cys Lys Ala
            180                 185                 190

Val Ala Gly Lys Pro Ala Ala His Ile Ser Trp Ile Pro Glu Gly Asp
        195                 200                 205

Cys Ala Thr Lys Gln Glu Tyr Trp Ser Asn Gly Thr Val Thr Val Lys
    210                 215                 220

Ser Thr Cys His Trp Glu Val His Asn Val Thr Val Thr Cys His
225                 230                 235                 240

Val Ser His Leu Thr Gly Asn Lys Ser Leu Tyr Ile Glu Leu Leu Pro
                245                 250                 255

Val Pro Gly Ala Lys Lys Ser Ala Lys Leu Tyr Ile Pro Tyr Ile Ile
```

```
                    260                 265                 270
Leu Thr Ile Ile Leu Thr Ile Val Gly Phe Ile Trp Leu Leu Lys
                275                 280                 285

Val Asn Gly Cys Arg Lys Tyr Lys Leu Asn Lys Thr Glu Ser Thr Pro
            290                 295                 300

Val Val Glu Glu Asp Glu Met Gln Pro Tyr Ala Ser Tyr Thr Glu Lys
305                 310                 315                 320

Asn Asn Pro Leu Tyr Asp Thr Thr Asn Lys Val Lys Ala Ser Glu Ala
                325                 330                 335

Leu Gln Ser Glu Val Asp Thr Asp Leu His Thr Leu
            340                 345

<210> SEQ ID NO 43
<211> LENGTH: 188
<212> TYPE: PRT
<213> ORGANISM: Homo sapiens

<400> SEQUENCE: 43

Met Leu Cys Pro Trp Arg Thr Ala Asn Leu Gly Leu Leu Leu Ile Leu
1               5                   10                  15

Thr Ile Phe Leu Val Ala Glu Ala Glu Gly Ala Ala Gln Pro Asn Asn
            20                  25                  30

Ser Leu Met Leu Gln Thr Ser Lys Glu Asn His Ala Leu Ala Ser Ser
        35                  40                  45

Ser Leu Cys Met Asp Glu Lys Gln Ile Thr Gln Asn Tyr Ser Lys Val
    50                  55                  60

Leu Ala Glu Val Asn Thr Ser Trp Pro Val Lys Met Ala Thr Asn Ala
65                  70                  75                  80

Val Leu Cys Cys Pro Pro Ile Ala Leu Arg Asn Leu Ile Ile Ile Thr
                85                  90                  95

Trp Glu Ile Ile Leu Arg Gly Gln Pro Ser Cys Thr Lys Ala Tyr Lys
            100                 105                 110

Lys Glu Thr Asn Glu Thr Lys Glu Thr Asn Cys Thr Asp Glu Arg Ile
        115                 120                 125

Thr Trp Val Ser Arg Pro Asp Gln Asn Ser Asp Leu Gln Ile Arg Thr
    130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Gly Lys Glu
                165                 170                 175

His His Ile Leu Arg Tyr Phe Thr Ser Pro Asp Leu
            180                 185

<210> SEQ ID NO 44
<211> LENGTH: 165
<212> TYPE: PRT
<213> ORGANISM: Homo sapiens

<400> SEQUENCE: 44

Met Leu Cys Pro Trp Arg Thr Ala Asn Leu Gly Leu Leu Leu Ile Leu
1               5                   10                  15

Thr Ile Phe Leu Val Ala Ala Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
```

```
        50                  55                  60
Ala Leu Arg Asn Leu Ile Ile Ile Thr Trp Glu Ile Ile Leu Arg Gly
 65                  70                  75                  80

Gln Pro Ser Cys Thr Lys Ala Tyr Lys Lys Glu Thr Asn Glu Thr Lys
                 85                  90                  95

Glu Thr Asn Cys Thr Asp Glu Arg Ile Thr Trp Val Ser Arg Pro Asp
                100                 105                 110

Gln Asn Ser Asp Leu Gln Ile Arg Thr Val Ala Ile Thr His Asp Gly
                115                 120                 125

Tyr Tyr Arg Cys Ile Met Val Thr Pro Asp Gly Asn Phe His Arg Gly
                130                 135                 140

Tyr His Leu Gln Val Leu Gly Lys Glu His His Ile Leu Arg Tyr Phe
145                 150                 155                 160

Thr Ser Pro Asp Leu
                165

<210> SEQ ID NO 45
<211> LENGTH: 325
<212> TYPE: PRT
<213> ORGANISM: Homo sapiens

<400> SEQUENCE: 45

Met Leu Cys Pro Trp Arg Thr Ala Asn Leu Gly Leu Leu Ile Leu
 1               5                  10                  15

Thr Ile Phe Leu Val Ala Ala Ser Ser Leu Cys Met Asp Glu Lys
                 20                  25                  30

Gln Ile Thr Gln Asn Tyr Ser Lys Val Leu Ala Glu Val Asn Thr Ser
                 35                  40                  45

Trp Pro Val Lys Met Ala Thr Asn Ala Val Leu Cys Cys Pro Pro Ile
                 50                  55                  60

Ala Leu Arg Asn Leu Ile Ile Ile Thr Trp Glu Ile Ile Leu Arg Gly
 65                  70                  75                  80

Gln Pro Ser Cys Thr Lys Ala Tyr Lys Lys Glu Thr Asn Glu Thr Lys
                 85                  90                  95

Glu Thr Asn Cys Thr Asp Glu Arg Ile Thr Trp Val Ser Arg Pro Asp
                100                 105                 110

Gln Asn Ser Asp Leu Gln Ile Arg Thr Val Ala Ile Thr His Asp Gly
                115                 120                 125

Tyr Tyr Arg Cys Ile Met Val Thr Pro Asp Gly Asn Phe His Arg Gly
                130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

His Ile Ser Trp Ile Pro Glu Gly Asp Cys Ala Thr Lys Gln Glu Tyr
                180                 185                 190

Trp Ser Asn Gly Thr Val Thr Val Lys Ser Thr Cys His Trp Glu Val
                195                 200                 205

His Asn Val Ser Thr Val Thr Cys His Val Ser His Leu Thr Gly Asn
                210                 215                 220

Lys Ser Leu Tyr Ile Glu Leu Leu Pro Val Pro Gly Ala Lys Lys Ser
225                 230                 235                 240

Ala Lys Leu Tyr Ile Pro Tyr Ile Ile Leu Thr Ile Ile Ile Leu Thr
                245                 250                 255
```

```
Ile Val Gly Phe Ile Trp Leu Leu Lys Val Asn Gly Cys Arg Lys Tyr
            260                 265                 270

Lys Leu Asn Lys Thr Glu Ser Thr Pro Val Val Glu Glu Asp Glu Met
            275                 280                 285

Gln Pro Tyr Ala Ser Tyr Thr Glu Lys Asn Asn Pro Leu Tyr Asp Thr
            290                 295                 300

Thr Asn Lys Val Lys Ala Ser Glu Ala Leu Gln Ser Glu Val Asp Thr
305                 310                 315                 320

Asp Leu His Thr Leu
                325

<210> SEQ ID NO 46
<211> LENGTH: 195
<212> TYPE: PRT
<213> ORGANISM: Homo sapiens

<400> SEQUENCE: 46

Met Val Thr Phe Ser Glu Asn His Gly Val Val Ile Gln Pro Ala Tyr
1               5                   10                  15

Lys Asp Lys Ile Asn Ile Thr Gln Leu Gly Leu Gln Asn Ser Thr Ile
            20                  25                  30

Thr Phe Trp Asn Ile Thr Leu Glu Asp Glu Gly Cys Tyr Met Cys Leu
            35                  40                  45

Phe Asn Thr Phe Gly Phe Gly Lys Ile Ser Gly Thr Ala Cys Leu Thr
50                  55                  60

Val Tyr Val Gln Pro Ile Val Ser Leu His Tyr Lys Phe Ser Glu Asp
65                  70                  75                  80

His Leu Asn Ile Thr Cys Ser Ala Thr Ala Arg Pro Ala Pro Met Val
                85                  90                  95

Phe Trp Lys Val Pro Arg Ser Gly Ile Glu Asn Ser Thr Val Thr Leu
            100                 105                 110

Ser His Pro Asn Gly Thr Thr Ser Val Thr Ser Ile Leu His Ile Lys
            115                 120                 125

Asp Pro Lys Asn Gln Val Gly Lys Glu Val Ile Cys Gln Val Leu His
            130                 135                 140

Leu Gly Thr Val Thr Asp Phe Lys Gln Thr Val Asn Lys Gly Tyr Trp
145                 150                 155                 160

Phe Ser Val Pro Leu Leu Leu Ser Ile Val Ser Leu Val Ile Leu Leu
                165                 170                 175

Val Leu Ile Ser Ile Leu Leu Tyr Trp Lys Arg His Arg Asn Gln Asp
            180                 185                 190

Arg Glu Pro
195
```